US011304932B2

(12) United States Patent
Friedhoff et al.

(10) Patent No.: US 11,304,932 B2
(45) Date of Patent: *Apr. 19, 2022

(54) DIARYL AND ARYLHETEROARYL UREA DERIVATIVES AS MODULATORS OF THE 5-HT$_{2A}$ SEROTONIN RECEPTOR USEFUL FOR THE PROPHYLAXIS AND TREATMENT OF HALLUCINATIONS ASSOCIATED WITH A NEURODEGENERATIVE DISEASE

(71) Applicant: Axovant Sciences GmbH, Basel (CH)

(72) Inventors: Lawrence Tim Friedhoff, Rivervale, NJ (US); Shankar Ramaswamy, Cincinnati, OH (US); Yandong Wen, Weston, CT (US)

(73) Assignee: Axovant Sciences GmbH, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/100,528

(22) Filed: Nov. 20, 2020

(65) Prior Publication Data

US 2021/0177804 A1 Jun. 17, 2021

Related U.S. Application Data

(63) Continuation of application No. 16/016,160, filed on Jun. 22, 2018, now abandoned, which is a continuation of application No. 15/211,638, filed on Jul. 15, 2016, now Pat. No. 10,034,859.

(60) Provisional application No. 62/261,381, filed on Dec. 1, 2015, provisional application No. 62/236,618, filed on Oct. 2, 2015, provisional application No. 62/192,939, filed on Jul. 15, 2015.

(51) Int. Cl.
| | |
|---|---|
| *A61K 31/415* | (2006.01) |
| *A61K 9/20* | (2006.01) |
| *A61K 45/06* | (2006.01) |
| *A61K 31/13* | (2006.01) |
| *A61K 31/135* | (2006.01) |
| *A61K 31/198* | (2006.01) |
| *A61K 31/27* | (2006.01) |
| *A61K 31/4045* | (2006.01) |
| *A61K 31/445* | (2006.01) |
| *A61K 31/55* | (2006.01) |
| *A61K 31/5513* | (2006.01) |
| *A61K 31/554* | (2006.01) |
| *A61P 25/00* | (2006.01) |

(52) U.S. Cl.
CPC .......... *A61K 31/415* (2013.01); *A61K 9/2018* (2013.01); *A61K 31/13* (2013.01); *A61K 31/135* (2013.01); *A61K 31/198* (2013.01); *A61K 31/27* (2013.01); *A61K 31/4045* (2013.01); *A61K 31/445* (2013.01); *A61K 31/55* (2013.01); *A61K 31/554* (2013.01); *A61K 31/5513* (2013.01); *A61K 45/06* (2013.01); *A61P 25/00* (2018.01)

(58) Field of Classification Search
CPC .... A61K 31/415; A61K 9/2018; A61K 31/13; A61K 31/135; A61K 31/198; A61K 31/27; A61K 31/4045; A61K 31/445; A61K 31/55; A61K 31/5513; A61K 31/554; A61K 45/06; A61P 25/00
USPC ...................................................... 514/406
See application file for complete search history.

(56) References Cited

U.S. PATENT DOCUMENTS

| | | | |
|---|---|---|---|
| 4,099,012 | A | 7/1978 | Gschwend |
| 4,405,644 | A | 9/1983 | Kabbe et al. |
| 4,409,231 | A | 10/1983 | Stenzel et al. |
| 4,482,534 | A | 11/1984 | Blank |
| 4,555,399 | A | 11/1985 | Hsiao |
| 4,985,352 | A | 1/1991 | Julius et al. |
| 5,077,409 | A | 12/1991 | Wissner |
| 5,128,351 | A | 7/1992 | Wissner |
| 5,346,906 | A | 9/1994 | Baker et al. |
| 5,523,280 | A | 6/1996 | Chene et al. |
| 5,576,338 | A | 11/1996 | Friesen et al. |
| 5,596,001 | A | 1/1997 | Hamanaka |
| 5,661,024 | A | 8/1997 | Kao et al. |
| 5,856,326 | A | 1/1999 | Anthony et al. |
| 5,861,431 | A | 1/1999 | Hildebrand et al. |
| 5,885,785 | A | 3/1999 | Kao et al. |
| 5,886,044 | A | 3/1999 | Widdowson et al. |
| 5,905,080 | A | 5/1999 | Duckworth et al. |
| 5,945,382 | A | 8/1999 | Cantegril et al. |
| 5,990,133 | A | 11/1999 | Gaster et al. |
| 6,005,008 | A | 12/1999 | Widdowson et al. |
| 6,028,083 | A | 2/2000 | Carr et al. |

(Continued)

FOREIGN PATENT DOCUMENTS

| | | |
|---|---|---|
| CA | 2135253 | 5/1996 |
| CA | 2169231 | 8/1996 |

(Continued)

OTHER PUBLICATIONS

"The Merck Manual of Diagnosis and Therapy," Merck Research Laboratories, pp. 1769-1781 (2006).

(Continued)

*Primary Examiner* — Kristin A Vajda
(74) *Attorney, Agent, or Firm* — Fish & Richardson P.C.

(57) ABSTRACT

The present invention relates to certain pyrazole derivatives of Formula (I) and pharmaceutical compositions thereof that modulate the activity of the 5-HT$_{2A}$ serotonin receptor and their uses for the treatment and prophylaxis of visual hallucinations associated with Lewy Body dementia.

28 Claims, 3 Drawing Sheets

(56) References Cited

U.S. PATENT DOCUMENTS

| | | | |
|---|---|---|---|
| 6,028,085 A | 2/2000 | Bromidge | |
| 6,054,472 A | 4/2000 | Armistead et al. | |
| 6,063,808 A | 5/2000 | Fabiano et al. | |
| 6,107,324 A | 8/2000 | Behan et al. | |
| 6,110,498 A | 8/2000 | Rudnic et al. | |
| 6,140,509 A | 10/2000 | Smith et al. | |
| 6,150,393 A | 11/2000 | Behan et al. | |
| 6,172,084 B1 | 1/2001 | Cuny et al. | |
| 6,180,138 B1 | 1/2001 | Engh et al. | |
| 6,187,805 B1 | 2/2001 | Pineiro et al. | |
| 6,204,285 B1 | 3/2001 | Fabiano et al. | |
| 6,207,679 B1 | 3/2001 | Cuny et al. | |
| 6,271,261 B1 | 8/2001 | Widdowson et al. | |
| 6,284,269 B1 | 9/2001 | Struengmann et al. | |
| 6,297,261 B1 | 10/2001 | Christophersen et al. | |
| 6,310,212 B1 | 10/2001 | Yuan et al. | |
| 6,316,450 B1 | 11/2001 | Bromidge et al. | |
| 6,358,698 B1 | 3/2002 | Weiner et al. | |
| 6,376,670 B1 | 4/2002 | Cuny et al. | |
| 6,380,199 B1 | 4/2002 | Reavill et al. | |
| 6,383,762 B1 | 5/2002 | Kao et al. | |
| 6,403,808 B1 | 6/2002 | Glennon et al. | |
| 6,417,393 B1 | 7/2002 | Christophersen et al. | |
| 6,420,541 B1 | 7/2002 | Behan et al. | |
| 6,469,006 B1 | 10/2002 | Blair et al. | |
| 6,479,480 B1 | 11/2002 | Moyes et al. | |
| 6,479,519 B1 | 11/2002 | Astles et al. | |
| 6,489,488 B2 | 12/2002 | Glennon et al. | |
| 6,518,297 B2 | 2/2003 | Glennon et al. | |
| 6,531,291 B1 | 3/2003 | Kabbash et al. | |
| 6,541,209 B1 | 4/2003 | Behan et al. | |
| 6,541,477 B2 | 4/2003 | Goehring et al. | |
| 6,548,504 B1 | 4/2003 | Bromidge et al. | |
| 6,608,085 B1 | 8/2003 | Gillespie et al. | |
| 6,627,661 B2 | 9/2003 | Reavill et al. | |
| 6,696,475 B2 | 2/2004 | Dahl et al. | |
| 6,706,749 B2 | 3/2004 | Dahl et al. | |
| 6,753,442 B1 | 6/2004 | Benedini et al. | |
| 6,784,183 B2 | 8/2004 | Lavielle et al. | |
| 6,787,535 B2 | 9/2004 | Beard et al. | |
| 6,846,919 B2 | 1/2005 | Behan et al. | |
| 6,849,644 B2 | 2/2005 | Bromidge et al. | |
| 7,084,169 B2 | 8/2006 | Zhao | |
| 7,087,750 B2 | 8/2006 | Caldirola et al. | |
| 7,091,236 B1 | 8/2006 | Roberts et al. | |
| 7,098,233 B2 | 8/2006 | Di Cesare et al. | |
| 7,262,188 B2 | 8/2007 | MacDonald et al. | |
| 7,368,539 B2 | 5/2008 | Behan et al. | |
| 7,452,888 B2 | 11/2008 | Ahmed et al. | |
| 7,601,837 B2 | 10/2009 | Ahmed et al. | |
| 7,754,724 B2 | 7/2010 | Lorsbach et al. | |
| 7,799,774 B2 | 9/2010 | Ahmed et al. | |
| 7,812,176 B2 | 10/2010 | Fritch et al. | |
| 7,943,639 B2 | 5/2011 | Johansson et al. | |
| 7,977,337 B2 | 7/2011 | Ahmed et al. | |
| 8,236,947 B2 | 8/2012 | Ahmed et al. | |
| 8,404,690 B2 | 3/2013 | Page et al. | |
| 8,481,535 B2 | 7/2013 | Gharbaoui et al. | |
| 8,754,238 B2 | 6/2014 | Teegarden et al. | |
| 8,871,797 B2 | 10/2014 | Teegarden et al. | |
| 9,029,379 B2 | 5/2015 | Korenberg et al. | |
| 9,034,911 B2 | 5/2015 | Selvey et al. | |
| 9,084,742 B2 | 7/2015 | Chuang et al. | |
| 9,126,946 B2 | 9/2015 | Carlos et al. | |
| 9,273,035 B2 | 3/2016 | Teegarden et al. | |
| 9,353,064 B2 | 5/2016 | Carlos et al. | |
| 9,434,692 B2 | 9/2016 | Xiong et al. | |
| 9,556,149 B2 | 1/2017 | Krishnan et al. | |
| 9,567,327 B2 | 2/2017 | Xiong et al. | |
| 9,732,039 B2 | 8/2017 | Xiong et al. | |
| 9,745,270 B2 | 8/2017 | Carlos et al. | |
| 9,775,829 B2 | 10/2017 | Teegarden et al. | |
| 9,801,856 B2 | 10/2017 | Selvey et al. | |
| 10,022,355 B2 | 7/2018 | Friedhoff et al. | |
| 10,034,859 B2 * | 7/2018 | Friedhoff | A61K 31/135 |
| 10,058,549 B2 | 8/2018 | Xiong et al. | |
| 10,059,691 B2 | 8/2018 | Krishnan et al. | |
| 10,071,075 B2 | 9/2018 | Carlos et al. | |
| 10,117,851 B2 | 11/2018 | Selvey et al. | |
| 2001/0022963 A1 | 9/2001 | Klaveness et al. | |
| 2001/0051719 A1 | 12/2001 | Bromidge et al. | |
| 2002/0025965 A1 | 2/2002 | Lavielle et al. | |
| 2002/0025967 A1 | 2/2002 | Smith | |
| 2002/0098548 A1 | 7/2002 | Kao et al. | |
| 2002/0115670 A1 | 8/2002 | Kelly et al. | |
| 2003/0037274 A1 | 2/2003 | Shikata et al. | |
| 2003/0144505 A1 | 7/2003 | Bromidge et al. | |
| 2004/0024210 A1 | 2/2004 | Johansson et al. | |
| 2004/0034036 A1 | 2/2004 | Bromidge et al. | |
| 2004/0077654 A1 | 4/2004 | Bouillot et al. | |
| 2004/0082644 A1 | 4/2004 | Korsten | |
| 2004/0092528 A1 | 5/2004 | Kelly et al. | |
| 2004/0102636 A1 | 5/2004 | Miller et al. | |
| 2004/0122076 A1 | 6/2004 | Bobb et al. | |
| 2004/0132742 A1 | 7/2004 | Bromidge et al. | |
| 2004/0167030 A1 | 8/2004 | Bernotas et al. | |
| 2004/0213816 A1 | 10/2004 | Weiner et al. | |
| 2005/0054691 A1 | 3/2005 | Potter et al. | |
| 2005/0080124 A1 | 4/2005 | Teegarden et al. | |
| 2005/0090485 A1 | 4/2005 | Bromidge et al. | |
| 2005/0090496 A1 | 4/2005 | Ahmed et al. | |
| 2005/0124628 A1 | 6/2005 | Ahmend et al. | |
| 2005/0176705 A1 | 8/2005 | Bromidge et al. | |
| 2005/0176759 A1 | 8/2005 | Ahmed et al. | |
| 2005/0215526 A1 | 9/2005 | Hulme et al. | |
| 2005/0267097 A1 | 12/2005 | Pinto et al. | |
| 2006/0014705 A1 | 1/2006 | Howitz et al. | |
| 2006/0018839 A1 | 1/2006 | Ieni et al. | |
| 2006/0035888 A1 | 2/2006 | Jonas et al. | |
| 2006/0063754 A1 | 3/2006 | Edgar et al. | |
| 2006/0142241 A1 | 6/2006 | Yooh | |
| 2006/0148818 A1 | 7/2006 | Johansson et al. | |
| 2006/0172992 A1 | 8/2006 | Yokoyama et al. | |
| 2006/0205792 A1 | 9/2006 | Wong et al. | |
| 2006/0229335 A1 | 10/2006 | Teegarden et al. | |
| 2006/0287334 A1 | 12/2006 | Johnson et al. | |
| 2007/0004750 A1 | 1/2007 | Lorsbach et al. | |
| 2007/0027139 A1 | 2/2007 | Johnson et al. | |
| 2007/0032504 A1 | 2/2007 | Gladwin | |
| 2007/0037827 A1 | 2/2007 | Nunes et al. | |
| 2007/0043058 A1 | 2/2007 | Bang-Anderson et al. | |
| 2007/0072857 A1 | 3/2007 | Teegarden et al. | |
| 2007/0078134 A1 | 4/2007 | Teegarden et al. | |
| 2007/0167431 A1 | 7/2007 | Comery et al. | |
| 2007/0191345 A1 | 8/2007 | Ahmed et al. | |
| 2007/0207994 A1 | 9/2007 | Teegarden et al. | |
| 2007/0244086 A1 | 10/2007 | Teegarden et al. | |
| 2007/0249603 A1 | 10/2007 | Johnson et al. | |
| 2007/0275979 A1 | 11/2007 | MacDonald et al. | |
| 2007/0293539 A1 | 12/2007 | Landbury et al. | |
| 2007/0293685 A1 | 12/2007 | Fitch et al. | |
| 2008/0015223 A1 | 1/2008 | Strah-Pleynet et al. | |
| 2008/0114014 A1 | 5/2008 | Rich | |
| 2008/0194836 A1 | 8/2008 | Gharbaoui et al. | |
| 2008/0200530 A1 | 8/2008 | Unett et al. | |
| 2008/0255359 A1 | 10/2008 | Wade | |
| 2009/0053306 A1 | 2/2009 | Agarwal et al. | |
| 2009/0076254 A1 | 3/2009 | Behan et al. | |
| 2009/0186895 A1 | 7/2009 | Teegarden et al. | |
| 2009/0197935 A1 | 8/2009 | Teegarden et al. | |
| 2010/0004264 A1 | 1/2010 | Xiong et al. | |
| 2010/0041672 A1 | 2/2010 | Bruton et al. | |
| 2010/0069367 A1 | 3/2010 | Boren et al. | |
| 2010/0226855 A1 | 9/2010 | Nangia et al. | |
| 2010/0240653 A1 | 9/2010 | Santora et al. | |
| 2010/0267691 A1 | 10/2010 | Chuang et al. | |
| 2011/0021538 A1 | 1/2011 | Krishnan et al. | |
| 2011/0178094 A1 | 7/2011 | Holm et al. | |
| 2011/0207790 A1 | 8/2011 | Carlos et al. | |
| 2011/0207791 A1 | 8/2011 | Selvey et al. | |
| 2011/0263592 A1 | 10/2011 | Xiong et al. | |
| 2012/0088785 A1 | 4/2012 | Rich | |
| 2013/0172379 A1 | 7/2013 | Rich | |
| 2013/0172398 A1 | 7/2013 | Rich | |

(56) References Cited

U.S. PATENT DOCUMENTS

| | | | |
|---|---|---|---|
| 2013/0217700 A1 | 8/2013 | Xiong et al. |
| 2013/0237541 A1 | 9/2013 | Teegarden et al. |
| 2013/0331399 A1 | 12/2013 | Leahy et al. |
| 2014/0073681 A1 | 3/2014 | Schmidt et al. |
| 2014/0142140 A1 | 5/2014 | Bird |
| 2014/0349976 A1 | 11/2014 | Hacksell et al. |
| 2015/0031897 A1 | 1/2015 | Rich |
| 2015/0045372 A1 | 2/2015 | Krishnan et al. |
| 2015/0073141 A1 | 3/2015 | Teegarden et al. |
| 2015/0210648 A1 | 7/2015 | Carlos et al. |
| 2015/0233698 A1 | 8/2015 | Huang et al. |
| 2015/0313888 A1 | 11/2015 | Mills et al. |
| 2016/0067216 A1 | 3/2016 | Selvey et al. |
| 2016/0075660 A1 | 3/2016 | Xiong et al. |
| 2016/0324851 A1 | 11/2016 | Friedhoff et al. |
| 2016/0324852 A1 | 11/2016 | Friedhoff et al. |
| 2016/0361296 A1 | 12/2016 | Friedhoff et al. |
| 2016/0374990 A1 | 12/2016 | Teegarden et al. |
| 2017/0014385 A1 | 1/2017 | Friedhoff et al. |
| 2017/0042876 A1 | 2/2017 | Mills et al. |
| 2017/0057924 A1 | 3/2017 | Carlos et al. |
| 2017/0137408 A1 | 5/2017 | Krishnan et al. |
| 2017/0151236 A1 | 6/2017 | Xiong et al. |
| 2017/0320831 A1 | 11/2017 | Xiong et al. |
| 2018/0072680 A1 | 3/2018 | Carlos et al. |
| 2018/0085351 A1 | 3/2018 | Selvey et al. |
| 2018/0169070 A1 | 6/2018 | Teegarden et al. |
| 2018/0344698 A1 | 12/2018 | Carlos et al. |
| 2019/0023691 A1 | 1/2019 | Krishnan et al. |
| 2019/0046506 A1 | 2/2019 | Friedhoff et al. |
| 2019/0151287 A1 | 5/2019 | Friedhoff et al. |

FOREIGN PATENT DOCUMENTS

| | | |
|---|---|---|
| DE | 102004061593 | 6/2006 |
| EP | 0030023 | 6/1981 |
| EP | 0371431 | 11/1989 |
| EP | 0605981 | 2/1996 |
| EP | 0818449 | 1/1998 |
| EP | 0631176 | 12/2000 |
| EP | 1108720 | 12/2000 |
| EP | 0867477 | 5/2002 |
| EP | 1734039 | 6/2005 |
| EP | 1558582 | 12/2005 |
| EP | 1683516 | 1/2006 |
| EP | 1695966 | 8/2006 |
| EP | 1727803 | 3/2012 |
| EP | 1956004 | 6/2012 |
| EP | 2190844 | 4/2013 |
| EP | 2066641 | 6/2014 |
| FR | 2722369 | 1/1996 |
| GB | 1147379 | 4/1969 |
| GB | 2341549 | 3/2000 |
| JP | H02262627 | 10/1990 |
| JP | H04334357 | 3/2010 |
| WO | WO 1995/011592 | 5/1995 |
| WO | WO 1996/002138 | 2/1996 |
| WO | WO 1996/010559 | 4/1996 |
| WO | WO 1996/023783 | 8/1996 |
| WO | WO 1996/032931 | 10/1996 |
| WO | WO 1997/003967 | 2/1997 |
| WO | WO 1997/032858 | 9/1997 |
| WO | WO 1997/045111 | 12/1997 |
| WO | WO 1998/024785 | 6/1998 |
| WO | WO 1998/027081 | 6/1998 |
| WO | WO 1998/047874 | 10/1998 |
| WO | WO 1998/054157 | 12/1998 |
| WO | WO 1998/054158 | 12/1998 |
| WO | WO 1998/057931 | 12/1998 |
| WO | WO 1998/057952 | 12/1998 |
| WO | WO 1999/006354 | 2/1999 |
| WO | WO 1999/032436 | 7/1999 |
| WO | WO 1999/032463 | 7/1999 |
| WO | WO 1999/032927 | 7/1999 |
| WO | WO 1999/042465 | 8/1999 |
| WO | WO 1999/047516 | 9/1999 |
| WO | WO 1999/052927 | 10/1999 |
| WO | WO 1999/065906 | 12/1999 |
| WO | WO 2000/012073 | 3/2000 |
| WO | WO 2000/013681 | 3/2000 |
| WO | WO 2000/034265 | 6/2000 |
| WO | WO 2000/042026 | 7/2000 |
| WO | WO 2000/057877 | 10/2000 |
| WO | WO 2000/058303 | 10/2000 |
| WO | WO 2000/058313 | 10/2000 |
| WO | WO 2000/063203 | 10/2000 |
| WO | WO 2000/064866 | 11/2000 |
| WO | WO 2000/064877 | 11/2000 |
| WO | WO 2001/007436 | 2/2001 |
| WO | WO 2001/016108 | 3/2001 |
| WO | WO 2001/017963 | 3/2001 |
| WO | WO 2001/021160 | 3/2001 |
| WO | WO 2001/029008 | 4/2001 |
| WO | WO 2001/032646 | 5/2001 |
| WO | WO 2001/032660 | 5/2001 |
| WO | WO 2001/040217 | 6/2001 |
| WO | WO 2001/046166 | 6/2001 |
| WO | WO 2001/064676 | 9/2001 |
| WO | WO 2001/098279 | 12/2001 |
| WO | WO 2002/008178 | 1/2002 |
| WO | WO 2002/020489 | 3/2002 |
| WO | WO 2002/028837 | 4/2002 |
| WO | WO 2002/036562 | 5/2002 |
| WO | WO 2002/039987 | 5/2002 |
| WO | WO 2002/044170 | 6/2002 |
| WO | WO 2002/051833 | 7/2002 |
| WO | WO 2002/076464 | 10/2002 |
| WO | WO 2002/078693 | 10/2002 |
| WO | WO 2002/089811 | 11/2002 |
| WO | WO 2002/098857 | 12/2002 |
| WO | WO 2002/102774 | 12/2002 |
| WO | WO 2003/002097 | 1/2003 |
| WO | WO 2003/011284 | 2/2003 |
| WO | WO 2003/013510 | 2/2003 |
| WO | WO 2003/014097 | 2/2003 |
| WO | WO 2003/020707 | 3/2003 |
| WO | WO 2003/035061 | 5/2003 |
| WO | WO 2003/037872 | 5/2003 |
| WO | WO 2003/062206 | 7/2003 |
| WO | WO 2003/066056 | 8/2003 |
| WO | WO 2003/072558 | 9/2003 |
| WO | WO 2003/080580 | 10/2003 |
| WO | WO 2003/080608 | 10/2003 |
| WO | WO 2003/095434 | 11/2003 |
| WO | WO 2003/104193 | 12/2003 |
| WO | WO 2004/000828 | 12/2003 |
| WO | WO 2004/026830 | 4/2004 |
| WO | WO 2004/026831 | 4/2004 |
| WO | WO 2004/028450 | 4/2004 |
| WO | WO 2004/035047 | 4/2004 |
| WO | WO 2004/041792 | 5/2004 |
| WO | WO 2004/045118 | 5/2004 |
| WO | WO 2004/046110 | 6/2004 |
| WO | WO 2004/050085 | 6/2004 |
| WO | WO 2004/058722 | 7/2004 |
| WO | WO 2004/064738 | 8/2004 |
| WO | WO 2004/071426 | 8/2004 |
| WO | WO 2004/074243 | 9/2004 |
| WO | WO 2004/078176 | 9/2004 |
| WO | WO 2004/080969 | 9/2004 |
| WO | WO 2004/085433 | 10/2004 |
| WO | WO 2004/096771 | 11/2004 |
| WO | WO 2005/012254 | 2/2005 |
| WO | WO 2005/021530 | 3/2005 |
| WO | WO 2005/021545 | 3/2005 |
| WO | WO 2005/026125 | 3/2005 |
| WO | WO 2005/030724 | 4/2005 |
| WO | WO 2005/040124 | 5/2005 |
| WO | WO 2005/066157 | 7/2005 |
| WO | WO 2005/077345 | 8/2005 |
| WO | WO 2005/095346 | 10/2005 |
| WO | WO 2005/103011 | 11/2005 |
| WO | WO 2005/113539 | 12/2005 |
| WO | WO 2005/121140 | 12/2005 |

(56) References Cited

FOREIGN PATENT DOCUMENTS

| | | |
|---|---|---|
| WO | WO 2006/018662 | 2/2006 |
| WO | WO 2006/038006 | 4/2006 |
| WO | WO 2006/049734 | 5/2006 |
| WO | WO 2006/049941 | 5/2006 |
| WO | WO 2006/053785 | 5/2006 |
| WO | WO 2006/055734 | 5/2006 |
| WO | WO 2006/059149 | 6/2006 |
| WO | WO 2006/060654 | 6/2006 |
| WO | WO 2006/070394 | 7/2006 |
| WO | WO 2006/076592 | 7/2006 |
| WO | WO 2006/078610 | 7/2006 |
| WO | WO 2006/079637 | 8/2006 |
| WO | WO 2006/081335 | 8/2006 |
| WO | WO 2006/086705 | 8/2006 |
| WO | WO 2006/089871 | 8/2006 |
| WO | WO 2006/094235 | 9/2006 |
| WO | WO 2006/095205 | 9/2006 |
| WO | WO 2006/097766 | 9/2006 |
| WO | WO 2006/100519 | 9/2006 |
| WO | WO 2006/112464 | 10/2006 |
| WO | WO 2006/116614 | 11/2006 |
| WO | WO 2007/002559 | 1/2007 |
| WO | WO 2007/026959 | 3/2007 |
| WO | WO 2007/039219 | 4/2007 |
| WO | WO 2007/039220 | 4/2007 |
| WO | WO 2007/039238 | 4/2007 |
| WO | WO 2007/041409 | 4/2007 |
| WO | WO 2007/120600 | 10/2007 |
| WO | WO 2007/129111 | 11/2007 |
| WO | WO 2007/136680 | 11/2007 |
| WO | WO 2007/136689 | 11/2007 |
| WO | WO 2007/136703 | 11/2007 |
| WO | WO 2007/136875 | 11/2007 |
| WO | WO 2007/147883 | 12/2007 |
| WO | WO 2008/027483 | 3/2008 |
| WO | WO 2008/042388 | 4/2008 |
| WO | WO 2008/054748 | 5/2008 |
| WO | WO 2008/113818 | 9/2008 |
| WO | WO 2009/023253 | 2/2009 |
| WO | WO 2009/074607 | 6/2009 |
| WO | WO 2009/123714 | 10/2009 |
| WO | WO 2010/062321 | 6/2010 |
| WO | WO 2010/062323 | 6/2010 |
| WO | WO 2014/065437 | 5/2014 |
| WO | WO-2014085362 A1 * 6/2014 ........... A61K 31/473 |
| WO | WO 2015/012554 | 1/2015 |
| WO | WO 2015/085004 | 6/2015 |
| WO | WO 2015/171547 | 11/2015 |
| WO | WO 2016/201373 | 12/2016 |
| WO | WO 2017/011767 | 1/2017 |
| WO | WO 2018/148737 | 8/2018 |
| WO | WO 2019/033068 | 2/2019 |

OTHER PUBLICATIONS

3D QSAR in Drug Design: Ligand-protein Interactions and Molecular Similarity, vol. 2, Kubinyi (ed.), 1998, 243 (abstract).
Adams et al., "Antithrombotic and Vascular effects of AR246686, a novel 5-HT2A receptor antagonist," 2007 EJM, pp. 1-22.
Affolter et al., "Ca2+ as messenger of 5HT2-receptor stimulation in human blood platelets," (1984) Naunyn-Schmiedeberg's Archives of Pharmacol. 325(4):337-42.
Ahmed et al., "Bicyclic heteroarylpiperazines as selective brain penetrant 5-HT6 receptor antagonists," (2005) Bioorganic & Medicinal Chem. Letters, 15:4867-4871.
Al-Shamma, "APD125: A 5-HT2A Inverse Agonist for the Treatment of Sleep Maintenance Insomnia," 2008 DDST 1-7.
Al-Shamma et al., "The Selective Serotonin 5HT2A Inverse Agonist APD 125 Promotes Sleep Onset and Consolidation in Male Wistar Rats During the Normal Active Phase," (2005) APSS Abstract 0005.
Al-Shamma et al., "Nelotanserin, a Novel Selective Human 5-Hydroxyttyptamine2A Inverse Agonist for the Treatment of Insomnia," (2010) J Pharmacol. Exp. Ther. 332:281-290.

Al-Shamma et al., "The Selective Serotonin 5HT2A Inverse Agonist APD125 Promotes Sleep Onset and Consolidation in Male Wistar Rats During the Normal Active Phase," 1994 APSS Slides, 1-5.
Ancelin et al., "Non-degenerative mild cognitive impairment in elderly people and use of anticholinergic drugs: longitudinal cohort study," Feb. 1, 2006, BMJ, 332(7539):455-459.
Ancoli-Israel et al., "Pimavanserin tartrate, a 5-HT2A Receptor Inverse Agonist, Increases Slow Wave Sleep as Measured by Polysomnography in Healthy Adult Volunteers," Sleep Med, Feb. 2011, 12(2):134-141.
Andrzejewska-Buczko et al., "[Serotonin in diabetic retinopathy]," Klin Oczna. Feb. 1996, 98(2):101-104 (abstract).
Anonymous, "Prevention of Atherosclerotic Complications: Controlled Trial of Ketanserin," (1989) Br. Med. J 298:424-430.
Anonymous, "Drug treats severe Alzheimer's," retrieved from <http://newsvote.bbc.co.uk/mpapps/pagetools/print/news.bbc.co.uk/2/hi/health/4832574.stm. > Mar. 23, 2006.
Antinori et al., "Diagnosis of AIDS-related focal brain lesions: A decision-making analysis based on clinical and neuroradiologic characteristics combined with polymerase chain reaction assays in CSF," (1997) Neurology 48:687-694.
Archie et al., "Clozapine en levodopa als behandeling van persisterende visuele hallucinaties en motorische symptomen bij dementie met lewylichaampjes," Tijdschrift Voor Psychiatrie, Apr. 1, 2013, 55(4):287-291 (English Abstract only).
Arena Pharmaceuticals [online], "Arena Pharmaceuticals Announces Preliminary Results of Phase 2B Clinical Trial of APD125 for the Treatment of Insomnia", dated Dec. 9, 2008, retrieved from < https://invest.arenapharm.com/news-releases/news-release-details/arena-pharmaceuticals-announces-preliminary-results-phase-2b >.
ARICEPT® Label, Jul. 2015.
Barluenga, Jr et al., "A New and Specific Method for the Monomethylation of Primary Amines," (1984) J Chem. Soc. Chem. Commun. 20:1334-1335.
Batey et al., "An Efficient New Protocol for the Formation of Unsymmetrical Tri- and Tretrasubstituted Ureas," (1998) Tetra. Lett. 39:6267-6270.
Bentley et al., "5-HT6 Antisense Oligonucleotide I.C.V. Affects Rat Performance in the Water Maze and Feedings," (1997) Journal of Psychopharma. (Supplement) A64:255 (abstract).
Bentley et al., "Effect of the 5-HT6 Antagonist, Ro 04-6790 on Food Consumption in Rats Trained to a Fixed Feeding Regime," (1999) British Journal of Pharmacol. 126(Suppl.):66 (abstract).
Bentley et al., "Investigation of stretching behaviour induced by the selective 5-HT6 receptor antagonist, Ro 04-6790, in rats" (1999) British Journal Pharmacol. 126:1537-1542.
Berge et al., "Pharmaceutical salts," (1977) J Pharmaceutical Sciences 66(1):1-19.
Berger et al., "Progressive Multifocal Leukoencephalopathy," (1999) Seminars in Neurology, 19:193-200.
Bernatowicz et al., "A Comparison of Acid Labile Linkage Agents for the Synthesis of Peptide C-Terminal Amides," (1989) Tetra. Let. 30(35):4645-4648.
Birks et al., "Donepezil for dementia due to Alzheimer's disease," Cochrane Database of Systematic Reviews, 2018, 349 pages.
Blier et al., "Putative mechanisms of action of antidepressant drugs in affective and anxiety disorders and pain," (2001) Journal of Psychiatry and Neuroscience, 26(1):37-43.
Bos et al., "5-HT(6) receptor antagonists: lead optimization and biological evaluation of N-aryl and N-heteroaryl 4-amino-benzene sulfonamides," (2001) Eur. J Med. Chem. 36(2):165-178.
Bourson et al., "Determination of the Role of the 5-HT6 Receptor in the Rat Brain: A Study Using Antisense Oligonucleotides," (1995) The Journal of Pharmacolofy & Experimental Therapeutics 274(1):173-180.
Bourson et al., "Involvement of 5-HT6 receptors in nigro-striatal function in rodents," (1998) British J Pharmacol. 125:1562-1566.
Branchek et al., "5-HT6 Receptors as Emerging Targets for Drug Discovery," (2000) Annu. Rev. Pharmcol. Toxicol. 40:319-334.
Bromidge et al., "Phenyl benzene sulfonamides are novel and selective 5-HT6 antagonists: identification of N-(2,5-dibromo-3-

(56) References Cited

OTHER PUBLICATIONS fluorophenyl)-4-methoxy-3-piperazin-1-ylbenzenesulfonamide (SB-357134)," (2001) Bioorganic & Medicinal Chemistiy Letters 11:55-58.
Burger, "Isosterism and bioisosterism in drug design," (1991) Prag. Drug Res. 37:287-371 (abstract).
Burla et al., "SIR2004: an improved tool for crystal structure determination and refinement," (2005) Journal of Applied Crystallography, 38:381-388 (abstract).
Buysse et al., "The Pittsburgh Sleep Quality Index: A New Instrument for Psychiatric Practice and Research" (1989) Psychiatry Research 28(2):193-213.
Byrn, "Solid-State Chemistiy of Drugs," 2nd Ed. (1999), Chapter 11—Hydrates and Solvates, 233-247 (TOC).
Byrn et al., "Pharmaceutical Solids: A Strategic Approach to Regulatory Considerations," (1995) Pharm. Res. 12(7):945-954 (abstract).
Callahan et al., "Characterization of the Selective 5-HT6 Receptor Antagonist SB 271046 in Behavioral Models of Cognition," 34th Annual Scientific Meeting of the Soc. for Neurosci., San Diego, Oct. 2004.
Cameron et al., "The effects of 5-hydroxytryptamine 5-HT2 receptor antagonists on nerve conduction velocity and endoneurial perfusion in diabetic rats," (Jun. 2003) Naunyn-Schmiedeberg's Archives of Pharmacology 367(6):607-614.
Campbell et al., "Use of anticholinergics and the risk of cognitive impairment in an African American population," (2010) Neurology 75:152-159.
Carnahan et al., "The Concurrent Use of Anticholinergics and Cholinesterase Inhibitors: Rare Event or Common Practice?" (2004) JAGS 52(12):2082-2087 (abstract).
Carter et al., "Carbobenzoxy Chloride and Derivatives," (1995) Org. Syn. Coll. 3:167-169.
Casey et al., "Constitutively active mutant 5HT2, serotonin receptors: inverse agonist activity of classical 5HT2A antagonists," (1996) Society for Neuroscience Abstracts 22:699 (abstract).
Castaneda-Corral et al., "Role of Peripheral and Spinal 5-HT6 Receptors According to the Rat Formalin Test," (2009) Neuroscience 162:444-452.
Catalan et al., "New ultraviolet stabilizers: 3- and 5-(2'-hydroxyphenyl)pyrazoles," (1992) J Am. Chem. Soc. 114:5039-5048.
Cazzola et al., "5-HT modifiers as a potential treatment of asthma," (2000) TIPS, 21:13-6 (2000).
Cazzola et al., "Central 5-HT1A Receptors and Vagal Tone to the Airways," (2000) Trends Pharmacol. Sci. 21:201-202.
Chambers et al., "Translocation of the 5-alkoxy substituent of 2,5-dialkoxyarylalkylamines to the 6-position: effects on 5-HT2A/2C receptor affinity," (2002) Bio. Med. Chem. Lett. 12:1997-1999.
Chang et al., "Isapirone and Ketanserin Protects Against Circulatory Shock, Intracranial Hypertension, and Cerebral Ischemia During Heatstroke," (2005) Shock 24(4):336-340.
Chang et al., "Mechanism of the Ocular Hypotensive Action of Ketanserin," (1985, Summer) J Ocul Pharmacol. 1(2):137-147.
Chang-Fong et al., "1,2,3,4-Tetrahydrocarbazoles as 5-HT6 serotonin receptor ligands," (2004) Bioorg Med. Chem. Lett. 14(8):1961-1964.
Chew et al., "Serum Anticholinergic Activity and Cognition in Patients with Moderate-to-Severe Dementia," (Jun. 2005) Am J Geriatr Psychiatry 13:6 (abstract).
Chuang et al., "P4-387: 5-HT6 receptor antagonist SB-742457 as a novel cognitive enhancing agent for Alzheimer's disease," (2006) Alzheimer's & Dementia, The Journal of the Alzheimer's Association, 2:S63 1-S632.
Clinical Trial Protocol Summaries (Five studies) [online], retrieved 3/9/7012, retrieved from < http://www.gsk-clinicalstudyregister.com/quick-search-list.jsp?item=SB742457&type=Compound&letterrange=Q-U&studyType=All&phase=All&population=All&marketin=All >.
Cohen-Mansfield et al., "Agitated behaviors in the elderly. I. A conceptual review," (Oct. 1986) J Am Geriatr Soc. 34(10):711-21.

Collier et al., "Radiosynthesis and in-vivo evaluation of the pseudopeptide-opioid antagonist [(123I]-ITIPP(psi)," (1999) Labeled Compd. Radiopharm, 42:S264-S266.
Collins et al., "N-Phenylamidines as Selective Inhibitors of Human Neuronal Nitric Oxide Synthase: Structure—Activity Studies and Demonstration of in Vivo Activity," (1998) J Med. Chem., Am. Chem. Soc. 41(15):2858-2871.
Cooke, "Glycopyrrolate in Bladder Dysfunction," Jan. 1, 1983, South African Medical Journal 63(1):3 (abstract).
Cuvposa, "Glycopyrrolate oral solution," Product Information Sheet, Rev. Jul. 2010.
Database Beilstein [Online] Beilstein Institute for Organic Chem., Frankfurt-Main,DE; XP002535545 Database Accession No. 5926580 (BRN), the whole document.
Davies et al., "Drug discovery targets: 5-HT6 receptor," (2005) Drugs of the Future, 30(5):479-495.
De Bie et al., "Modulation of airway hyperresponsiveness and eosinophilia by selective histamine and 5-HT receptor antagonists in a mouse model of allergic asthma," (1998) British Journal of Pharmacology 124:857-864.
Defilippi et al., "Drug Interactions with Cholinesterase Inhibitors," (2003) Drugs Aging 20(6):437-444 (abstract).
Deuchar et al., "The role of 5-hydroxytryptamine in the control of pulmonary vascular tone in a rabbit model of pulmonary hypertension secondary to left ventricular dysfunction," (2005) Pulm. Pharmacol. Ther. 18(1):23-31.
Diagnostic and Statistical Manual of Mental Disorders, Fourth Edition, Text Revision: DSM-IV-TR, Washington, DC, American Psychiatric Association, 2000 (abstract).
Dosa et al., "MEDI 44-Synthesis and SAR of pyridinyl-pyrazole derivatives as selective 5HT (2A) inverse-agonists for platelet aggregation," Abstracts of Papers of the American Chemical Society, 2008, vol. 235.
Dosa et al., "Solubilized phenyl-pyrazole ureas as potent, selective 5-HT2A inverse agonists and their application as antiplatelet agents," (2010) BMCL pp. 1-15.
Dosa et al., "Synthesis and SAR of solubilized pyrazole derivatives as 5-HT2A inverse-agonists for platelet aggregation," 232nd ACS National Meeting, Medi. vol. 431, 2006, 1 page (abstract).
Dosa et al., "Synthesis and SAR of solubilized pyrazole derivatives as 5-HT2A inverse-agonists for platelet aggregation," 232nd ACS National Meeting, Medi. vol. 431, 2006, poster.
Douaud et al., "Preventing Alzheimer's disease-related gray matter atrophy by B vitamin treatment," (2013) PNAS 110:9523-9528.
Drinka, "Antimuscarinic Drugs for Overactive Bladder and Their Potential Effects on Cognitive Function in Older Patients," 2006 JAGS 54(6):1004-1005 (abstract).
Drug Therapy in Nursing, 3rd edition, Aschenbrenner et al., 2009, Table of Contents.
East et al., "5-HT6 receptor binding sites in schizophrenia and following antipsychotic drug administration: Autoradiographic studies with [125I]SB-258585," (2002) Synapse 45:191-199.
Edwards et al., "Risk of delirium with concomitant use of tolterodine and acetycholinesterase inhibitors," 2002, J Amer Geriatric Society 50(6):1165-1166 (abstract).
Elliott et al., "4-Oxospiro[benzopyran-2,4' -piperidines] as class III antiarrhythmic agents. Pharmacological studies on 3,4-dihydro-1' -[2-(benzofurazan-5-yl)ethyl]-6-methanesulfonamidospiro[(2H)-1-benzopyran-2,4' -piperidin]-4-one (L-691,121))," (1992) J Med. Chem. 35:3973-3976.
Elphick et al., "The human polyomavirus, JCV, uses serotonin to infect cells," (2004) Science 306:1380-1383.
EP Office Action in European Appln. No. 16808478.8, dated May 11, 2020.
Extended European Search Report in EP Application 16808478.8, dated Jan. 14, 2019.
Extended European Search Report in EP Application 16825262.5, dated Feb. 12, 2019.
Ferguson, "Modulation of lymphatic smooth muscle contraction responses by the endothelium," (1992) Journal of Surgical Research 52:359-363 (abstract).

(56) References Cited

OTHER PUBLICATIONS

File, "Anxiolytic Action of a Neurokininl Receptor Antagonist in the Social Interaction Test," (Nov. 1997) Pharmacol. Biochem. Behav. 58(3):747-752.
File, "The use of social interaction as a method for detecting anxiolytic activity of chlordiazepoxide-like drugs," (Jun. 1980) J. Neuro. Methods 2(3):219-238.
Foley et al., "The 5-HT6 Receptor Antagonist SB-271046 Reverses Scopolamine-Disrupted Consolidation of a Passive Avoidance Task and Ameliorates Spatial Task Deficits in Aged Rats," (2004) Neuropsychopharmacology, 29:93-100.
Fujita et al., "Sarpogrelate Treatment Reduces Restenosis After Coronary Stenting," (2003) Am. Heart J 145:e16.
Fujiwara, "Augmented Responses to 5-HT2-Receptor-Mediated Vascoconstrictions in Atherosclerotic Rabbit Common Carotid Arteries," (1995) Journal of Cardiovascular Pharmacology 26:503-510.
Fullerton et al., "A Phase 2 clinical trial of PF-05212377 (SAM-760) in subjects with mild to moderate Alzheimer's disease with existing neuropsychiatric symptoms on a stable daily dose of donepezil," Alzheimer's Research & Therapy, 2018, 10:1-10.
Garcia-Alloza et al., "Differential Involvement of 5-HT1B/1D and 5-HT6 Receptors in Cognitive and Non-cognitive Symptoms in Alzheimer's Disease," (2004) Neuropsychopharmacology, 29:410-416.
Gardner, "Distress Vocalization in Rat Pups a Simple Screening Method for Anxiolytic Drags," (Nov. 1985) J Pharma. Meth. 14(3): 181-187.
Geldmacher, "Donepezil (Aricept®) for treatment of Alzheimer's disease and other dementing conditions," (2004) Expert Rev. Neurotherapeutics 4(1):5-16.
Gill et al., "A Prescribing Cascade Involving Cholinesterase Inhibitors and Anticholinergic Drugs," (2005) Arch. Intern. Med. 165:808-813.
Gillman, "The serotonin syndrome and its treatment," Journal of Psychopharmacology (1999), 31(1):100-109.
Gish et al., "Memorandum: Age-dependent manifestations of central anticholinergic effects," Department of Health and Human Services Public Health Service Food and Drug Administration Center for Drug Evaluation and Research (2007).
GlaxoSmithKline Clinical Trial [online], Sep. 21, 2011, retrieved from < http://www.gsk-clinicalstudyregister.com/result-comp-list.jsp?compound=SB742457&studyType=All&phase=All&population=All&marketing=All. >.
Glaxosmithkline Pharmacology Study Report, "A study in healthy volunteers to characterise [11C]GSK215083A as a positron emission tomography (PET) tracer ligand for the 5-HT6 receptor and to assess the occupancy at the 5-HT6 receptor of SB-742457 in the brain using PET and a tracer dose of [11C]GSK215083A," (Sep. 24, 2009).
Glaxosmithkline, "Dose Ranging Study to Investigate the Efficacy and Safety of SB-742457 in Alzheimer's Disease," NCT ID No. NCT00224497 (Verified 2007) Clinical Study.
Glaxosmithkline, "SB-742457 and donepezil in Alzheimer disease: a randomized, placebo-controlled study," NCT ID No. NCT00348192 (2006) Clinical Study.
Glennon et al., "2-Substituted Tryptamines: Agents with Selectivity for 5-HT6 Serotonin Receptors," (2000) J. Med. Chem., 43:1011-1018.
Glennon et al., "Behavioral and serotonin receptor properties of 4-substituted derivatives of the hallucinogen 1-(2.5-dimethoxyphenyl)-2-aminopropane," (1982) J Med. Chem. 25(10):1163-1168.
Goldman et al., "Finding Balance: New Strategies to Optimize Care for Patients With Parkinson's Disease Psychosis," Supplement to Neurology Reviews, Aug. 2016, 12 pages.
Gottlieb et al., "NMR Chemical Shifts of Common Laboratory Solvents as Trace Impurities," (1997) J Org,. Chem. 62:7512-7515.
Greene et al., "Protecting Groups in Organic Synthiesis," 3rd Edition, 1999 (Wiley) (abstract).

Grotewiel et al., "Receptors Exhibit Constitutive Activity that is Blocked by Inverse Agonists," (May 1994) Faseb J., Abstract 353:8(7), 1 page.
Grunder et al., "Time course of 5-HT2A receptor occupancy in the human brain after a single oral dose of the putative antipsychotic drug MDL 100,907 measured by positron emission tomography," (Sep. 1997) Neuropsychopharmacology, 17(3): 175-185.
Gsk-studyregister [online] "Phase 1 Study, result summary. Study AZ3105822, a single-blind, randomized, placebo-controlled study to evaluate the effect of repeated dosing of an investigational product on the pharmacokinetics and pharmacodynamics of Warfarin in healthy adult subjects," retrieved from < http://www.gsk-clinicalstudyregister.com/result_detail.jsp?protocolId=105822&studyId=BC2066FF-1606-487D-B093-189458F0AE76&compound=SB742457 >(undated).
Gsk-studyregister [online] "Phase 2, Study 1, result summary. Study AZ3110865, a study comparing SB-74257 or donepezil versus placebo in subjects with mild-to-moderate Alzheimer's disease," retrieved from < http: www.gsk-clinicaistudyregister.com/result_detail.jsp?protocolId=AZ3110865&studyId=242C4974-9729-4D30-8F91-327CF0631014&compound=SB742457>(undated).
Gsk-studyregister [online] "Phase 2, Study 2, result summary. Study AZ3 11 0866, a fixed dose study of SB-742457 versus placebo when added to existing donepezil treatment in subjects with mild-to-moderate Alzheimer's disease," retrieved from < http://www.gsk-clinicalstudyresgister.com/result_detail.jsp?protocolID=AZ3110866&studyId=B8176D5B-C33 1-4621-9303-2BBF51E4690B&compound=SB742457 > (undated).
Guillory, "Generation of Polymorphs, Hydrates, Solvates, and Amorphous Solids, in Polymorphism in the Pharmaceutical Industry," (1999) Harry G. Britain ed. 183-226, 202-209.
Gutsche et al., "2-Phenylcycloheptanone," (1963) Org Syn. Coll. 4:780-783.
Guy, "C.G.I.—Clinical global impression," Assessment manual for Psychopharmacology, (1976): 217-222.
Halberstadt et al., "5-HT2A and 5-HT2c Receptors Exert Opposing Effects on Locomotor Activity in Mice," (Jul. 2009) Neuropsychopharmacology 34(8):1958-1967.
Hamiilton, "A Rating Scale for Depression," (1960) J Neural. Neurosurg. Psychiatry, 23:56-62.
Hamilton, "Development of a Rating Scale for Primary Depressive Illness," (Dec. 1967) Br. J Clin. Psvch. 6(4):278-296.
Hashimoto et al., "Urinary Incontinence: an Unrecognized Adverse Effect with Donepezil," (Aug. 12, 2000) The Lancet 356:568 (abstract).
Hayashi et al., "Sarpogrelate HC1, a selective 5-HT2A Antagonist, Retards the Progression of Atherosclerosis Through a Novel Mechanism," (2003) Atherosclerosis 168:23-31.
Helm et al., "GABAb receptor antagonist SGS742 improves spatial memory and reduces protein binding to the cAMP response element (CRE) in the hippocampus," (2005) Neuropharmacology 48:956-964.
Herrick-Davis et al., "Activating mutations of the serotonin 5-HT2C receptor," (Sep. 1997) J Neurochem. 69(3): 1138-44.
Herrick-Davis et al., "Constitutively active 5HT2C serotonin receptor created by site-directed mutagenesis," Society for Neuroscience Abstracts 22:699.18.
Higuchi et al., "Pro-Drugs as Novel Delivery Systems," vol. 14 of the ACS Symposium Series; and in Bioreversible Carriers in Drug Design, ed. Edward B. Roche, American Pharmaceutical Association and Pergamon Press, 1987.
Hirst et al., "Characterization of [ 125I]-SB-258585 binding to human recombinant and native 5-HT6 receptors in rat, pig and human brain tissue," (2000) British Journal of Pharmacology 130: 1597-1605.
Hirst et al., "Differences in the Central Nervous System Distribution and Pharmacology of the Mouse 5-Hydroxytryptamine-6 Receptor Compared with Rat and Human Receptors Investigated by Radioligand Binding, Site-Directed Mutagenesis, and Molecular Modeling," (2003) Mol. Pharmacol. 64:1295-1308.
Hittner et al., "A Selective 5-HT2A Receptor Inverse Agonist with Preclinical Antipsychotic Profile in Rats," 2000, Neuro, poster.

(56) References Cited

OTHER PUBLICATIONS

Holenz et al., "Medicinal Chemistry Driven Approaches Toward Novel and Selective Serotonin 5-HT6 Receptor Ligands," (2005) J Med. Chem. 48(6):1781-1795.
Holtje, "Pharmacophore Identification and Receptor Mapping," (2003) The Practice of Medicinal Chemistry, 2nd ed., Wermuth (editor), Academic Press, Chap. 24, pp. 387-403.
Horibe et al., "Sarpogrelate, a 5-HT2 Receptor Blocker, may Have a Preconditioning-Like Effect in Patients with Coronary Artery Disease," (2004) Circulation Research 68:68-72.
Ibach et al., "Acetylcholinesterase Inhibition in Alzheimer's Disease," (2004) Current Pharmaceutical Design 10:231-251.
ICSD—International Classification of Sleep Disorders: Revised Diagnostic and Coding Manual, American Academy of Sleep Medicine (2001) pp. 1-336 (also includes table of contents and glossary).
Ieni et al., "The 5-HT1A receptor probe [3H]8-OH-DPAT labels the 5-HT transporter in human platelets," (1988) Life Sciences 42:311-320.
Ikeguchi et al., "Mianserin Treatment of Patients with Psychosis Induced by Antiparkinsonian Drugs," (1995) Eur. Arch. Psych. Clin. Neurosci. 244:320-324.
Iliff et al., "A Paravascular Pathway Facilitates CSF Flow Through the Brain Parenchyma and the Clearance of Interstitial Solutes, Including Amyloid β," (2012) Sci. Transl. Med. 4(147):147ra111.
Inorganic Structural Chemistry, Müller, Apr. 15, 1993, pp. 14-15.
International Preliminary Report on Patentability in International Appln. No. PCT/US2007/021182, dated Nov. 4, 2008.
International Preliminary Report on Patentability in International Appln. No. PCT/US2005/041726, dated Sep. 21, 2006.
International Preliminary Report on Patentability in International Appln. No. PCT/US2007/0I1810, dated Jul. 16, 2008.
International Search Report and Written Opinion in International Appln No. PCT/US2005/041726, dated May 18, 2006.
International Search Report and Written Opinion in International Appln No. PCT/US2006/001516, dated Jun. 7, 2006.
International Search Report and Written Opinion in International Appln No. PCT/US2007/011810, dated Oct. 30, 2007.
International Search Report and Written Opinion in International Appln. No. PCT/EP2003/003197, dated Dec. 11, 2003.
International Search Report and Written Opinion in International Appln. No. PCT/EP2005/012463, dated Feb. 20. 2006.
International Search Report and Written Opinion in International Appln. No. PCT/EP2006/009460, dated Dec. 14, 2006.
International Search Report and Written Opinion in International Appln. No. PCT/US2004/023880, dated Nov. 15, 2004.
International Search Report and Written Opinion in International Appln. No. PCT/US2006/002721, dated Feb. 20, 2007.
International Search Report and Written Opinion in International Appln. No. PCT/US2007/021182, dated Mar. 14, 2005.
International Search Report and Written Opinion in International Appln. No. PCT/US2008/009740, dated Feb. 18, 2009.
International Search Report and Written Opinion in International Appln. No. PCT/US2009/005811, dated Jul. 8, 2010.
International Search Report and Written Opinion in International Appln. No. PCT/US2016/031359, dated Jul. 29, 2016.
International Search Report and Written Opinion in International Appln. No. PCT/US2016/037090, dated Sep. 9, 2016.
International Search Report and Written Opinion in International Appln. No. PCT/US2018/018026, dated Apr. 5, 2018.
International Search Report and Written Opinion in International Appln. No. PCT/EP2004/010843, dated Mar. 14, 2005.
International Search Report and Written Opinion in International Appln. No. PCT/EP2008/053285, dated Jul. 29, 2008.
International Search Report and Written Opinion in International Appln. No. PCT/EP2008/067225, dated March 23, 2009.
International Search Report and Written Opinion in International Appln. No. PCT/US2004/023488, dated Oct. 12, 2004.
International Search Report and Written Opinion in International Appln. No. PCT/US2009/002019, dated Dec. 14, 2009.
International Search Report and Written Opinion in International Appln. No. PCT/US2009/005809, dated Apr. 28, 2010.
International Search Report and Written Opinion in International Appln. No. PCT/US2016/042556, dated Dec. 23, 2016.
International Search Report and Written Opinion in International Appln. No. PCT/US2018/046363, dated Oct. 15, 2018.
Isaac et al., "6-bicyclopiperazinyl-1-arylsulfonylindoles and 6-bicyclopiperidinyl-1-arylsulfonylindoles derivatives as novel, potent, and selective 5-HT6 receptor antagonists," (2000) Bioorganic & Med. Chem. Letters 10:1719-1721.
Janos et al., "Overactive bladder medicines and cognitive testing," (Nov. 2008) Int. J. Clin. Prac. 62(11):1637-1642 (abstract).
Jayakumar et al., "Synthesis and SAR of Alkoxyphenyl Pyrazole as 5-HT2A Inverse Agonists," (2006) ACS, 232nd ACS National Meeting, Medi 430, poster.
Jayakumar et al., "Synthesis and SAR of Novel-Phenyl-Pyrazole Urea derivatives," (2006) ACS, abstract.
Jayakumar et al., "Synthesis and SAR of Substituted Diphenylamines as 5HT2A Inverse-Agonists," (2004) ACS, meeting abstract.
Jayakumar et al., "Synthesis and SAR of Substituted Diphenylamines as 5HT2A Inverse-Agonists," (2005) ACS, 229th ACS National Meeting, Medi 049, poster.
Jeon et al., "The Synthesis of a New Pyrazolylimidazolinone via 1,3-Dipolar Cycloaddition Reaction of N-Methyl Sydnone with Methyl Propiolate," (1998) Bull. Korean Chem. Soc. 19(7):725-726.
Jewart et al., "Cognitive, Behavioral and Physiological Changes in Alzheimer Disease Patients as a Function of Incontinence Medications" (Apr. 2005) Am J. Geriatr. Psychiatry 13(4):324-328 (abstract).
Jhee et al., "Centrally Acting Antiemetics Mitigate Nausea and Vomiting in Patients with Alzheimer's Disease Who Receive Rivastigmine," (Mar./Apr. 2002) Clinical Neuropharmacology 25(2):122-123 (abstract).
Johnell et al., "Concurrent Use of Anticholinergic Drugs and Cholinesterase Inhibitors," (2008) Drugs Aging 25(10):871-877 (abstract).
Johnson et al., "5-HT6 receptor antagonists: Prospects for the treatment of cognitive disorders including dementia," (2008) Current Opinion in Drug Discovery and Development 11(5):642-654.
Julius et al., "The 5HT2 Receptor Defines a Family of Structurally Distinct but Functionally Conserved Serotonin Receptors," (1990) PNAS USA 87:928-932.
Kaduszkiewicz et al., "Cholinesterase inhibitors for patients with Alzheimer's disease: systematic review of randomized clinical trials," (2005) BMJ online 331-321.
Kalueff et al., "Hypolocomotion, anxiety and serotonin syndrome-like behavior contribute to the complex phenotype of serotonin transporter knockout mice," Genes, Brain and Behavior (2007), 6:389-400.
Kan et al., "Association of the HTR6 Polymorphism C267T With Late-Onset Alzheimer's Disease in Chinese," (1995) J Pharmacol. & Exp. Therapeutics 274:173-180.
Kanayama et al., "New treatment of lumbar disc herniation involving 5-hydroxytryptamine2A receptor inhibitor: a randomized controlled trial," (2005) Journal of Neurosurgery: Spine 2:441-446.
Kaneniwa et al., "Solubilization of Water-Insoluble Organic Powders by Ball-Milling in the Presence of Polyvinylpyrrolidone," (1975) Chem. Pharm. Bull. 23(11):2973-2986.
Katz et al., "Comparison of risperidone and placebo for psychosis and behavioral disturbances associated with dementia: a randomized, double-blind trial. Risperidone Study Group," (Feb. 1999) J Clin Psychiatry. 60(2):107-15.
Kay et al., "Antimuscarinic Drugs for Overactive Bladder and Their Potential Effects on Cognitive Function in Older Patients," (2005) JAGS 53:2195-2201 (abstract).
Kay et al., "Preserving cognitive function for patients with overactive bladder: evidence for a differential effect with darifenacin," (Nov. 2008) Int J Clin Pract. 62(11):1792-1800.
Khoshkhoo et al., "Crystallization of polymorphs: the effect of solvent," (1993) J. Phys. DD Appl.Phys. 26:B90-B93.
Khullar et al., "Prevalence of Faecal Incontinence Among Women with Urinary Incontinence," (1998) Br. J Obslet. Gynaecol. 105:1211-1213.

(56) References Cited

OTHER PUBLICATIONS

Kitagawa et al., "Beckmann Rearrangement of 0-4 Pentenyl Oxime through N-Bromosuccinimide-Mediated Activating Process," (1997) Chem. Pharm. Bull. 45(1):32-35.

Konig et al., "A New Method for Synthesis of Peptides: Activation of the Carboxyl Group with Dicyclohexylcarbodiimide using 1-Hydroxybenzotriazoles as Additives," (1970) Chem. Ber. 103:788-798 (English abstract included).

Koss et al., "Assessing patterns of agitation in Alzheimer's disease patients with the Cohen-Mansfield Agitation Inventory. The Alzheimer's Disease Cooperative Study," (1997) Alzheimer Dis Assoc Disord. 11(Suppl 2):545-550.

Krieger et al., "Novel Immunosuppressants," (2004) Pediatr. Transplantation 8:594-599.

Krystal et al., "The effects of APD125, a selective serotonin 5-HT2A, on sleep quality and sleep maintenance in a subjective study in patients with primary insomnia," (2009) Sleep pp. 1-23.

Landolt et al., "Serotonin-2 receptors and human sleep: effect of a selective antagonist on EEG power spectra," (1999) Neuropsychopharmacology 21(3):455-66.

Le Bas et al., "Radioiodinated analogs of EP 00652218 for the exploration of the tachykinin NK1 receptor by SPECT," (2001) J Labeled Compd. Radiopharm. 44:S280-S282.

Levin et al., "Direct measurement of the anticholinergic activity of a series of pharmacological compounds on the canine and rabbit, urinary bladder," (1982) J Urology 128(2):396-398 (abstract).

Lewy Body Dementia Association, Inc. [online], "Treatment Options Page," retrieved from <http://www.lbda.org/content/treatment-options> 2015.

Liang et al., "Olanzapine in the treatment of schizophrenia: an open trial clinical study," (1999) Chinese Journal of Psychiatry 4:Title page/TOC only.

Lieben et al.. "The Selective 5-HT6 Receptor Antagonist Ro4368554 Restores Memory Performance in Cholinergic and Serotonergic Models of Memory Deficiency in tire Rat," (2005) Neuropsychopharmacology 30:2169-2179.

Liem-Moolenaar et al., "Central Nervous System Effects of the Interaction Between Risperidone (single dose) and the 5-HT6 Antagonist SB742457 (repeated doses) in Healthy Men," (2010) Br. J Clin. Pharma. 71(6):907-916.

Lightowler el al., "Anxiolytic-like Effect of Paroxetine in a Rat Social Interaction Test," (Oct. 1994) Pharmacol. Biochem. Behav. 49(2):281-285 (abstract).

Lindner et al., "An Assessment of the Effects of Serotonin 6 (5-HT6) Receptor Antagonists in Rodent Models of Learning," (2003) J Pharmacol. Exp. Ther. 307(2):682-691.

Lombardo et al., CTAD Poster Presentation, Figure 4, entitled "Phase 1 PET Study to Evaluate the Receptor Occupancy of RVT-101," Sep. 21, 2011.

London Stock Exchange Announcement—GlaxoSmithKline (GSK) plc, Issued on Thursday, Dec. 13, 2007, New York, New York.

Lopez et al., "Predictors of progression in patients with AD and Lewy bodies," (2000) Neurology 54:1774-1779 (abstract).

Lu et al., "Chronic Exposure to Anticholinergic Medications Adversely Affects the Course of Alzheimer Disease," (Jul.-Aug. 2003) Am J Geriatr Psychiatiy 11(4):458-461 (abstract).

Luthringer et al., "Pharmacokinetic and Pharmacodynamic Effects of the Selective 5HT2A Inverse Agonist APD125 in Healthy Adults," 2005 APSS, abstract.

Maher-Edwards et al., "Double-blind, controlled phase II study of a 5-HT6 receptor antagonist, SB-742457, in Alzheimer's disease," (2010) Current Alzheimer Research 7:374-385.

Maher-Edwards et al., "SB-742457 and donepezil in Alzheimer disease: a randomized, placebo-controlled study," (2011) Int. J Geriatr. Psychiatry 26:536-544.

Major et al., "Establishment of a Line of Human Fetal Glial Cells That Supports JC Virus Multiplication," (1985) Proceedings of the National Academy of Sciences of the United States of America, 82:1257-1261.

Marchini et al., "Sodium borohydride-carboxylic acid systems. Useful reagents for the alkylation of amines," (1975) J. Org. Chem. 40(23):3453-3456.

Marcos, "Serotonin-Induced Smooth Muscle Hyperplasia in Various Forms of Human Pulmonary Hypertension," (2004) Circ. Res. 94(9):1263-1270.

Martarello et al., "Radiolabelling and in vivo evaluation of [11C]GSK215083 as potential PET radioligand for the 5-HT6 receptor in the porcine brain," (2005) J. Label Compd. Radiopharm. 48:S7.

Martarello et al., "Radiolabelling and in vivo evaluation of [11C]GSK215083 as potential PET radioligand for the 5-HT6 receptor in the porcine brain," (2005) Journal of Cerebral Blood Flow & Metabolism 25:S598.

Mastropasqua et al., "Ocular hypotensive effect of ketanserin in patients with primary open angle glaucoma," (1997) Acta Ophthalmol Scand Suppl. (224):24-5.

McKeith et al., "Efficacy of rivastigmine in dementia with Lewy bodies: a randomised, doubleblind, placebo-controlled international study," (2000) The Lancet 356:2031-2036 (abstract).

MedlinePlus, MedlinePlus Medical Encyclopedia, 2009, pp. 1-5 (abstract).

Menzaghi et al., "ARI 16081, A Novel Selective 5-HT2A Inverse Agonist as a Putative Atypical Antipsychotic: Comparative Studies with Clozapine and Haloperidol," 2000 CINP, poster.

Menzaghi et al., "ARI 18081, A Novel High Affinity 5-HT2A Receptor Inverse Agonist With in Vivo Efficacy," Nov. 1999 Neuro, poster.

Menzaghi et al., "Identification of Novel Selective 5-HT2A Inverse Agonists as Putative Atypical Antipsychotics Using Constitutively Activated Human 5-HT Receptors," Jun. 2000 ASPET, poster.

Menzaghi et al., "Therapeutic Potential of Selective Serotonin 5HT2A Receptor Inverse Agonists: Pre-Clinical Evaluation of ARI 16081 as Antipsychotics in Rodents," 2002 FESN, abstract.

Mestre et al., "5-Hydroxytryptamine 2A receptor antagonists as potential treatment for psychiatric disorders," (2013) Expert Opinion on Investigational Drugs 22(4):411-421.

Miao et al., "Ketanserin Stabilizes Blood Pressure in Conscious Spontaneously Hypertensive Rats," (2003) Clin. Exp. Pharmacol. Physiol. 30(3):189-193.

Mitchell et al., "5-HT6 receptors: a novel target for cognitive enhancement," (2005) Pharmacol & Therapeutics 108:320-333.

Mizuki et al., "Effects of mianserin on negative symptoms in schizophrenia," (1990) International Clinical Psychopharmacology 5:83-95.

Montgomery et al., "A New Depression Scale Designed to be Sensitive to Change," (Apr. 1979) Br. J Psychiatry 134(4):382-389.

Monti, "Serotonin 5-HT2A Receptor Antagonists in the Treatment of Insomnia: Present Status and Future Prospects," 2010 Drugs of Today 46(3):183-193.

Morairty et al., "Selective 5HT2A and 5HT6 Receptor Antagonists Promote Sleep in Rats," (2008) Sleep 31(1).

Morissette et al., "High-throughput crystallization: polymorphs, salts, co-crystals and solvates of pharmaceutical solids," (2004) Advanced Drug Deliveiy Review 56:275-300.

Mueller, "Drug Immunosuppression Therapy for Adult Heart Transplantation Part 1: Immune Response to Allograft and Mechanism of Action of Immunosuppressants," (2004) The Annals of Thoracic Surgery 77(1):354-362.

Muto et al., "Protective effects of sarpogrelate, a 5HT2A antagonist, against postischemic myocardial dysfunction in guinea-pig hearts," (2005) Molecular and Cellular Biochemistry 272:119-32.

National Institutes of Health, National Heart, Lung and Blood Institute, "Facts about Insomnia," (Oct. 1995) NIH Publication No. 95-3801:1-4.

Newton et al., "Mianserin-Induced Down-Regulation of Human 5-Hydroxytryptamine2A and 5-Hydroxytryptamine2c Receptors Stably Expressed in the Human Neuroblastoma Cell Line SH-SY5Y," (1997) Journal of Neurochemistry 69:1031-1038.

Nichols et al., "2,3-Dihydrobenzofuran Analogs of Hallucinogenic Phenethvlamines," (Jan. 1, 1991) J Med. Chem. 34(1):276-281.

(56) References Cited

OTHER PUBLICATIONS

Nishiyama "Effects of 5HT2A receptor antagonist, sarpogrelate on thermal or inflammatory pain," (2005) European Journal of Pharmacology 516:18-22.
Nomura et al., "5-HT2A receptor antagonist, increases circulating adiponectin in patients with type 2 diabetes," (2005) Blood Coagulation and Fibrinolysis 16(6):423-428.
Nordberg et al., "Cholinesterase Inhibitors in the Treatment of Alzheimer's Disease," (1998) Drug Safety 19(6):465-480.
Office Action in U.S. Appl. No. 11/883,043, dated Sep. 8, 2009, 10 pages.
Oken, "Antihistamines, a Possible Risk Factor for Alzheimer's Disease," (1995) Medical Hypotheses 44:47-48 (abstract).
Olichney et al., "Cognitive Decline is Faster in Lewy Body Variant than in Alzheimer's Disease," (1998) Neurology 51:351-357 (abstract).
Olson et al., "Rapid eye movement sleep behaviour disorder: demographic, clinical and laboratory findings in 93 cases," Brain: A Journal of Neurology, Feb. 2000, 123(2):331-339.
Ono Pharmaceutical Co., Ltd. [online], "Launch of Rivastach Patch, for the Treatment of Dementia of Alzheimer's Type—To Offer New Treatment Option for Dementia of Alzheimer's Type (Transdermal Patch)," dated Jul. 19, 2011, retrieved from < https://www.ono-pharma.com/sites/default/files/en/news/press/sm_cn110719.pdf>, 2 pages.
Otwinowski et al., "Processing of X-ray diffraction data collected in oscillation mode," (1997) Methods in Enzymology 276:307-326 (abstract).
Parker et al., "Human Kinetic Modeling of the 5HT6 PET Radioligand 11CGSK215083 and Its Utility for Determining Occupancy at Both 5HT6 and 5HT2A Receptors by SB742457 as a Potential Therapeutic Mechanism of Action in Alzheimer Disease," (2015) J Nucl. Med. 56:1901-1909.
Pawlak et al., "A Potent 5-Hydroxytryptamine Receptor (5-HT2A) Antagonist, DV-7028, Delays Arterial Thrombosis Development in Rats," (1998) Thrombosis Research 90:259-270.
Pietraszek et al., "Blood serotonergic mechanisms in type 2 (non-insulin-dependent) diabetes mellitus," Thromb Res., Jun. 15, 1992;66(6):765-74.
Pineiro-Nunez et al., "Discovery and SAR studies of 2,6-difluorobenzenesulfonic acid 1-methyl-3-(methylopiperidin-4-yl)-1H-indol-5-ylester, a novel and potent 5-HT6 antagonist treatment of cognitive deficit," 299th ACS Natl. Mtg., Mar. 13-17, San Diego, Abst. Medi 282 (2005).
Polymorphism: in the Pharmaceutical Industry, Hilfiker (ed), 2006, Chapter 8, 211-233, 23 pages.
Porsolt et al., "Behavioral despair in mice: a primary screening test for antidepressants," (1977) Arch. Int. Pharmac. Ther. 229(2):327-336 abstract.
Portegies et al., "Guidelines for the Diagnosis and Management of Neurological Complications of HIV Infection," (2004) Eur. J Neural. 11:297-304.
Product Information Sheet Detrol.RTM. LA (tolterodine tartrate) capsules, Rev. Mar. 2008.
Product Information Sheet, Enablex.RTM. (darifenacin) tablets, T2010-XX.
Product Information Sheet, Exelon.RTM. Patch (rivastigmine transdermal system), LTS Lohmann Therapie Systems AG, 2000.
Product Information Sheet, Sanctura.RTM. (trospium chloride), Rev. Jan. 2011.
Product Information Sheet, VESicare.RTM. (solifenacin succinate) tablets, Rev. Apr. 2010.
Prosser et al., "Selective serotonin 5-HT2A, inverse agonists promote sleep consolidation in male Wistar rats during the normal inactive phase," Sleep 27:2 pages 2004.
Przyklenk et al., "Targeted inhibition of the serotonin 5HT2A receptor improves coronary patency in an in vivo model of recurrent thrombosis," (2010) Journal of Thrombosis and Haemostasis 8(2):331-340.

"QuaSAR—Quantitative Structure Activity Relationships of Analgesics, Narcotic Antagonists, and Hallucinogens," Research Monograph 22, 1978, NIDA, Barnett and Willette (eds.), 1-487.
Querbes et al., "A JC Virus-Induced Signal is Required for Infection of Glial Cells by a Clathtin-and epsl5-Dependent Pathway," (2004) J Virology 78:250-256.
Ramage, "Central 5-HT1A Receptors and Vagal Tone to the Airways." Trends in Pharmacological Sciences, Jun. 2000, 21(6):201-203.
Raschetti et al., "Cholinesterase Inhibitors in Mild Cognitive Impairment: A Systematic Review of Randomised Trials," (2007) PloS Med. 4(11):1818-1828.
Ray et al., "Central Anticholinergic Hypersensitivity in Aging," (Apr.-Jun. 1992) Journal of Geriatric Psychiatry and Neurology 5:72-77 (abstract).
Remington, "The Science and Practice of Pharmacy," 20th Edition, 2000 (Lippincott Williams & Wilkins), Table of Contents.
Riemer et al., "Influence of the 5-HT6 Receptor on Acetylcholine Release in the Cortex: Pharmacological Characterization of 4-(2-Bromo-6-pyrrolidin-1-ylpyridine-4-sulfonyl)phenylamine, a Potent and Selective 5-HT6 Receptor Antagonist," (2003) Brief Articles, J Med. Chem. 46:1273-1276.
Roberts et al., "The distribution of 5-HT6 receptors in rat brain: an autoradiographic binding study using the radiolabeled 5-HT6 receptor antagonist 125ISB-258585," (2002) Brain Research 934:49-57.
Robichaud et al., "Ch. 2: Recent Advances in Selective Serotonin Receptor Modulation," (2000) Annual Reports in Medicinal Chemistry 36: 11-20.
Robinul RTM. glycopyrrolate tablets Product Information Sheet, Rev. Apr. 2010.
Roche, "Bioreversible Carriers in Drug Design," (1987) (Table of Contents only).
Roe et al., "Use of Anticholinergic Medications by Older Adults with Dementia," (2002) JAGS 50:836-842 (abstract).
Rogers et al., "5-HT6 Receptor Antagonists Enhance Retention of a Water Maze Task in the Rat," (2001) Psychopharmacology 158:114-119.
Rojas-Fernandez "Successful Use of Donepezil for the Treatment of Dementia with Lewy Bodies," (2001) Annals of Pharmacotherapy 35(2):202-205.
Rosenberg et al., "APD125, a selective serotonin 5-HT2A receptor inverse agonist, significantly improves the key PSG parameters of sleep maintenance in patients with primary insomnia." (2008) Sleep, poster.
Rosenberg et al., "APD125, a selective serotonin 5-HT2A receptor inverse agonist, significantly improves the key parameters of sleep maintenance in patients with primary insomnia," (2007) AASM (abstract).
Rosenberg et al., "APD125, a Selective Serotonin 5-HT2A Receptor Inverse Agonist, Significantly Improves Sleep Maintenance in Primary Insomnia," Sleep, Dec. 2008, 31(12):1663-1671.
Roth et al., "APD125, a selective serotonin 5-HT2A receptor inverse agonist, significantly improves the key parameters of sleep maintenance inpatients with primary insomnia," (2008) APSS pp. 1-19.
Roth et al., "Serotonin receptors represent highly favorable molecular targets for cognitive enhancement in schizophrenia and other disorders," (2004) Psychopharmacology 174:17-24.
Rudolph et al., "The Anticholinergic Risk Scale and Anticholinergic Adverse Effects in Older Persons," (Mar. 10. 2008) Arch Intern Med 168(5):508-513.
Russell et al., "N-Arylsulfonylindole Derivatives as Serotonin 5-HT6 Receptor Ligands," (2001) J Med. Chem. 44(23):3881-3895.
Sahgal, "Practical behavioural neuroscience: problems, pitfalls and suggestions," (1993) Behavioural Neuroscience: A Practical Approach, IRL Press, New York, 1:1-8.
Satomura et al., "Sarpogrelate, a specific 5HT2-receptor antagonist, improves the coronary microcirculation in coronary artery disease," (Jan. 2002) Clin Cardiol. 25(1):28-32.
Sawnyok et al., "Antidepressants as analgesics: an overview of central and peripheral mechanisms of action," (2001) Journal of Psychiatry and Neurosciences 26(1):21-29.

(56) References Cited

OTHER PUBLICATIONS

Schmidt et al., "The Role of 5-HT2A Receptors in Antipsychotic Activity," (1995) Life Sciences 56(25):2209-2222.
Search Report in European Appln. No. 16808478.8, dated Jan. 14, 2019, 6 pages.
Search Report in European Appln. No. EP05025004.2, dated Jun. 30, 2006, 7 pages.
Search Report in European Appln. No. EP08157490.7, dated Jul. 8, 2008, 4 pages.
Search Report in European Appln. No. EP12170019.9, dated Aug. 16, 2012, 6 pages.
Search Report in European Appln. No. 16825262.5, dated Feb. 12, 2019, 7 pages.
Shan et al., "Investigation of Non-Aqueous Vehicles for a Poorly Soluble Compound Intended for Softgel Dosage Form Development," 2005 APSS, abstract.
Shan et al., "Physicochemical Characterization During Salt Selection Process" 2005 AAPS, poster.
Shan et al., "Physicochemical Characterization During Salt Selection Process" 2006 AAPS, poster.
Shapiro et al., "Differential Modes of Agonist Binding to 5-Hydroxytryptamine2A Serotonin Receptors Revealed by Mutation and Molecular Modeling of Conserved Residues in Transmembrane Region 5," (2000) Molecular Pharmacology 58(5):877-886.
Sharpley et al., "Slow wave sleep in humans: role of 5HT2A and 5-HT2C receptors," (Mar.-Apr. 1994) Neuropharmacology, 33(3-4):467-471.
Sheehan et al., "1-Ethyl-3-(3-Dimethylamino) Proplycarbodimide Hydrochloride and Methiodide," (1973) Org Syn. Coll. 5:555-558.
Shibata et al., "Adiponectin protects against myocardial ischemiareperfusion injury throush AMPK- and COX-2 dependent mechanisms," (2005) Nature Medicine pp. 1-8.
Shua-Haim et al., "Safety, Tolerability, and Caregiver's Impressions of Combination Therapy With Rivastigmine and Memantine for the Treatment of Alzheimer's Disease," (2004) Neurobiology & Aging S205:P1-377.
Silva et al., "Chronic treatment with mianserin prevents DOCA-salt hypertension in rats-evidence for the involvement of central 5-HT2 receptors," (2005) J Pharmacol. 518(2-3):152-157, 2005.
Singh et al., "Immunosuppressive-associated Leukoencephalopathy in Organ Transplant Recipients," (2000) Transplantation 69:467-472.
Sink et al., "Dual Use of Bladder Anticholinergics and Cholinesterase Inhibitors: Long-Term Functional and Cognitive Outcomes," (2008) JAGS 56:847-853.
Sleight et al., "Characterization of Ro 04-6790 and Ro 63-0563: potent, and selective antagonists at human and rat 5-HT6 receptors," (1998) British Journal of Phamacol. 124:556-562.
Smirnova, et al., "Analiz kristallicheskoy i prostranstvennoy struktury lekarstvennykh veshchestv [Analysis of crystalline structure and chirality of drug substances]," Vestn. Mosk. Un-ta. Ser. 2, (2012):234-240 (English Abstract only).
Smith et al., "Test-retest variability of serotonin 5-HT2A receptor binding measured with positron emission tomography and [18F]altanserin in the human brain," (1998) Synapse, Dec. 30(4):380-392.
Sorenson et al., "Characterization of the 5-HT2 Receptor Antagonist MDL 100907 as Putative Atypical Antipsychotic: Behavioral, Electrophysiological and Neurochemical Studies," (1993) J Pharacol. Exp. Ther. 266(2):684-691.
Speer et al., "Intrinsic Dissolution Characterization of Different Morphic Forms of a Poorly Water Soluble Compound," 2006, AAPS, abstract.
Speer et al., "Influence of Digestive Enzymes Combined with Sodium Lauryl Sulfate on Dissolution of Cross-linked Gelatin Capsules," 2005 AAPS, poster.
Speer et al., "Influence of Digestive Enzymes on Dissolution of a Poorly Water Soluble Compound From Cross-Linked Gelatin Capsules in Sodium Lauryl Sulfate Medium," 2005 AAPS, abstract.
Stadler et al., "5-HT6 antagonists: a novel approach for the symptomatic treatment of Alzheimer's Disease," 37th IUPAC Cong. Aug. 14-19, 1999, Berlin, Abst. MM-7.
Staley et al., "Comparison of [(18)F]altanserin and [(18)F]deuteroaltanserin for PET imaging of serotonin(2A) receptors in baboon brain: pharmacological studies," (Apr. 2001) Nucl Med Biol. 28(3):271-279.
Storey et al., "Automation of Solid Form Screening Procedures in the Pharmaceutical industry—How to Avoid the Bottlenecks," (2004) Crystallography Review's 10(1):45-56.
Strah-Pleynet et al., "5HT2A Receptor Inverse Agonists: Design and SAR of Novel Pyrazole Derivatives," (2006) meeting abstract.
Strah-Pleynet et al., "5-HT2A Receptor Inverse-Agonists: Design and Structure-Activity Relationship of Novel Pyrazole Derivatives," 2005 ACS, 231st ACS National Meeting, Medi 145, poster.
Strah-Pleynet et al., "Bioisosteric Modifications of Urea Derivatives as 5HT2A Inverse-Agonists," 2004 ACS, meeting abstract.
Strah-Pleynet et al., "Bioisosteric Modifications of Urea Derivatives as 5HT2A Inverse-Agonists," 2005 ACS, meeting poster.
Strah-Pleynet et al., "Discovery and SAR of novel 5-HT2A inverse agonists," 227th ACS National Meeting, MED 1 270, Arena Pharmaceutical Inc. (Mar. 2004), 1 page, poster.
Strah-Pleynet et al., "Discovery and SAR of Novel 5-HT2A Inverse-Agonists," 2004 ACS, 227th ACS National Meeting, Medi 270, abstract.
Street et al., "Olanzapine treatment of psychotic and behavioral symptoms in patients with Alzheimer disease in nursing care facilities: a double-blind, randomized, placebo-controlled trial. The HGEU Study Group," (Oct. 2000) Arch Gen Psychiatry. 57(10):968-976.
Takahashi et al., "Sarpogrelate hydrochloride, a serotonin2A receptor antagonist, reduces albuminuria in diabetic patients with early-stage diabetic nephropathy," (Nov. 2002) Diabetes Res Clin Pract. 58(2):123-129.
Takenaka et al., "The effect of anplag (sarpogrelate HCl), novel selective 5-HT2 antagonist on intraocular pressure in glaucoma patients," (1995) Investig Ophthalmol Iris Sci. 36(4):S724 (abstract 3390-377).
Talvik-Lotfi et al., "High 5HT2A receptor occupancy in M100907-treated schizophrenic patients," (2000) Psychopharmacology 148:400-403.
Tang et al., "Anilinopyrazole as selective CDK2 inhibitors: design, synthesis, biological evaluation, and x-ray crystallographic analysis," (2003) Bioorg. Med. Chem. Letters 13(18):2985-2988 (abstract).
Teegarden et al., "5-HT2A Inverse-Agonists for the Treatment of Insomnia," (2008) Current Topics in Medicinal Chemistiy, pp. 1-28.
Teegarden et al., "Discovery of 1-[3-(4-Bromo-2-methyl-2H-pyrazol-3-yl]-4-methoxy-phenyl]-3-(2,4-difluorophenyl)-urea (APD 125) and Related 5-HT2A Inverse Agonists for the Treatment of insomnia," (2009) J Med. Chem pp. 1-50.
Teegarden et al., "Discovery of 1-[3-(4-Bromo-2-methyl-2H-pyrazol-3-yl)-4-methoxyphenyl]-3-(2,4-difluoropheny)urea (Nelotanserin) and Related 5-Hydroxytryptamine2A Inverse Agonists for the Treatment of Insomnia," (2003) J Med. Chem. 53:1923-193.
Teramura-Gronblad et al., "Use of Anticholinergic Drugs and Cholinesterase Inhibitors and Their Association with Psychological Well-Being Among Frail Older Adults in Residential Care Facilities," (2011) Ann Pharmacotherapy 45:596-602 (abstract).
Terry et al., "The Cholinergic Hypothesis of Age and Alzheimer's Disease-Related Cognitive Deficits: Recent Challenges and Their Implications for Novel Drug Development," (2003) JPET 306(3):821-827.
The Practice of Medicinal Chemistry, 2nd ed., Wermuth (author), 2003, Chapters 9-10.
The Statistical Analysis of Experimental Data, Mandel (author), 1964, Chapter 3, pp. 28-57.
The Statistical Analysis of Experimental Data, Mandel (author), 1964, Chapter 9, pp. 204-207.
Thome et al., "Association analysis ofHTR6 and HTR2A polymorphisms in sporadic Alzheimer's disease," (2001) Journal of Neural Transmission 108:1175-1180.
Topliss, "A Manual Method for Applying the Hansch Approach to Drug Design," (Apr. 1, 1977) J Med. Chem. 20(4):463-469.

(56) References Cited

OTHER PUBLICATIONS

Totterdell, "Synaptic Circuitry of Interactions Between Limbic and Dopaminergic Afferents to the Ventral Striatum," (2004) International Journal of Neuropsychopharmacology 7:S14-S14.
Tsai et al., "Association Analysis of the 5-HT6 Receptor Polymorphism C267T in Alzheimer's Disease," (1999) Neuroscience Letters 276:138-139.
Tsao et al., "Transient Memory Impairment and Hallucinations Associated with Tolterodine Use," (Dec. 4, 2003) New England Journal of Medicine 349(23):2274-2275 (abstract).
Upton et al., "5-HT6 Receptor antagonists as novel cognitive enhancing agents for Alzheimer's Disease," (2008) Neurotherapeutics 5(3):458-469.
Vacante et al., "Extension of JC Virus Host Range to Monkey Cells by Insertion of a Simian Virus 40 Enhancer into the JC Virus Regulatory Region," Virology 170:353-361.
Van Eijk et al., "Effect of rivastigmine as an adjunct to usual care with haloperidol on duration of delirium and mortality in critically ill patients: a multicentre, double blind, placebo-controlled randomised trial." (2010) The Lancet 376: 1829-1837 (abstract).
Van Zwieten, "Receptors Involved in the Regulation of Vascular Tone" (1985) Arzneimittelfirschung 35(12A):1904-1909.
Vanover et al., "Role of 5-HT2A receptor antagonists in the treatment of insomnia," (2010) Nature and Science of Sleep 2:139-150.
Vanover et al., "Pharmacokinetics, Tolerability, and Safety of ACP-103 Following Single or Multiple Oral Dose Administration in Healthy Volunteers," (2007) J Clinical Pharmacol. 47(6):704-714.
Vanover et al., "Pharmacological and Behavioral Profile of N-(4-Fluorophenylmethyl)-N-(1-methylpiperidin-4-yl)-N'-(4-(2-methylpropyloxy)phenylmethyl) Carbamide (2R,3R)-Dihydroxybutanedioate (2:1) (ACP-103), a Novel 5-Hydroxytryptamine2A Receptor Inverse Agonist," (2006) J Pharmacol Exp Ther. 317:910-918.
Vasilevskii, "Oxidative Iodination of Substituted N-Methylpyrazoles," (1980) Bull. Acad. Sci. USSR 29(5):778-784.
Vasilevsky et al., "Study of the heterocyclization of vic-substituted hydrazides of acetylenylpyrazolecarboxylic acids into N-amino pyrazolopyridinones," (2002) J. Hetercycl. Chem. 39:1229-1233.
Verdejo et al., "Tratamiento con propantelina de la incontinencia urinaria por inestabilidad vesical en pacientes ancianos," (1992) Anales de Medicina 9(3): 1160120.
Verstraete, "Prevention of atherosclerotic complications: controlled trial of ketanserin," (1989) British Medical Journal 298:424-430.
Vikenes et al., "Serotonin is Associated with Coronary Artery Disease and Cardiac Events," (1999) Circulation 100:483-489.
Vippagunta et al., "Crystalline Solids," (2001) Advanced Drug Delivery Reviews 48:3-26.
Westkaemper et al., "Application of Ligand SAR, Receptor Modeling and Receptor Mutagenesis to the Discovery and Development of a New Class of 5-HT2A Ligands," (2002) Curr. Topics Med. Chem. 2:575-598 (abstract).
White, "Deamination of amines. 2-phenylethyl benzoate via the nitrosoamide decomposition," (1973) Org. Syn. Coll. 5:336-339.
Wikstrom et al., "Synthesis and Pharmacological Testing of 1,2,3,4,10,14b-Hexahydro-6-methoxy-2-methyldibenzo[c,f]pyrazino[1,2-a]azepin and Its Enantiomers in Comparison with the Two Antidepressants Mianserin and Mirtazapine," (2002) J Med. Chem.45(15):3280-3285.
Williams et al., "Survival and mortality differences between dementia with Lewy bodies vs Alzheimer disease," (1935) Neurology 67:1935-1941 (abstract).
Willner, "Animal Models as Simulations of Depression," (1991) Trends Pharmacol. Sci. 12(4):131-136 (abstract).
Wilson et al., "LY53857, a 5HT2 Receptor Antagonist, Delays Occlusion and Inhibits Platelet Aggregation in a Rabbit Model of Carotid Artery Occlusion," (Sep. 2, 1991) Thrombosis and Haemostasis 66(3):355-360.
Wilson et al., "The Psychopharmacology of Agitation: Consensus Statement of the American Association for Emergency Psychiatry Project BETA Psychopharmacology Workgroup," Western Journal of Emergency Medicine, Feb. 2012, 13(1):26-34.
Winokur et al., "Acute effects of mirtazapine on sleep continuity and sleep architecture in depressed patients: a pilot study," (Jul. 1, 2000) Biol Psychiatry 48(1):75-78.
Woolley et al., "5-HT6 Receptors," (2004) Current Drug Targets—CNS & Neurological Disorders 3:59-79.
Woolley et al., "A role for 5-HT6 Receptors in Retention of Spatial Learning in the Morris Water Maze," (2001) Neuropharmacology 41:210-219.
Woolley et al., "Reversal of a cholinergic-induced deficit in a rodent model of recognition memory by the selective 5-HT6 receptor antagonist, Ro 04-6790," (2003) Psychopharmacology 170:358-367.
Xiong et al., "Discovery and SAR of Highly Selective 5-HT$_{2A}$ Receptor Subtype Inverse-Agonists for Inhibition of Platelet Aggregation," 2008 ACS, 235th National Meeting, Medi 45, poster.
Xiong et al., "Synthesis and in Vivo Evaluation of Phenethylpiperazine Amides: Selective 5-Hydroxytryptamine2A Receptor Antagonists for the Treatment of Insomnia," (2010) Journal of Medical Chemistry 53:5696-5706.
Yamada et al., "Phase I/II trial of didanosine (2',3'-dideoxyinosine) in hemophiliac patients with AIDS or AIDS-related complex," (1993) Clinical and Diagnostic Virology 1:245-256.
Yamashita et al., "Conjunctive effects of the 5HT2 receptor antagonist, sarpogrelate, on thrombolysis with modified tissue plasminogen activator in different laser-induced thrombosis models," (2000) Haemostatis 30:321-332 (abstract).
Yevich et al., "Second generation antimigraine 5-HT lb/D agonists: structure activity relationship and preclinical pharmacological distinctions," (1997) Curr. Med. Chem. 4(5):295-312 (abstract).
Zhu et al., "Synthesis and Mode of Action of 125I- and 3H-Labeled Thieno[2,3-c]pyridine Antagonists of Cell Adhesion Molecule Expression," (2000) J Org. Chem. 67:943-948.

* cited by examiner

DIARYL AND ARYLHETEROARYL UREA DERIVATIVES AS MODULATORS OF THE 5-HT$_{2A}$ SEROTONIN RECEPTOR USEFUL FOR THE PROPHYLAXIS AND TREATMENT OF HALLUCINATIONS ASSOCIATED WITH A NEURODEGENERATIVE DISEASE

CROSS REFERENCE TO RELATED APPLICATIONS

This application is a continuation of U.S. patent application Ser. No. 16/016,160 filed Jun. 22, 2018, which is a continuation of U.S. patent application Ser. No. 15/211,638 filed Jul. 15, 2016 now issued as U.S. Pat. No. 10,034,859, which claims the priority benefit under 35 U.S.C. 119(e) of U.S. Provisional Application No. 62/192,939 filed Jul. 15, 2015, U.S. Provisional Application No. 62/236,618 filed Oct. 2, 2015, and U.S. Provisional Application No. 62/261,381 filed Dec. 1, 2015, the disclosures of which are incorporated by reference in their entireties.

SUMMARY

The present invention relates to certain diaryl and arylheteroaryl urea derivatives of Formula (I) and pharmaceutical compositions thereof that modulate the activity of the 5-HT$_{2A}$ serotonin receptor. Compounds and pharmaceutical compositions thereof are directed to methods useful in the prophylaxis and/or treatment of neuropsychiatric symptoms such as, but not limited to hallucinations. In some embodiments the hallucinations may be associated with a neurodegenerative disease. In some embodiments, the hallucinations may be associated with Lewy Body dementia. In some embodiments, the hallucinations are visual hallucinations.

One aspect of the present invention encompasses certain diaryl and arylheteroaryl urea derivatives as shown in Formula I:

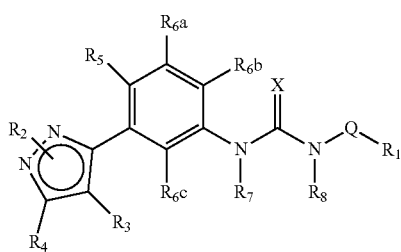

I or a pharmaceutically acceptable salt, hydrate or solvate thereof;
wherein:
i) $R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$cycloalkyl group or heterocyclic group each optionally substituted with F, Cl, or Br; and wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$alkynyl, $C_{1-6}$ alkylsulfonamide, $C_{1-6}$ alkylsulfinyl, $C_{1-6}$alkylsulfonyl, $C_{1-6}$ alkylthio, $C_{1-6}$ alkylureyl, amino, $C_{1-6}$alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$haloalkylsulfonyl, $C_{1-6}$ haloalkylthio, hydroxyl, thiol and nitro;
ii) $R_2$ is selected from the group consisting of H, $C_{1-6}$ alkyl, $C_{2-6}$alkenyl, $C_{2-6}$ alkynyl and $C_{3-7}$ cycloalkyl;
iii) $R_3$ is selected from the group consisting of H, $C_{2-6}$ alkenyl, $C_{1-6}$alkyl, $C_{1-6}$ alkylcarboxamide, $C_{2-6}$ alkynyl, $C_{1-6}$alkylsulfonamide, carbo-$C_{1-6}$-alkoxy, carboxamide, carboxy, cyano, $C_{3-7}$ cycloalkyl, $C_{2-8}$ dialkylcarboxamide, halogen, heteroaryl and phenyl; and wherein each of said $C_{2-6}$ alkenyl, $C_{1-6}$ alkyl, $C_{2-6}$ alkynyl, $C_{1-6}$alkylsulfonamide, $C_{3-7}$ cycloalkyl, heteroaryl and phenyl groups can be optionally substituted with 1 to 5 substituents selected independently from the group consisting of $C_{1-5}$ acyl, $C_{1-5}$ acyloxy, $C_{2-6}$alkenyl, $C_{1-4}$alkoxy, $C_{1-8}$alkyl, $C_{1-6}$alkylamino, $C_{2-8}$dialkylamino, $C_{1-4}$ alkylcarboxamide, $C_{2-6}$ alkynyl, $C_{1-4}$alkylsulfonamide, $C_{1-4}$ alkylsulfinyl, $C_{1-4}$ alkylsulfonyl, $C_{1-4}$alkylthio, $C_{1-4}$ alkylureyl, amino, carbo-$C_{1-6}$-alkoxy, carboxamide, carboxy, cyano, $C_{3-6}$cycloalkyl, $C_{2-6}$ dialkylcarboxamide, halogen, $C_{1-4}$haloalkoxy, $C_{1-4}$haloalkyl, $C_{1-4}$ haloalkylsulfinyl, $C_{1-4}$haloalkylsulfonyl, $C_{1-4}$ haloalkylthio, hydroxyl, nitro and sulfonamide;
iv) $R_4$ is selected from the group consisting of H, $C_{1-6}$ acyl, $C_{1-6}$acyloxy, $C_{2-6}$ alkenyl, $C_{1-6}$ alkoxy, $C_{1-6}$ alkyl, $C_{1-6}$alkylcarboxamide, $C_{2-6}$ alkynyl, $C_{1-6}$ alkylsulfonamide, $C_{1-6}$alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$dialkylcarboxamide, $C_{2-8}$ dialkylsulfonamide, halogen, $C_{1-6}$haloalkoxy, $C_{1-6}$ haloalkyl, $C_{1-6}$ haloalkylsulfinyl, $C_{1-6}$haloalkylsulfonyl, $C_{1-6}$ haloalkylthio, hydroxyl, thiol, nitro and sulfonamide;
v) $R_5$ is selected from the group consisting of $C_{1-6}$ acyl, $C_{1-6}$acyloxy, $C_{2-6}$ alkenyl, $C_{1-6}$ alkoxy, $C_{1-6}$ alkyl, $C_{1-6}$alkylcarboxamide, $C_{2-6}$ alkynyl, $C_{1-6}$ alkylsulfonamide, $C_{1-6}$alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$cycloalkyl, $C_{2-8}$dialkylcarboxamide, $C_{2-8}$ dialkylsulfonamide, halogen, $C_{1-6}$haloalkoxy, $C_{1-6}$ haloalkyl, $C_{1-6}$haloalkylsulfinyl, $C_{1-6}$haloalkylsulfonyl, $C_{1-6}$ haloalkylthio, hydroxyl, thiol, nitro and sulfonamide, wherein said $C_{1-6}$ alkoxy group can be optionally substituted with 1 to 5 substituents selected independently from the group consisting of $C_{1-5}$ acyl, $C_{1-5}$ acyloxy, $C_{2-6}$ alkenyl, $C_{1-4}$alkoxy, $C_{1-8}$ alkyl, amino, $C_{1-6}$ alkylamino, $C_{2-8}$dialkylamino, $C_{1-4}$alkylcarboxamide, $C_{2-6}$ alkynyl, $C_{1-4}$ alkylsulfonamide, $C_{1-4}$alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$cycloalkyl, $C_{2-6}$ dialkylcarboxamide, halogen, $C_{1-4}$haloalkoxy, $C_{1-4}$haloalkyl, $C_{1-4}$ haloalkylsulfinyl, $C_{1-4}$haloalkylsulfonyl, $C_{1-4}$haloalkylthio, hydroxyl, nitro and phenyl; and wherein said amino and phenyl are each optionally substituted with 1 to 5 further substituents selected from the group consisting of halogen and carbo-$C_{1-6}$-alkoxy;

vi) $R_{6a}$, $R_{6b}$, and $R_{6c}$ are each independently selected from the group consisting of H, $C_{1-6}$ acyl, $C_{1-6}$ acyloxy, $C_{2-6}$ alkenyl, $C_{1-6}$alkoxy, $C_{1-6}$ alkyl, $C_{1-6}$ alkylcarboxamide, $C_{2-6}$ alkynyl, $C_{1-6}$alkylsulfonamide, $C_{1-6}$ alkylsulfinyl, $C_{1-6}$ alkylsulfonyl, $C_{1-6}$alkylthio, $C_{1-6}$ alkylureyl, amino, $C_{1-6}$ alkylamino, $C_{2-8}$dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

vii) $R_7$ and $R_8$ are independently H or $C_{1-8}$ alkyl;

viii) X is O or S; and ix) Q is $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl, halogen and oxo; or Q is a bond.

One aspect of the present invention encompasses pharmaceutical compositions comprising a compound of the present invention and a pharmaceutically acceptable carrier.

One aspect of the present invention encompasses methods for the prophylaxis and/or treatment of neuropsychiatric symptoms such as, but not limited to hallucinations, associated with a neurodegenerative disease in an individual comprising administering to said individual in need thereof a therapeutically effective amount of a 5-$HT_{2A}$ inverse agonist. One aspect of the present invention encompasses methods for the prophylaxis and/or treatment of hallucinations associated with Lewy Body dementia in an individual comprising administering to said individual in need thereof a therapeutically effective amount of a 5-$HT_{2A}$ inverse agonist. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One aspect of the present invention encompasses methods for the prophylaxis and/or treatment of visual hallucinations associated with a neurodegenerative disease in an individual comprising administering to said individual in need thereof a therapeutically effective amount of a 5-$HT_{2A}$ inverse agonist. One aspect of the present invention encompasses methods for the prophylaxis and/or treatment of visual hallucinations associated with Lewy Body dementia in an individual comprising administering to said individual in need thereof a therapeutically effective amount of a 5-$HT_{2A}$ inverse agonist.

Some embodiments are directed to methods for the prophylaxis and/or treatment of neuropsychiatric symptoms such as, but not limited to hallucinations, in a subject in need thereof, comprising administering to said subject a therapeutically effective amount of a 5-$HT_{2A}$ inverse agonist. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

Some embodiments are directed to methods for the prophylaxis and/or treatment of visual hallucinations, in a subject in need thereof, comprising administering to said subject a therapeutically effective amount of a 5-$HT_{2A}$ inverse agonist.

In some embodiments, the 5-$HT_{2A}$ inverse agonist is selected from nelotanserin, pimavanserin, pruvanserin, eplivanserin, volinanserin, glemanserin, ketanserin, ritanserin, clozapine, or a pharmaceutically acceptable salt, hydrate, polymorph, or solvate thereof. In some embodiments, the 5-$HT_{2A}$ inverse agonist is nelotanserin or a pharmaceutically acceptable salt, hydrate, polymorph, or solvate thereof. In some embodiments, the nelotanserin or a pharmaceutically acceptable salt, hydrate, polymorph, or solvate thereof is selected from the group consisting of Form I of 1-[3-(4-bromo-2-methyl-2H-pyrazol-3-yl)-4-methoxy-phenyl]-3-(2,4-difluoro-phenyl)-urea, Form II of 1-[3-(4-bromo-2-methyl-2H-pyrazol-3-yl)-4-methoxy-phenyl]-3-(2,4-difluoro-phenyl)-urea and a combination thereof. In some embodiments, the therapeutically effective amount of nelotanserin or a pharmaceutically acceptable salt, hydrate, polymorph, or solvate thereof is from about 10 mg to about 160 mg. In some embodiments, the therapeutically effective amount of nelotanserin or a pharmaceutically acceptable salt, hydrate, polymorph, or solvate thereof is about 10 mg, about 20 mg, about 40 mg, about 80 mg, or about 160 mg. In some embodiments, the therapeutically effective amount of nelotanserin is about 10 mg, about 20 mg, about 40 mg, about 80 mg, or about 160 mg. In some embodiments, the therapeutically effective amount of nelotanserin is about 10 mg. In some embodiments, the therapeutically effective amount of nelotanserin is about 20 mg. In some embodiments, the therapeutically effective amount of nelotanserin is about 40 mg. In some embodiments, the therapeutically effective amount of nelotanserin is about 80 mg. In some embodiments, the therapeutically effective amount of nelotanserin is about 160 mg. In some embodiments, the therapeutically effective amount of the 5-$HT_{2A}$ inverse agonist is administered once a day, twice a day, three times a day, or four times a day. In some embodiments, the 5-$HT_{2A}$ inverse agonist is in a pharmaceutical composition configured for immediate release, for extended release, for delayed release, or any combination thereof. In some embodiments, the 5-$HT_{2A}$ inverse agonist is in a pharmaceutical composition, and wherein the pharmaceutical composition is formulated for oral administration. In some embodiments, the therapeutically effective amount of the 5-$HT_{2A}$ inverse agonist is administered about one to about four times per day, once daily in the morning, once daily about 1 hour prior to the subject's bedtime, or twice daily.

In some embodiments, the subject is a human. In some embodiments, the human is an adult with a diagnosis of a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the human has a concurrent diagnosis of hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the human has a concurrent diagnosis of visual hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the human has a diagnosis of probable Dementia with Lewy Bodies. In some embodiments, the diagnosis of probable DLB is defined by the presence of dementia and at least one of: at least two Core Criteria selected from visual hallucinations, cognitive fluctuations, and Parkinsonism, and any combination thereof; and one Core Criteria selected from visual hallucinations, cognitive fluctuations, and Parkinsonism, and any combination thereof; and at least one Suggestive Criteria selected from REM Sleep Behavior Disorder, Severe Neuroleptic Sensitivity, Low Dopamine Transporter Uptake on DaT SPECT Imaging Scan; and any combination thereof. In some embodiments, the human has a diagnosis of Dementia with Lewy Bodies. In some embodiments, the human has a Mini Mental State Examination score of greater than, or equal to, about 18. In some embodiments, the human is an adult with a diagnosis of visual hallucinations associated with Dementia with Lewy Bodies. In some embodiments, the human is an adult aged 50-85 inclusive. In some embodiments, the human has experienced persistent visual hallucinations. In some embodiments, the presence of persistent hallucinations is defined by a score of four or greater on the hallucinations component of the Neuropsychiatric Inventory (NPI Item B) at screening. In some embodiments, the human has experienced visual hallucinations on at least five days in a week.

In some embodiments, the subject is concurrently receiving a therapeutically effective amount of at least one additional therapeutic agent selected from the group consisting of melatonin, quetiapine, clonazepam, levodopa, carbidopa, an antiparkinsonian drug, an acetylcholinesterase inhibitor, NMDA receptor antagonist, and a combination thereof. In some embodiments, the antiparkinsonian drug is selected from an MAO-B inhibitor, a COMT inhibitor, a dopamine agonist or any combination thereof. In some embodiments, the acetylcholinesterase inhibitor is selected from the group consisting of donepezil, rivastigmine, galantamine, and pharmaceutically acceptable salts, hydrates, polymorphs, or solvates thereof. In some embodiments, the acetylcholinesterase inhibitor is donepezil or a pharmaceutically acceptable salt, hydrate, polymorph, or solvate thereof. In some embodiments, the acetylcholinesterase inhibitor is rivastigmine or a pharmaceutically acceptable salt, hydrate, polymorph, or solvate thereof. In some embodiments, the acetylcholinesterase inhibitor is galantamine or a pharmaceutically acceptable salt, hydrate, polymorph, or solvate thereof. In some embodiments, NMDA receptor antagonist is selected from the group consisting of memantine, amantadine, ketamine, and pharmaceutically acceptable salts, hydrates, polymorphs, or solvates thereof. In some embodiments, the NMDA receptor antagonist is memantine or a pharmaceutically acceptable salt, hydrate, polymorph, or solvate thereof. In some embodiments, the NMDA receptor antagonist is amantadine or a pharmaceutically acceptable salt, hydrate, polymorph, or solvate thereof.

In some embodiments, administration of a therapeutically effective amount of a 5-HT$_{2A}$ inverse agonist results in treatment, and/or prophylaxis of neuropsychiatric symptoms such as, but not limited to hallucinations. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, administration of a therapeutically effective amount of a 5-HT$_{2A}$ inverse agonist results in treatment, and/or prophylaxis of visual hallucinations. In some embodiments, treating or prophylaxis results in a decrease in the frequency, severity, or a combination thereof of visual hallucinations. In some embodiments, the subject has a score of three or greater on SAPS-H prior to administration of a therapeutically effective amount of a 5-HT$_{2A}$ inverse agonist. In some embodiments, treatment results in an improvement in the hallucinations component of the Scale for Assessment of Positive Symptoms (SAPS-H) after 22 days of treatment. In some embodiments, treatment results in an improvement in the hallucinations component of the Scale for Assessment of Positive Symptoms (SAPS-H) after 43 days of treatment. In some embodiments, treatment results in an improvement in the delusions component of the Scale for Assessment of Positive Symptoms (SAPS-D) after 22 days of treatment. In some embodiments, treatment results in an improvement in the delusions component of the Scale for Assessment of Positive Symptoms (SAPS-D) after 43 days of treatment. In some embodiments, treatment results in an improvement in investigator assessments of global function as measured by the change in the CGI-I and CGI-S scores after 22 days of treatment. In some embodiments, treatment results in an improvement in investigator assessments of global function as measured by the change in the CGI-I and CGI-S scores after 43 days of treatment. In some embodiments, treatment results in an improvement in caregiver burden as measured by the Zarit Caregiver Burden Score after 22 days of treatment. In some embodiments, treatment results in an improvement in caregiver burden as measured by the Zarit Caregiver Burden Score after 43 days of treatment. In some embodiments, treatment results in an improvement in subjective sleep quality as measured by change in the SCOPA-night and SCOPA day wake scores after 22 days of treatment. In some embodiments, treatment results in an improvement in subjective sleep quality as measured by change in the SCOPA-night and SCOPA day wake scores after 43 days of treatment. In some embodiments, treating or prophylaxis results in a decrease in the severity, frequency, or a combination thereof, of visual hallucinations. In some embodiments, treating or prophylaxis results in an improvement in the subject's Mini-Mental State Examination score.

Some embodiments are directed to methods for the prophylaxis and/or treatment of neuropsychiatric symptoms such as, but not limited to hallucinations associated with Lewy Body Dementia, in a subject in need thereof comprising administering to said subject a daily dose of about 40 mg of nelotanserin. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, the daily dose of about 40 mg of nelotanserin is administered once a day, twice a day, three times a day, or four times a day. In some embodiments, the subject has a concurrent diagnosis of hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of visual hallucinations associated with Lewy Body Dementia, in a subject in need thereof comprising administering to said subject a daily dose of about 40 mg of nelotanserin. In some embodiments, the daily dose of about 40 mg of nelotanserin is administered once a day, twice a day, three times a day, or four times a day. In some embodiments, the subject has a concurrent diagnosis of visual hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of neuropsychiatric symptoms such as, but not limited to hallucinations, in a subject in need thereof, comprising administering to said subject a daily oral dose of about 40 mg of nelotanserin. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, the daily dose of about 40 mg of nelotanserin is administered once a day, twice a day, three times a day or four times a day. In some embodiments, the subject has a concurrent diagnosis of hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of visual hallucinations, in a subject in need thereof, comprising administering to said subject a daily oral dose of about 40 mg of nelotanserin. In some embodiments, the daily dose of about 40 mg of nelotanserin is administered once a day, twice a day, three times a day or four times a day. In some embodiments, the subject has a concurrent diagnosis of visual hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of neuropsychiatric symptoms such as, but not limited to hallucinations, in a subject in need thereof, comprising administering to said subject a daily oral dose of about 80 mg of nelotanserin. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, the daily dose of about 80 mg of nelotanserin is administered once a day, twice a day, three times a day or four times a day. In some embodiments, the subject has a concurrent diagnosis of hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of visual hallucinations, in a subject in need thereof, comprising administering to said subject a daily oral dose of about 80 mg of nelotanserin. In some embodiments, the daily dose of about 80 mg of nelotanserin is administered once a day, twice a day, three times a day or four times a day. In some embodiments, the subject has a concurrent diagnosis of visual hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, Alzheimer's agitation, aggression, REM sleep behavior disorder, schizophrenia, and any combination thereof.

Some embodiments are directed to methods for the prophylaxis and/or treatment of neuropsychiatric symptoms such as, but not limited to hallucinations, in a subject in need thereof, comprising administering to said subject a daily oral dose of about 160 mg of nelotanserin. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, the daily dose of about 160 mg of nelotanserin is administered once a day, twice a day, three times a day or four times a day. In some embodiments, the subject has a concurrent diagnosis of hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of visual hallucinations, in a subject in need thereof, comprising administering to said subject a daily oral dose of about 160 mg of nelotanserin. In some embodiments, the daily dose of about 160 mg of nelotanserin is administered once a day, twice a day, three times a day or four times a day. In some embodiments, the subject has a concurrent diagnosis of visual hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of neuropsychiatric symptoms such as, but not limited to hallucinations in a subject in need thereof comprising administering to said subject a dose of about 40 mg of nelotanserin for a first time period followed by administering to said subject a dose of about 80 mg of nelotanserin for a second time period. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, the subject is a human adult with a diagnosis of a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of visual hallucinations in a subject in need thereof comprising administering to said subject a dose of about 40 mg of nelotanserin for a first time period followed by administering to said subject a dose of about 80 mg of nelotanserin for a second time period. In some embodiments, the subject is a human adult with a diagnosis of a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of dementia with Lewy Bodies in a subject in need thereof, comprising administering to said subject a therapeutically effective amount of a $5-HT_{2A}$ inverse agonist. In some embodiments, the $5-HT_{2A}$ inverse agonist is selected from nelotanserin, pimavanserin, pruvanserin, eplivanserin, volinanserin, glemanserin, ketanserin, ritanserin, clozapine, or a pharmaceutically acceptable salt, hydrate, polymorph, or solvate thereof. In some embodiments, the $5-HT_{2A}$ inverse agonist is nelotanserin or a pharmaceutically acceptable salt, hydrate, polymorph, or solvate thereof. In some embodiments, the nelotanserin or a pharmaceutically acceptable salt, hydrate, polymorph, or solvate thereof is selected from the group consisting of Form I of 1-[3-(4-bromo-2-methyl-2H-pyrazol-3-yl)-4-methoxy-phenyl]-3-(2,4-difluoro-phenyl)-urea, Form II of 1-[3-(4-bromo-2-methyl-2H-pyrazol-3-yl)-4-methoxy-phenyl]-3-(2,4-difluoro-phenyl)-urea and a combination thereof. In some embodiments, the therapeutically effective amount of nelotanserin or a pharmaceutically acceptable salt, hydrate, polymorph, or solvate thereof is from 10 mg to about 160 mg. In some embodiments, the therapeutically effective amount of nelotanserin or a pharmaceutically acceptable salt, hydrate, polymorph, or solvate thereof is about 10 mg, about 20 mg, about 40 mg, about 80 mg, or about 160 mg. In some embodiments, the therapeutically effective amount of nelotanserin is about 10 mg, about 20 mg, about 40 mg, about 80 mg, or about 160 mg. In some embodiments, the therapeutically effective amount of nelotanserin is about 10 mg. In some embodiments, the therapeutically effective amount of nelotanserin is about 20 mg. In some embodiments, the therapeutically effective amount of nelotanserin is about 40 mg. In some embodiments, the therapeutically effective amount of nelotanserin is about 80 mg. In some embodiments, the therapeutically effective amount of nelotanserin is about 160 mg. In some embodiments, the therapeutically effective amount of the $5-HT_{2A}$ inverse agonist is administered once a day, twice a day, three times a day, or four times a day. In some embodiments, the $5-HT_{2A}$ inverse agonist is in a pharmaceutical composition configured for immediate release, for extended release, for delayed release, or any combination thereof. In some embodiments, the $5-HT_{2A}$ inverse agonist is in a pharmaceutical composition, and wherein the pharmaceutical composition is formulated for oral administration. In some embodiments, the therapeutically effective amount of the $5-HT_{2A}$ inverse agonist is administered about one to about four times per day, once daily in the morning, once daily about 1 hour prior to the subject's bedtime, or twice daily.

In some embodiments, the subject is a human. In some embodiments, the human is an adult with a diagnosis of a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the human has a concurrent diagnosis of neuropsychiatric symptoms such as, but not limited to hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, hallucinations are visual hallucinations. In some embodiments, the human has a concurrent diagnosis of hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, the human has a concurrent diagnosis of visual hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the human has a diagnosis of probable Dementia with Lewy Bodies. In some embodiments, the diagnosis of probable Dementia with Lewy Bodies is defined by the presence of dementia and at least one of: at least two Core Criteria selected from visual hallucinations, cognitive fluctuations, and Parkinsonism, and any combination thereof; and one Core Criteria selected from visual hallucinations, cognitive fluctuations, and Parkinsonism, and any combination thereof; and at least one Suggestive Criteria selected from REM Sleep Behavior Disorder, Severe Neuroleptic Sensitivity, Low Dopamine Transporter Uptake on DaT SPECT Imaging Scan; and any combination thereof. In some embodiments, the human has a diagnosis of Dementia with Lewy Bodies. In some embodiments, the human has a Mini Mental State Examination score of greater than, or equal to, about 18. In some embodiments, the human is an adult with a diagnosis of visual hallucinations associated with Dementia with Lewy Bodies. In some embodiments, the human is an adult aged 50-85 inclusive. In some embodiments, the human has experienced persistent visual hallucinations. In some embodiments, the presence of persistent hallucinations is defined by a score of four or greater on the hallucinations component of the Neuropsychiatric Inventory (NPI Item B) at screening. In some embodiments, the human has experienced hallucinations on at least five days in a week. In some embodiments, the human has experienced visual hallucinations on at least five days in a week.

In some embodiments, the subject is concurrently receiving a therapeutically effective amount of at least one additional therapeutic agent selected from the group consisting of melatonin, quetiapine, clonazepam, levodopa, carbidopa, an antiparkinsonian drug, an acetylcholinesterase inhibitor, an NMDA receptor antagonist, and a combination thereof. In some embodiments, the antiparkinsonian drug is selected from an MAO-B inhibitor, a COMT inhibitor, a dopamine agonist or any combination thereof. In some embodiments, the acetylcholinesterase inhibitor is selected from the group consisting of donepezil, rivastigmine, galantamine, and pharmaceutically acceptable salts, hydrates, polymorphs, or solvates thereof. In some embodiments, the acetylcholinesterase inhibitor is donepezil or a pharmaceutically acceptable salt, hydrate, polymorph, or solvate thereof. In some embodiments, the acetylcholinesterase inhibitor is rivastigmine or a pharmaceutically acceptable salt, hydrate, polymorph, or solvate thereof. In some embodiments, the acetylcholinesterase inhibitor is galantamine or a pharmaceutically acceptable salt, hydrate, polymorph, or solvate thereof. In some embodiments, NMDA receptor antagonist is selected from the group consisting of memantine, amantadine, ketamine, and pharmaceutically acceptable salts, hydrates, polymorphs, or solvates thereof. In some embodiments, the NMDA receptor antagonist is memantine or a pharmaceutically acceptable salt, hydrate, polymorph, or solvate thereof. In some embodiments, the NMDA receptor antagonist is amantadine or a pharmaceutically acceptable salt, hydrate, polymorph, or solvate thereof.

In some embodiments, administration of a therapeutically effective amount of a $5\text{-HT}_{2A}$ inverse agonist results in treatment, and/or prophylaxis of Lewy Body Dementia or the symptoms thereof in a subject experiencing neuropsychiatric symptoms such as, but not limited to hallucinations. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, administration of a therapeutically effective amount of a $5\text{-HT}_{2A}$ inverse agonist results in treatment, and/or prophylaxis of Lewy Body Dementia or the symptoms thereof in a subject experiencing visual hallucinations. In some embodiments, treating or prophylaxis results in an improvement in the subject's Mini-Mental State Examination score, cognition, attention, Clinician's Interview-Based Impression of Change with caregiver input (CIBIC+) rating, neuropsychiatric inventory (NPI), North-East Visual Hallucinations Interview (NEVHI), Cognitive Drug Research (CDR) computerized assessment system, Scale for the Assessment of Positive Symptoms (SAPS), Parkinson's Disease-adapted Scale for the Assessment of Positive Symptoms (SAPS-PD), Positive and Negative Syndrome Scale (PANSS), Clinical Global Impression (CGI) scale or any combination thereof. In some embodiments, treating or prophylaxis results in fluctuations in cognition, attention or a combination thereof.

These and other aspects of the invention disclosed herein will be set forth in greater detail as the patent disclosure proceeds.

DETAILED DESCRIPTION

Figure 1:
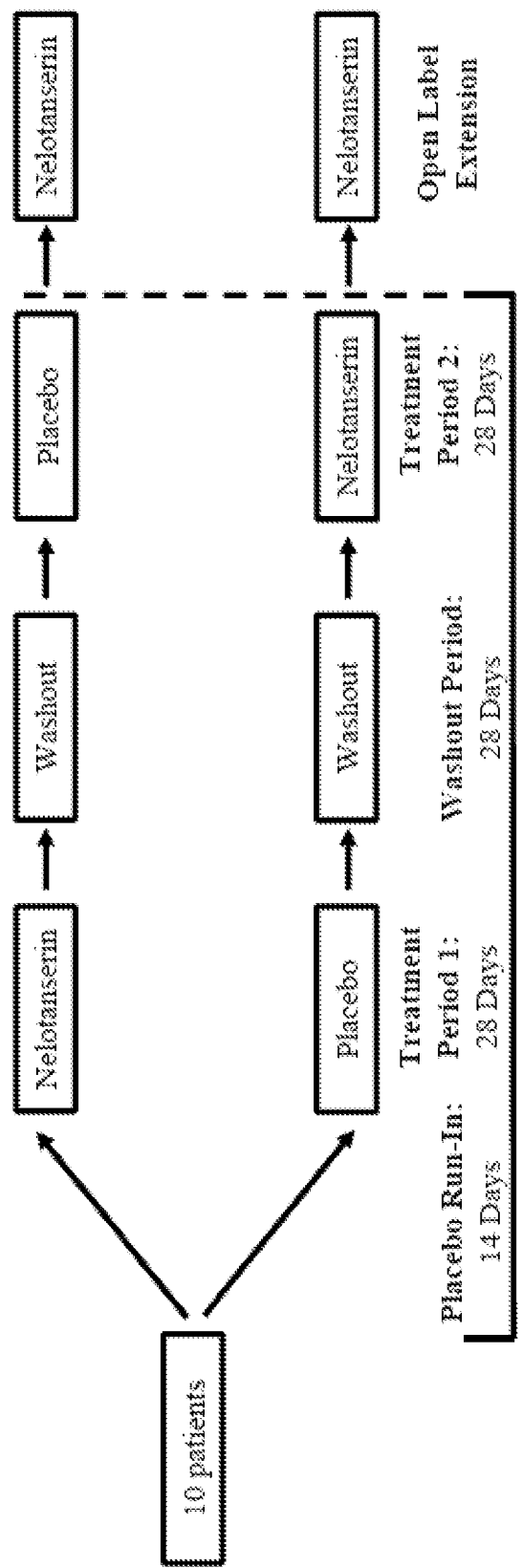
FIG. 1 shows the design of a multi-center, double-blind, randomized, placebo-controlled, cross-over study in subjects with visual hallucinations associated with Lewy Body Dementia.

Although any methods and materials similar or equivalent to those described herein can be used in the practice or testing of embodiments of the present invention, the exemplary methods, devices, and materials are now described.

In each of the embodiments described herein, the method may comprise administering a therapeutically effective amount of 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof. In some embodiments, 1-[3-(4-bromo-2-methyl-2H-pyrazol-3-yl)-4-methoxy-phenyl]-3-(2,4-difluoro-phenyl)-urea may also be known as nelotanserin or RVT-102 and these terms may be used interchangeably. In each of the embodiments described herein, the method may consist essentially of administering a therapeutically effective amount of 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof. In each of the embodiments described herein, the method may consist of administering a therapeutically effective amount of 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof. The term "comprising" means "including, but not limited to." The term "consisting essentially of" means the method or composition includes the steps or components specifically recited, and may also include those that do not materially affect the basic and novel characteristics of the present invention. The term "consisting of" means the method or composition includes only the steps or components specifically recited. It must be noted that, as used herein, and in the appended claims, the singular forms "a", "an" and "the" include plural reference unless the context clearly dictates otherwise.

As used herein, the term "neuropsychiatric symptom" shall mean one or more psychiatric manifestation or non-cognitive disturbances associated with neurodegenerative diseases, such as, but not limited to depression, euphoria, delirium, delusions, flattening of affect, anxiety, dissociation, irritability, apathy, agitation, aggression, aberrant vocalizations, hallucinations, psychosis, wandering, sleep disturbances, sundowning, psychomotor retardation, cognitive impairment, disturbances of consciousness, behavioral changes, neurotic symptoms, mood disorders, Parkinsonism, nuclal rigidity, stiffness, personality change, neurological signs, somatic complaints, dementia, subcortical dementia, or disinhibition.

As used herein, the term "hallucination" means a perception in the absence of external stimulus that has qualities of real perception. In some embodiments, hallucinations may vivid, substantial, and are perceived to be located in external objective space. As used herein, hallucinations may occur in any sensory modality including, but not limited to visual, auditory, olfactory, gustatory, tactile, proprioceptive, equilibrioceptive, nociceptive, thermoceptive and chronoceptive. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

As used herein, the term "Lewy body dementia" or "LBD" means a chronic, progressive neurodegenerative disorder. LBD is characterized by a build-up of abnormal proteins known as Lewy bodies in the brain. Lewy Body dementia includes two similar conditions—dementia with Lewy bodies, or DLB, and Parkinson's disease dementia, or PDD.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the described includes instances where the event occurs and instances where it does not.

"Administering" when used in conjunction with a therapeutic means to administer a therapeutic directly or indirectly into or onto a target tissue to administer a therapeutic to a patient whereby the therapeutic positively impacts the tissue to which it is targeted. "Administering" a composition may be accomplished by oral nasal, sublingual, buccal, transdermal, vaginal or rectal administration, injection, infusion, inhalation, absorption or by any method in combination with other known techniques. "Administering" may include the act of self-administration or administration by another person such as a health care provider.

The term "improves" is used to convey that the present invention changes the appearance, form, characteristics, structure, function and/or physical attributes of the tissue to which it is being provided, applied or administered. "Improves" may also refer to the overall physical state of an individual to whom an active agent has been administered. For example, the overall physical state of an individual may "improve" if one or more symptoms of the disease, condition or disorder are alleviated by administration of an active agent.

As used herein, the term "therapeutic" means an agent utilized to treat, combat, ameliorate or prevent an unwanted disease, condition or disorder of a patient.

In each of the embodiments disclosed herein, the compounds and methods may be utilized with or on a subject in need of such treatment, which may also be referred to as "in need thereof." As used herein, the phrase "in need thereof" means that the subject has been identified as having a need for the particular method or treatment and that the treatment has been given to the subject for that particular purpose. "In need thereof" as used herein also refers to a judgment made by a caregiver (e.g. physician, nurse, nurse practitioner, etc. in the case of humans; veterinarian in the case of animals, including non-human mammals) that an individual or animal requires or will benefit from prophylaxis and/or treatment. This judgment is made based on a variety of factors that are in the realm of a caregiver's expertise, but that includes the knowledge that the individual or animal is ill, or will be ill, as the result of a disease, condition or disorder that is treatable by the compounds of the invention. In general, "in need of prophylaxis" refers to the judgment made by the caregiver that the individual will become ill. In this context, the compounds of the invention are used in a protective or preventive manner. However, "in need of treatment" refers to the judgment of the caregiver that the individual is already ill; therefore, the compounds of the present invention are used to alleviate, inhibit or ameliorate the disease, condition or disorder.

As used herein, the term "patient" and "subject" or "individual" are interchangeable and may be taken to mean any living organism, which may be treated with compounds of the present invention. As such, the terms "patient" and "subject" may include, but are not limited to, any non-human mammal, primate or human. In some embodiments, the "patient" or "subject" is an adult, an elderly adult, child, infant, or fetus. In some embodiments, an elderly adult is an adult of about 50 years of age or older. In yet other embodiments, an elderly adult is an adult aged between about 50 and 85 years of age. In some embodiments, the "patient" or "subject" is a human. In some embodiments, the "patient" or "subject" is a mammal, such as mice, rats, other rodents, rabbits, dogs, cats, swine, cattle, sheep, horses, primates, or humans.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology). In some embodiments, the therapeutically effective amount of 1-[3-(4-bromo-2-methyl-2H-pyrazol-3-yl)-4-methoxy-phenyl]-3-(2,4-difluoro-phenyl)-urea is from about 0.0001 to about 1,000 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 10 to about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 10 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 20 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 40 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 80 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is from about 0.001 mg to about 1,000 mg, about 0.001 mg to about 160 mg or about 10 to about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is about 10 mg, about 20 mg, about 40 mg, about 80 mg or about 160 mg.

The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to alleviating the symptoms associated with the specific disorder, disease or condition. In some embodiments, the term refers to restoring function which was impaired or lost due to a specific disease, disorder or condition.

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. A pharmaceutical composition may, for example, contain 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof as the active ingredient. Alternatively, a pharmaceutical composition may contain 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof as the active ingredient.

"Pharmaceutically acceptable salts, hydrates or solvates" is meant to indicate those salts, hydrates or solvates which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, describes pharmaceutically acceptable salts in detail. A pharmaceutical acceptable "salt" is any acid addition salt, preferably a pharmaceutically acceptable acid addition salt, including, but not limited to, halogenic acid salts such as hydrobromic, hydrochloric, hydrofloric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesufonic, acetic, malic, fumaric, succinic, citric, benzoic gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogic, di-sulfuric, di-phosphoric or di-organic acid salt. In all cases, the acid addition salt is used as an achiral reagent which is not selected on the basis of any expected or known preference for the interaction with or precipitation of a specific optical isomer of the products of this disclosure.

As used herein, the term "daily dose" refers to the amount of 1-[3-(4-bromo-2-methyl-2H-pyrazol-3-yl)-4-methoxy-phenyl]-3-(2,4-difluoro-phenyl)-urea or pharmaceutically acceptable salts, hydrates or solvates thereof, per day that is administered or prescribed to a patient. This amount can be administered in multiple unit doses or in a single unit dose, at a single time during the day or at multiple times during the day. Multiple doses may be administered during the day, for example 2, 3 or 4, doses. In some embodiments, the dose is administered once daily in the morning, afternoon, evening, or once daily about 1 hour prior to the subject's bedtime. In some embodiments, the dose is administered about one to about four times per day, once daily in the morning, once daily about 1 hour prior to the subject's bedtime, or twice daily. In some embodiments, the dose is administered twice daily. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is from about 0.0001 to about 1,000 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is from about 10 to about 160 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is about 10 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is about 20 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is about 40 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is about 80 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is about 160 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is from about 0.001 mg to about 1,000 mg, about 0.001 mg to about 160 mg or about 10 to about 160 mg. In some embodiments, the daily dose of 1-[3-(4-bromo-2-methyl-2H-pyrazol-3-yl)-4-methoxy-phenyl]-3-(2,4-difluoro-phenyl)-urea or a pharmaceutically acceptable salt, hydrate, polymorph, or solvate thereof is about 10 mg, about 20 mg, about 40 mg, about 80 mg or about 160 mg.

"Composition" shall mean a material comprising at least two compounds or two components; for example, and without limitation, a Pharmaceutical Composition is a Composition comprising a compound of the present invention and a pharmaceutically acceptable carrier.

"Compound efficacy" shall mean a measurement of the ability of a compound to inhibit or stimulate receptor functionality, as opposed to receptor binding affinity.

"Constitutively activated receptor" shall mean a receptor subject to constitutive receptor activation.

"Constitutive receptor activation" shall mean stabilization of a receptor in the active state by means other than binding of the receptor with its endogenous ligand or a chemical equivalent thereof.

"Contact" or "contacting" shall mean bringing the indicated moieties together, whether in an in vitro system or an in vivo system. Thus, "contacting" a 5-HT$_{2A}$ receptor with a compound of the invention includes the administration of a compound of the present invention to an individual, preferably a human, having a 5-HT$_{2A}$ receptor, as well as, for example, introducing a compound of the invention into a sample containing a cellular or more purified preparation containing a 5-HT$_{2A}$ receptor.

"Endogenous" shall mean a material that a mammal naturally produces. Endogenous in reference to, for example and without limitation, the term "receptor" shall mean that which is naturally produced by a mammal (for example, and without limitation, a human) or a virus.

In contrast, the term "non-Endogenous" in this context shall mean that which is not naturally produced by a mammal (for example, and without limitation, a human) or a virus. For example, and without limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and without limitation, in a screening approach, the endogenous or non-endogenous receptor may be in reference to an in vitro screening system. As a further example and without limitation, where the genome of a mammal has been manipulated to include a non-endogenous constitutively activated receptor, screening of a candidate compound by means of an in vivo system is viable.

"Inhibit" or "inhibiting", in relationship to the term "response" shall mean that a response is decreased or prevented in the presence of a compound as opposed to in the absence of the compound.

"Inverse agonists" shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

"Ligand" shall mean an endogenous, naturally occurring molecule specific for an endogenous, naturally occurring receptor.

As used herein, the terms "modulate" or "modulating" shall mean to refer to an increase or decrease in the amount, quality, response or effect of a particular activity, function or molecule.

The scientific literature that has evolved around receptors has adopted a number of terms to refer to ligands having various effects on receptors. For clarity and consistency, the following definitions will be used throughout this patent document.

"Agonists" shall mean moieties that interact and activate the receptor, such as the 5-HT$_{2A}$ receptor, and initiate a physiological or pharmacological response characteristic of that receptor. For example, when moieties activate the intracellular response upon binding to the receptor, or enhance GTP binding to membranes.

The term "antagonists" is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

The term "$C_{1-6}$ acyl" denotes a $C_{1-6}$ alkyl radical attached to a carbonyl wherein the definition of alkyl has the same definition as described herein; some examples include but are not limited to, acetyl, propionyl, n-butanoyl, iso-butanoyl, sec-butanoyl, t-butanoyl (i.e., pivaloyl), pentanoyl and the like.

The term "$C_{1-6}$ acyloxy" denotes an acyl radical attached to an oxygen atom wherein acyl has the same definition has described herein; some examples include but are not limited to acetyloxy, propionyloxy, butanoyloxy, iso-butanoyloxy, sec-butanoyloxy, t-butanoyloxy and the like.

The term "$C_{2-6}$ alkenyl" denotes a radical containing 2 to 6 carbons wherein at least one carbon-carbon double bond is present, some embodiments have 2 to 4 carbons, some embodiments have 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present, then the bonds may be all E or Z or a mixture of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2,4-hexadienyl and the like.

The term "$C_{1-6}$ alkoxy" as used herein denotes a radical alkyl, as defined herein, attached directly to an oxygen atom. Examples include methoxy, ethoxy, n-propoxy, iso-propoxy, n-butoxy, t-butoxy, iso-butoxy, sec-butoxy and the like.

The term "$C_{1-8}$ alkyl" denotes a straight or branched carbon radical containing 1 to 8 carbons, some embodiments have 1 to 6 carbons, some embodiments have 1 to 4 carbons, some embodiments have 1 to 3 carbons, and some embodiments have 1 or 2 carbons. Examples of an alkyl include, but are not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "$C_{1-6}$ alkylcarboxamido" or "$C_{1-6}$ alkylcarboxamide" denotes a single $C_{1-6}$ alkyl group attached to the nitrogen of an amide group, wherein alkyl has the same definition as found herein. The $C_{1-6}$ alkylcarboxamido may be represented by Formula II:

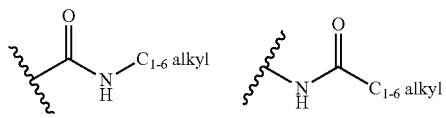

II

Examples include, but are not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-3}$ alkylene" refers to a $C_{1-3}$ divalent straight carbon group. In some embodiments $C_{1-3}$ alkylene refers to, for example, —CH$_2$—, —CH$_2$CH$_2$—, —CH$_2$CH$_2$CH$_2$—, and the like. In some embodiments, $C_{1-3}$ alkylene refers to —CH—, —CHCH$_2$—, —CHCH$_2$CH$_2$—, and the like wherein these examples relate generally to the variable or claim element "Q".

The term "$C_{1-6}$ alkylimino" denotes a $C_{1-6}$ alkyl radical attached directly to the carbon of the —C(=NH)— group wherein the definition of alkyl has the same definition as described herein; some examples include but are not limited to, 1-imino-ethyl [i.e., —C(=NH)CH$_3$], 1-imino-propyl [i.e., —C(=NH)CH$_2$CH$_3$], 1-imino-2-methyl-propyl [i.e., —C(=NH)CH(CH$_3$)$_2$], and the like.

The term "$C_{1-6}$ alkylsulfinyl" denotes a $C_{1-6}$ alkyl radical attached to a sulfoxide radical of the formula: —S(O)— wherein the alkyl radical has the same definition as described herein. Examples include, but are not limited to, methylsulfinyl, ethylsulfinyl, n-propylsulfinyl, iso-propylsulfinyl, n-butylsulfinyl, sec-butylsulfinyl, iso-butylsulfinyl, t-butylsulfinyl, and the like.

The term "$C_{1-6}$ alkylsulfonamide" refers to the groups of Formula III:

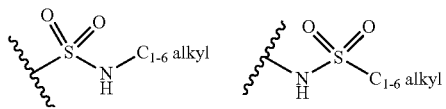

III wherein $C_{1-6}$ alkyl has the same definition as described herein.

The term "$C_{1-6}$ alkylsulfonyl" denotes a $C_{1-6}$ alkyl radical attached to a sulfone radical of the formula: —S(O)$_2$— wherein the alkyl radical has the same definition as described herein. Examples include, but are not limited to, methylsulfonyl, ethylsulfonyl, n-propylsulfonyl, iso-propylsulfonyl, n-butylsulfonyl, sec-butylsulfonyl, iso-butylsulfonyl, t-butylsulfonyl, and the like.

The term "$C_{1-6}$ alkylthio" denotes a $C_{1-6}$ alkyl radical attached to a sulfide of the formula: —S— wherein the alkyl radical has the same definition as described herein. Examples include, but are not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butylsulfanyl, and the like.

The term "$C_{1-6}$ alkylthiocarboxamide" denotes a thioamide of the following Formula IV:

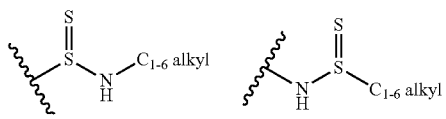

IV wherein $C_{1-4}$ alkyl has the same definition as described herein.

The term "$C_{1-6}$ alkylthioureyl" denotes the group of the formula: —NC(S)N— wherein one or both of the nitrogens are substituted with the same or different $C_{1-6}$ alkyl groups and alkyl has the same definition as described herein. Examples of an alkylthioureyl include, but are not limited to, CH$_3$NHC(S)NH—, NH$_2$C(S)NCH$_3$—, (CH$_3$)$_2$N(S)NH—, (CH$_3$)$_2$N(S)NH—, (CH$_3$)$_2$N(S)NCH$_3$—, CH$_3$CH$_2$NHC(S)NH—, CH$_3$CH$_2$NHC(S)NCH$_3$—, and the like.

The term "$C_{1-6}$ alkylureyl" denotes the group of the formula: —NC(O)N— wherein one or both of the nitrogens are substituted with the same or different $C_{1-6}$ alkyl group wherein alkyl has the same definition as described herein. Examples of an alkylureyl include, but are not limited to, CH$_3$NHC(O)NH—, NH$_2$C(O)NCH$_3$—, (CH$_3$)$_2$NC(O)NH—, (CH$_3$)$_2$NC(O)NH—, (CH$_3$)$_2$NC(O)NCH$_3$—, CH$_3$CH$_2$NHC(O)NH—, CH$_3$CH$_2$NHC(O)NCH$_3$—, and the like.

The term "$C_{2-6}$ alkynyl" denotes a radical containing 2 to 6 carbons and at least one carbon-carbon triple bond, some embodiments have 2 to 4 carbons, some embodiments have 2 to 3 carbons, and some embodiments have 2 carbons. Examples of an alkynyl include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and triynes.

The term "amino" denotes the group —NH$_2$.

The term "$C_{1-6}$alkylamino" denotes one alkyl radical attached to an amino radical wherein the alkyl radical has the same meaning as described herein. Some examples include, but are not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "arylalkyl" defines a $C_1$-$C_4$ alkylene, such as —$CH_2$—, —$CH_2CH_2$— and the like, which is further substituted with an aryl group. Examples of an "arylalkyl" include benzyl, phenethylene and the like.

The term "arylcarboxamido" denotes a single aryl group attached to the nitrogen of an amide group, wherein aryl has the same definition as found herein. An example is N-phenylcarboxamide.

The term "arylureyl" denotes the group —NC(O)N— where one of the nitrogens are substituted with an aryl.

The term "benzyl" denotes the group —$CH_2C_6H_5$.

The term "carbo-$C_{1-6}$-alkoxy" refers to a $C_{1-6}$ alkyl ester of a carboxylic acid, wherein the alkyl group is as defined herein. Examples include, but are not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neo-pentoxy, carbo-n-hexyloxy, and the like.

The term "carboxamide" refers to the group —$CONH_2$.

The term "carboxy" or "carboxyl" denotes the group —$CO_2H$; also referred to as a carboxylic acid group.

The term "cyano" denotes the group —CN.

The term "$C_{4-7}$cycloalkenyl" denotes a non-aromatic ring radical containing 4 to 7 ring carbons and at least one double bond; some embodiments contain 4 to 6 carbons; some embodiments contain 4 to 5 carbons; some embodiments contain 4 carbons. Examples include cyclobutenyl, cyclopentenyl, cyclopentenyl, cyclohexenyl, and the like.

The term "$C_{3-7}$ cycloalkyl" denotes a saturated ring radical containing 3 to 7 carbons; some embodiments contain 3 to 6 carbons; some embodiments contain 3 to 5 carbons; some embodiments contain 5 to 7 carbons; some embodiments contain 3 to 4 carbons. Examples include cyclopropyl, cyclobutyl, cyclopentyl, cyclohexyl, cycloheptyl and the like.

The term "$C_{2-8}$ dialkylamino" denotes an amino substituted with two of the same or different $C_{1-4}$ alkyl radicals wherein alkyl radical has the same definition as described herein. Some examples include, but are not limited to, dimethylamino, methylethylamino, diethylamino, methylpropylamino, methylisopropylamino, ethylpropylamino, ethylisopropylamino, dipropylamino, propylisopropylamino and the like. Some embodiments are "$C_{2-4}$ dialkylamino."

The term "$C_{2-8}$ dialkylcarboxamido" or "$C_{2-8}$ dialkylcarboxamide" denotes two alkyl radicals, that are the same or different, attached to an amide group, wherein alkyl has the same definition as described herein. A $C_{2-8}$ dialkylcarboxamido may be represented by Formula V:

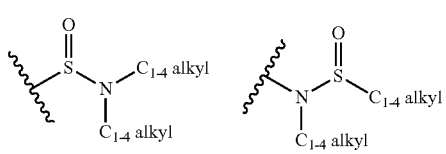

wherein $C_{1-4}$ has the same definition as described herein. Examples of a dialkylcarboxamide include, but are not limited to, N,N-dimethylcarboxamide, N-methyl-N-ethylcarboxamide, N,N-diethylcarboxamide, N-methyl-N-isopropylcarboxamide, and the like.

The term "$C_{2-8}$ dialkylsulfonamide" refers to one of the following groups shown in Formula VI:

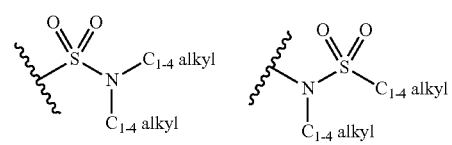

wherein $C_{1-4}$ has the same definition as described herein, for example but not limited to, methyl, ethyl, n-propyl, isopropyl, and the like.

The term "$C_{2-8}$ dialkylthiocarboxamido" or "$C_{2-8}$ dialkylthiocarbox-amide" denotes two alkyl radicals, that are the same or different, attached to a thioamide group, wherein alkyl has the same definition as described herein. A $C_{2-8}$ dialkylthiocarboxamido or $C_{2-8}$ dialkylthiocarboxamide may be represented by the Formula VII:

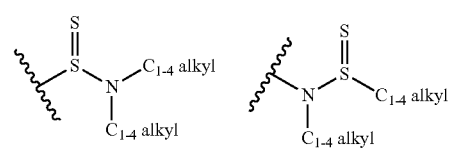

Examples of a dialkylthiocarboxamide include, but are not limited to, N,N-dimethylthiocarboxamide, N-methyl-N-ethylthiocarboxamide and the like.

The term "ethynylene" refers to the carbon-carbon triple bond group as represented Formula VIII:

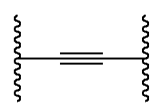

The term "formyl" refers to the group —CHO.

The term "$C_{1-6}$ haloalkoxy" denotes a haloalkyl, as defined herein, which is directly attached to an oxygen atom. Examples include, but are not limited to, difluoromethoxy, trifluoromethoxy, 2,2,2-trifluoroethoxy, pentafluoroethoxy and the like.

The term "$C_{1-6}$ haloalkyl" denotes an $C_{1-6}$ alkyl group, defined herein, wherein the alkyl is substituted with one halogen up to fully substituted and a fully substituted $C_{1-6}$haloalkyl can be represented by the formula $C_nL_{2n+1}$ wherein L is a halogen and "n" is 1, 2, 3 or 4. When more than one halogen is present, they may be the same or different and selected from the group consisting of F, Cl, Br and I, preferably F. Examples of $C_{1-4}$ haloalkyl groups include, but are not limited to, fluoromethyl, difluoromethyl, trifluoromethyl, chlorodifluoromethyl, 2,2,2-trifluoroethyl, pentafluoroethyl and the like.

The term "$C_{1-6}$ haloalkylcarboxamide" denotes an alkylcarboxamide group, defined herein, wherein the alkyl is substituted with one halogen up to fully substituted represented by the formula $C_nL_{2n+1}$ wherein L is a halogen and "n" is 1, 2, 3 or 4. When more than one halogen is present, they may be the same or different and selected from the group consisting of F, Cl, Br and I, preferably F.

The term "$C_{1-6}$ haloalkylsulfinyl" denotes a haloalkyl radical attached to a sulfoxide group of the formula: —S(O)— wherein the haloalkyl radical has the same definition as described herein. Examples include, but are not limited to, trifluoromethylsulfinyl, 2,2,2-trifluoroethylsulfinyl, 2,2-difluoroethylsulfinyl and the like.

The term "$C_{1-6}$ haloalkylsulfonyl" denotes a haloalkyl radical attached to a sulfone group of the formula: —S(O)$_2$— wherein haloalkyl has the same definition as described herein. Examples include, but are not limited to, trifluoromethylsulfonyl, 2,2,2-trifluoroethylsulfonyl, 2,2-difluoroethylsulfonyl and the like.

The term "$C_{1-6}$ haloalkylthio" denotes a haloalkyl radical directly attached to a sulfur wherein the haloalkyl has the same meaning as described herein. Examples include, but are not limited to, trifluoromethylthio (i.e., CF$_3$S—, also referred to as trifluoromethylsulfanyl), 1,1-difluoroethylthio, 2,2,2-trifluoroethylthio and the like.

The term "halogen" or "halo" denotes a fluoro, chloro, bromo or iodo group.

The term "heteroaryl" denotes an aromatic ring system that may be a single ring, two fused rings or three fused rings wherein at least one ring carbon is replaced with a heteroatom selected from, but are not limited to, the group consisting of O, S and N wherein the N can be optionally substituted with H, $C_{1-4}$ acyl or $C_{1-4}$ alkyl. Examples of heteroaryl groups include, but are not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline and the like. In some embodiments, the heteroaryl atom is O, S, NH. Examples include, but are not limited to, pyrrole, indole, and the like. Other examples include, but are not limited to, those in Table 1, Table 2, and the like.

The term "heterocyclic" denotes a non-aromatic carbon ring (i.e., $C_{3-7}$cycloalkyl or $C_{4-7}$cycloalkenyl as defined herein) wherein one, two or three ring carbons are replaced by a heteroatom selected from, but are not limited to, the group consisting of O, S, N, wherein the N can be optionally substituted with H, $C_{1-4}$ acyl or $C_{1-4}$ alkyl, and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include, but are not limited to, aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like.

The term "heterocycliccarboxamido" denotes a heterocyclic group, as defined herein, with a ring nitrogen where the ring nitrogen is bonded directly to the carbonyl forming an amide. Examples include those in Formula IX, but are not limited to,

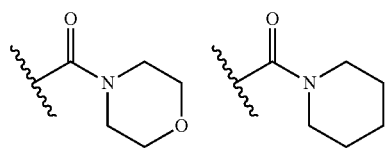

IX

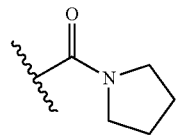

and the like.

The term "heterocyclicsulfonyl" denotes a heterocyclic group, as defined herein, with a ring nitrogen where the ring nitrogen is bonded directly to an —SO$_2$-group forming an sulfonamide. Examples include those in Formula X, but are not limited to,

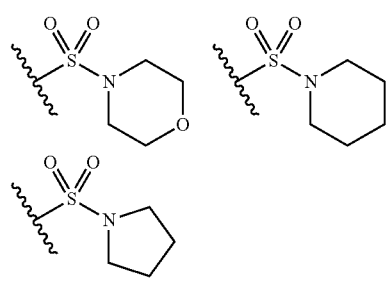

X and the like.

The term "hydroxyl" refers to the group —OH.
The term "hydroxylamino" refers to the group —NHOH.
The term "nitro" refers to the group —NO$_2$.
The term "$C_{4-7}$ oxo-cycloalkyl" refers to a $C_{4-7}$ cycloalkyl, as defined herein, wherein one of the ring carbons is replaced with a carbonyl. Examples of $C_{4-7}$ oxo-cycloalkyl include, but are not limited to, 2-oxo-cyclobutyl, 3-oxo-cyclobutyl, 3-oxo-cyclopentyl, 4-oxo-cyclohexyl, and the like and represented by the structures respectively in Formula XI:

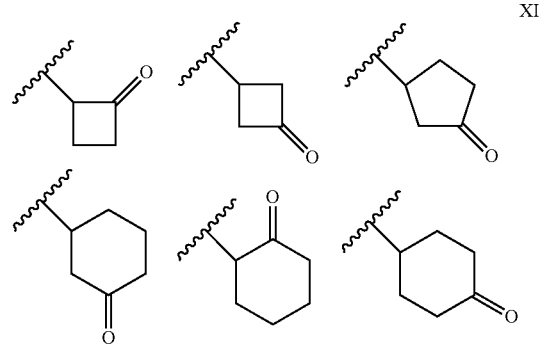

XI

The term "perfluoroalkyl" denotes the group of the formula —C$_n$F$_{2n+1}$; stated differently, a perfluoroalkyl is an alkyl as defined herein wherein the alkyl is fully substituted with fluorine atoms and is therefore considered a subset of haloalkyl. Examples of perfluoroalkyls include CF$_3$, CF$_2$CF$_3$, CF$_2$CF$_2$CF$_3$, CF(CF$_3$)$_2$, CF$_2$CF$_2$CF$_2$CF$_3$, CF$_2$CF(CF$_3$)$_2$, CF(CF$_3$)CF$_2$CF$_3$ and the like.

The term "phenoxy" refers to the group C$_6$H$_5$O—.
The term "phenyl" refers to the group C$_6$H$_5$—.
The term "sulfonic acid" refers to the group —SO$_3$H.
The term "thiol" denotes the group —SH.

"Codon" shall mean a grouping of three nucleotides (or equivalents to nucleotides) which generally comprise a nucleoside [adenosine (A), guanosine (G), cytidine (C), uridine (U) and thymidine (T)] coupled to a phosphate group and which, when translated, encodes an amino acid.

Before the present compositions and methods are described, it is to be understood that this invention is not limited to the particular processes, compositions, or methodologies described, as these may vary. Moreover, the processes, compositions, and methodologies described in particular embodiments are interchangeable. Therefore, for example, a composition, dosages regimen, route of administration, and so on described in a particular embodiment may be used in any of the methods described in other particular embodiments. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

Compounds of the Invention:

One aspect of the present invention encompasses certain diaryl and arylheteroaryl urea derivatives as shown in Formula I:

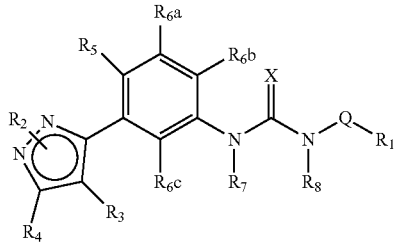

I or a pharmaceutically acceptable salt, hydrate or solvate thereof; wherein $R_1$, $R_2$, $R_3$, $R_4$, $R_5$, $R_{6a}$, $R_{6b}$, $R_{6c}$, $R_7$, $R_8$, X, and Q have the same definitions as described herein, supra and infra.

Some embodiments of the present invention encompass certain diaryl and arylheteroaryl urea derivatives as shown in the following Formula II

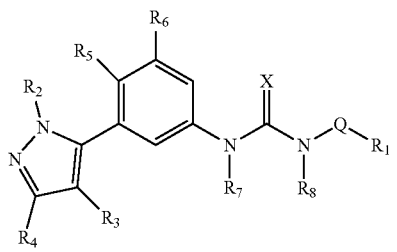

II wherein:

i) $R_1$ is aryl or heteroaryl optionally substituted with $R_9$, $R_{10}$, $R_{11}$, $R_{12}$, $R_{13}$, $R_{14}$, and $R_{15}$ selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$haloalkylsulfinyl, $C_{1-6}$ haloalkylsulfonyl, $C_{1-6}$ haloalkylthio, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$cycloalkyl group or heterocyclic group each optionally substituted with F, Cl, or Br; and wherein each of said $C_{2-6}$ alkenyl, $C_{1-6}$alkyl, $C_{2-6}$ alkynyl and phenyl groups can be optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$cycloalkyl, $C_{2-8}$ dialkylcarboxamide, halogen, $C_{1-6}$ haloalkoxy, $C_{1-6}$ haloalkyl, $C_{1-6}$haloalkylsulfinyl, $C_{1-6}$ haloalkylsulfonyl, $C_{1-6}$ haloalkylthio, hydroxyl, thiol and nitro;

ii) $R_2$ is selected from the group consisting of $C_{1-6}$ alkyl, $C_{2-6}$ alkenyl, $C_{2-6}$ alkynyl and $C_{3-7}$ cycloalkyl;

iii) $R_3$ is selected from the group consisting of H, $C_{2-6}$ alkenyl, $C_{1-6}$ alkyl, $C_{1-6}$ alkylcarboxamide, $C_{2-6}$alkynyl, $C_{1-6}$alkylsulfonamide, carbo-$C_{1-6}$-alkoxy, carboxamide, carboxy, cyano, $C_{3-7}$ cycloalkyl, $C_{2-8}$dialkylcarboxamide, halogen, heteroaryl and phenyl; and wherein each of said $C_{2-6}$ alkenyl, $C_{1-6}$ alkyl, $C_{2-6}$alkynyl, $C_{1-6}$ alkylsulfonamide, $C_{3-7}$cycloalkyl, heteroaryl and phenyl groups can be optionally substituted with 1 to 5 substituents selected independently from the group consisting of $C_{1-5}$ acyl, $C_{1-5}$acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$alkynyl, $C_{1-4}$alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$cycloalkyl, $C_{2-6}$dialkylcarboxamide, halogen, $C_{1-4}$haloalkoxy, $C_{1-4}$haloalkyl, $C_{1-4}$ haloalkylsulfinyl, $C_{1-4}$ haloalkylsulfonyl, $C_{1-4}$ haloalkylthio, hydroxyl, nitro and sulfonamide;

iv) $R_4$ is selected from the group consisting of H, $C_{1-6}$ acyl, $C_{1-6}$ acyloxy, $C_{2-6}$ alkenyl, $C_{1-6}$ alkoxy, $C_{1-6}$alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$dialkylsulfonamide, halogen, $C_{1-6}$ haloalkoxy, $C_{1-6}$haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

v) $R_5$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$alkynyl, $C_{1-6}$ alkylsulfonamide, $C_{1-6}$ alkylsulfinyl, $C_{1-4}$ alkylsulfonyl, $C_{1-6}$alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$cycloalkyl, $C_{2-8}$ dialkylcarboxamide, $C_{2-8}$dialkylsulfonamide, halogen, $C_{1-6}$haloalkoxy, $C_{1-6}$haloalkyl, $C_{1-6}$haloalkylsulfinyl, $C_{1-6}$ haloalkylsulfonyl, $C_{1-6}$ haloalkylthio, hydroxyl, thiol, nitro and sulfonamide, wherein said $C_{1-6}$ alkoxy group can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$cycloalkyl, $C_{2-6}$dialkylcarboxamide, halogen, $C_{1-4}$haloalkoxy, $C_{1-4}$haloalkyl, $C_{1-4}$haloalkylsulfinyl, $C_{1-4}$haloalkylsulfonyl, $C_{1-4}$ haloalkylthio, hydroxyl, nitro and phenyl, and wherein said phenyl is optionally substituted with 1 to 5 halogen atoms;

vi) $R_6$ is selected from the group consisting of H, $C_{1-6}$ acyl, $C_{1-6}$ acyloxy, $C_{2-6}$ alkenyl, $C_{1-6}$ alkoxy, $C_{1-6}$alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$alkylthio, $C_{1-6}$ alkylureyl, amino, $C_{1-6}$ alkylamino, $C_{2-8}$dialkylamino, carbo-$C_{1-6}$-alkoxy, carboxamide, carboxy, cyano, $C_{3-7}$ cycloalkyl, $C_{2-8}$dialkylcarboxamide, $C_{2-8}$dialkylsulfonamide, halogen, $C_{1-6}$haloalkoxy, $C_{1-6}$haloalkyl, $C_{1-6}$haloalkylsulfinyl, $C_{1-6}$ haloalkylsulfonyl, $C_{1-6}$ haloalkylthio, hydroxyl, thiol, nitro and sulfonamide;

vii) $R_7$ and $R_8$ are independently H or $C_{1-8}$ alkyl;

viii) X is O or S; and ix) Q is $C_{1-3}$ alkylene optionally substituted with 1 to 4 substituents selected from the group consisting of $C_{1-3}$alkyl, $C_{1-4}$ alkoxy, carboxy, cyano, $C_{1-3}$ haloalkyl, halogen and oxo; or Q is a bond; or a pharmaceutically acceptable salt, hydrate or solvate thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers, and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of the present invention may have one or more chiral centers, and therefore can exist as enantiomers and/or diastereomers. The invention is understood to extend to and embrace all such enantiomers, diastereomers and mixtures thereof, including but not limited to racemates. Accordingly, some embodiments of the present invention pertain to compounds of the present invention that are R enantiomers. Further, some embodiments of the present invention pertain to compounds of the present invention that are S enantiomers. In examples where more than one chiral center is present, some embodiments of the present invention include compounds that are RS or SR enantiomers. In further embodiments, compounds of the present invention are RR or SS enantiomers. It is understood that compounds of the present invention are intended to represent all individual enantiomers and mixtures thereof, unless stated or shown otherwise.

In some embodiments, $R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, Cu-6 alkylsulfinyl, $C_{1-6}$alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro;

Some embodiments of the present invention pertain to compounds wherein $R_1$ is phenyl or naphthyl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ alkoxy, $C_{1-6}$ alkyl, $C_{1-6}$ alkylsulfonyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$cycloalkyl, halogen, $C_{1-6}$ haloalkoxy, $C_{1-6}$haloalkyl, heterocyclic, hydroxyl, nitro, and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$alkyl, $C_{1-6}$alkylimino, and heterocyclic are each optionally substituted with 1 to 5 substituents selected independently from the group consisting of $C_{1-6}$ acyl, $C_{1-6}$ alkoxy, $C_{1-6}$ alkyl, $C_{1-6}$ alkylsulfonyl, amino, $C_{1-6}$ alkylamino, $C_{2-8}$ dialkylamino, carboxamide, cyano, $C_{3-7}$cycloalkyl, halogen, $C_{1-6}$ haloalkoxy, $C_{1-6}$ haloalkyl, and hydroxyl.

Some embodiments of the present invention pertain to compounds wherein $R_1$ is phenyl optionally substituted with $R_9$, $R_{10}$, $R_{11}$, $R_{12}$, and $R_{13}$ each selected independently from the group consisting of $C_{1-6}$ acyl, $C_{1-6}$ alkoxy, $C_{1-6}$ alkyl, $C_{1-6}$alkylsulfonyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, and $R_{13}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ acyl, $C_{1-6}$alkoxy, $C_{1-6}$alkyl, $C_{1-6}$alkylsulfonyl, amino, $C_{1-6}$alkylamino, $C_{2-8}$dialkylamino, carboxamide, cyano, $C_{3-7}$cycloalkyl, halogen, $C_{1-6}$haloalkoxy, $C_{1-6}$ haloalkyl, and hydroxyl.

Some embodiments of the present invention pertain to compounds wherein $R_1$ is phenyl or naphthyl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ alkoxy, $C_{1-6}$ alkyl, amino, $C_{1-6}$ alkylamino, $C_{2-8}$dialkylamino, $C_{1-6}$ alkylimino, cyano, halogen, $C_{1-6}$ haloalkoxy, $C_{1-6}$haloalkyl, heterocyclic, hydroxyl, nitro, and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$alkyl, $C_{1-6}$alkylimino, and heterocyclic are each optionally substituted with 1 to 5 substituents selected independently from the group consisting of $C_{1-6}$ alkyl, amino, $C_{1-6}$ alkylamino, $C_{2-8}$dialkylamino, and hydroxyl.

Some embodiments of the present invention pertain to compounds wherein $R_1$ is phenyl optionally substituted with $R_9$, $R_{10}$, $R_{11}$, $R_{12}$, and $R_{13}$ each selected independently from the group consisting of $C_{1-6}$ acyl, $C_{1-6}$ alkoxy, $C_{1-6}$ alkyl, amino, $C_{1-6}$alkylamino, $C_{2-8}$ dialkylamino, $C_{1-6}$ alkylimino, cyano, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, and $R_{13}$ together with the atoms to which they are attached form a $C_{5-7}$cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$alkyl, amino, $C_{1-6}$ alkylamino, $C_{2-8}$ dialkylamino, and hydroxyl.

Some embodiments of the present invention pertain to compounds wherein $R_1$ is phenyl or naphthyl optionally substituted with $R_9$, $R_{10}$, $R_{11}$, $R_{12}$, $R_{13}$, $R_{14}$, and $R_{15}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylamino-ethyl)-methyl-amino [i.e., —N(CH$_3$)CH$_2$CH$_2$N(CH$_3$)$_2$], (3-dimethylamino-propyl)-methyl-amino [i.e., —N(CH$_3$)CH$_2$CH$_2$CH$_2$N(CH$_3$)$_2$], —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

Some embodiments of the present invention pertain to compounds wherein $R_1$ is phenyl optionally substituted with $R_9$, $R_{10}$, $R_{11}$, $R_{12}$, and $R_{13}$, $R_{14}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylamino-ethyl)-methyl-amino [i.e., —N(CH$_3$)CH$_2$CH$_2$N(CH$_3$)$_2$], (3-dimethylamino-propyl)-methyl-amino [i.e., —N(CH$_3$)CH$_2$CH$_2$CH$_2$N(CH$_3$)$_2$], —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

Some embodiments of the present invention pertain to compounds wherein $R_1$ is phenyl or naphthyl optionally substituted with $R_9$, $R_{10}$, $R_{11}$, $R_{12}$, $R_{13}$, $R_{14}$, and $R_{15}$ each selected independently from the group consisting of —OCH$_3$, —CH$_3$, cyano, —F, —Cl, —Br, —OCF$_3$, and —CF$_3$.

Some embodiments of the present invention pertain to compounds wherein $R_1$ is phenyl optionally substituted with $R_9$, $R_{10}$, $R_{11}$, $R_{12}$, and $R_{13}$ each selected independently from the group consisting of —OCH$_3$, —CH$_3$, cyano, —F, —Cl, —Br, —OCF$_3$, and —CF$_3$.

Some embodiments of the present invention pertain to compounds wherein $R_1$ is phenyl and can be represented by the Formula XIII shown below:

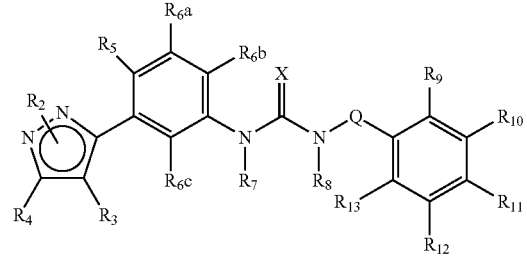

XIII wherein each variable in the above formula has the same meaning as described herein, supra and infra. In some embodiments, $R_7$ and $R_8$ are both —H, Q is a bond, and X is O.

Some embodiments of the present invention pertain to compounds wherein $R_1$ is phenyl and can be represented by Formula XIV as shown below:

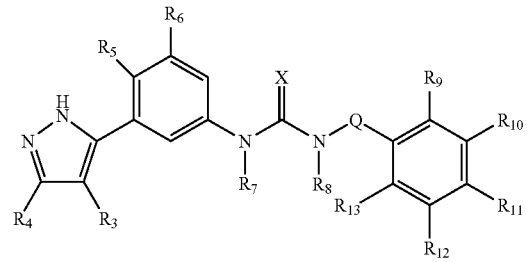

XIV wherein:
$R_9$ to $R_{13}$ substituents are each selected independently from the group consisting of H, $C_{1-6}$ acyl, $C_{1-6}$ acyloxy, $C_{1-6}$ alkoxy, $C_{1-6}$ alkyl, $C_{1-6}$ alkylcarboxamide, $C_{1-6}$ alkylsulfonamide, $C_{1-6}$ alkylsulfinyl, $C_{1-6}$ alkylsulfonyl, $C_{1-6}$ alkylthio, amino, $C_{1-6}$alkylamino, $C_{2-8}$ dialkylamino, carbo-$C_{1-6}$-alkoxy, carboxamide, carboxy, cyano, halogen, $C_{1-6}$haloalkoxy, $C_{1-6}$haloalkyl, hydroxyl, nitro and phenyl, or two adjacent substituents together with the phenyl form a $C_{5-7}$ cycloalkyl optionally comprising 1 to 2 oxygen atoms; and wherein each said $C_{1-6}$ alkyl and phenyl groups can be optionally substituted with 1 to 5 substituents selected independently from the group consisting of $C_{1-6}$ alkoxy, $C_{1-6}$ alkyl, amino, cyano, halogen, $C_{1-6}$haloalkoxy, $C_{1-6}$haloalkyl, hydroxyl and nitro.

In some embodiments, $R_1$ is phenyl optionally substituted with $R_9$ to $R_{13}$ substituents selected independently from the group consisting of $C_{1-6}$ acyl, $C_{1-6}$ alkoxy, $C_{1-6}$ alkyl, cyano, halogen, $C_{1-6}$haloalkoxy, $C_{1-6}$haloalkyl, nitro and phenyl; and wherein said phenyl can be optionally substituted with 1 to 5 substituents selected independently from the group consisting of $C_{1-6}$alkoxy, $C_{1-6}$ alkyl, cyano, halogen, $C_{1-6}$haloalkoxy, $C_{1-6}$haloalkyl and nitro.

In some embodiments, $R_1$ is phenyl optionally substituted with $R_9$ to $R_{13}$ substituents selected independently from the group consisting of $C_{1-6}$ acyl, $C_{1-6}$ alkoxy, $C_{1-6}$alkyl, cyano, halogen, $C_{1-6}$ haloalkoxy, $C_{1-6}$ haloalkyl, nitro and phenyl.

In some embodiments, $R_1$ is phenyl optionally substituted with $R_9$ to $R_{13}$ substituents selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, F, Cl, Br, I, —OCF$_3$, —OCHF$_2$, —OCFH$_2$, —OCF$_2$CF$_3$, —OCH$_2$CF$_3$, —CF$_3$, —CHF$_2$, —CFH$_2$, —CF$_2$CF$_3$, —CH$_2$CF$_3$, nitro and phenyl.

In some embodiments, $R_1$ is phenyl optionally substituted with $R_9$ to $R_{13}$ substituents are each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylamino-ethyl)-methyl-amino, (3-dimethylamino-propyl)-methyl-amino, —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

In some embodiments, $R_1$ is phenyl optionally substituted with $R_9$, $R_{10}$, $R_{11}$, $R_{12}$ and $R_{13}$ substituents selected independently from the group consisting of —C(O)CH$_3$, —OCH$_3$, —CH$_3$, cyano, —F, —Cl, —Br, —OCF$_3$, —CF$_3$, nitro and phenyl.

Some embodiments of the present invention pertain to compounds wherein $R_1$ is naphthyl optionally substituted with $R_9$ $R_{10}$ $R_{11}$ $R_{12}$ $R_{13}$ $R_{14}$ and $R_{15}$ substituents selected independently from the group consisting of $C_{1-6}$ acyl, $C_{1-6}$ acyloxy, $C_{1-6}$alkoxy, $C_{1-6}$ alkyl, $C_{1-6}$ alkylcarboxamide, $C_{1-6}$ alkylsulfonamide, $C_{1-6}$ alkylsulfinyl, $C_{1-6}$ alkylsulfonyl, $C_{1-6}$ alkylthio, amino, $C_{1-6}$ alkylamino, $C_{2-8}$dialkylamino, carbo-$C_{1-6}$-alkoxy, carboxamide, carboxy, cyano, halogen, $C_{1-6}$ haloalkoxy, $C_{1-6}$haloalkyl, hydroxyl and nitro; and wherein said $C_{1-6}$ alkyl can be optionally substituted with 1 to 5 substituents selected independently from the group consisting of $C_{1-6}$ alkoxy, $C_{1-6}$ alkyl, amino, cyano, halogen, $C_{1-6}$ haloalkoxy, $C_{1-6}$ haloalkyl, hydroxyl and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of $C_{1-6}$ acyl, $C_{1-6}$ alkoxy, $C_{1-6}$alkyl, cyano, halogen, $C_{1-6}$haloalkoxy, $C_{1-6}$haloalkyl and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, —F, —Cl, —Br, —I, —OCF$_3$, —OCHF$_2$, —OCFH$_2$, —OCF$_2$CF$_3$, —OCHF$_2$CF$_3$, —CF$_3$, —CHF$_2$, —CFH$_2$, —CF$_2$CF$_3$, —CH$_2$CF$_3$ and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, —F, —Cl, —Br, —I, —OCF$_3$, —OCHF$_2$, —OCFH$_2$, —OCF$_2$CF$_3$, —OCH$_2$CF$_3$, —CF$_3$, —CHF$_2$, —CFH$_2$, —CF$_2$CF$_3$, —CH$_2$CF$_3$ and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of —C(O)CH$_3$, —OCH$_3$, —CH$_3$, cyano, —F, —Cl, —Br, —OCF$_3$, —CF$_3$ and nitro.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of $C_{1-6}$ acyl, $C_{1-6}$ alkoxy, $C_{1-6}$alkyl, amino, $C_{1-6}$ alkylamino, $C_{2-8}$ dialkylamino, $C_{1-6}$ alkylimino, cyano, halogen, $C_{1-6}$haloalkoxy, $C_{1-6}$ haloalkyl, heterocyclic, hydroxyl, nitro, and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$ alkyl, $C_{1-6}$alkylimino, and heterocyclic are each optionally substituted with 1 to 5 substituents selected independently from the group consisting of $C_{1-6}$alkyl, amino, $C_{1-6}$ alkylamino, $C_{2-8}$ dialkylamino, and hydroxyl.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylamino-ethyl)-methyl-amino, (3-dimethylamino-propyl)-methyl-amino, —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of —OCH$_3$, —CH$_3$, cyano, —F, —Cl, —Br, —OCF$_3$, and —CF$_3$.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of $C_{1-6}$ acyl, $C_{1-6}$ acyloxy, $C_{1-6}$ alkoxy, $C_{1-6}$alkyl, $C_{1-6}$ alkylcarboxamide, $C_{1-6}$ alkylsulfonamide, $C_{1-6}$ alkylsulfinyl, $C_{1-6}$ alkylsulfonyl, $C_{1-6}$ alkylthio, amino, $C_{1-6}$alkylamino, $C_{2-8}$ dialkylamino, carbo-$C_{1-6}$-alkoxy, carboxamide, carboxy, cyano, halogen, $C_{1-6}$ haloalkoxy, $C_{1-6}$ haloalkyl, hydroxyl, nitro and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group; and wherein each of said $C_{1-6}$ alkyl and phenyl groups can be optionally substituted with 1 to 5 substituents selected independently from the group consisting of $C_{1-6}$ alkoxy, $C_{1-6}$ alkyl, amino, cyano, halogen, $C_{1-6}$ haloalkoxy, $C_{1-6}$haloalkyl, hydroxyl and nitro.

In some embodiments, $R_1$ is heteroaryl optionally substituted with $R_9$, $R_{10}$, $R_{11}$, $R_{12}$ and $R_{13}$ each selected independently from the group consisting of $C_{1-6}$ acyl, $C_{1-6}$alkoxy, $C_{1-6}$ alkyl, cyano, halogen, $C_{1-6}$ haloalkoxy, $C_{1-6}$ haloalkyl, nitro and phenyl; and wherein said phenyl can be optionally substituted with 1 to 5 substituents selected independently from the group consisting of $C_{1-6}$ alkoxy, $C_{1-6}$ alkyl, cyano, halogen, $C_{1-6}$ haloalkoxy, $C_{1-6}$ haloalkyl and nitro.

In some embodiments, $R_1$ is heteroaryl optionally substituted with $R_9$, $R_{10}$, $R_{11}$, $R_{12}$ and $R_{13}$ each selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl, nitro and phenyl.

In some embodiments, $R_1$ is heteroaryl optionally substituted with $R_9$, $R_{10}$, $R_{11}$, $R_{12}$, and $R_{13}$ each selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)

CH₂CH(CH₃)₂, —OCH₃, —OCH₂CH₃, —OCH(CH₃)₂, —OCH₂CH₂CH₃, —OCH₂CH(CH₃)₂, —CH₃, —CH₂CH₃, —CH(CH₃)₂, —CH₂CH₂CH₃, —CH₂CH(CH₃)₂, —CH₂CH₂CH₂CH₃, cyano, —F, —Cl, —Br, —I, —OCF₃, —OCHF₂, —OCFH₂, —OCF₂CF₃, —OCH₂CF₃, —CF₃, —CHF₂, —CFH₂, —CF₂CF₃, —CH₂CF₃, nitro and phenyl.

In some embodiments, R₁ is heteroaryl optionally substituted with R₉, R₁₀, Rn, R₁₂, and R₁₃ each selected independently from the group consisting of —C(O)CH₃, —OCH₃, —CH₃, cyano, —F, —Cl, —Br, —OCF₃, —CF₃, nitro and phenyl. In some embodiments, R₁ is heteroaryl optionally substituted with R₉, R₁₀, R₁₁, R₁₂, and R₁₃ selected independently from the group consisting of H, —C(O)CH₃, —OCH₃, —CH₃, cyano, —F, —Cl, —Br, —OCF₃, —CF₃, nitro and phenyl.

In some embodiments, R₁ is heteroaryl having 5-atoms in the aromatic ring, examples of which are represented by the following formulae in Table 1:

TABLE 1

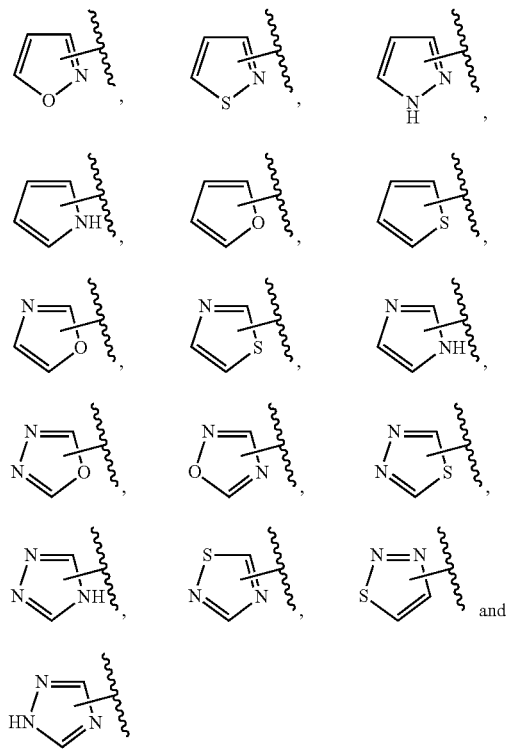

wherein the 5-membered heteroaryl is bonded at any available position of the ring, for example, a imidazolyl ring can be bonded at one of the ring nitrogens (i.e., imidazol-1-yl group) or at one of the ring carbons (i.e., imidazol-2-yl, imidazol-4-yl or imidazol-5-yl group).

In some embodiments, R₁ is a 6-membered heteroaryl, for example, a 6-membered heteroaryl as shown in Table 2:

TABLE 2

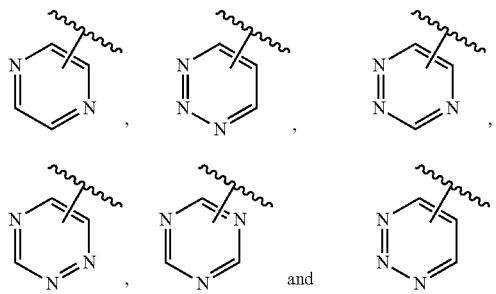

TABLE 2-continued

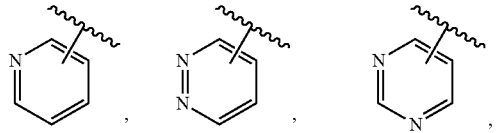

wherein the heteroaryl group is bonded at any ring carbon. In some embodiments, R₁ is selected from the group consisting of pyridinyl, pyridazinyl, pyrimidinyl and pyrazinyl. In some embodiments, R₁ is pyridinyl.

In some embodiments R₁ is a heteroaryl, for example but is not limited to those shown in Tables 1 and 2, optionally substituted with 1 to 3 substituents selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$haloalkylsulfonyl, $C_{1-6}$ haloalkylthio, hydroxyl, thiol, nitro, phenoxy and phenyl; and wherein each of said $C_{2-6}$ alkenyl, $C_{1-6}$alkyl, $C_{2-6}$ alkynyl and phenyl groups can be optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$dialkylamino, carbo-$C_{1-6}$-alkoxy, carboxamide, carboxy, cyano, $C_{3-7}$cycloalkyl, $C_{2-8}$dialkylcarboxamide, halogen, $C_{1-6}$haloalkoxy, $C_{1-6}$haloalkyl, $C_{1-6}$ haloalkylsulfinyl, $C_{1-6}$ haloalkylsulfonyl, $C_{1-6}$ haloalkylthio, hydroxyl, thiol and nitro.

Some embodiments of the present invention pertain to compounds wherein R₂ is H or $C_{1-6}$ alkyl.

Some embodiments of the present invention pertain to compounds wherein R₂ is $C_{1-6}$ alkyl. In some embodiments, R₂ is selected from the group consisting of —CH₃, —CH₂CH₃, —CH(CH₃)₂, —CH₂CH₂CH₃, —CH₂CH(CH₃)₂ and —CH₂CH₂CH₂CH₃. In some embodiments, R₂ is —CH₃ or —CH(CH₃)₂.

Some embodiments of the present invention can be represented by Formulae IIb and IIc respectively as shown below:

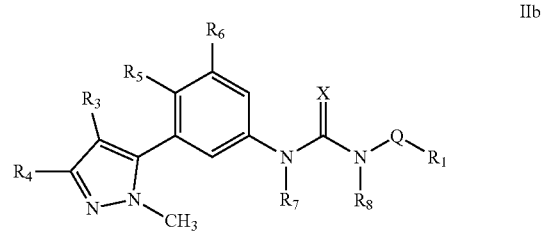

IIb

-continued

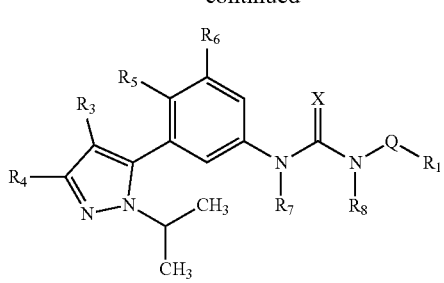

IIc wherein each variable in Formulae IIb and IIc has the same meaning as described herein, supra and infra.

Some embodiments of the present invention pertain to compounds wherein $R_2$ is H.

It is understood that when $R_2$ is H, then tautomers are possible. It is well understood and appreciated in the art that pyrazoles can exist in various tautomeric forms. Two possible tautomeric forms are illustrated below as Formula IId and IId':

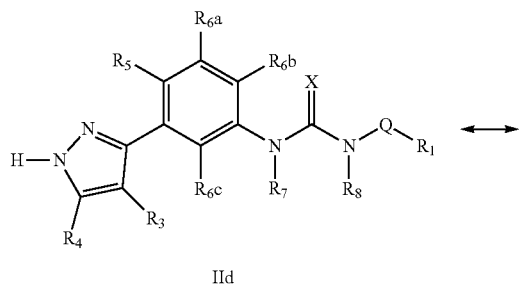

IId

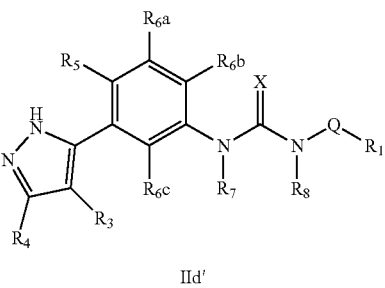

IId'

It is further understood that tautomeric forms can also have corresponding nomenclature for each represented tautomer, for example, Formula IId and Formula IId' can be represented by the general chemical names 1H-pyrazol-3-yl and 2H-pyrazole-3-yl respectively. Therefore, the present invention includes all tautomers and the various nomenclature designations.

Some embodiments of the present invention pertain to compounds wherein $R_2$ is $C_{2-6}$ alkenyl. In some embodiments, $R_2$ is —$CH_2CH$=$CH_2$.

Some embodiments of the present invention pertain to compounds wherein $R_2$ is $C_{2-6}$ alkynyl.

Some embodiments of the present invention pertain to compounds wherein $R_2$ is $C_{3-7}$ cycloalkyl. In some embodiments, $R_2$ is cyclopropyl.

Some embodiments of the present invention pertain to compounds wherein $R_3$ is selected from the group consisting of H, $C_{2-6}$ alkenyl, $C_{1-6}$ alkyl, $C_{1-6}$ alkylcarboxamide, $C_{2-6}$ alkynyl, carbo-$C_{1-6}$-alkoxy, carboxamide, carboxy, cyano, $C_{3-7}$cycloalkyl, halogen, heteroaryl or phenyl; and wherein each of said $C_{2-6}$ alkenyl, $C_{1-6}$ alkyl, $C_{2-6}$ alkynyl, heteroaryl and phenyl groups can be optionally substituted with 1 to 5 substituents selected independently from the group consisting of $C_{1-6}$ alkylamino, $C_{2-8}$ dialkylamino, $C_{2-6}$ alkenyl, $C_{1-4}$ alkoxy, $C_{1-8}$ alkyl, $C_{2-6}$ alkynyl, amino, halogen, $C_{1-4}$ haloalkoxy and hydroxyl.

In some embodiments, $R_3$ is selected from the group consisting of H, $C_{2-6}$ alkenyl, $C_{1-6}$ alkyl, $C_{2-6}$ alkynyl, carbo-$C_{1-6}$-alkoxy, carboxy, cyano, $C_{3-7}$ cycloalkyl, halogen, heteroaryl or phenyl; and wherein each of said $C_{2-6}$ alkenyl, $C_{1-6}$ alkyl, $C_{2-6}$ alkynyl and phenyl groups can be optionally substituted with 1 to 5 substituents selected independently from the group consisting of $C_{2-8}$ dialkylamino, $C_{2-6}$ alkenyl, $C_{1-4}$ alkoxy, $C_{2-6}$ alkynyl, halogen, $C_{1-4}$ haloalkoxy and hydroxyl.

In some embodiments, $R_3$ is selected from the group consisting of H, —CH=$CH_2$, —$CH_3$, —$CH_2CH_3$, —CH$(CH_3)_2$, —$CH_2CH_2CH_3$, —$CH_2CH(CH_3)_2$, —$CH_2CH_2CH_2CH_3$, —C≡CH, —C(O)O$CH_3$, —C(O)O$CH_2CH_3$, carboxy, cyano, cyclopropyl, F, Cl, Br, I, thiophen-2-yl, thiophen-3-yl, phenyl, —$CH_2CH_2N(CH_3)_2$, 2-methoxyphenyl, 3-methoxyphenyl, 4-methoxyphenyl, —CH=CH—C≡CH, 4-fluorophenyl, 4-trifluoromethoxyphenyl, —$CH_2OH$ and —$CH_2CH_2OH$.

Some embodiments of the present invention pertain to compounds wherein $R_3$ is H or halogen.

In some embodiments, $R_3$ is H, F, Cl or Br.

Some embodiments of the present invention pertain to compounds of Formula IIe and Ie as shown below:

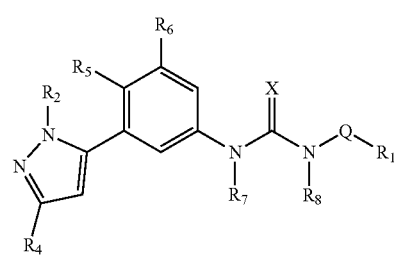

IIe

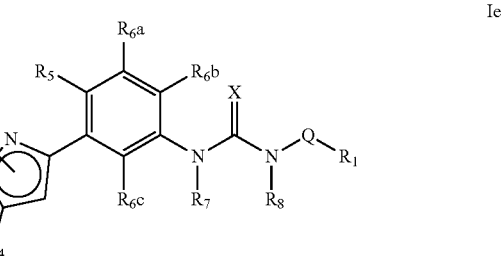

Ie wherein each variable in Formula IIe and Ie has the same meaning as described herein, supra and infra.

Some embodiments of the present invention pertain to compounds of Formula IIf and If as shown below:

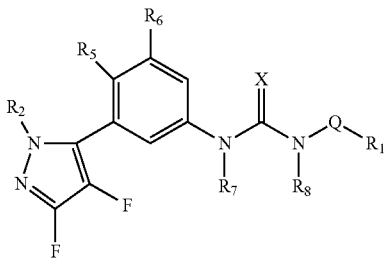

IIf

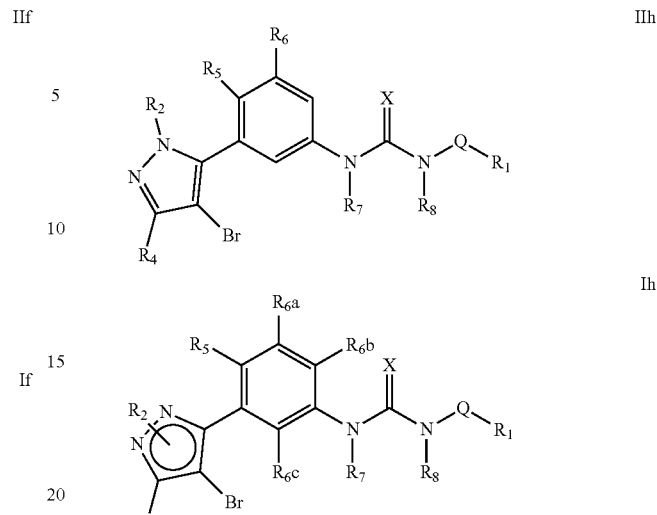

Ih wherein each variable in Formula IIh and Ih has the same meaning as described herein, supra and infra.

Some embodiments of the present invention pertain to compounds wherein $R_4$ is selected from the group consisting of H, $C_{1-6}$ alkyl and $C_{1-6}$ haloalkyl.

In some embodiments, $R_4$ is selected from the group consisting of H, —$CH_3$, —$CH_2CH_3$, —$CH(CH_3)_2$, —$CH_2CH_2CH_3$, —$CH_2CH(CH_3)_2$, —$CH_2CH_2CH_2CH_3$, —$CF_3$, —$CHF_2$, —$CFH_2$, —$CF_2CF_3$ and —$CH_2CF_3$.

In some embodiments, $R_4$ is selected from the group consisting of H or —$CF_3$.

Some embodiments of the present invention can be represented by Formula IIi and IIj as shown below:

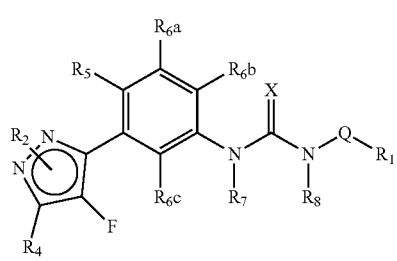

If wherein each variable in Formula IIf and If has the same meaning as described herein, supra and infra.

Some embodiments of the present invention pertain to compounds of Formula IIg and Ig as shown below:

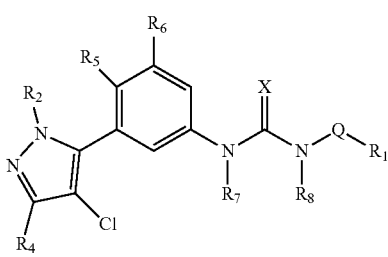

IIg

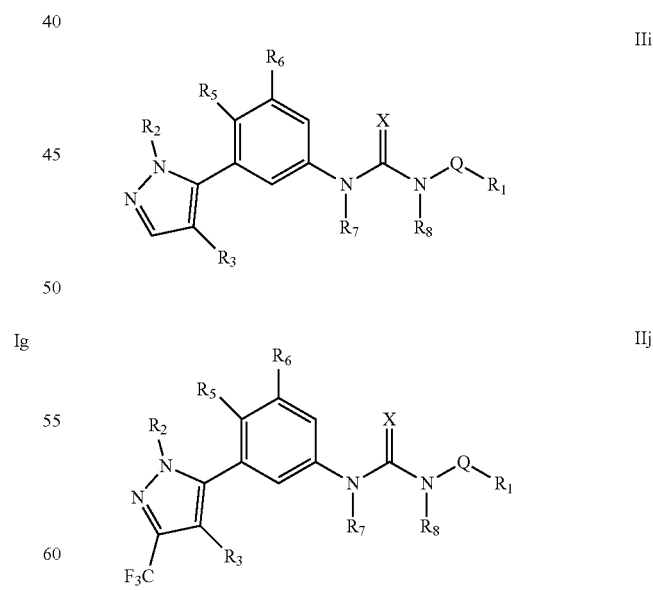

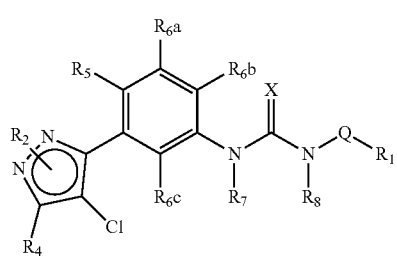

Ig wherein each variable in Formula IIg and Ig has the same meaning as described herein, supra and infra.

Some embodiments of the present invention pertain to compounds of Formula IIh or Ih as shown below:

wherein each variable in Formula IIi and IIj has the same meaning as described herein, supra and infra.

Some embodiments of the present invention can be represented by Formula Ii and Ij as shown below:

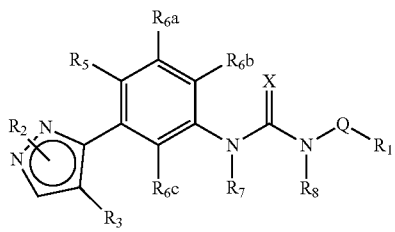

Ii

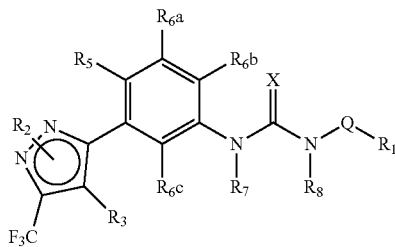

Ij wherein each variable in Formula Ii and Ij has the same meaning as described herein, supra and infra.

Some embodiments of the present invention pertain to compounds wherein R₅ is selected from the group consisting of $C_{1-6}$alkoxy, $C_{1-6}$ alkylthio, amino, $C_{1-6}$ alkylamino, $C_{2-8}$ dialkylamino, halogen, $C_{1-6}$ haloalkoxy, and hydroxyl, wherein said $C_{1-6}$alkoxy group can be optionally substituted with 1 to 5 substituents selected independently from the group consisting of amino, $C_{1-6}$ alkylamino, $C_{2-8}$ dialkylamino, amino, carbo-$C_{1-6}$-alkoxy, carboxamide, carboxy, cyano, halogen, and phenyl, and wherein said amino and phenyl are each optionally substituted with 1 to 5 further substituents selected from the group consisting of halogen and carbo-$C_{1-6}$-alkoxy.

Some embodiments of the present invention pertain to compounds wherein R₅ is $C_{1-6}$ alkoxy, or hydroxyl, wherein said $C_{1-6}$alkoxy group can be optionally substituted with 1 to 5 substituents selected independently from the group consisting of $C_{1-4}$alkoxy, $C_{1-6}$ alkylamino, $C_{2-8}$dialkylamino, alkylsulfinyl, $C_{1-4}$alkylsulfonyl, $C_{1-4}$ alkylthio, amino, halogen, $C_{1-4}$ haloalkoxy, $C_{1-4}$ haloalkyl, $C_{1-4}$ haloalkylsulfinyl, $C_{1-4}$haloalkylsulfonyl, $C_{1-4}$haloalkylthio, hydroxyl and phenyl, and wherein said phenyl is optionally substituted with 1 to 5 halogen atoms.

Some embodiments of the present invention pertain to compounds wherein R₅ is selected from the group consisting of $C_{1-6}$alkoxy, $C_{1-6}$ haloalkoxy, and hydroxyl, wherein said $C_{1-6}$ alkoxy group can be optionally substituted with 1 to 5 substituents selected independently from the group consisting of amino, $C_{2-8}$ dialkylamino, carboxy, and phenyl, and wherein said amino and phenyl are each optionally substituted with 1 to 5 further substituents selected from the group consisting of halogen and carbo-$C_{1-6}$-alkoxy.

In some embodiments, R₅ is $C_{1-6}$ alkoxy, or hydroxyl, and wherein said $C_{1-6}$ alkoxy group can be optionally substituted with 1 to 5 substituents selected independently from the group consisting of $C_{1-4}$ alkoxy, $C_{1-6}$alkylamino, $C_{2-8}$dialkylamino, amino, $C_{1-4}$ haloalkoxy, hydroxyl and phenyl, wherein said phenyl is optionally substituted with 1 to 5 halogen atoms.

Some embodiments of the present invention pertain to compounds wherein R₅ is selected from the group consisting of —OCH₃, —OCH₂CH₃, —OCH(CH₃)₂, —OCF₃, hydroxyl, benzyloxy, 4-chloro-benzyloxy, phenethyloxy, 2-dimethylamino-ethoxy [i.e., —OCH₂CH₂N(CH₃)₂], 3-di-methylamino-propoxy [i.e., —OCH₂CH₂CH₂N(CH₃)₂], carboxymethoxy [i.e., —OCHC(O)OH], and 2-tert-butoxy-carbonylamino-ethoxy [i.e., —OCH₂CH₂NHC(O)OC(CH₃)₃].

In some embodiments, R₅ is selected from the group consisting of —OCH₃, —OCH₂CH₃, —OCH(CH₃)₂, —OCH₂CH₂CH₃, —OCH₂CH(CH₃)₂, hydroxyl, —OCH₂CH₂OH, —OCH₂CH₂OCH₃, —OCH₂CH₂OCH₂CH₃, —OCH₂CH₂OCH(CH₃)₂, —OCH₂CH₂OCH₂CH₂CH₃, —OCH₂CH₂OCH₂CH(CH₃)₂, —OCH₂CH₂NH₂, —OCH₂CH₂NHCH₃, —OCH₂CH₂N(CH₃)₂, —OCH₂CH₂OCF₃, —OCH₂CH₂OCHF₂, —OCH₂CH₂OCFH₂, —OCH₂C₆H₅, —OCH₂CH₂C₆H₅, —OCH₂C₆H₅-o-Cl, —OCH₂C₆H₅-m-Cl and —OCH₂C₆H₅-p-Cl.

In some embodiments, R₅ is selected from the group consisting of —OCH₃, —OCH₂CH₃, —OCH(CH₃)₂, hydroxyl, —OCH₂CH₂N(CH₃)₂, —OCH₂C₆H₅, —OCH₂CH₂C₆H₅ and —OCH₂C₆H₅-p-Cl.

In some embodiments, R₅ is —OCH₃.

Some embodiments of the present invention pertain to compounds wherein R₆ is selected from the group consisting of H, $C_{1-6}$ alkoxy, carbo-$C_{1-6}$-alkoxy, carboxamide, carboxy, cyano, halogen and hydroxyl.

In some embodiments, R₆ is H.

Some embodiments of the present invention pertain to compounds wherein $R_{6a}$, $R_{6b}$, and $R_{6c}$ are each independently selected from the group consisting of H, $C_{1-6}$ alkoxy, $C_{1-6}$ alkyl, amino, $C_{1-6}$ alkylamino, $C_{2-8}$ dialkylamino, cyano, halogen, $C_{1-6}$ haloalkoxy, $C_{1-6}$ haloalkyl, hydroxyl, and nitro.

Some embodiments of the present invention pertain to compounds wherein $R_{6a}$, $R_{6b}$, and $R_{6c}$ are each independently selected from the group consisting of H, —OCH₃, —CH₃, —N(CH₃)₂, cyano, —F, —Cl, —Br, —OCF₃, hydroxyl, and nitro.

Some embodiments of the present invention pertain to compounds wherein $R_{6a}$, $R_{6b}$, and $R_{6c}$ are each independently selected from the group consisting of H, $C_{1-6}$ alkoxy, carbo-$C_{1-6}$-alkoxy, carboxamide, carboxy, cyano, halogen and hydroxyl.

Some embodiments of the present invention pertain to compounds wherein $R_{6a}$, $R_{6b}$, and $R_{6c}$ are all H.

Some embodiments of the present invention pertain to compounds wherein R₅ is $C_{1-6}$ alkoxy and $R_{6a}$, $R_{6b}$, and $R_{6c}$ are all H.

In some embodiments, R₅ is —OCH₃.

Some embodiments of the present invention pertain to compounds represented by Formula IIk and Ik as shown below:

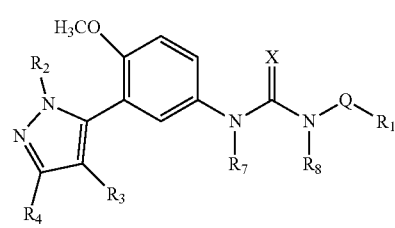

IIk

-continued

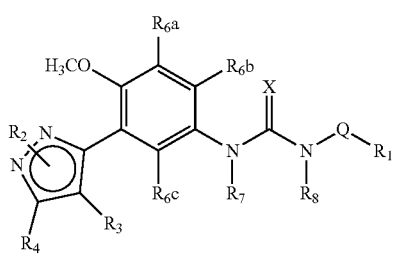

Ik wherein each variable in Formula IIK has the same meaning as described herein, supra and infra. In some embodiments, compounds of the present invention have Formula IIK and Q is a bond.

Some embodiments of the present invention pertain to compounds represented by Formula IK wherein each variable in Formula IK has the same meaning as described herein, supra and infra. In some embodiments, compounds of the present invention have Formula IK and Q is a bond.

Some embodiments of the present invention pertain to compounds wherein $R_7$ is H or $C_{1-8}$ alkyl.

In some embodiments, $R_7$ is selected from the group consisting of H, —$CH_3$, —$CH_2CH_3$, —$CH(CH_3)_2$, —$CH_2CH_2CH_3$, —$CH_2CH(CH_3)_2$ and —$CH_2CH_2CH_2CH_3$.

In some embodiments, $R_7$ is H.

Some embodiments of the present invention pertain to compounds wherein $R_8$ is H or $C_{1-8}$ alkyl.

In some embodiments, $R_5$ is selected from the group consisting of H, —$CH_3$, —$CH_2CH_3$, —$CH(CH_3)_2$, —$CH_2CH_2CH_3$, —$CH_2CH(CH_3)_2$ and —$CH_2CH_2CH_2CH_3$.

In some embodiments, $R_8$ is H.

Some embodiments of the present invention pertain to compounds wherein both $R_7$ and $R_8$ are H.

Some embodiments of the present invention pertain to compounds represented by Formula IIm and Im as shown below:

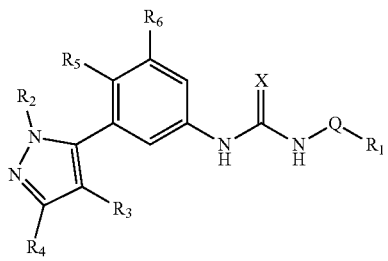

IIm

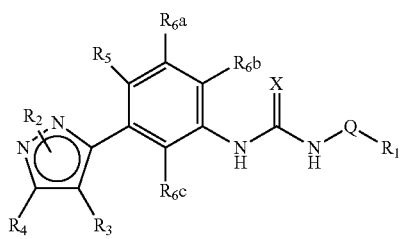

Im wherein each variable in Formula IIm and Im has the same meaning as described herein, supra and infra.

Some embodiments of the present invention pertain to compounds wherein X is O (i.e., oxygen).

Some embodiments of the present invention pertain to compounds wherein X is S (i.e., sulfur).

Some embodiments of the present invention pertain to compounds wherein Q is $C_{1-3}$ alkylene optionally substituted with $C_{1-3}$ alkyl, $C_{1-3}$ haloalkyl, halogen and oxo.

Some embodiments of the present invention pertain to compounds wherein Q is a $C_{1-3}$ alkylene optionally substituted with oxo. As used herein, oxo refers to a double bonded oxygen. In some embodiments, Q is —C(O)— (i.e., a carbonyl).

In some embodiments, Q is —$CH_2$—.

Some embodiments of the present invention pertain to compounds wherein Q is a bond.

Some embodiments of the present invention pertain to compounds represented by Formula IIn and In as shown below:

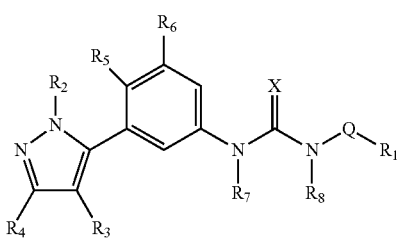

IIn

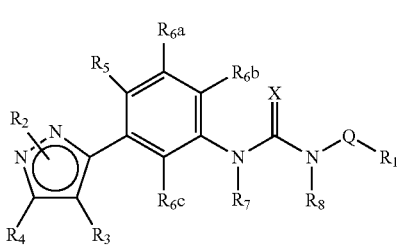

In wherein each variable in Formula IIn and In has the same meaning as described herein, supra and infra.

In some embodiments, $R_1$ is phenyl and can be represented by Formula XIIIa as shown below:

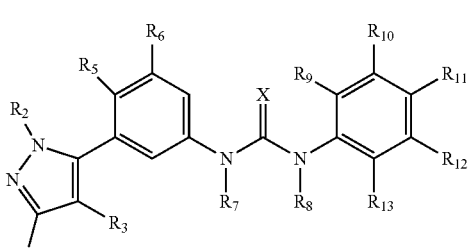

XIIIa wherein each variable in Formula XIIIa has the same meaning as described herein, supra and infra. In some embodiments, $R_7$ and $R_8$ are both H. In some embodiments, X is O (i.e., oxygen).

In some embodiments, $R_1$ is phenyl and can be represented by Formula XIVa as shown below:

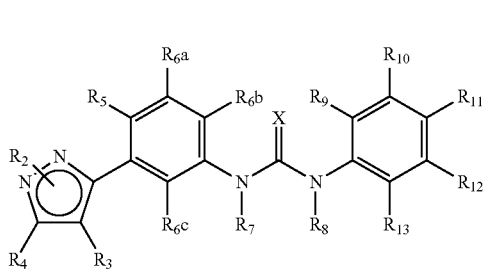

XIVa wherein each variable in Formula XIVa has the same meaning as described herein, supra and infra. In some embodiments, $R_7$ and $R_8$ are both H. In some embodiments, X is O (i.e., oxygen).

Some embodiments of the present invention pertain to compounds of Formula IIa:

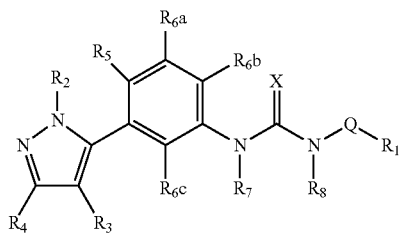

IIa wherein:
$R_1$ is phenyl or naphthyl optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ alkoxy, $C_{1-6}$ alkyl, amino, $C_{1-6}$alkylamino, $C_{2-8}$dialkylamino, $C_{1-6}$alkylimino, cyano, halogen, $C_{1-6}$haloalkoxy, $C_{1-6}$haloalkyl, heterocyclic, hydroxyl, nitro, and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$alkyl, $C_{1-6}$alkylimino, and heterocyclic are each optionally substituted with 1 to 5 substituents selected independently from the group consisting of $C_{1-6}$ alkyl, amino, $C_{1-6}$ alkylamino, $C_{2-8}$ dialkylamino, and hydroxyl;
$R_2$ is $C_{1-6}$ alkyl;
$R_3$ is H or halogen;
$R_4$ is selected from the group consisting of H, $C_{1-6}$ alkyl and $C_{1-6}$ haloalkyl;
$R_5$ is selected from the group consisting of $C_{1-6}$alkoxy, $C_{1-6}$ haloalkoxy, and hydroxyl, wherein said $C_{1-6}$alkoxy group can be optionally substituted with 1 to 5 substituents selected independently from the group consisting of amino, $C_{2-8}$ dialkylamino, carboxy, and phenyl, and wherein said amino and phenyl are each optionally substituted with 1 to 5 further substituents selected from the group consisting of halogen and carbo-$C_{1-6}$-alkoxy;
$R_{6a}$, $R_{6b}$, and $R_{6c}$ are each independently selected from the group consisting of H, $C_{1-6}$ alkoxy, $C_{1-6}$ alkyl, amino, $C_{1-6}$ alkylamino, $C_{2-8}$ dialkylamino, cyano, halogen, $C_{1-6}$ haloalkoxy, $C_{1-6}$ haloalkyl, hydroxyl, and nitro
$R_7$ and $R_8$ are both H;
X is O; and
Q is a bond.

Some embodiments of the present invention pertain to compounds of Formula IIa:

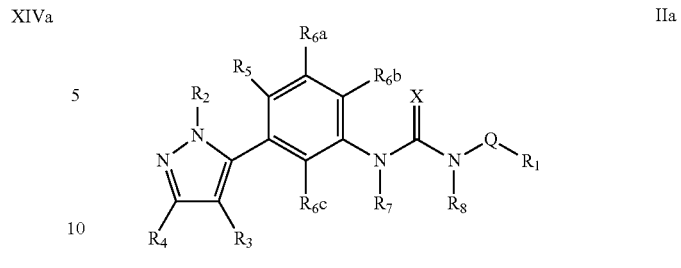

IIa wherein:
$R_1$ is phenyl or naphthyl optionally substituted with $R_9$, $R_{10}$, $R_{11}$, $R_{12}$, $R_{13}$, $R_{14}$, and $R_{15}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylamino-ethyl)-methyl-amino, (3-dimethylamino-propyl)-methyl-amino, —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl;
$R_2$ is —CH$_3$ or —CH(CH$_3$)$_2$;
$R_3$ is H, F, Cl, or Br;
$R_4$ is —H, or —CF$_3$;
$R_5$ is selected from the group consisting of —OCH$_3$, —OCH$_2$CH$_3$, —OCH(CH$_3$)$_2$, —OCF$_3$, hydroxyl, benzyloxy, 4-chloro-benzyloxy, phenethyloxy, 2-dimethylamino-ethoxy, 3-dimethylamino-propoxy, carboxymethoxy, and 2-tert-butoxycarbonylamino-ethoxy;
$R_{6a}$, $R_{6b}$, and $R_{6c}$ are each independently selected from the group consisting of H, —OCH$_3$, —CH$_3$, —N(CH$_3$)$_2$, cyano, —F, —Cl, —Br, —OCF$_3$, hydroxyl, and nitro;
$R_7$ and $R_8$ are both H;
X is O; and
Q is a bond.

Some embodiments of the present invention pertain to compounds of Formula IIa:

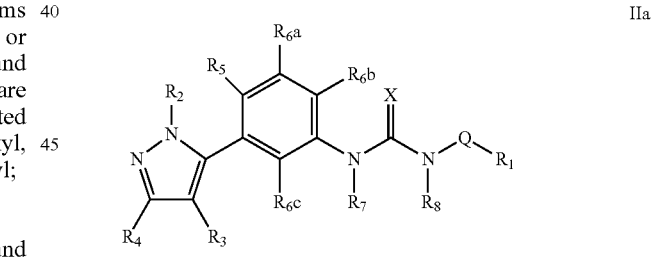

IIa wherein:
$R_1$ is phenyl optionally substituted with $R_9$, $R_{10}$, $R_{11}$, $R_{12}$, and $R_{13}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylamino-ethyl)-methyl-amino, (3-dimethylamino-propyl)-methyl-amino, —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl;
$R_2$ is —CH$_3$ or —CH(CH$_3$)$_2$;
$R_3$ is —H, —F, —Cl, or —Br;
$R_4$ is —H, or —CF$_3$;
$R_5$ is selected from the group consisting of —OCH$_3$, —OCH$_2$CH$_3$, —OCH(CH$_3$)$_2$, —OCF$_3$, hydroxyl, benzyloxy, 4-chloro-benzyloxy, phenethyloxy, 2-dimethylamino-ethoxy, 3-dimethylamino-propoxy, carboxymethoxy, and 2-tert-butoxycarbonylamino-ethoxy;

$R_{6a}$, $R_{6b}$, and $R_{6c}$ are each independently selected from the group consisting of —H, —OCH$_3$, —CH$_3$, —N(CH$_3$)$_2$, cyano, F, Cl, Br, —OCF$_3$, hydroxyl, and nitro;

$R_7$ and $R_8$ are both H;

X is O; and

Q is a bond.

Some embodiments of the present invention pertain to compounds of Formula IIa:

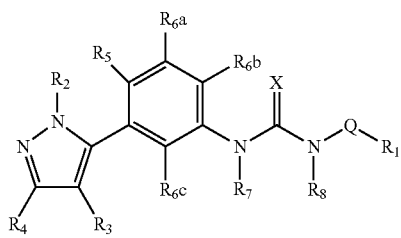

wherein:

$R_1$ is phenyl optionally substituted with $R_9$, $R_{10}$, $R_{11}$, $R_{12}$, and $R_{13}$ each selected independently from the group consisting of —C(O)CH$_3$, —OCH$_3$, —CH$_3$, —CH(CH$_3$)$_2$, —N(CH$_3$)$_2$, cyano, —F, —Cl, —Br, —OCF$_3$, —CF$_3$, hydroxyl, and nitro;

$R_2$ is —CH$_3$;

$R_3$ is —H, —F, —Cl, or —Br;

$R_4$ is —H;

$R_5$ is selected from the group consisting of —OCH$_3$, —OCH$_2$CH$_3$, —OCH(CH$_3$)$_2$, —OCF$_3$, hydroxyl, benzyloxy, 4-chloro-benzyloxy, phenethyloxy, 2-dimethylamino-ethoxy, 3-dimethylamino-propoxy, carboxymethoxy, and 2-tert-butoxycarbonylamino-ethoxy;

$R_{6a}$, $R_{6b}$, and $R_{6c}$ are each —H;

$R_7$ and $R_8$ are both —H;

X is O; and

Q is a bond.

Some embodiments of the present invention include compounds illustrated in Table 3 as shown below:

TABLE 3

| Cmpd # | Structure | Chemical Name |
|---|---|---|
| 1 | 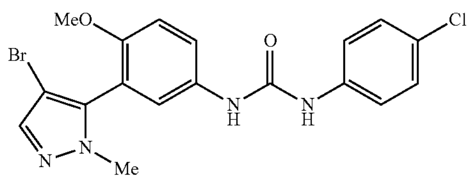 | 1-[3-(4-Bromo-2-methyl-2H-pyrazol-3-yl)-4-methoxy-phenyl]-3-(4-chloro-phenyl)-urea |
| 2 | 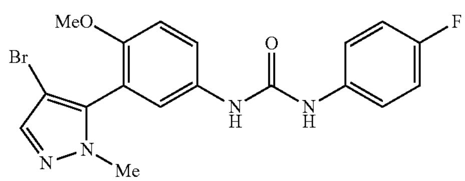 [SMILES: COc1ccc(NC(=O)Nc2ccc(F)cc2)cc1-c1c(Br)cnn1C] | 1-[3-(4-Bromo-2-methyl-2H-pyrazol-3-yl)-4-methoxy-phenyl]-3-(4-fluoro-phenyl)-urea |
| 3 | 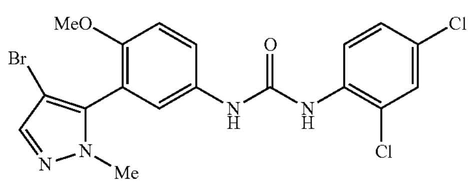 [SMILES: COc1ccc(NC(=O)Nc2ccc(Cl)cc2Cl)cc1-c1c(Br)cnn1C] | 1-[3-(4-Bromo-2-methyl-2H-pyrazol-3-yl)-4-methoxy-phenyl]-3-(2,4-dichloro-phenyl)-urea |
| 4 | 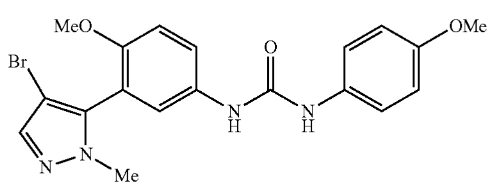 [SMILES: COc1ccc(NC(=O)Nc2ccc(OC)c(-c3c(Br)cnn3C)c2)cc1] | 1-[3-(4-Bromo-2-methyl-2H-pyrazol-3-yl)-4-methoxy-phenyl]-3-(4-methoxy-phenyl)-urea |
| 5 | 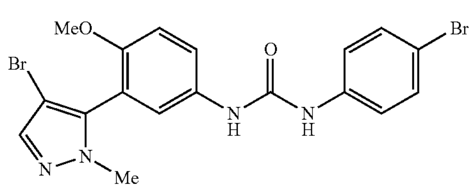 | 1-[3-(4-Bromo-2-methyl-2H-pyrazol-3-yl)-4-methoxy-phenyl]-3-(4-bromo-phenyl)-urea |

TABLE 3-continued

| Cmpd # | Structure | Chemical Name |
|---|---|---|
| 6 | 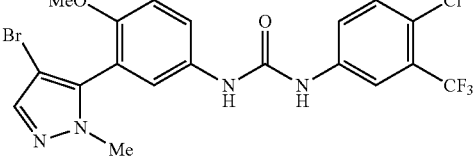 | 1-[3-(4-Bromo-2-methyl-2H-pyrazol-3-yl)-4-methoxy-phenyl]-3-(4-chloro-3-trifluoromethyl-phenyl)-urea |
| 7 | 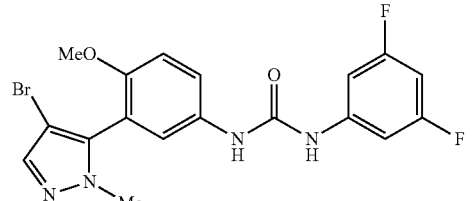 | 1-[3-(4-Bromo-2-methyl-2H-pyrazol-3-yl)-4-methoxy-phenyl]-3-(3,5-difluoro-phenyl)-urea |
| 8 | 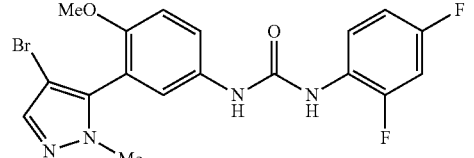 | 1-[3-(4-Bromo-2-methyl-2H-pyrazol-3-yl)-4-methoxy-phenyl]-3-(2,4-difluoro-phenyl)-urea |
| 9 | 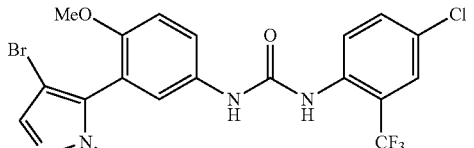 | 1-[3-(4-Bromo-2-methyl-2H-pyrazol-3-yl)-4-methoxy-phenyl]-3-4-chloro-2-trifluoromethyl-phenyl)-urea |
| 10 | 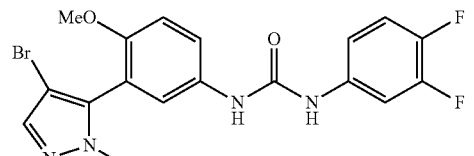 | 1-[3-(4-Bromo-2-methyl-2H-pyrazol-3-yl)-4-methoxy-phenyl]-(3,4-difluoro-phenyl)-urea |
| 11 | 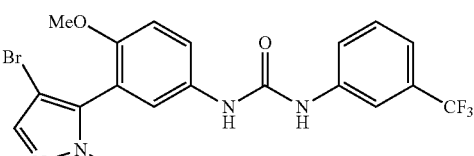 | 1-[3-(4-Bromo-2-methyl-2H-pyrazol-3-yl)-4-methoxy-phenyl]-3-(3-trifluoromethyl-phenyl)-urea |
| 12 | 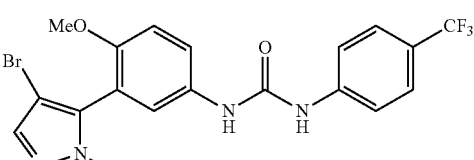 | 1-[3-(4-Bromo-2-methyl-2H-pyrazol-3-yl)-4-methoxy-phenyl]-3-(4-trifluoromethyl-phenyl)-urea |
| 13 | 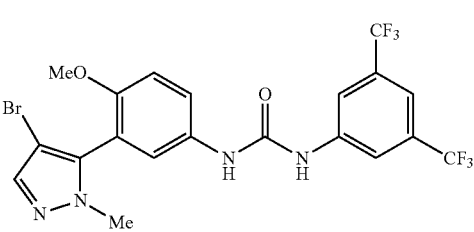 [SMILES: COc1ccc(NC(=O)Nc2cc(C(F)(F)F)cc(C(F)(F)F)c2)cc1-c1c(Br)cnn1C] | 1-(3,5-Bis-trifluoromethyl-phenyl)-3-[3-(4-bromo-2-methyl-2H-pyrazol-3-yl)-4-methoxy-phenyl]-urea |

TABLE 3-continued

| Cmpd # | Structure | Chemical Name |
|---|---|---|
| 14 | 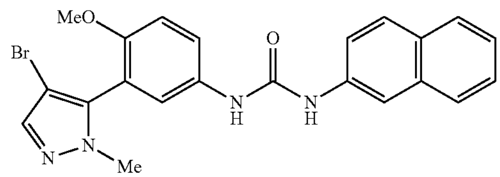 [SMILES: COc1ccc(NC(=O)Nc2ccc3ccccc3c2)cc1-c1c(Br)cnn1C] | 1-[3-(4-Bromo-2-methyl-2H-pyrazol-3-yl)-4-methoxy-phenyl]-3-naphthalen-2-yl-urea |
| 15 | 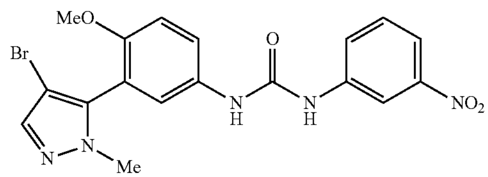 | 1-[3-(4-Bromo-2-methyl-2H-pyrazol-3-yl)-4-methoxy-phenyl]-3-(3-nitro-phenyl)-urea |
| 16 | 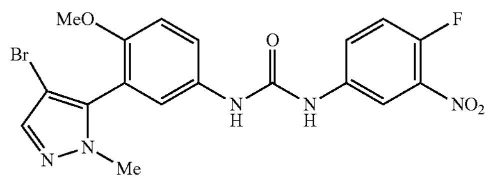 [SMILES: COc1ccc(NC(=O)Nc2ccc(F)c([N+](=O)[O-])c2)cc1-c1c(Br)cnn1C] | 1-[3-(4-Bromo-2-methyl-2H-pyrazol-3-yl)-4-methoxy-phenyl]-3-(4-fluoro-3-nitro-phenyl)-urea |
| 17 | 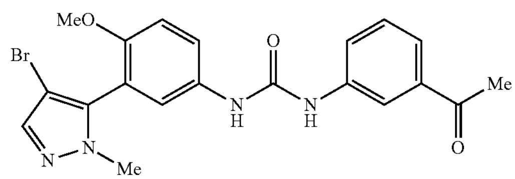 | 1-(3-Acetyl-phenyl)-3-[3-(4-bromo-2-methyl-2H-pyrazol-3-yl)-4-methoxy-phenyl]-urea |
| 18 | 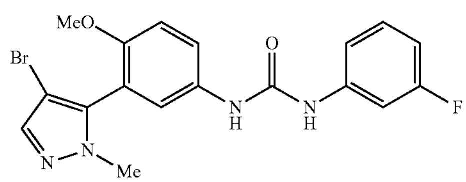 | 1-[3-(4-Bromo-2-methyl-2H-pyrazol-3-yl)-4-methoxy-phenyl]-3-(3-fluoro-phenyl)-urea |
| 19 | 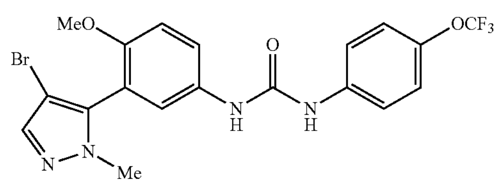 [SMILES: COc1ccc(NC(=O)Nc2ccc(OC(F)(F)F)cc2)cc1-c1c(Br)cnn1C] | 1-[3-(4-Bromo-2-methyl-2H-pyrazol-3-yl)-4-methoxy-phenyl]-3-(4-trifluoromethoxy-phenyl)-urea |
| 20 | 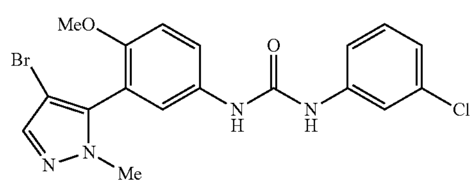 [SMILES: COc1ccc(NC(=O)Nc2cccc(Cl)c2)cc1-c1c(Br)cnn1C] | 1-[3-(4-Bromo-2-methyl-2H-pyrazol-3-yl)-4-methoxy-phenyl]-3-(3-chloro-phenyl)-urea |
| 21 | 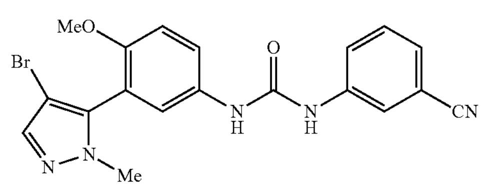 | 1-[3-(4-Bromo-2-methyl-2H-pyrazol-3-yl)-4-methoxy-phenyl]-3-(3-cyano-phenyl)-urea |

TABLE 3-continued

| Cmpd # | Structure | Chemical Name |
|---|---|---|
| 22 | 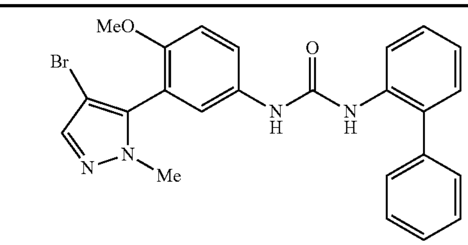 | 1-Biphenyl-2-yl-3-[3-(4-bromo-2-methyl-2H-pyrazol-3-yl)-4-methoxy-phenyl]-urea |
| 23 | 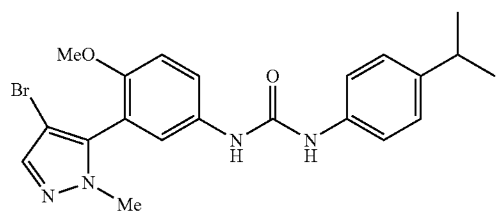 | 1-[3-(4-Bromo-2-methyl-2H-pyrazol-3-yl)-4-methoxy-phenyl]-3-(4-isopropyl-phenyl)-urea |
| 24 | 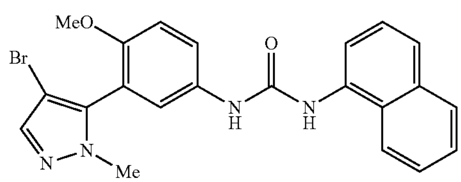 | 1-[3-(4-Bromo-2-methyl-2H-pyrazol-3-yl)-4-methoxy-phenyl]-3-napthalen-1-yl-urea |
| 25 | 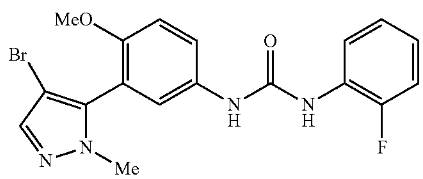 | 1-[3-(4-Bromo-2-methyl-2H-pyrazol-3-yl)-4-methoxy-phenyl]-3-(2-fluoro-phenyl)-urea |
| 26 | 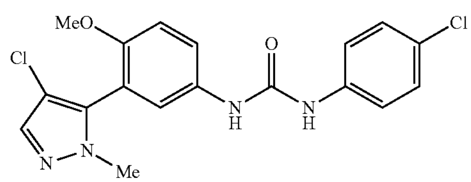 [SMILES: COc1ccc(NC(=O)Nc2ccc(Cl)cc2)cc1-c1c(Cl)cnn1C] | 1-[3-(4-Chloro-2-methyl-2H-pyrazol-3-yl)-4-methoxy-phenyl]-3-(4-chloro-phenyl)-urea |
| 27 | 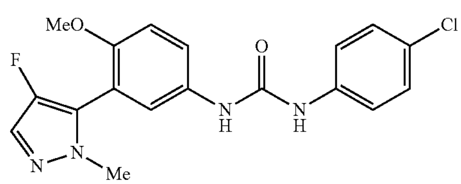 [SMILES: COc1ccc(NC(=O)Nc2ccc(Cl)cc2)cc1-c1c(F)cnn1C] | 1-(4-Chloro-phenyl)-3-[3-(4-fluoro-2-methyl-2H-pyrazol-3-yl)-4-methoxy-phenyl]-urea |
| 28 | 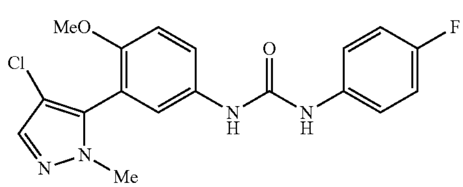 [SMILES: COc1ccc(NC(=O)Nc2ccc(F)cc2)cc1-c1c(Cl)cnn1C] | 1-[3-(4-Chloro-2-methyl-2H-pyrazol-3-yl)-4-methoxy-phenyl]-3-(4-fluoro-phenyl)-urea |
| 29 | 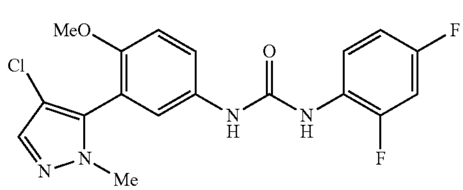 [SMILES: COc1ccc(NC(=O)Nc2ccc(F)cc2F)cc1-c1c(Cl)cnn1C] | 1-[3-(4-Chloro-2-methyl-2H-pyrazol-3-yl)-4-methoxy-phenyl]-3-(2,4-difluoro-phenyl)-urea |

TABLE 3-continued

| Cmpd # | Structure | Chemical Name |
|---|---|---|
| 30 | 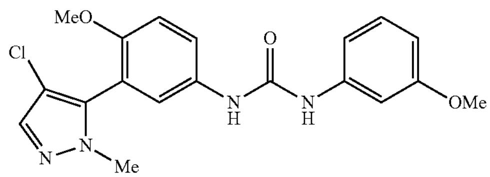 [SMILES: COc1cccc(NC(=O)Nc2ccc(OC)c(-c3c(Cl)cnn3C)c2)c1] | 1-[3-(4-Chloro-2-methyl-2H-pyrazol-3-yl)-4-methoxy-phenyl]-3-(3-methoxy-phenyl)-urea |
| 31 | 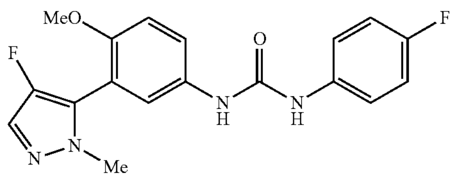 [SMILES: COc1ccc(NC(=O)Nc2ccc(F)cc2)cc1-c1c(F)cnn1C] | 1-[3-(4-Fluoro-2-methyl-2H-pyrazol-3-yl)-4-methoxy-phenyl]-3-(4-fluoro-phenyl)-urea |
| 32 | 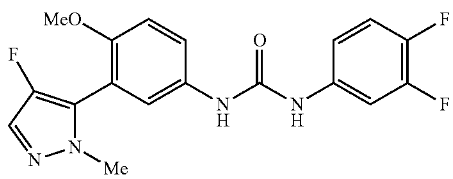 [SMILES: COc1ccc(NC(=O)Nc2ccc(F)c(F)c2)cc1-c1c(F)cnn1C] | 1-(3,4-Difluoro-phenyl)-3-[3-(4-fluoro-2-methyl-2H-pyrazol-3-yl)-4-methoxy-phenyl]-urea |
| 33 | 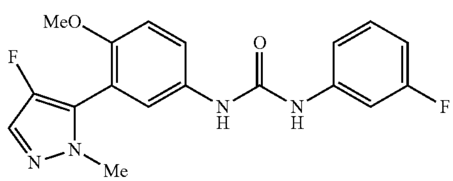 [SMILES: COc1ccc(NC(=O)Nc2cccc(F)c2)cc1-c1c(F)cnn1C] | 1-[3-(4-Fluoro-2-methyl-2H-pyrazol-3-yl)-4-methoxy-phenyl]-3-(3-fluoro-phenyl)-urea |
| 34 | 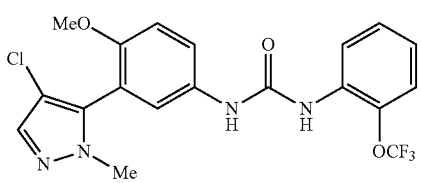 [SMILES: COc1ccc(NC(=O)Nc2ccccc2OC(F)(F)F)cc1-c1c(Cl)cnn1C] | 1-[3-(4-Chloro-2-methyl-2H-pyrazol-3-yl)-4-methoxy-phenyl]-3-(2-trifluoromethoxy-phenyl)-urea |
| 35 | 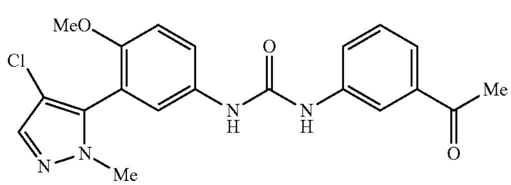 [SMILES: COc1ccc(NC(=O)Nc2cccc(C(C)=O)c2)cc1-c1c(Cl)cnn1C] | 1-(3-Acetyl-phenyl)-3-[3-(4-chloro-2-methyl-2H-pyrazol-3-yl)-4-methoxy-phenyl]-urea |
| 36 | 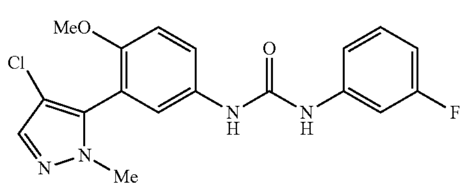 [SMILES: COc1ccc(NC(=O)Nc2cccc(F)c2)cc1-c1c(Cl)cnn1C] | 1-[3-(4-Chloro-2-methyl-2H-pyrazol-3-yl)-4-methoxy-phenyl]-3-(3-fluoro-phenyl)-urea |
| 37 | 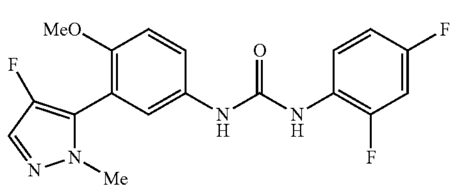 [SMILES: COc1ccc(NC(=O)Nc2ccc(F)cc2F)cc1-c1c(F)cnn1C] | 1-(2,4-Difluoro-phenyl)-3-[3-(4-fluoro-2-methyl-2H-pyrazol-3-yl)-4-methoxy-phenyl]-urea |

TABLE 3-continued

| Cmpd # | Structure | Chemical Name |
|---|---|---|
| 38 | 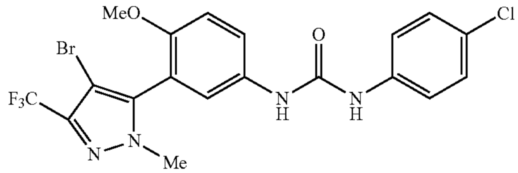 [SMILES: COc1ccc(NC(=O)Nc2ccc(Cl)cc2)cc1-c1c(Br)c(C(F)(F)F)nn1C] | 1-[3-(4-Bromo-2-methyl-5-trifluoromethyl-2H-pyrazol-3-yl)-4-methoxy-phenyl]-3-(4-chloro-phenyl)-urea |
| 39 | 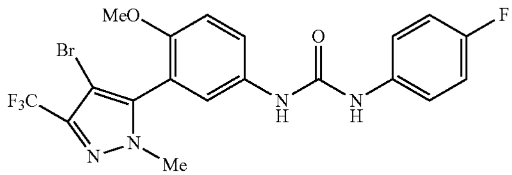 [SMILES: COc1ccc(NC(=O)Nc2ccc(F)cc2)cc1-c1c(Br)c(C(F)(F)F)nn1C] | 1-[3-(4-Bromo-2-methyl-5-trifluoromethyl-2H-pyrazol-3-yl)-4-methoxy-phenyl]-3-(4-fluoro-phenyl)-urea |
| 40 | 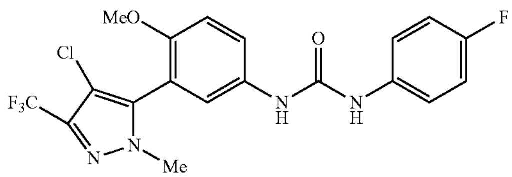 [SMILES: COc1ccc(NC(=O)Nc2ccc(F)cc2)cc1-c1c(Cl)c(C(F)(F)F)nn1C] | 1-[3-(4-Chloro-2-methyl-5-trifluoromethyl-2H-pyrazol-3-yl)-4-methoxy-phenyl]-3-(4-fluoro-phenyl)-urea |
| 41 | 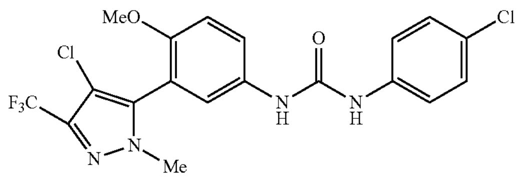 [SMILES: COc1ccc(NC(=O)Nc2ccc(Cl)cc2)cc1-c1c(Cl)c(C(F)(F)F)nn1C] | 1-[3-(4-Chloro-2-methyl-5-trifluoromethyl-2H-pyrazol-3-yl)-4-methoxy-phenyl]-3-(4-chloro-phenyl)-urea |
| 42 | 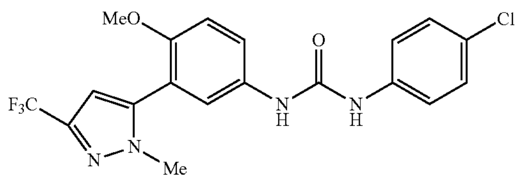 [SMILES: COc1ccc(NC(=O)Nc2ccc(Cl)cc2)cc1-c1cc(C(F)(F)F)nn1C] | 1-(4-Chloro-phenyl)-3-[4-methoxy-3-(2-methyl-5-trifluoromethyl-2H-pyrazol-3-yl)-phenyl]-urea |
| 43 | 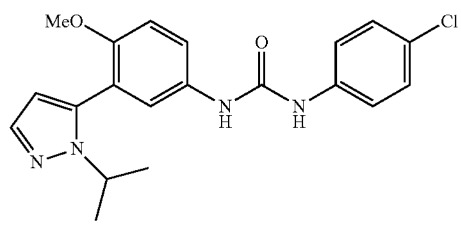 [SMILES: COc1ccc(NC(=O)Nc2ccc(Cl)cc2)cc1-c1ccnn1C(C)C] | 1-(4-Chloro-phenyl)-3-[3-(2-isopropyl-2H-pyrazol-3-yl)-4-methoxy-phenyl]-urea |
| 44 | 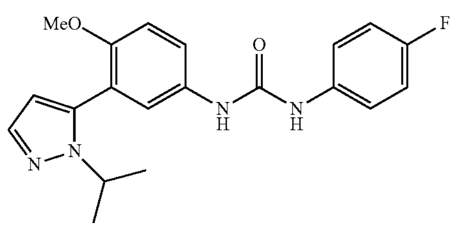 [SMILES: COc1ccc(NC(=O)Nc2ccc(F)cc2)cc1-c1ccnn1C(C)C] | 1-(4-Fluoro-phenyl)-3-[3-(2-isopropyl-2H-pyrazol-3-yl)-4-methoxy-phenyl]-urea |
| 45 | 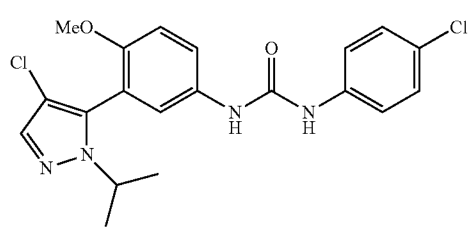 [SMILES: COc1ccc(NC(=O)Nc2ccc(Cl)cc2)cc1-c1c(Cl)cnn1C(C)C] | 1-[3-(4-Chloro-2-isopropyl-2H-pyrazol-3-yl)-4-methoxy-phenyl]-3-(4-chloro-phenyl)-urea |

TABLE 3-continued

| Cmpd # | Structure | Chemical Name |
|---|---|---|
| 46 | 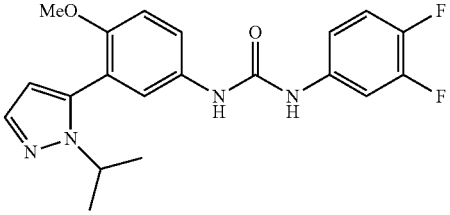 [SMILES: COc1ccc(NC(=O)Nc2ccc(F)c(F)c2)cc1-c1ccnn1C(C)C] | 1-(3,4-Difluoro-phenyl)-3-[3-(2-isopropyl-2H-pyrazol-3-yl)-4-methoxy-phenyl]-urea |
| 47 | 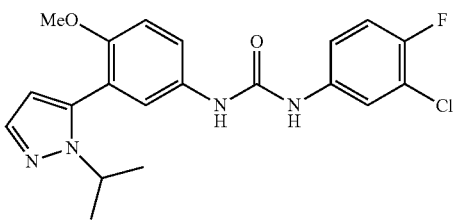 [SMILES: COc1ccc(NC(=O)Nc2ccc(F)c(Cl)c2)cc1-c1ccnn1C(C)C] | 1-(3-Chloro-4-fluoro-phenyl)-3-[3-(2-isopropyl-2H-pyrazol-3-yl)-4-methoxy-phenyl]-urea |
| 48 | 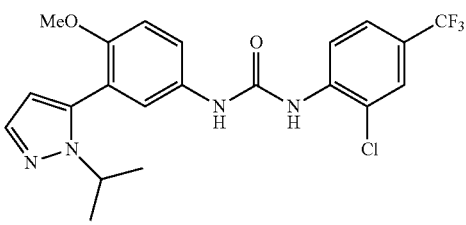 [SMILES: COc1ccc(NC(=O)Nc2ccc(C(F)(F)F)cc2Cl)cc1-c1ccnn1C(C)C] | 1-(2-Chloro-4-trifluoromethyl-phenyl)-3-[3-(2-isopropyl-2H-pyrazol-3-yl)-4-methoxy-phenyl]-urea |
| 49 | 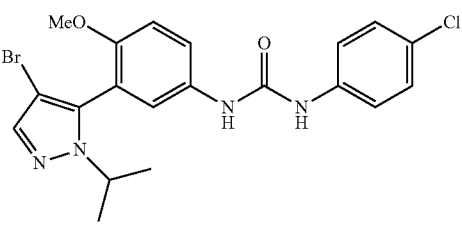 [SMILES: COc1ccc(NC(=O)Nc2ccc(Cl)cc2)cc1-c1c(Br)cnn1C(C)C] | 1-[3-(4-Bromo-2-isopropyl-2H-pyrazol-3-yl)-4-methoxy-phenyl]-3-(4-chloro-phenyl)-urea |
| 50 | 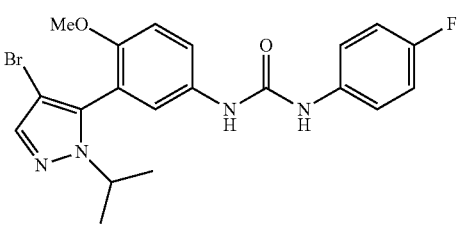 | 1-[3-(4-Bromo-2-isopropyl-2H-pyrazol-3-yl)-4-methoxy-phenyl]-3-(4-fluoro-phenyl)-urea |
| 51 | 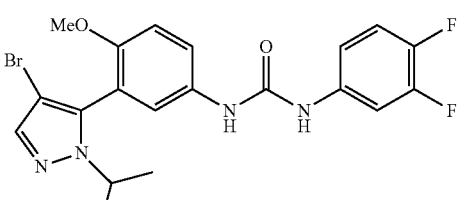 | 1-[3-(4-Bromo-2-isopropyl-2H-pyrazol-3-yl)-4-methoxy-phenyl]-3-(3,4-difluoro-phenyl)-urea |
| 52 | 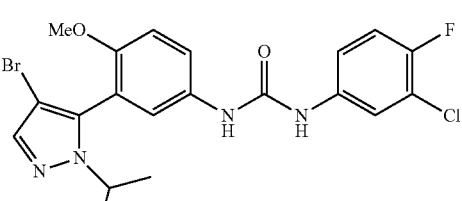 | 1-[3-(4-Bromo-2-isopropyl-2H-pyrazol-3-yl)-4-methoxy-phenyl]-3-(3-chloro-4-fluoro-phenyl)-urea |

TABLE 3-continued

| Cmpd # | Structure | Chemical Name |
|---|---|---|
| 53 | 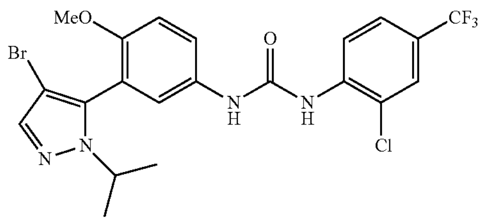 | 1-[3-(4-Bromo-2-isopropyl-2H-pyrazol-3-yl)-4-methoxy-phenyl]-3-(2-Chloro-4-trifluoromethyl-phenyl)-urea |
| 54 | 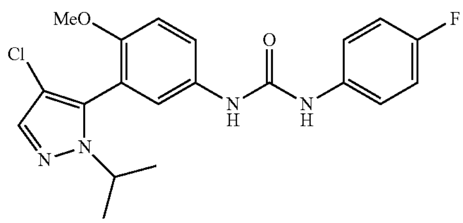 [SMILES: COc1ccc(NC(=O)Nc2ccc(F)cc2)cc1-c1c(Cl)cnn1C(C)C] | 1-[3-(4-Chloro-2-isopropyl-2H-pyrazol-3-yl)-4-methoxy-phenyl]-3-(4-fluoro-phenyl)-urea |
| 55 | 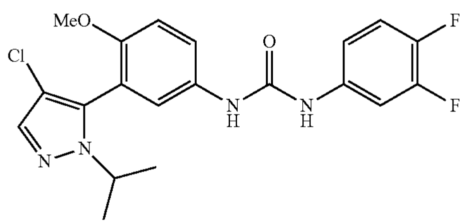 [SMILES: COc1ccc(NC(=O)Nc2ccc(F)c(F)c2)cc1-c1c(Cl)cnn1C(C)C] | 1-[3-(4-Chloro-2-isopropyl-2H-pyrazol-3-yl)-4-methoxy-phenyl]-3-(3,4-difluoro-phenyl)-urea |
| 56 | 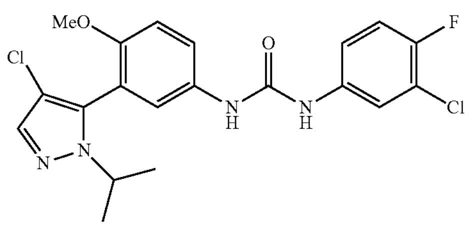 [SMILES: COc1ccc(NC(=O)Nc2ccc(F)c(Cl)c2)cc1-c1c(Cl)cnn1C(C)C] | 1-(3-Chloro-4-fluoro-phenyl)-3-[3-(4-Chloro-2-isopropyl-2H-pyrazol-3-yl)-4-methoxy-phenyl]-urea |
| 57 | 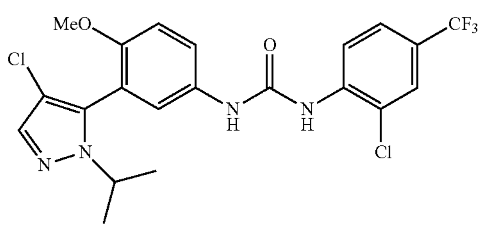 [SMILES: COc1ccc(NC(=O)Nc2ccc(C(F)(F)F)cc2Cl)cc1-c1c(Cl)cnn1C(C)C] | 1-[3-(4-Chloro-2-isopropyl-2H-pyrazol-3-yl)-4-methoxy-phenyl]-3-(2-Chloro-4-trifluoromethyl-phenyl)-urea |
| 58 | 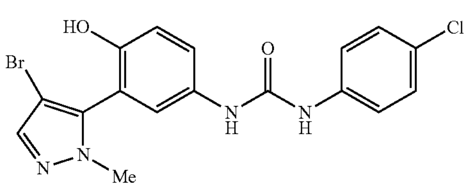 [SMILES: Cn1ncc(Br)c1-c1cc(NC(=O)Nc2ccc(Cl)cc2)ccc1O] | 1-[3-(4-Bromo-2-methyl-2H-pyrazol-3-yl)-4-hydroxy-phenyl]-3-(4-chloro-phenyl)-urea |
| 59 | 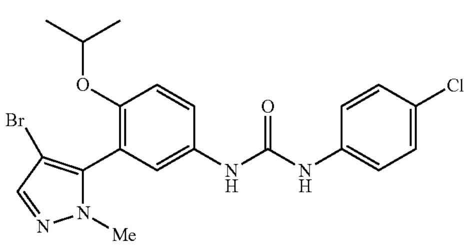 [SMILES: CC(C)Oc1ccc(NC(=O)Nc2ccc(Cl)cc2)cc1-c1c(Br)cnn1C] | 1-[3-(4-Bromo-2-methyl-2H-pyrazol-3-yl)-4-isopropoxy-phenyl]-3-(4-chloro-phenyl)-urea |

TABLE 3-continued

| Cmpd # | Structure | Chemical Name |
|---|---|---|
| 60 | 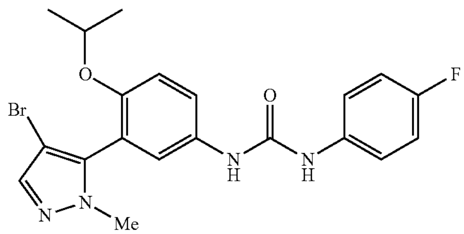 [SMILES: CC(C)Oc1ccc(NC(=O)Nc2ccc(F)cc2)cc1-c1c(Br)cnn1C] | 1-[3-(4-Bromo-2-methyl-2H-pyrazol-3-yl)-4-isopropoxy-phenyl]-3-(4-fluoro-phenyl)-urea |
| 61 | 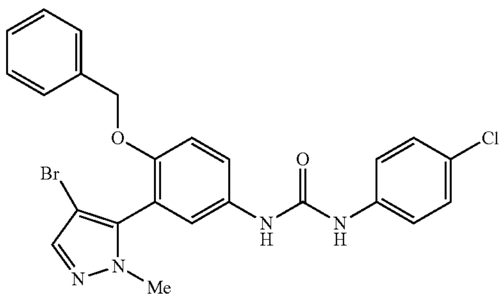 [SMILES: Cn1ncc(Br)c1-c1cc(NC(=O)Nc2ccc(Cl)cc2)ccc1OCc1ccccc1] | 1-[4-Benzyloxy-3-(4-bromo-2-methyl-2H-pyrazol-3-yl)-phenyl]-3-(4-chloro-phenyl)-urea |
| 62 | 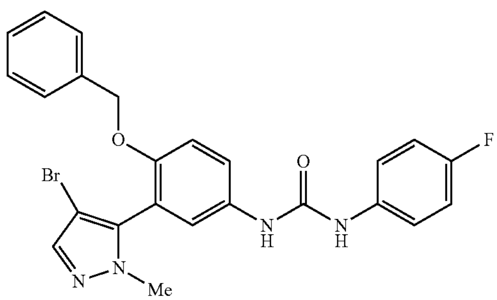 [SMILES: Cn1ncc(Br)c1-c1cc(NC(=O)Nc2ccc(F)cc2)ccc1OCc1ccccc1] | 1-[4-Benzyloxy-3-(4-bromo-2-methyl-2H-pyrazol-3-yl)-phenyl]-3-(4-fluoro-phenyl)-urea |
| 63 | 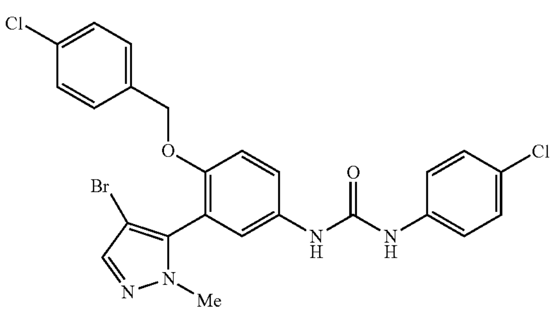 [SMILES: Cn1ncc(Br)c1-c1cc(NC(=O)Nc2ccc(Cl)cc2)ccc1OCc1ccc(Cl)cc1] | 1-[3-(4-Bromo-2-methyl-2H-pyrazol-3-yl)-4-(4-chloro-benzyloxy)-phenyl]-3-(4-chloro-phenyl)-urea |
| 64 | 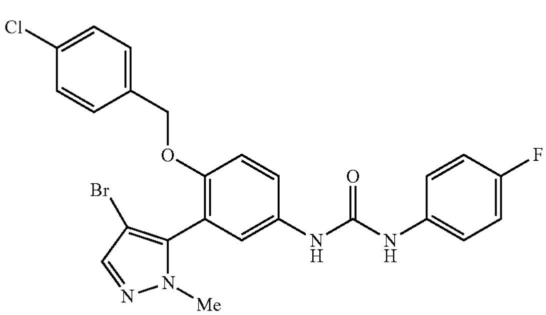 [SMILES: Cn1ncc(Br)c1-c1cc(NC(=O)Nc2ccc(F)cc2)ccc1OCc1ccc(Cl)cc1] | 1-[3-(4-Bromo-2-methyl-2H-pyrazol-3-yl)-4-(4-chloro-benzyloxy)-phenyl]-3-(4-fluoro-phenyl)-urea |

TABLE 3-continued

| Cmpd # | Structure | Chemical Name |
|---|---|---|
| 65 | 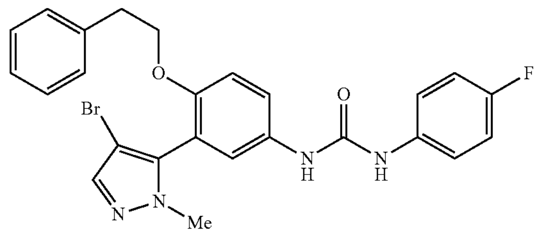 [SMILES: Cn1ncc(Br)c1-c1cc(NC(=O)Nc2ccc(F)cc2)ccc1OCCc1ccccc1] | 1-[3-(4-Bromo-2-methyl-2H-pyrazol-3-yl)-4-phenethyloxy-phenyl]-3-(4-fluoro-phenyl)-urea |
| 66 | 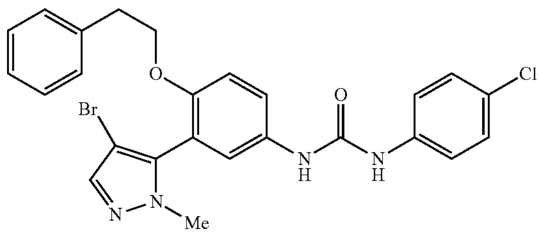 [SMILES: Cn1ncc(Br)c1-c1cc(NC(=O)Nc2ccc(Cl)cc2)ccc1OCCc1ccccc1] | 1-[3-(4-Bromo-2-methyl-2H-pyrazol-3-yl)-4-phenethyloxy-phenyl]-3-(4-chloro-phenyl)-urea |
| 67 | 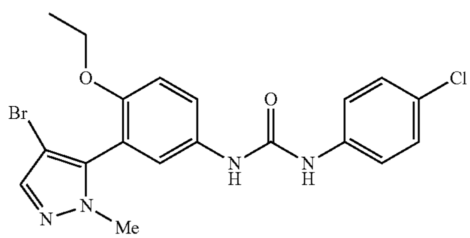 [SMILES: CCOc1ccc(NC(=O)Nc2ccc(Cl)cc2)cc1-c1c(Br)cnn1C] | 1-[3-(4-Bromo-2-methyl-2H-pyrazol-3-yl)-4-ethoxy-phenyl]-3-(4-chloro-phenyl)-urea |
| 68 | 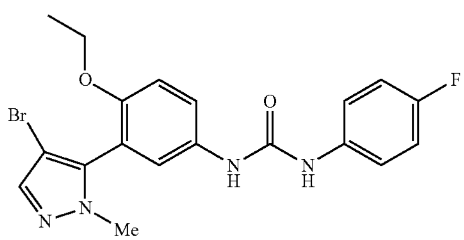 [SMILES: CCOc1ccc(NC(=O)Nc2ccc(F)cc2)cc1-c1c(Br)cnn1C] | 1-[3-(4-Bromo-2-methyl-2H-pyrazol-3-yl)-4-ethoxy-phenyl]-3-(4-fluoro-phenyl)-urea |
| 69 | 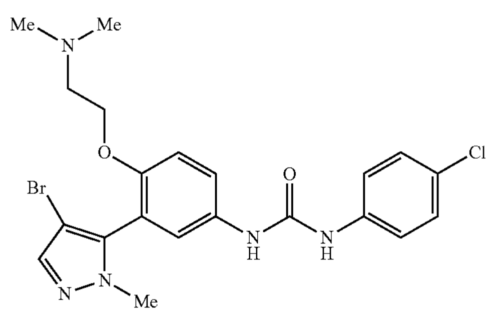 [SMILES: CN(C)CCOc1ccc(NC(=O)Nc2ccc(Cl)cc2)cc1-c1c(Br)cnn1C] | 1-[3-(4-Bromo-2-methyl-2H-pyrazol-3-yl)-4-(2-dimethylamino-ethoxy)-phenyl]-3-(4-chloro-phenyl)-urea |
| 70 | 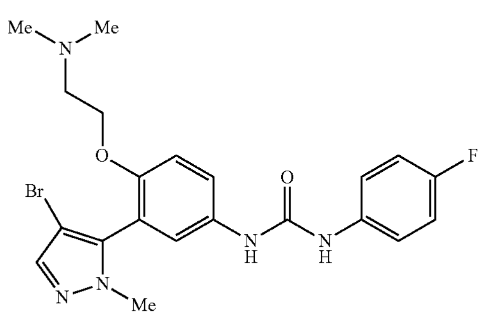 [SMILES: CN(C)CCOc1ccc(NC(=O)Nc2ccc(F)cc2)cc1-c1c(Br)cnn1C] | 1-[3-(4-Bromo-2-methyl-2H-pyrazol-3-yl)-4-(2-dimethylamino-ethoxy)-phenyl]-3-(4-fluoro-phenyl)-urea |

TABLE 3-continued

| Cmpd # | Structure | Chemical Name |
|---|---|---|
| 71 | 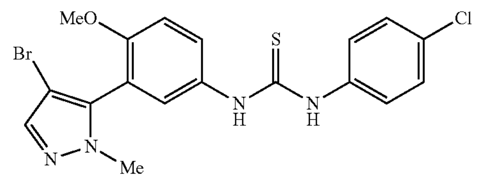 | 1-[3-(4-Bromo-2-methyl-2H-pyrazol-3-yl)-4-methoxy-phenyl]-3-(4-chloro-phenyl)-thiourea |
| 72 | 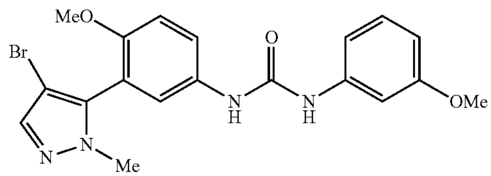 | 1-[3-(4-Bromo-2-methyl-2H-pyrazol-3-yl)-4-methoxy-phenyl]-3-(3-methoxy-phenyl)-urea |
| 73 | 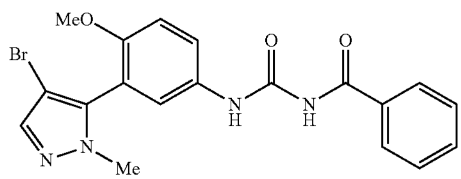 | 1-Benzoyl-3-[3-(4-bromo-2-methyl-2H-pyrazol-3-yl)-4-methoxy-phenyl]-urea |
| 74 | 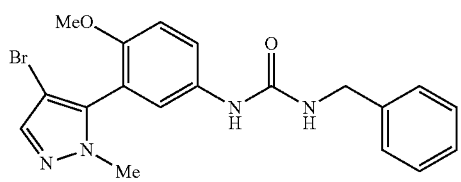 | 1-Benzyl-3-[3-(4-bromo-2-methyl-2H-pyrazol-3-yl)-4-methoxy-phenyl]-urea |
| 75 | 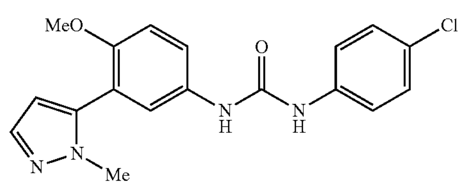 [SMILES: COc1ccc(NC(=O)Nc2ccc(Cl)cc2)cc1-c1ccnn1C] | 1-(4-Chloro-phenyl)-3-[4-methoxy-3-(2-methyl-2H-pyrazol-3-yl)-phenyl]-urea |
| 76 | 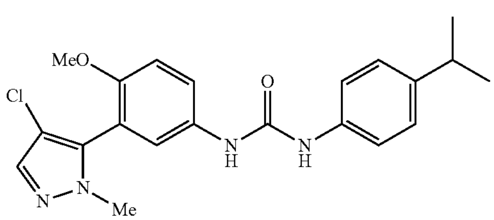 [SMILES: COc1ccc(NC(=O)Nc2ccc(C(C)C)cc2)cc1-c1c(Cl)cnn1C] | 1-[3-(4-Chloro-2-methyl-2H-pyrazol-3-yl)-4-methoxy-phenyl]-3-(4-isopropyl-phenyl)-urea |
| 77 | 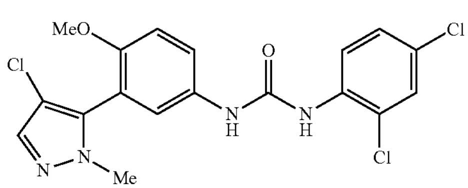 [SMILES: COc1ccc(NC(=O)Nc2ccc(Cl)cc2Cl)cc1-c1c(Cl)cnn1C] | 1-[3-(4-Chloro-2-methyl-2H-pyrazol-3-yl)-4-methoxy-phenyl]-(2,4-dichloro-phenyl)-urea |
| 78 | 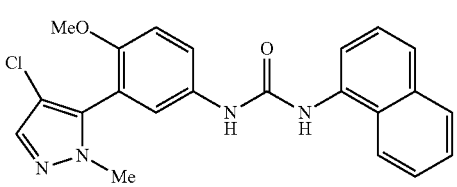 [SMILES: COc1ccc(NC(=O)Nc2cccc3ccccc23)cc1-c1c(Cl)cnn1C] | 1-[3-(4-Chloro-2-methyl-2H-pyrazol-3-yl)-4-methoxy-phenyl]-3-naphthalen-1-yl-urea |

TABLE 3-continued

| Cmpd # | Structure | Chemical Name |
|---|---|---|
| 79 | 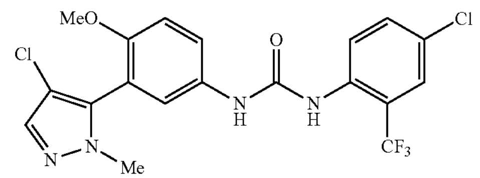 [SMILES: COc1ccc(NC(=O)Nc2ccc(Cl)cc2C(F)(F)F)cc1-c1c(Cl)cnn1C] | 1-[3-(4-Chloro-2-methyl-2H-pyrazol-3-yl)-4-methoxy-phenyl]-3-(4-chloro-2-trifluoromethyl-phenyl)-urea |
| 80 | 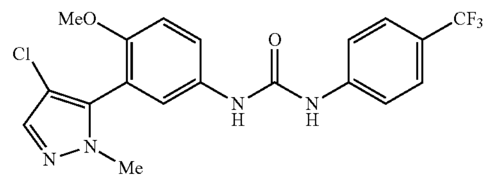 [SMILES: COc1ccc(NC(=O)Nc2ccc(C(F)(F)F)cc2)cc1-c1c(Cl)cnn1C] | 1-[3-(4-Chloro-2-methyl-2H-pyrazol-3-yl)-4-methoxy-phenyl]-3-(4-trifluoromethyl-phenyl)-urea |
| 81 | 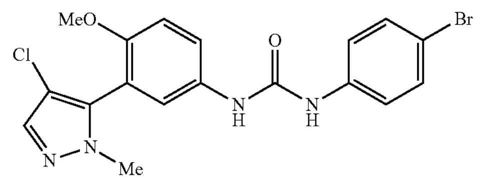 [SMILES: COc1ccc(NC(=O)Nc2ccc(Br)cc2)cc1-c1c(Cl)cnn1C] | 1-(4-Bromo-phenyl)-3-[3-(4-chloro-2-methyl-2H-pyrazol-3-yl)-4-methoxy-phenyl]-urea |
| 82 | 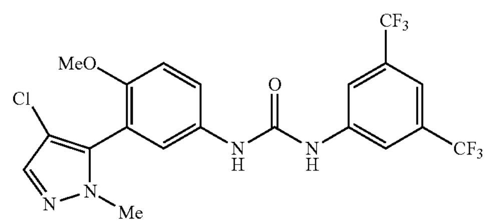 [SMILES: COc1ccc(NC(=O)Nc2cc(C(F)(F)F)cc(C(F)(F)F)c2)cc1-c1c(Cl)cnn1C] | 1-(3,5-Bis-trifluoromethyl-phenyl)-3-[3-(4-chloro-2-methyl-2H-pyrazol-3-yl)-4-methoxy-phenyl]-urea |
| 83 | 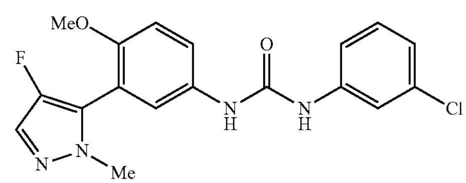 [SMILES: COc1ccc(NC(=O)Nc2cccc(Cl)c2)cc1-c1c(F)cnn1C] | 1-(3-Chloro-phenyl)-3-[3-(4-fluoro-2-methyl-2H-pyrazol-3-yl)-4-methoxy-phenyl]-urea |
| 84 | 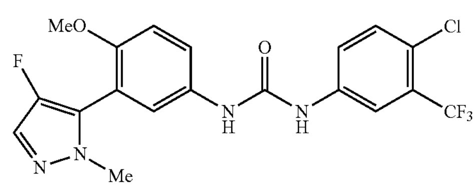 [SMILES: COc1ccc(NC(=O)Nc2ccc(Cl)c(C(F)(F)F)c2)cc1-c1c(F)cnn1C] | 1-(4-Chloro-3-trifluoromethyl-phenyl)-3-[3-(4-fluoro-2-methyl-2H-pyrazol-3-yl)-4-methoxy-phenyl]-urea |
| 85 | 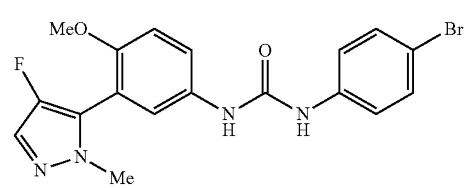 [SMILES: COc1ccc(NC(=O)Nc2ccc(Br)cc2)cc1-c1c(F)cnn1C] | 1-(4-Bromo-phenyl)-3-[3-(4-fluoro-2-methyl-2H-pyrazol-3-yl)-4-methoxy-phenyl]-urea |
| 86 | 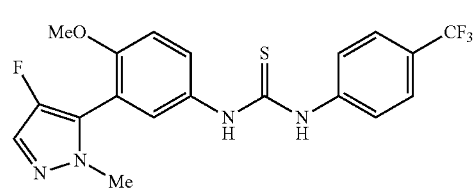 [SMILES: COc1ccc(NC(=S)Nc2ccc(C(F)(F)F)cc2)cc1-c1c(F)cnn1C] | 1-[3-(4-Fluoro-2-methyl-2H-pyrazol-3-yl)-4-methoxy-phenyl]-3-(4-trifluoromethyl-phenyl)-thiourea |

TABLE 3-continued

| Cmpd # | Structure | Chemical Name |
|---|---|---|
| 87 | 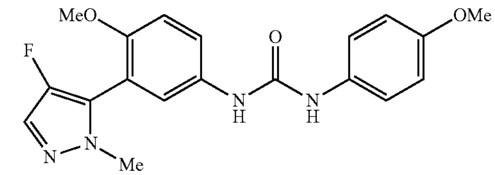 [SMILES: COc1ccc(NC(=O)Nc2ccc(OC)c(-c3c(F)cnn3C)c2)cc1] | 1-[3-(4-Fluoro-2-methyl-2H-pyrazol-3-yl)-4-methoxy-phenyl]-3-(4-methoxy-phenyl)-urea |
| 88 | 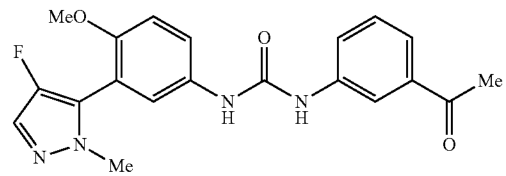 [SMILES: COc1ccc(NC(=O)Nc2cccc(C(C)=O)c2)cc1-c1c(F)cnn1C] | 1-(3-Acetyl-phenyl)-3-[3-(4-fluoro-2-methyl-2H-pyrazol-3-yl)-4-methoxy-phenyl]-urea |
| 89 | 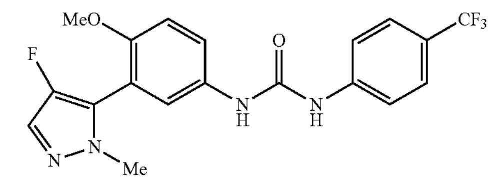 [SMILES: COc1ccc(NC(=O)Nc2ccc(C(F)(F)F)cc2)cc1-c1c(F)cnn1C] | 1-[3-(4-Fluoro-2-methyl-2H-pyrazol-3-yl)-4-methoxy-phenyl]-3-(4-trifluoromethyl-phenyl)-urea |
| 90 | 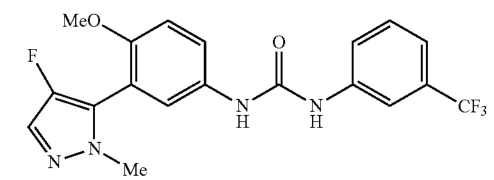 [SMILES: COc1ccc(NC(=O)Nc2cccc(C(F)(F)F)c2)cc1-c1c(F)cnn1C] | 1-[3-(4-Fluoro-2-methyl-2H-pyrazol-3-yl)-4-methoxy-phenyl]-3-(3-trifluoromethyl-phenyl)-urea |
| 91 | 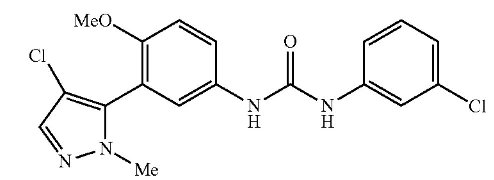 [SMILES: COc1ccc(NC(=O)Nc2cccc(Cl)c2)cc1-c1c(Cl)cnn1C] | 1-[3-(4-Chloro-2-methyl-2H-pyrazol-3-yl)-4-methoxy-phenyl]-3-(3-chloro-phenyl)-urea |
| 92 | 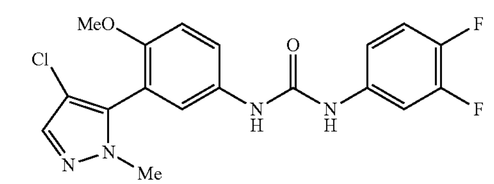 [SMILES: COc1ccc(NC(=O)Nc2ccc(F)c(F)c2)cc1-c1c(Cl)cnn1C] | 1-[3-(4-Chloro-2-methyl-2H-pyrazol-3-yl)-4-methoxy-phenyl]-3-(3,4-difluoro-phenyl)-urea |
| 93 | 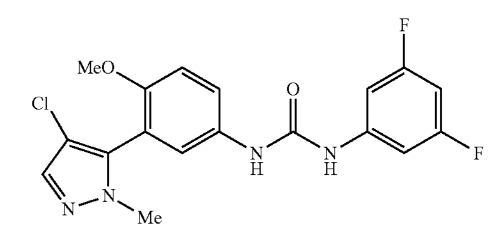 [SMILES: COc1ccc(NC(=O)Nc2cc(F)cc(F)c2)cc1-c1c(Cl)cnn1C] | 1-[3-(4-Chloro-2-methyl-2H-pyrazol-3-yl)-4-methoxy-phenyl]-3-(3,5-difluoro-phenyl)-urea |
| 94 | 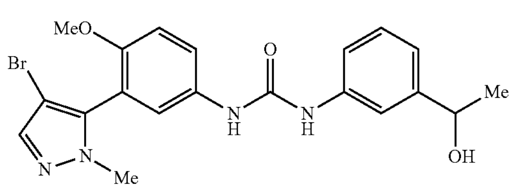 [SMILES: COc1ccc(NC(=O)Nc2cccc(C(C)O)c2)cc1-c1c(Br)cnn1C] | 1-[3-(4-Bromo-2-methyl-2H-pyrazol-3-yl)-4-methoxy-phenyl]-3-[3-(1-hydroxy-ethyl)-phenyl]-urea |

TABLE 3-continued

| Cmpd # | Structure | Chemical Name |
| --- | --- | --- |
| 95 | 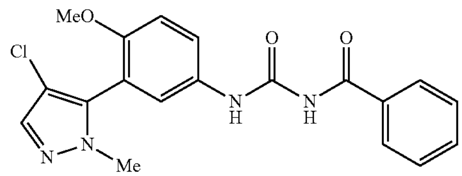 [SMILES: COc1ccc(NC(=O)NC(=O)c2ccccc2)cc1-c1c(Cl)cnn1C] | 1-Benzoyl-3-[3-(4-chloro-2-methyl-2H-pyrazol-3-yl)-4-methoxy-phenyl]-urea |
| 96 | 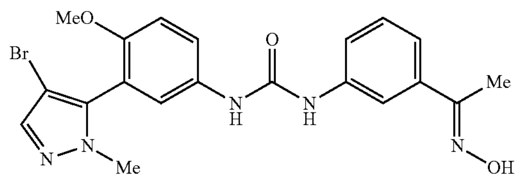 [SMILES: COc1ccc(NC(=O)Nc2cccc(/C(C)=N/O)c2)cc1-c1c(Br)cnn1C] | 1-[3-(4-Bromo-2-methyl-2H-pyrazol-3-yl)-4-methoxy-phenyl]-3-[3-(1-hydroxyimino-ethyl)-phenyl]-urea |
| 97 | 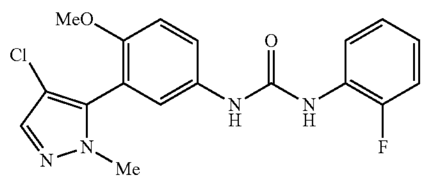 [SMILES: COc1ccc(NC(=O)Nc2ccccc2F)cc1-c1c(Cl)cnn1C] | 1-[3-(4-Chloro-2-methyl-2H-pyrazol-3-yl)-4-methoxy-phenyl]-3-(2-fluoro-phenyl)-urea |
| 98 | 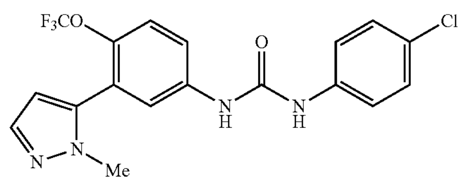 [SMILES: Cn1nccc1-c1cc(NC(=O)Nc2ccc(Cl)cc2)ccc1OC(F)(F)F] | 1-(4-Chloro-phenyl)-3-[3-(2-methyl-2H-pyrazol-3-yl)-4-trifluoromethoxy-phenyl]-urea |
| 99 | 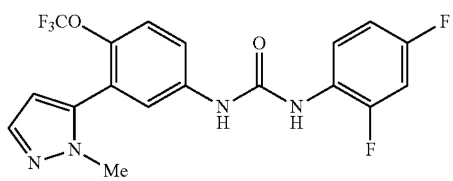 [SMILES: Cn1nccc1-c1cc(NC(=O)Nc2ccc(F)cc2F)ccc1OC(F)(F)F] | 1-(2,4-Difluoro-phenyl)-3-[3-(2-methyl-2H-pyrazol-3-yl)-4-trifluoromethoxy-phenyl]-urea |
| 100 | 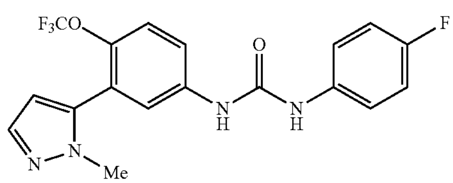 [SMILES: Cn1nccc1-c1cc(NC(=O)Nc2ccc(F)cc2)ccc1OC(F)(F)F] | 1-(4-Fluoro-phenyl)-3-[3-(2-methyl-2H-pyrazol-3-yl)-4-trifluoromethoxy-phenyl]-urea |
| 101 | 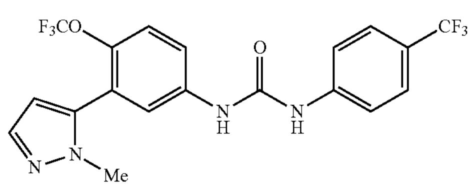 [SMILES: Cn1nccc1-c1cc(NC(=O)Nc2ccc(C(F)(F)F)cc2)ccc1OC(F)(F)F] | 1-[3-(2-Methyl-2H-pyrazol-3-yl)-4-trifluoromethoxy-phenyl]-3-(4-trifluoromethyl-phenyl)-urea |
| 102 | 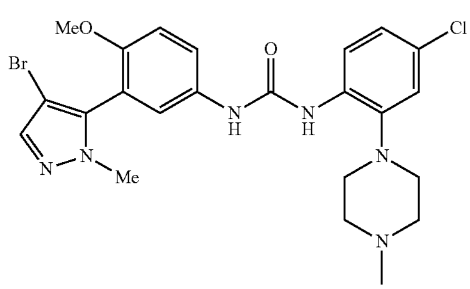 [SMILES: COc1ccc(NC(=O)Nc2ccc(Cl)cc2N2CCN(C)CC2)cc1-c1c(Br)cnn1C] | 1-[3-(4-Bromo-2-methyl-2H-pyrazol-3-yl)-4-methoxy-phenyl]-3-[4-chloro-2-(4-methyl-piperazin-1-yl)-phenyl]-urea |

TABLE 3-continued

| Cmpd # | Structure | Chemical Name |
| --- | --- | --- |
| 103 | 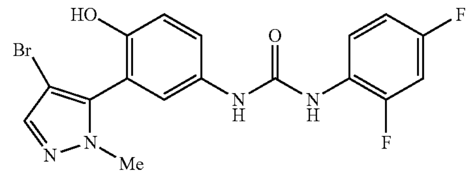 | 1-[3-(4-Bromo-2-methyl-2H-pyrazol-3-yl)-4-hydroxy-phenyl]-3-(2,4-difluoro-phenyl)-urea |
| 104 | 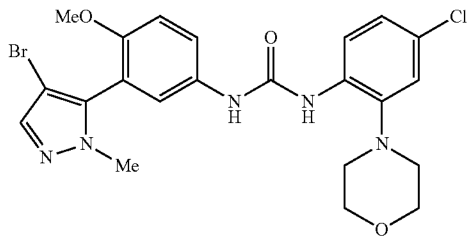 [SMILES: COc1ccc(NC(=O)Nc2ccc(Cl)cc2N2CCOCC2)cc1-c1c(Br)cnn1C] | 1-[3-(4-Bromo-2-methyl-2H-pyrazol-3-yl)-4-methoxy-phenyl]-(4-chloro-2-morpholin-4-yl-phenyl)-urea |
| 105 | 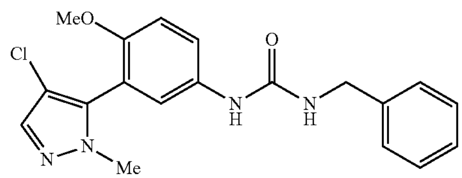 [SMILES: COc1ccc(NC(=O)NCc2ccccc2)cc1-c1c(Cl)cnn1C] | 1-Benzyl-3-[3-(4-chloro-2-methyl-2H-pyrazol-3-yl)-4-methoxy phenyl]-urea |
| 106 | 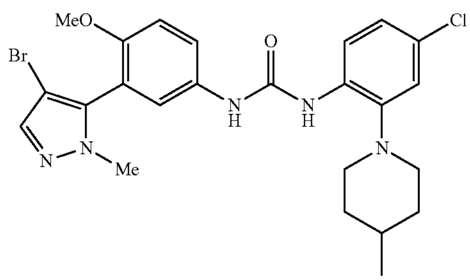 [SMILES: COc1ccc(NC(=O)Nc2ccc(Cl)cc2N2CCC(C)CC2)cc1-c1c(Br)cnn1C] | 1-[3-(4-Bromo-2-methyl-2H-pyrazol-3-yl)-4-methoxy-phenyl]-3-[4-chloro-2-(4-methyl-piperidin-1-yl)-phenyl]-urea |
| 107 | 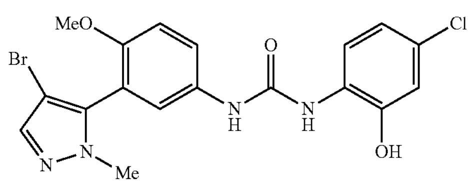 [SMILES: COc1ccc(NC(=O)Nc2ccc(Cl)cc2O)cc1-c1c(Br)cnn1C] | 1-[3-(4-Bromo-2-methyl-2H-pyrazol-3-yl)-4-methoxy-phenyl]-3-(4-chloro-2-hydroxy-phenyl)-urea |
| 108 | 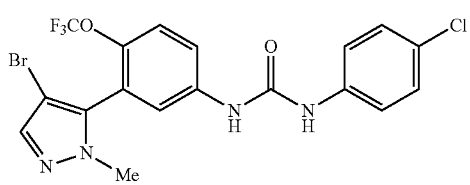 | 1-[3-(4-Bromo-2-methyl-2H-pyrazol-3-yl)-4-trifluoromethoxy-phenyl]-3-(4-chloro-phenyl)-urea |
| 109 | 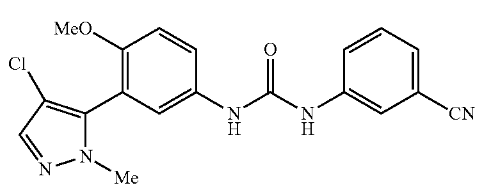 [SMILES: COc1ccc(NC(=O)Nc2cccc(C#N)c2)cc1-c1c(Cl)cnn1C] | 1-[3-(4-Chloro-2-methyl-2H-pyrazol-3-yl)-4-methoxy-phenyl]-3-(3-cyano-phenyl)-urea |

TABLE 3-continued

| Cmpd # | Structure | Chemical Name |
|---|---|---|
| 110 | 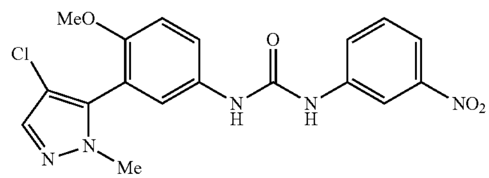 [SMILES: COc1ccc(NC(=O)Nc2cccc([N+](=O)[O-])c2)cc1-c1c(Cl)cnn1C] | 1-[3-(4-Chloro-2-methyl-2H-pyrazol-3-yl)-4-methoxy-phenyl]-3-(3-nitro-phenyl)-urea |
| 111 | 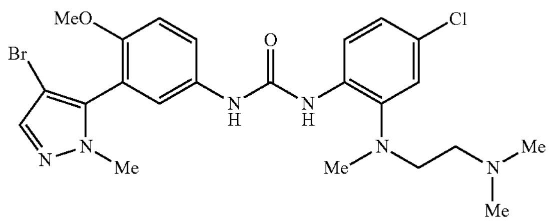 [SMILES: COc1ccc(NC(=O)Nc2ccc(Cl)cc2N(C)CCN(C)C)cc1-c1c(Br)cnn1C] | 1-[3-(4-Bromo-2-methyl-2H-pyrazol-3-yl)-4-methoxy-phenyl]-3-{4-chloro-2-[(2-dimethylamino-ethyl)-methyl-amino]-phenyl}-urea |
| 112 | 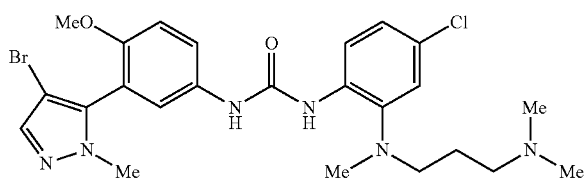 [SMILES: COc1ccc(NC(=O)Nc2ccc(Cl)cc2N(C)CCCN(C)C)cc1-c1c(Br)cnn1C] | 1-[3-(4-Bromo-2-methyl-2H-pyrazol-3-yl)-4-methoxy-phenyl]-3-{4-chloro-2-[(3-dimethylamino-propyl)-methyl-amino]-phenyl}-urea |
| 113 | 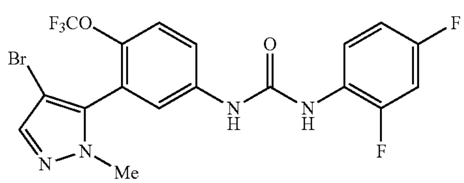 | 1-[3-(4-Bromo-2-methyl-2H-pyrazol-3-yl)-4-trifluoromethoxy-phenyl]-3-(2,4-difluoro-phenyl)-urea |
| 114 | 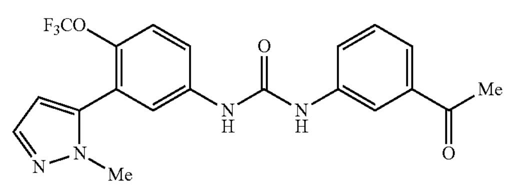 [SMILES: CC(=O)c1cccc(NC(=O)Nc2ccc(OC(F)(F)F)c(-c3ccnn3C)c2)c1] | 1-(3-Acetyl-phenyl)-3-[3-(2-methyl-2H-pyrazol-3-yl)-4-trifluoromethoxy-phenyl]-urea |
| 115 | 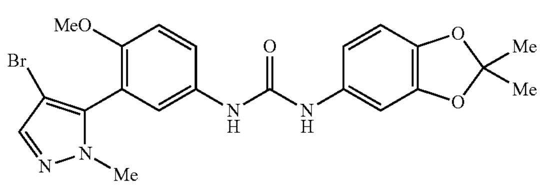 [SMILES: COc1ccc(NC(=O)Nc2ccc3c(c2)OC(C)(C)O3)cc1-c1c(Br)cnn1C] | 1-[3-(4-Bromo-2-methyl-2H-pyrazol-3-yl)-4-methoxy-phenyl]-3-(2,2-difluoro-benzo[1,3]dioxol-5-yl)-urea |
| 116 | 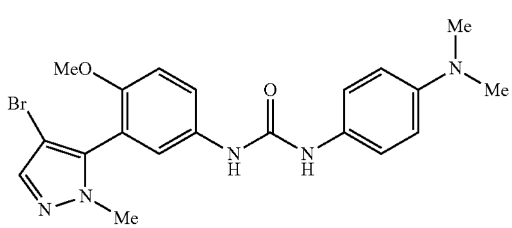 [SMILES: COc1ccc(NC(=O)Nc2ccc(N(C)C)cc2)cc1-c1c(Br)cnn1C] | 1-[3-(4-Bromo-2-methyl-2H-pyrazol-3-yl)-4-methoxy-phenyl]-3-(4-dimethylamino-phenyl)-urea |

TABLE 3-continued

| Cmpd # | Structure | Chemical Name |
| --- | --- | --- |
| 117 | 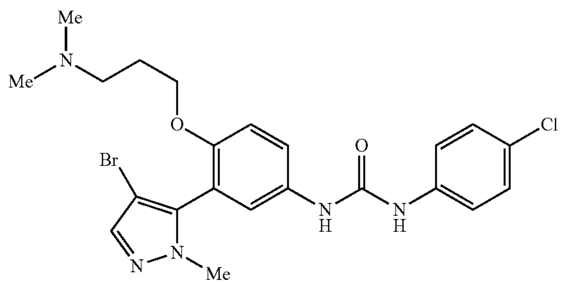 [SMILES: CN(C)CCCOc1ccc(NC(=O)Nc2ccc(Cl)cc2)cc1-c1c(Br)cnn1C] | 1-[3-(4-Bromo-2-methyl-2H-pyrazol-3-yl)-4-(3-dimethylamino-propoxy)-phenyl]-3-(4-chloro-phenyl)-urea |
| 118 | 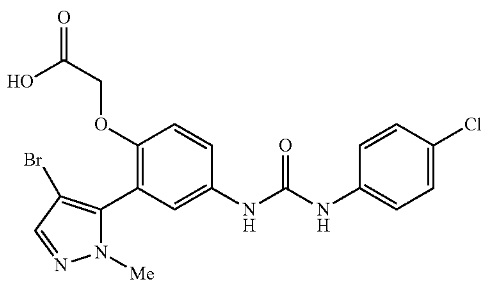 [SMILES: Cn1ncc(Br)c1-c1cc(NC(=O)Nc2ccc(Cl)cc2)ccc1OCC(=O)O] | {2-(4-Bromo-2-methyl-2H-pyrazol-3-yl)-4-[3-(4-chloro-phenyl)-ureido]-phenoxy}-acetic acid |
| 119 | 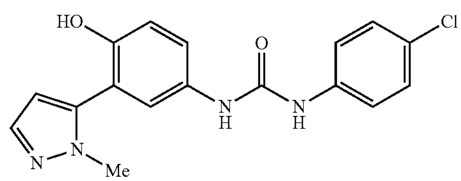 [SMILES: Cn1nccc1-c1cc(NC(=O)Nc2ccc(Cl)cc2)ccc1O] | 1-(4-Chloro-phenyl)-3-[4-hydroxy-3-(2-methyl-2H-pyrazol-3-yl)-phenyl]-urea |
| 120 | 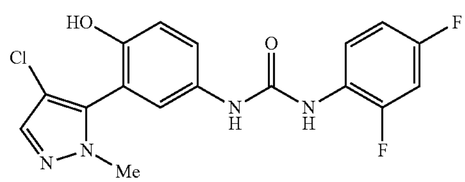 [SMILES: Cn1ncc(Cl)c1-c1cc(NC(=O)Nc2ccc(F)cc2F)ccc1O] | 1-[3-(4-Chloro-2-methyl-2H-pyrazol-3-yl)-4-hydroxy-phenyl]-3-(2,4-difluoro-phenyl)-urea |
| 121 | 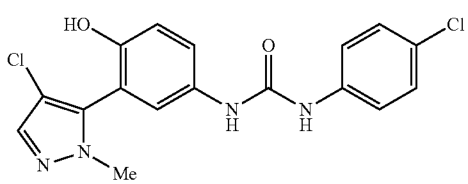 [SMILES: Cn1ncc(Cl)c1-c1cc(NC(=O)Nc2ccc(Cl)cc2)ccc1O] | 1-[3-(4-Chloro-2-methyl-2H-pyrazol-3-yl)-4-hydroxy-phenyl]-3-(4-chloro-phenyl)-urea |
| 122 | 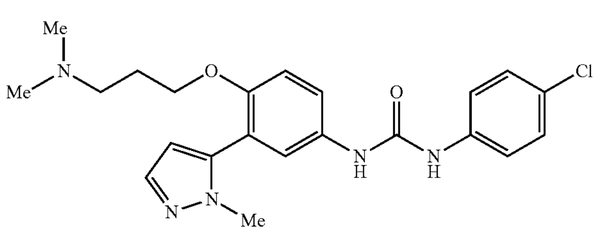 [SMILES: CN(C)CCCOc1ccc(NC(=O)Nc2ccc(Cl)cc2)cc1-c1ccnn1C] | 1-(4-Chloro-phenyl)-3-[4-(3-dimethylamino-propoxy)-3-(2-methyl-2H-pyrazol-3-yl)-phenyl]-urea |

TABLE 3-continued

| Cmpd # | Structure | Chemical Name |
|---|---|---|
| 123 | 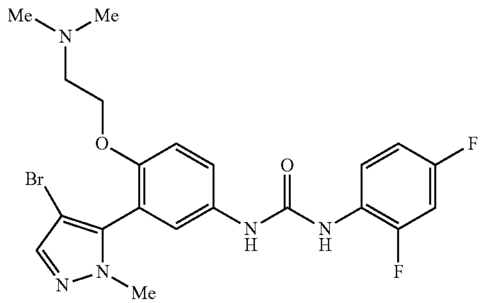 [SMILES: CN(C)CCOc1ccc(NC(=O)Nc2ccc(F)cc2F)cc1-c1c(Br)cnn1C] | 1-[3-(4-Bromo-2-methyl-2H-pyrazol-3-yl)-4-(2-dimethylamino-ethoxy)-phenyl]-3-(2,4-difluoro-pheny)-urea |
| 124 | 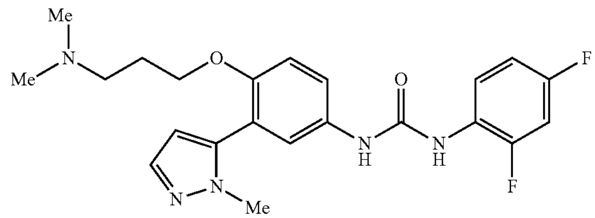 [SMILES: CN(C)CCCOc1ccc(NC(=O)Nc2ccc(F)cc2F)cc1-c1ccnn1C] | 1-(2,4-Difluoro-phenyl)-3-[4-(3-dimethylamino-propoxy)-3-(2-methyl-2H-pyrazol-3-yl)-phenyl]-urea |
| 125 | 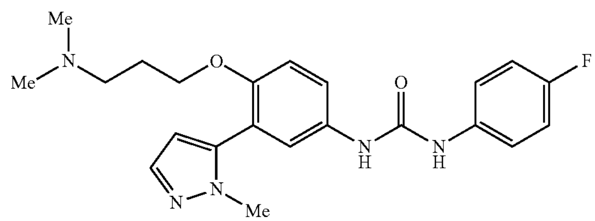 [SMILES: CN(C)CCCOc1ccc(NC(=O)Nc2ccc(F)cc2)cc1-c1ccnn1C] | 1-[4-(3-Dimethylamino-propoxy)-3-(2-methyl-2H-pyrazol-3-yl)-phenyl]-3-(4-fluoro-phenyl)-urea |
| 126 | 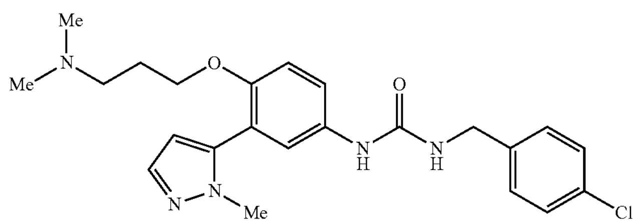 [SMILES: CN(C)CCCOc1ccc(NC(=O)NCc2ccc(Cl)cc2)cc1-c1ccnn1C] | 1-(4-Chloro-benzyl)-3-[4-(3-dimethylamino-propoxy)-3-(2-methyl-2H-pyrazol-3-yl)-phenyl]-urea |
| 127 | 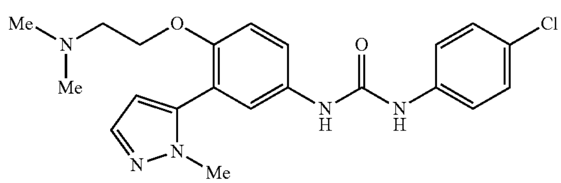 [SMILES: CN(C)CCOc1ccc(NC(=O)Nc2ccc(Cl)cc2)cc1-c1ccnn1C] | 1-(4-Chloro-phenyl)-3-[4-(2-dimethylamino-ethoxy)-3-(2-methyl-2H-pyrazol-3-yl)-phenyl]-urea |
| 128 | 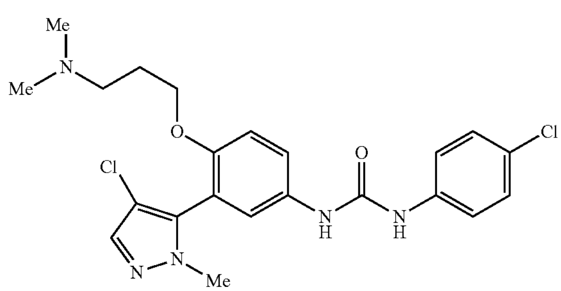 [SMILES: CN(C)CCCOc1ccc(NC(=O)Nc2ccc(Cl)cc2)cc1-c1c(Cl)cnn1C] | 1-[3-(4-Chloro-2-methyl-2H-pyrazol-3-yl)-4-(3-dimethylamino-(propoxy)-phenyl]-3-(4-chloro-phenyl)-urea |

TABLE 3-continued

| Cmpd # | Structure | Chemical Name |
|---|---|---|
| 129 | 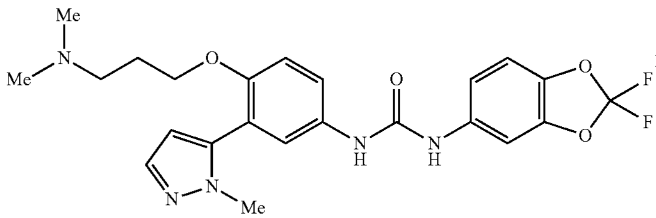 [SMILES: CN(C)CCCOc1ccc(NC(=O)Nc2ccc3c(c2)OC(F)(F)O3)cc1-c1ccnn1C] | 1-(2,2-Difluoro-benzo[1,3]dioxol-5-yl)-3-[4-(3-dimethylamino-propoxy)-3-(2-methyl-2H-pyrazol-3-yl)-phenyl]-urea |
| 130 | 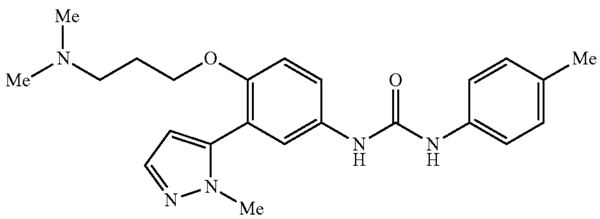 [SMILES: Cc1ccc(NC(=O)Nc2ccc(OCCCN(C)C)c(-c3ccnn3C)c2)cc1] | 1-[4-(3-Dimethylamino-propoxy)-3-(2-methyl-2H-pyrazol-3-yl)-phenyl]-3-p-tolyl-urea |
| 131 | 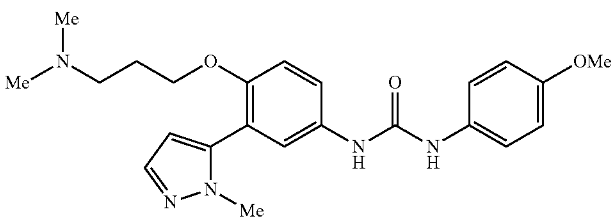 [SMILES: COc1ccc(NC(=O)Nc2ccc(OCCCN(C)C)c(-c3ccnn3C)c2)cc1] | 1-[4-(3-Dimethylamino-propoxy)-3-(2-methyl-2H-pyrazol-3-yl)-phenyl]-3-(4-methoxy-phenyl)-urea |
| 132 | 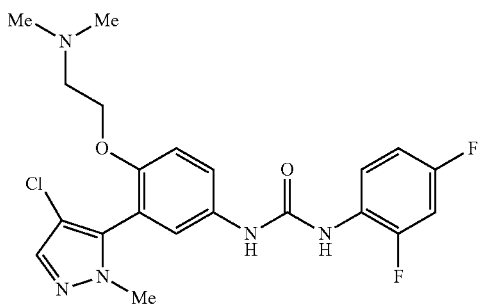 | 1-[3-(4-Chloro-2-methyl-2H-pyrazol-3-yl)-4-(2-dimethylamino-ethoxy)-phenyl]-3-(2,4-difluoro-phenyl)-urea |
| 133 | 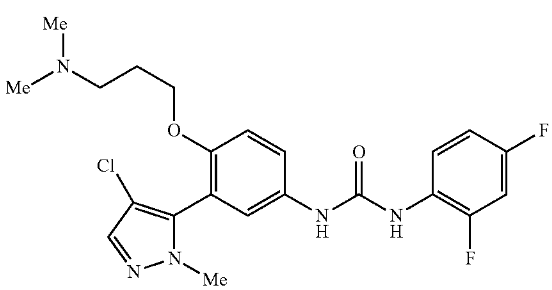 [SMILES: CN(C)CCCOc1ccc(NC(=O)Nc2ccc(F)cc2F)cc1-c1c(Cl)cnn1C] | 1-[3-(4-Chloro-2-methyl-2H-pyrazol-3-yl)-4-(3-dimethylamino-propoxy)-phenyl]-3-(2,4-difluoro-phenyl)-urea |
| 134 | 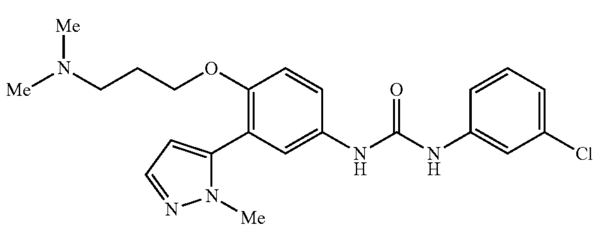 [SMILES: CN(C)CCCOc1ccc(NC(=O)Nc2cccc(Cl)c2)cc1-c1ccnn1C] | 1-(3-Chloro-phenyl)-3-[4-(3-dimethylamino-propoxy)-3-(2-methyl-2H-pyrazol-3-yl)-phenyl]-urea |

TABLE 3-continued

| Cmpd # | Structure | Chemical Name |
|---|---|---|
| 135 | 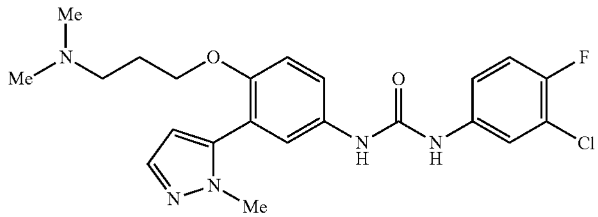 [SMILES: CN(C)CCCOc1ccc(NC(=O)Nc2ccc(F)c(Cl)c2)cc1-c1ccnn1C] | 1-(3-Chloro-4-fluoro-phenyl)-3-[4-(3-dimethylamino-propoxy)-3-(2-methyl-2H-pyrazol-3-yl)-phenyl]-urea |
| 136 | 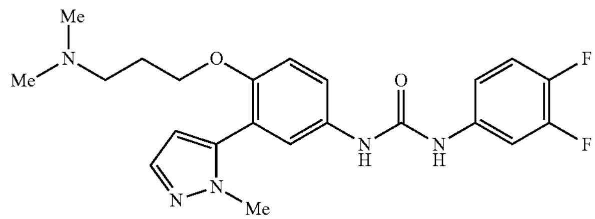 [SMILES: CN(C)CCCOc1ccc(NC(=O)Nc2ccc(F)c(F)c2)cc1-c1ccnn1C] | 1-(3,4-Difluoro-phenyl)-3-[4-(3-dimethylamino-propoxy)-3-(2-methyl-2H-pyrazol-3-yl)-phenyl]-urea |
| 137 | 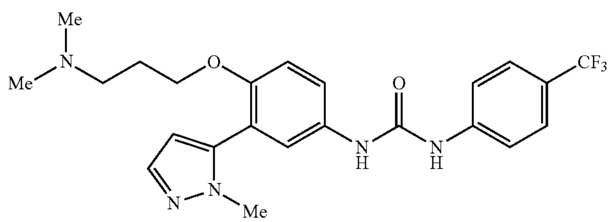 [SMILES: CN(C)CCCOc1ccc(NC(=O)Nc2ccc(C(F)(F)F)cc2)cc1-c1ccnn1C] | 4-[4-Dimethylammo-propoxy)-3-(2-methyl-2H-pyrazol-3-yl)-phenyl]-3-(4-trifluoromethyl-phenyl)-urea |
| 138 | 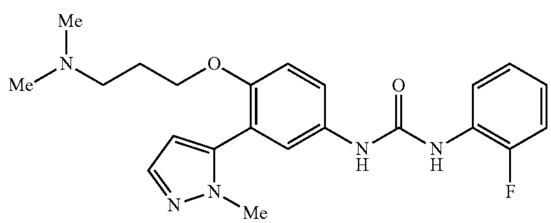 | 1-[4-(3-Dimethylamino-propoxy)-3-(2-methyl-2H-pyrazol-3-yl)-phenyl]-3-(2-fluoro-phenyl)-urea |
| 139 | 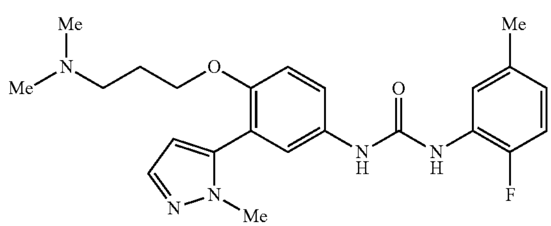 [SMILES: Cc1ccc(F)c(NC(=O)Nc2ccc(OCCCN(C)C)c(-c3ccnn3C)c2)c1] | 1-[4-(3-Dimethylamino-propoxy-3-(2-methyl-2H-pyrazol-3-yl)-phenyl]-3-(2-fluoro-5-methyl-phenyl)-urea |
| 140 | 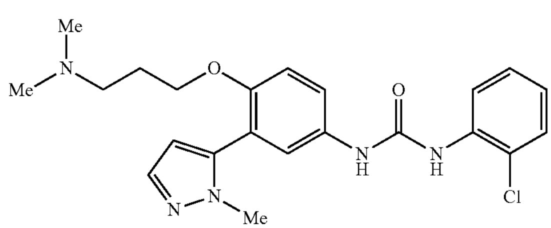 [SMILES: CN(C)CCCOc1ccc(NC(=O)Nc2ccccc2Cl)cc1-c1ccnn1C] | 1-(2-Chloro-phenyl)-3-[4-(3-dimethylamino-propoxy)-3-(2-methyl-2H-pyrazol-3-yl)-phenyl]-urea |
| 141 | 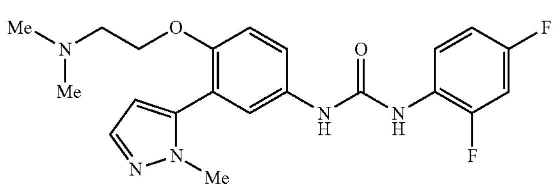 [SMILES: CN(C)CCOc1ccc(NC(=O)Nc2ccc(F)cc2F)cc1-c1ccnn1C] | 1-(2,4-Difluoro-phenyl)-3-[4-(2-dimethylamino-ethoxy)-3-(2-methyl-2H-pyrazol-3-yl)-phenyl]-urea |

TABLE 3-continued

| Cmpd # | Structure | Chemical Name |
| --- | --- | --- |
| 142 | 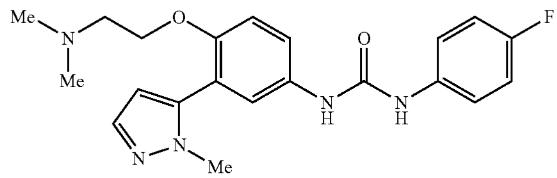 [SMILES: CN(C)CCOc1ccc(NC(=O)Nc2ccc(F)cc2)cc1-c1ccnn1C] | 1-[4-(2-Dimethylamino-ethoxy)-3-(2-methyl-2H-pyrazol-3-yl)-phenyl]-3-(4-fluoro-phenyl)-urea |
| 143 | 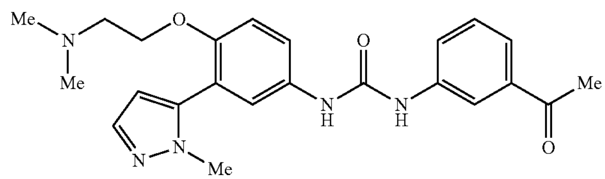 [SMILES: CC(=O)c1cccc(NC(=O)Nc2ccc(OCCN(C)C)c(-c3ccnn3C)c2)c1] | 1-(3-Acetyl-phenyl)-3-[4-(2-dimethylamino-ethoxy)-3-(2-methyl-2H-pyrazol-3-yl)-pbenyl]-urea |
| 144 | 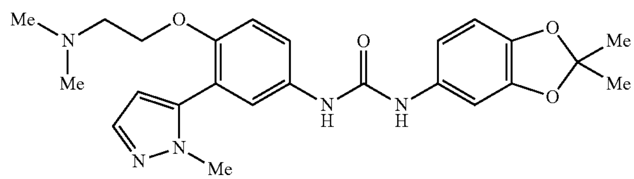 [SMILES: CN(C)CCOc1ccc(NC(=O)Nc2ccc3c(c2)OC(C)(C)O3)cc1-c1ccnn1C] | 1-(2,2-Difluoro-benzo[1,3]dioxol-5-yl)-3-[4-(2-dimethylamino-ethoxy)-3-(2-methyl-2H-pyrazol-3-yl)-phenyl]-urea |
| 145 | 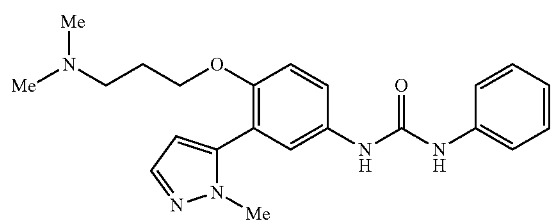 [SMILES: CN(C)CCCOc1ccc(NC(=O)Nc2ccccc2)cc1-c1ccnn1C] | 1-[4-(3-Dimethylamino-propoxy)-3-(2-methyl-2H-pyrazol-3-yl)-phenyl]-3-phenyl-urea |
| 146 | 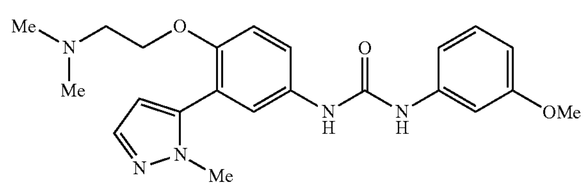 [SMILES: COc1cccc(NC(=O)Nc2ccc(OCCN(C)C)c(-c3ccnn3C)c2)c1] | 1-[4-(2-Dimethylamino-ethoxy)-3-(2-methyl-2H-pyrazol-3-yl)-phenyl]-3-(3-methoxy-phenyl)-urea |
| 147 | 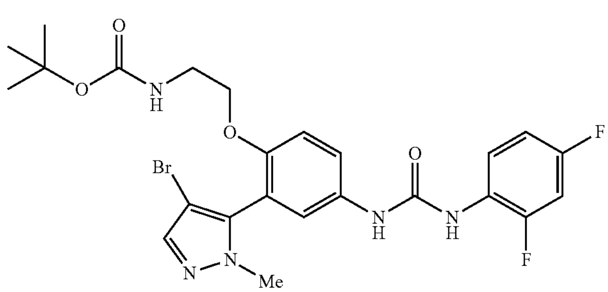 [SMILES: Cn1ncc(Br)c1-c1cc(NC(=O)Nc2ccc(F)cc2F)ccc1OCCNC(=O)OC(C)(C)C] | (2-{2-(4-Bromo-2-methyl-2H-pyrazol-3-yl)-4-[3-(2,4-difluoro-phenyl)-ureido]-phenoxy}-ethyl)-carbamic acid tert-butyl ester |
| 148 | 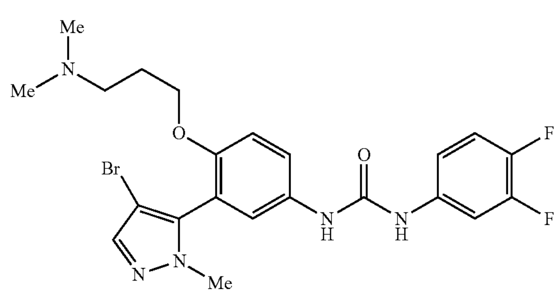 [SMILES: CN(C)CCCOc1ccc(NC(=O)Nc2ccc(F)c(F)c2)cc1-c1c(Br)cnn1C] | 1-[3-(4-Bromo-2-methyl-2H-pyrazol-3-yl)-4-(3-dimethylamino-propoxy)-phenyl]-3-(3,4-difluoro-phenyl)-urea |

TABLE 3-continued

| Cmpd # | Structure | Chemical Name |
|---|---|---|
| 149 | 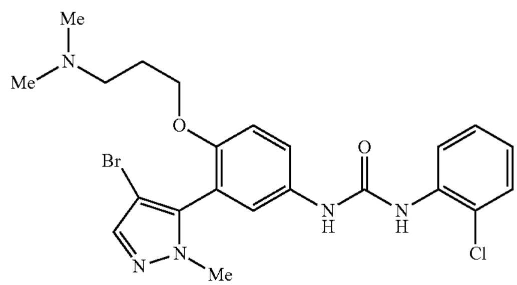 [SMILES: CN(C)CCCOc1ccc(NC(=O)Nc2ccccc2Cl)cc1-c1c(Br)cnn1C] | 1-[3-(4-Bromo-2-methyl-2H-pyrazol-3-yl)-4-(3-dimethylamino-propoxy)-phenyl]-3-(2-chloro-phenyl)-urea |
| 150 | 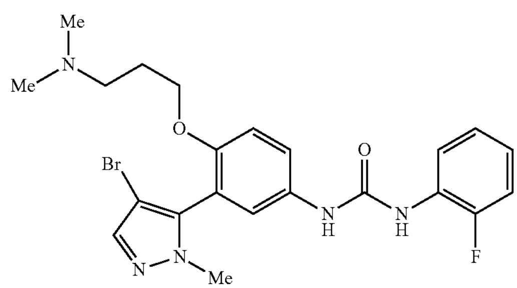 [SMILES: CN(C)CCCOc1ccc(NC(=O)Nc2ccccc2F)cc1-c1c(Br)cnn1C] | 1-[3-(4-Bromo-2-methyl-2H-pyrazol-3-yl)-4-(3-dimethylamino-propoxy)-phenyl]-3-(2-fluoro-phenyl)-urea |
| 151 | 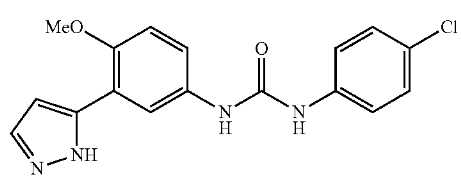 [SMILES: COc1ccc(NC(=O)Nc2ccc(Cl)cc2)cc1-c1ccn[nH]1] | 1-(4-Chloro-phenyl)-3-[4-methoxy-3-(2H-pyrazol-3-yl)-phenyl]-urea |
| 152 | 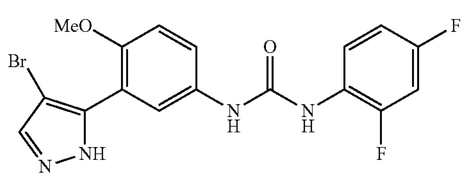 [SMILES: COc1ccc(NC(=O)Nc2ccc(F)cc2F)cc1-c1[nH]ncc1Br] | 1-[3-(4-Bromo-2H-pyrazol-3-yl)-4-methoxy-phenyl]-3-(2,4-difluoro-phenyl)-urea |
| 153 | 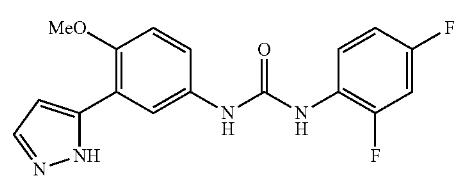 [SMILES: COc1ccc(NC(=O)Nc2ccc(F)cc2F)cc1-c1ccn[nH]1] | 1-(2,4-Difluoro-phenyl)-3-[4-methoxy-3-(2H-pyrazol-3-yl)-phenyl]-urea |
| 154 | 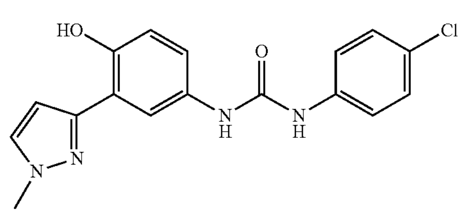 [SMILES: Cn1ccc(-c2cc(NC(=O)Nc3ccc(Cl)cc3)ccc2O)n1] | 1-(4-Chloro-phenyl)-3-[4-hydroxy-3-(1-methyl-1H-pyrazol-3-yl)-phenyl]-urea |

TABLE 3-continued

| Cmpd # | Structure | Chemical Name |
|---|---|---|
| 155 | 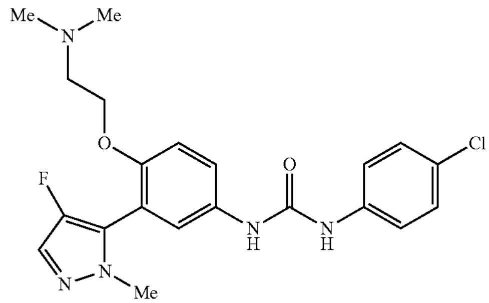 [SMILES: CN(C)CCOc1ccc(NC(=O)Nc2ccc(Cl)cc2)cc1-c1c(F)cnn1C] | 1-(4-Chloro-phenyl)-3-[4-(2-dimethylamino-ethoxy)-3-(4-fluoro-2-methyl-2H-pyrazol-3-yl)-phenyl]-urea |
| 156 | 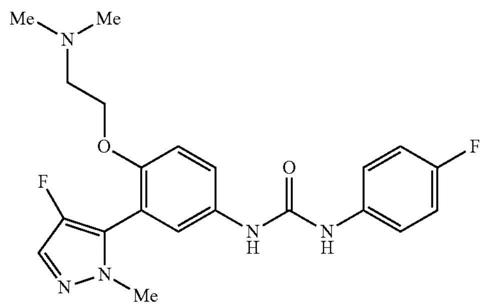 [SMILES: CN(C)CCOc1ccc(NC(=O)Nc2ccc(F)cc2)cc1-c1c(F)cnn1C] | 1-[4-(2-Dimethylamino-ethoxy)-3-(4-fluoro-2-methyl-2H-pyrazol-3-yl)-phenyl]-3-(4-fluoro-phenyl)-urea |
| 157 | 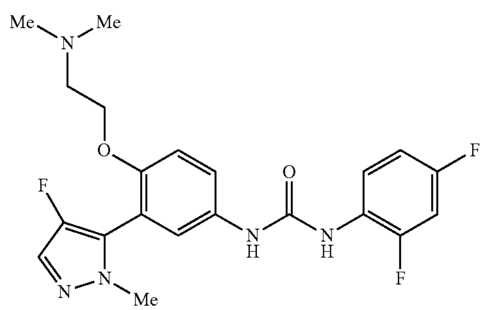 [SMILES: CN(C)CCOc1ccc(NC(=O)Nc2ccc(F)cc2F)cc1-c1c(F)cnn1C] | 1-(2,4-Difluoro-phenyl)-3-[4-(2-dimethylamino-ethoxy)-3-(4-fluoro-2-methyl-2H-pyrazol-3-yl)-phenyl]-urea |
| 158 | 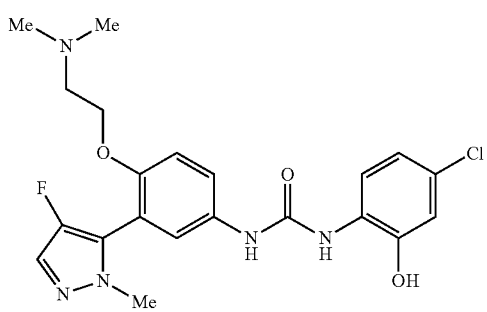 | 1-(4-Chloro-2-hydroxy-pbenyl)-3-[4-(2-dimethylamino-ethoxy)-3-(4-fluoro-2-methyl-2H-pyrazol-3-yl)-phenyl]-urea |
| 159 | 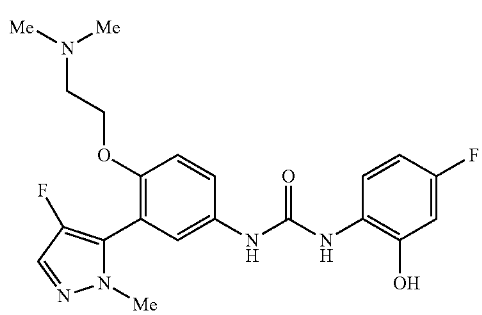 | 1-[4-(2-Dimethylamino-ethoxy)-3-(4-fluoro-2-methyl-2H-pyrazol-3-yl)-phenyl]-3-(4-fluoro-2-hydroxy-phenyl)-urea |

TABLE 3-continued

| Cmpd # | Structure | Chemical Name |
|---|---|---|
| 160 | 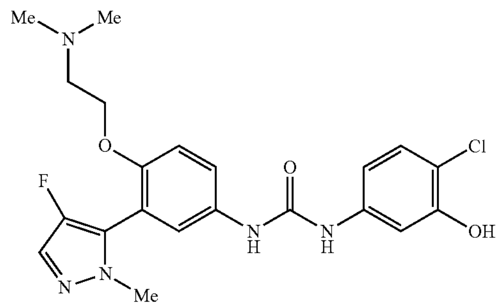 | 1-(4-Chloro-3-hydroxy-phenyl)-3-[4-(2-dimethylamino-ethoxy)-3-(4-fluoro-2-methyl-2H-pyrazol-3-yl)-phenyl]-urea |
| 161 | 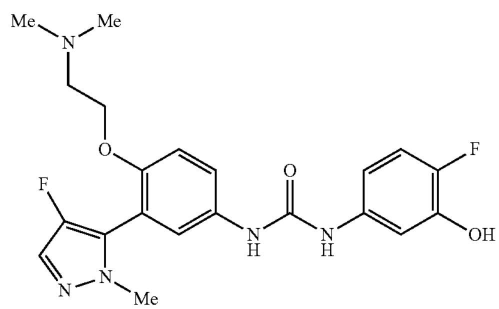 | 1-[4-(2-Dimethylamino-ethoxy)-3-(4-fluoro-2-methyl-2H-pyrazol-3-yl)-phenyl]-3-(4-fluoro-3-hydroxy-phenyl)-urea |
| 162 | 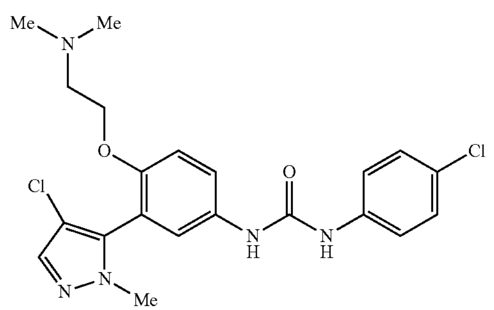 [SMILES: CN(C)CCOc1ccc(NC(=O)Nc2ccc(Cl)cc2)cc1-c1c(Cl)cnn1C] | 1-[3-(4-Chloro-2-methyl-2H-pyrazol-3-yl)-4-(2-dimethylamino-ethoxy)-phenyl]-3-(4-chloro-phenyl)-urea |
| 163 | 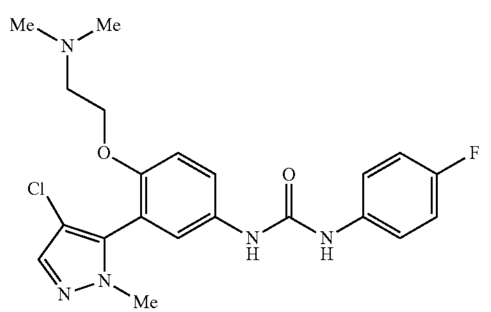 [SMILES: CN(C)CCOc1ccc(NC(=O)Nc2ccc(F)cc2)cc1-c1c(Cl)cnn1C] | 1-[3-(4-Chloro-2-methyl-2H-pyrazol-3-yl)-4-(2-dimethylamino-ethoxy)-phenyl]-3-(4-fluoro-phenyl)-urea |
| 164 | 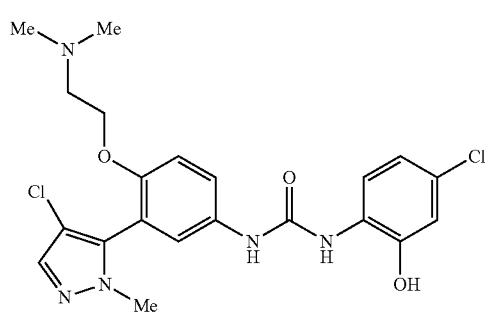 [SMILES: CN(C)CCOc1ccc(NC(=O)Nc2ccc(Cl)cc2O)cc1-c1c(Cl)cnn1C] | 1-(4-Chloro-2-hydroxy-phenyl)-3-[3-(4-chloro-2-methyl-2H-pyrazol-3-yl)-4-(2-dimethylamino-ethoxy)-phenyl]-urea |

TABLE 3-continued

| Cmpd # | Structure | Chemical Name |
| --- | --- | --- |
| 165 | 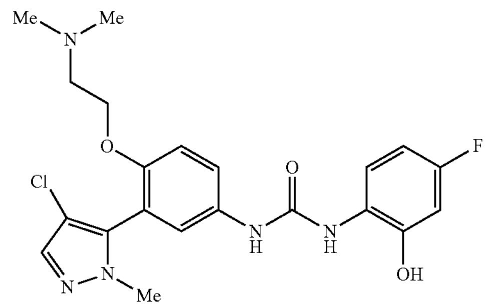 [SMILES: CN(C)CCOc1ccc(NC(=O)Nc2ccc(F)cc2O)cc1-c1c(Cl)cnn1C] | 1-[3-(4-Chloro-2-methyl-2H-pyrazol-3-yl)-4-(2-dimethylamino-ethoxy)-phenyl]-3-(4-fluoro-2-hydroxy-phenyl)-urea |
| 166 | 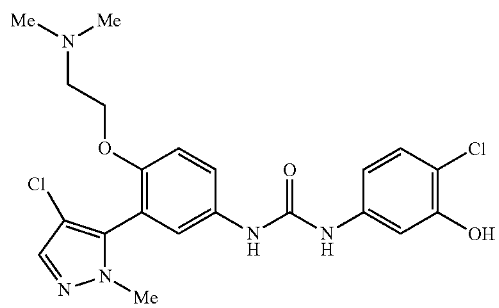 [SMILES: CN(C)CCOc1ccc(NC(=O)Nc2ccc(Cl)c(O)c2)cc1-c1c(Cl)cnn1C] | 1-(4-Chloro-3-hydroxy-phenyl)-3-[3-(4-chloro-2-methyl-2H-pyrazol-3-yl)-4-(2-dimethylamino-ethoxy)-phenyl]-urea |
| 167 | 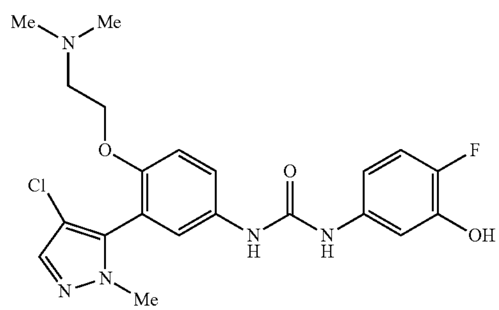 [SMILES: CN(C)CCOc1ccc(NC(=O)Nc2ccc(F)c(O)c2)cc1-c1c(Cl)cnn1C] | 1-[3-(4-Chloro-2-methyl-2H-pyrazol-3-yl)-4-(2-dimethylamino-ethoxy)-phenyl]-3-(4-fluoro-3-hydroxy-phenyl)-urea |
| 168 | 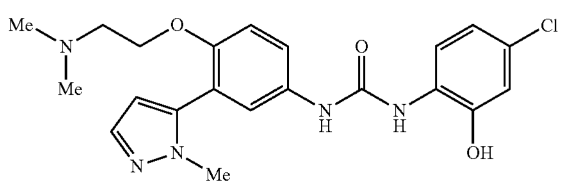 [SMILES: CN(C)CCOc1ccc(NC(=O)Nc2ccc(Cl)cc2O)cc1-c1ccnn1C] | 1-(4-Chloro-2-hydroxy-phenyl)-3-[4-(2-dimethylamino-ethoxy)-3-(2-methyl-2H-pyrazol-3-yl)-phenyl]-urea |
| 169 | 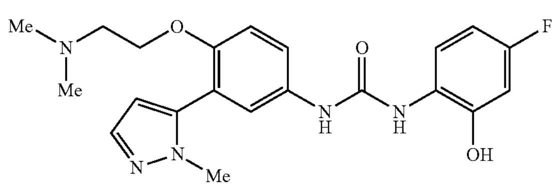 [SMILES: CN(C)CCOc1ccc(NC(=O)Nc2ccc(F)cc2O)cc1-c1ccnn1C] | 1-[4-(2-Dimethylamino-ethoxy)-3-(2-methyl-2H-pyrazol-3-yl)-phenyl]-3-(4-fluoro-2-hydroxy-phenyl)-urea |
| 170 | 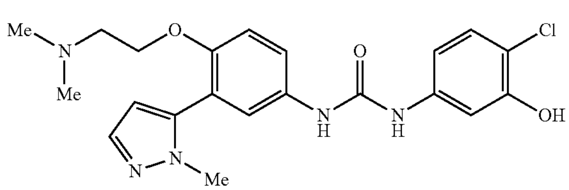 [SMILES: CN(C)CCOc1ccc(NC(=O)Nc2ccc(Cl)c(O)c2)cc1-c1ccnn1C] | 1-(4-Chloro-3-hydroxy-phenyl)-3-[4-(2-dimethylamino-ethoxy)-3-(2-methyl-2H-pyrazol-3-yl)-phenyl]-urea |

TABLE 3-continued

| Cmpd # | Structure | Chemical Name |
|---|---|---|
| 171 | 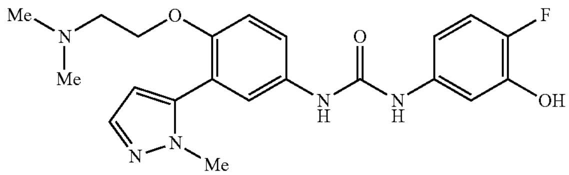 [SMILES: CN(C)CCOc1ccc(NC(=O)Nc2ccc(F)c(O)c2)cc1-c1ccnn1C] | 1-[4-(2-Dimethylamino-ethoxy)-3-(2-methyl-2H-pyrazol-3-yl)-phenyl]-3-(4-fluoro-3-hydroxy-phenyl)-urea |
| 172 | 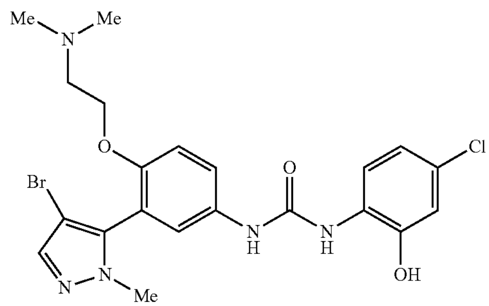 | 1-[3-(4-Bromo-2-methyl-2H-pyrazol-3-yl)-4-(2-dimethylamino-ethoxy)-phenyl]-3-(4-chloro-2-hydroxy-phenyl)-urea |
| 173 | 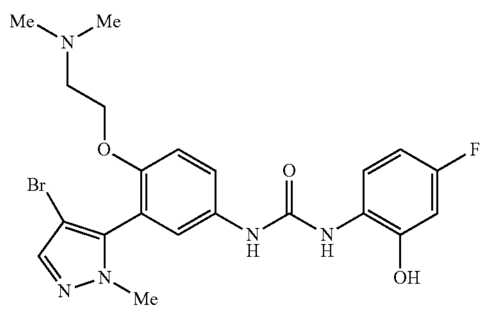 | 1-[3-(4-Bromo-2-methyl-2H-pyrazol-3-yl)-4-(2-dimethylamino-ethoxy)-phenyl]-3-(4-fluoro-2-hydroxy-phenyl)-urea |
| 174 | 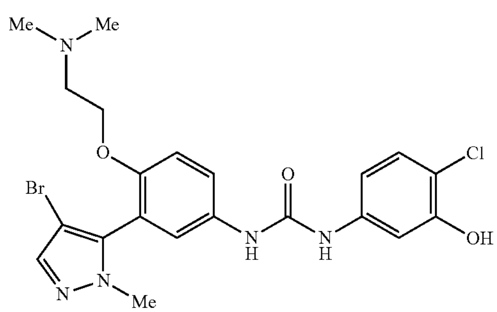 | 1-[3-(4-Bromo-2-methyl-2H-pyrazol-3-yl)-4-(2-dimethylamino-ethoxy)-phenyl]-3-(4-chloro-3-hydroxy-phenyl)-urea |
| 175 | 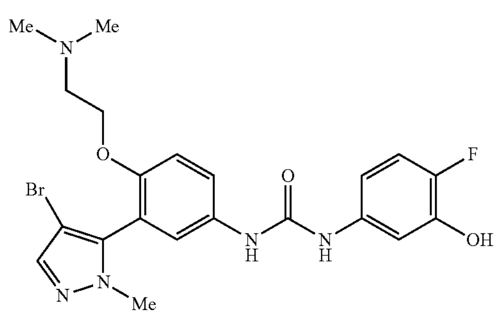 | 1-[3-(4-Bromo-2-methyl-2H-pyrazol-3-yl)-4-(2-dimethylamino-ethoxy)-phenyl]-3-(4-fluoro-3-hydroxy-phenyl)-urea |

TABLE 3-continued

| Cmpd # | Structure | Chemical Name |
|---|---|---|
| 176 | 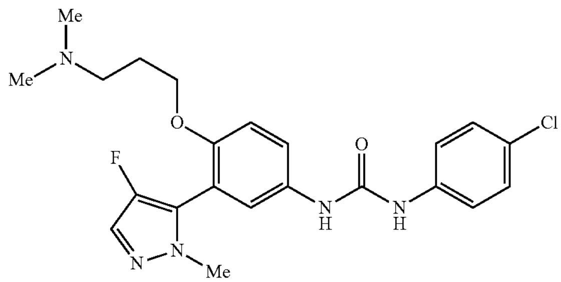 [SMILES: CN(C)CCCOc1ccc(NC(=O)Nc2ccc(Cl)cc2)cc1-c1c(F)cnn1C] | 1-(4-Chloro-phenyl)-3-[4-(3-dimethylamino-propoxy)-3-(4-fluoro-2-methyl-2H-pyrazol-3-yl)-phenyl]-urea |
| 177 | 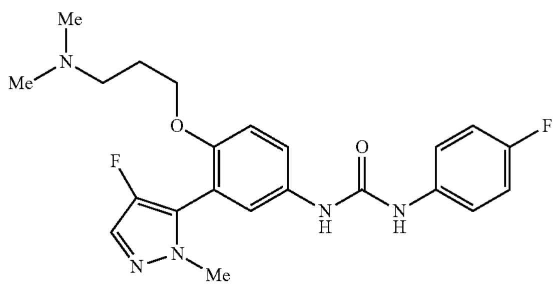 [SMILES: CN(C)CCCOc1ccc(NC(=O)Nc2ccc(F)cc2)cc1-c1c(F)cnn1C] | 1-[4-(3-Dimethylamino-propoxy)-3-(4-fluoro-2-methyl-2H-pyrazol-3-yl)-phenyl]-3-(4-fluoro-phenyl)-urea |
| 178 | 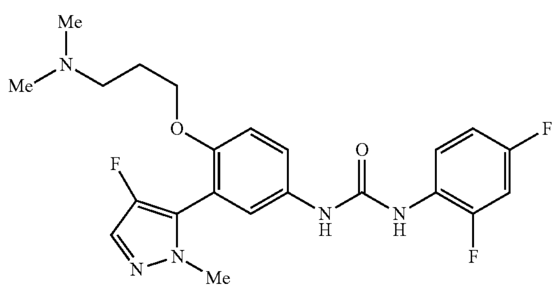 [SMILES: CN(C)CCCOc1ccc(NC(=O)Nc2ccc(F)cc2F)cc1-c1c(F)cnn1C] | 1-(2,4-Difluoro-phenyl)-3-[4-(3-dimethylamino-propoxy)-3-(4-fluoro-2-methyl-2H-pyrazol-3-yl)-phenyl]-urea |
| 179 | 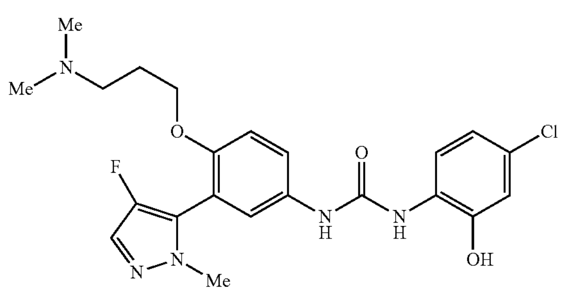 [SMILES: CN(C)CCCOc1ccc(NC(=O)Nc2ccc(Cl)cc2O)cc1-c1c(F)cnn1C] | 1-(4-Chloro-2-hydroxy-phenyl)-3-[4-(3-dimethylamino-propoxy)-3-(4-fluoro-2-methyl-2H-pyrazol-3-yl)-phenyl]-urea |
| 180 | 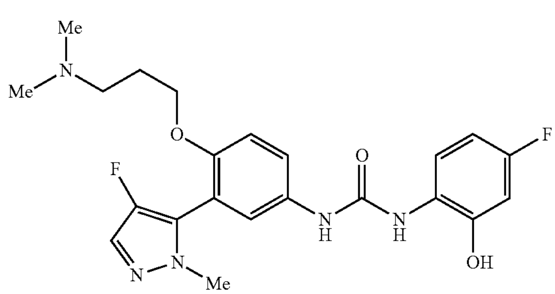 [SMILES: CN(C)CCCOc1ccc(NC(=O)Nc2ccc(F)cc2O)cc1-c1c(F)cnn1C] | 1-[4-(3-Dimethylamino-propoxy)-3-(4-fluoro-2-methyl-2H-pyrazol-3-yl)-phenyl]-3-(4-fluoro-2-hydroxy-phenyl)-urea |

TABLE 3-continued

| Cmpd # | Structure | Chemical Name |
|---|---|---|
| 181 | 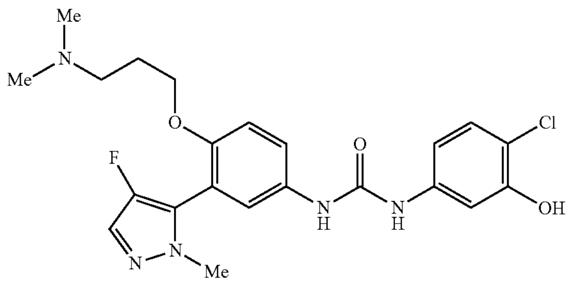 [SMILES: CN(C)CCCOc1ccc(NC(=O)Nc2ccc(Cl)c(O)c2)cc1-c1c(F)cnn1C] | 1-(4-Chloro-3-hydroxy-phenyl)-3-[4-(3-dimethylamino-propoxy)-3-(4-fluoro-2-methyl-2H-pyrazol-3-yl)-phenyl]-urea |
| 182 | 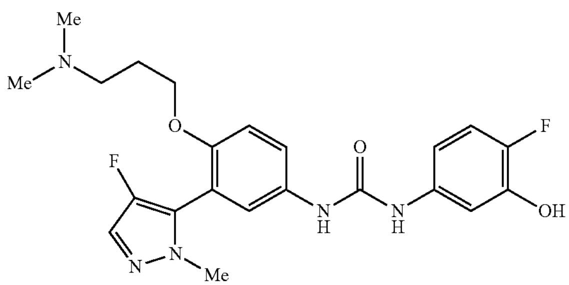 [SMILES: CN(C)CCCOc1ccc(NC(=O)Nc2ccc(F)c(O)c2)cc1-c1c(F)cnn1C] | 1-[4-(3-Dimethylamino-propoxy)-3-(4-fluoro-2-methyl-2H-pyrazol-3-yl)-phenyl]-3-(4-fluoro-3-hydroxy-phenyl)-urea |
| 183 | 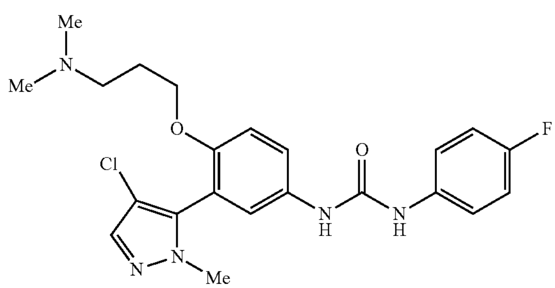 [SMILES: CN(C)CCCOc1ccc(NC(=O)Nc2ccc(F)cc2)cc1-c1c(Cl)cnn1C] | 1-[3-(4-Chloro-2-methyl-2H-pyrazol-3-yl)-4-(3-dimethylamino-propoxy)-phenyl]-3-(4-fluoro-phenyl)-urea |
| 184 | 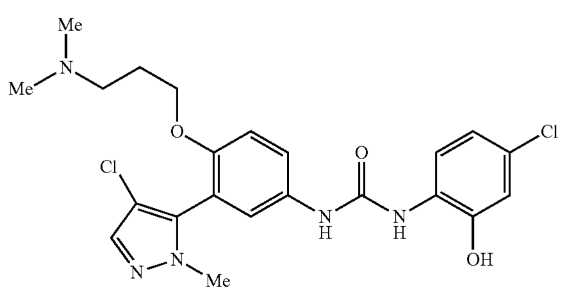 [SMILES: CN(C)CCCOc1ccc(NC(=O)Nc2ccc(Cl)cc2O)cc1-c1c(Cl)cnn1C] | 1-(4-Chloro-2-hydroxy-phenyl)-3-[3-(4-chloro-2-methyl-2H-pyrazol-3-yl)-4-(3-dimethylamino-propoxy)-phenyl]-urea |
| 185 | 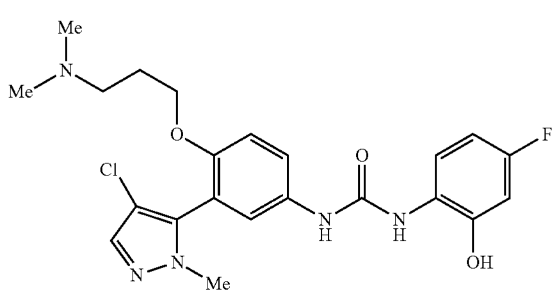 [SMILES: CN(C)CCCOc1ccc(NC(=O)Nc2ccc(F)cc2O)cc1-c1c(Cl)cnn1C] | 1-[3-(4-Chloro-2-methyl-2H-pyrazol-3-yl)-4-(3-dimethylamino-propoxy)-phenyl]-3-(4-fluoro-2-hydroxy-phenyl)-urea |

TABLE 3-continued

| Cmpd # | Structure | Chemical Name |
|---|---|---|
| 186 | 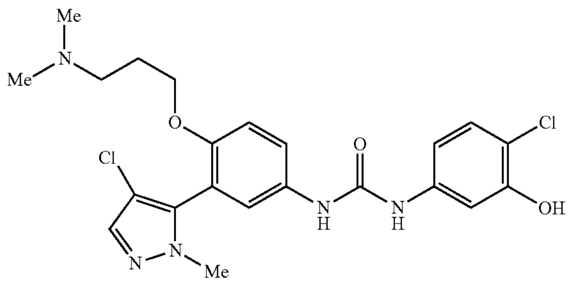 [SMILES: CN(C)CCCOc1ccc(NC(=O)Nc2ccc(Cl)c(O)c2)cc1-c1c(Cl)cnn1C] | 1-(4-Chloro-3-hydroxy-phenyl)-3-[3-(4-chloro-2-methyl-2H-pyrazol-3-yl)-4-(3-dimethylantino-propoxy)-phenyl]-urea |
| 187 | 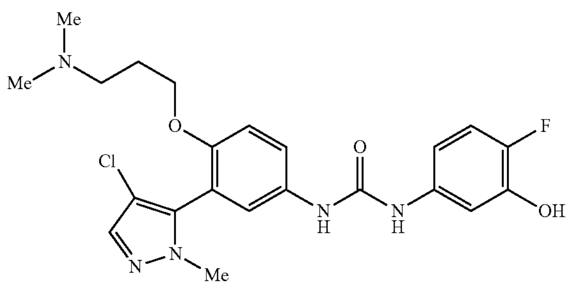 [SMILES: CN(C)CCCOc1ccc(NC(=O)Nc2ccc(F)c(O)c2)cc1-c1c(Cl)cnn1C] | 1-[3-(4-Chloro-2-methyl-2H-pyrazol-3-yl)-4-(3-dimethylamino-propoxy)-phenyl]-3-(4-fluoro-3-hydroxy-phenyl)-urea |
| 188 | 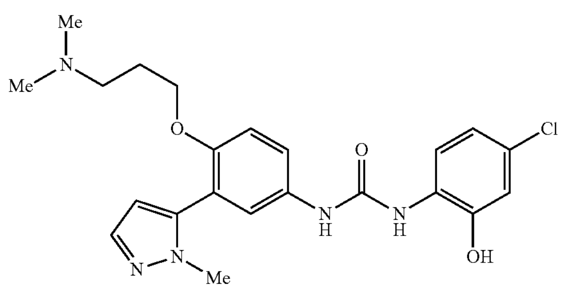 [SMILES: CN(C)CCCOc1ccc(NC(=O)Nc2ccc(Cl)cc2O)cc1-c1ccnn1C] | 1-(4-Chloro-2-hydroxy-phenyl)-3-[4-(3-dimethylamino-propoxy)-3-(2-methyl-2H-pyrazol-3-yl)-phenyl]-urea |
| 189 | 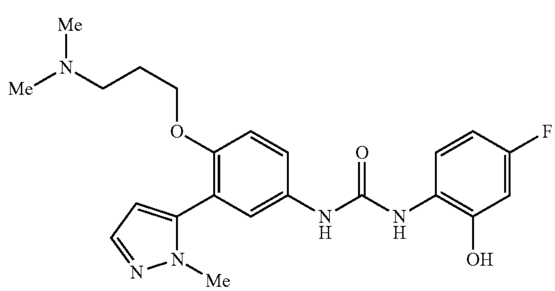 [SMILES: CN(C)CCCOc1ccc(NC(=O)Nc2ccc(F)cc2O)cc1-c1ccnn1C] | 1-[4-(3-Dimethylamino-propoxy)-3-(2-methyl-2H-pyrazol-3-yl)-phenyl]-3-(4-fluoro-2-hydroxy-phenyl)-urea |
| 190 | 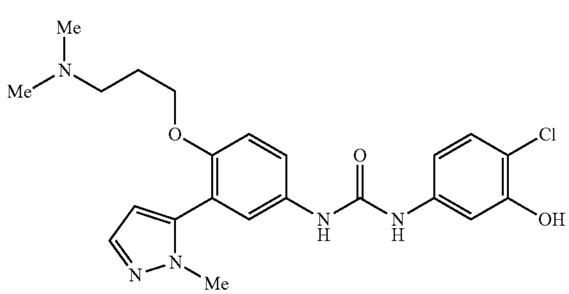 [SMILES: CN(C)CCCOc1ccc(NC(=O)Nc2ccc(Cl)c(O)c2)cc1-c1ccnn1C] | 1-(4-Chloro-3-hydroxy-phenyl)-3-[4-(3-dimethylamino-propoxy)-3-(2-methyl-2H-pyrazol-3-yl)-phenyl]-urea |

TABLE 3-continued

| Cmpd # | Structure | Chemical Name |
|---|---|---|
| 191 | 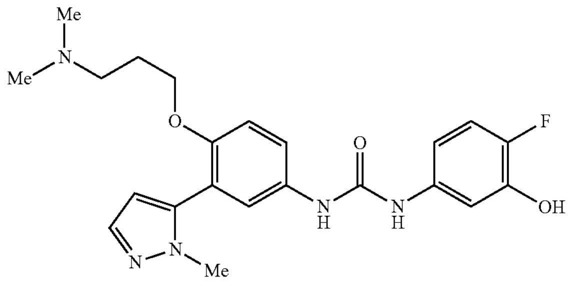 [SMILES: CN(C)CCCOc1ccc(NC(=O)Nc2ccc(F)c(O)c2)cc1-c1ccnn1C] | 1-[4-(3-Dimethylamino-propoxy)-3-(2-methyl-2H-pyrazol-3-yl)-phenyl]-3-(4-fluoro-3-hydroxy-phenyl)-urea |
| 192 | 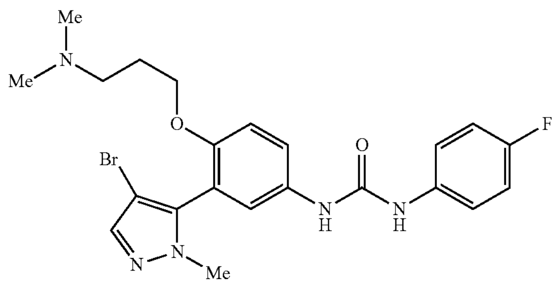 [SMILES: CN(C)CCCOc1ccc(NC(=O)Nc2ccc(F)cc2)cc1-c1c(Br)cnn1C] | 1-[3-(4-Bromo-2-methyl-2H-pyrazol-3-yl)-4-(3-dimethylamino-propoxy)-phenyl]-3-(4-fluoro-phenyl)-urea |
| 193 | 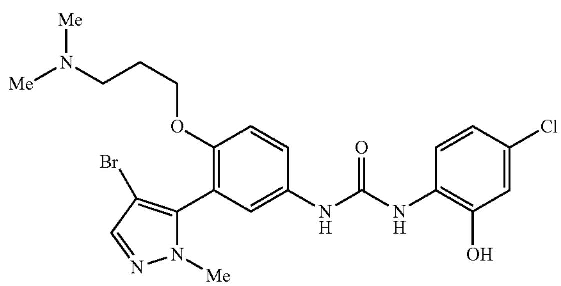 [SMILES: CN(C)CCCOc1ccc(NC(=O)Nc2ccc(Cl)cc2O)cc1-c1c(Br)cnn1C] | 1-[3-(4-Bromo-2-methyl-2H-pyrazol-3-yl)-4-(3-dimethylamino-propoxy)-phenyl]-3-(4-chloro-2-hydroxy-phenyl)-urea |
| 194 | 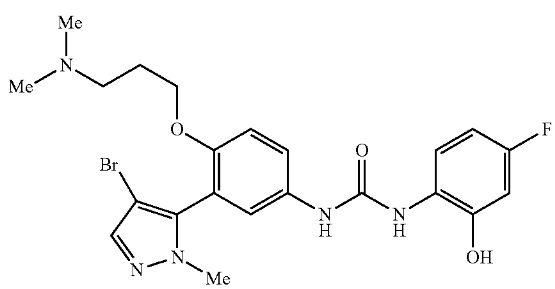 [SMILES: CN(C)CCCOc1ccc(NC(=O)Nc2ccc(F)cc2O)cc1-c1c(Br)cnn1C] | 1-[3-(4-Bromo-2-methyl-2H-pyrazol-3-yl)-4-(3-dimethylamino-propoxy)-phenyl]-3-(4-fluoro-2-hydroxy-phenyl)-urea |
| 195 | 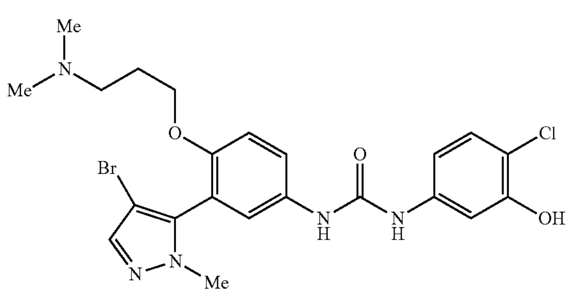 [SMILES: CN(C)CCCOc1ccc(NC(=O)Nc2ccc(Cl)c(O)c2)cc1-c1c(Br)cnn1C] | 1-[3-(4-Bromo-2-methyl-2H-pyrazol-3-yl)-4-(3-dimethylamino-propoxy)-phenyl]-3-(4-chloro-3-hydroxy-phenyl)-urea |

TABLE 3-continued

| Cmpd # | Structure | Chemical Name |
|---|---|---|
| 196 | 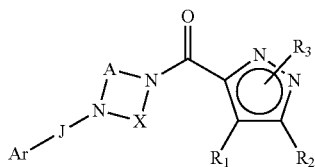 | 1-[3-(4-Bromo-2-methyl-2H-pyrazol-3-yl)-4-(3-dimethylamino-propoxy)-phenyl]-3-(4-fluoro-3-hydroxy-phenyl)-urea |

One aspect of the present invention pertains to certain compounds as shown in Formula 2a:

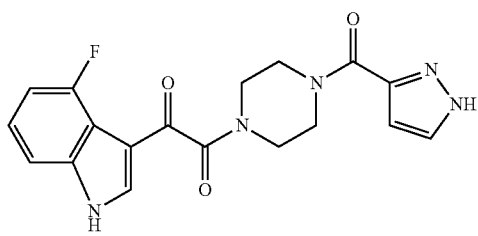

or a pharmaceutically acceptable salt, hydrate or solvate thereof; wherein $R_1$, $R_2$, $R_3$, Ar, A, X and J have the same definitions as described herein, supra and infra.

In some embodiments, the compounds of the present invention are other than 1-(4-(1H-pyrazole-3-carbonyl)piperazin-1-yl)-2-(4-fluoro-1H-indol-3-yl)ethane-1,2-dione, represented by the Formula 3 below:

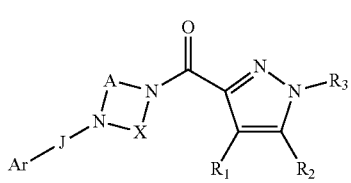

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R_1$, $R_2$, $R_3$, Ar, A, X and J) contained within the generic chemical formulae described herein for example, (Ia, Ic and Ie), are specifically embraced by the present invention just as if they were explicitly disclosed, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each of such subcombination of chemical groups and subcombination of uses and medical indications were explicitly disclosed herein.

It is understood and appreciated that compounds of Formula 2a and formulae related therefrom may have one or more chiral centers, and therefore can exist as enantiomers and/or diastereomers. The invention is understood to extend to and embrace all such enantiomers, diastereomers and mixtures thereof, including but not limited to racemates. It is understood that compounds of Formula 2a and formulae used throughout this disclosure are intended to represent all individual enantiomers and mixtures thereof, unless stated or shown otherwise.

Some embodiments of the present invention pertain to compounds of Formula 2c:

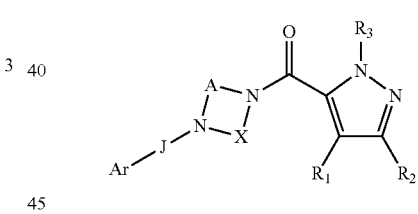

Some embodiments of the present invention pertain to compounds of Formula 2e:

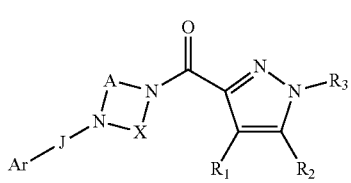

In some embodiments, each $R_1$ and $R_2$ is selected independently from the group consisting of H, $C_1$-$C_6$ alkyl, $C_1$-$C_6$ alkylaryl, aryl, $C_3$-$C_7$ cycloalkyl, $C_1$-$C_6$ haloalkyl, halogen, heteroaryl, and nitro.

In some embodiments, $R_1$ and $R_2$ is selected independently from the group consisting of H, methyl, ethyl, isopropyl, t-butyl, 2-methylphenyl, phenyl, cyclopropyl, trifluoromethyl, fluoro, chloro, bromo, iodo, furan-2-yl and nitro.

In some embodiments, $R_1$ is H, halogen or $C_1$-$C_6$ alkylaryl; and $R_2$ is H, $C_1$-$C_6$ alkyl, aryl, $C_3$-$C_7$ cycloalkyl, $C_1$-$C_6$ haloalkyl, heteroaryl or nitro.

In some embodiments, $R_1$ is H, fluoro, chloro, bromo, iodo or 2-methylphenyl and $R_2$ is H, methyl, ethyl, isopropyl, t-butyl, phenyl, cyclopropyl, trifluoromethyl, furan-2-yl or nitro.

In some embodiments, $R_1$ and $R_2$ together with the carbon atoms to which they are bonded form a $C_3$-$C_7$ carbocyclyl.

In some embodiments, $R_1$ and $R_2$ together with the carbon atoms to which they are bonded form a $C_5$ carbocyclyl.

In some embodiments, $R_3$ is selected from the group consisting of H, $C_1$-$C_6$ alkyl and aryl; and wherein aryl is optionally substituted with $C_1$-$C_6$ alkoxy.

In some embodiments, $R_3$ is selected from the group consisting of H, $C_1$-$C_6$ alkyl and aryl; and wherein aryl is optionally substituted with methoxy.

In some embodiments, $R_3$ is selected from the group consisting of H, methyl, ethyl, t-butyl, phenyl and 4-methoxyphenyl.

In some embodiments, A and X are each —$CH_2CH_2$—, each optionally substituted with $C_1$-$C_3$ alkyl.

In some embodiments, A and X are each —$CH_2CH_2$—, each optionally substituted with methyl.

In some embodiments, A and X are each independently —$CH_2CH_2$— or —$CH(CH_3)CH_2$—.

In some embodiments, J is —$CH_2CH_2$— optionally substituted with 1, 2, 3 or 4 substituents selected independently from the group consisting of $C_1$-$C_3$ alkyl, hydroxyl, oxo and =NO—$C_1$-$C_3$ alkyl.

In some embodiments, J is —$CH_2CH_2$— optionally substituted with 1, 2, 3 or 4 substituents selected independently from the group consisting of methyl, hydroxyl, oxo and =NOCH$_3$.

In some embodiments, J is —$CH_2CH_2$—, —$C(=NOCH_3)CH_2$—, —C=OCH$_2$—, —$CH(CH_3)CH_2$—, —$C(CH_3)_2CH_2$—, or —CHOHCH$_2$—.

In some embodiments, Ar is aryl or heteroaryl each optionally substituted with 1, 2, 3, 4 or 5 substituents selected independently from the group consisting of $C_1$-$C_6$ alkoxy, $C_1$-$C_6$ alkylsulfonyl, $C_1$-$C_6$ haloalkoxy, $C_1$-$C_6$ haloalkyl, halogen and heterocyclyl.

In some embodiments, Ar is aryl or heteroaryl each optionally substituted with 1, 2, 3, 4 or 5 substituents selected independently from the group consisting of methoxy, methanesulfonyl, trifluoromethoxy, trifluoromethyl, fluoro, chloro and pyrrolidin-1-yl.

In some embodiments, Ar is naphthyl, 2-methoxyphenyl, 4-methoxyphenyl, 4-methanesulfonylphenyl, 4-trifluoromethoxyphenyl, 4-trifluoromethylphenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl and 6-chloro-1,3-dihydro-indol-2-one.

Some embodiments of the present invention pertain to compounds of Formula 2c:

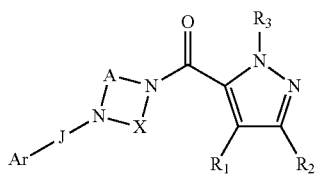

or a pharmaceutically acceptable salt, solvate or hydrate thereof;
wherein:
$R_1$ is H, halogen or $C_1$-$C_6$ alkylaryl;
$R_2$ is H, $C_1$-$C_6$ alkyl, aryl, $C_3$-$C_7$cycloalkyl, $C_1$-$C_6$ haloalkyl, heteroaryl, or nitro; or
$R_1$ and $R_2$ together with the carbon atoms to which they are bonded form a $C_3$-$C_7$ carbocyclyl;
$R_3$ is H, $C_1$-$C_6$alkyl, aryl, or aryl substituted with $C_1$-$C_6$alkoxy;
A and X are each —$CH_2CH_2$—, each optionally substituted with $C_1$-$C_3$ alkyl;
J is —$CH_2CH_2$— optionally substituted with 1, 2, 3 or 4 substituents selected independently from the group consisting of $C_1$-$C_3$ alkyl, hydroxyl, oxo and =NO—$C_1$-$C_3$ alkyl; and
Ar is aryl or heteroaryl each optionally substituted with 1, 2, 3, 4 or 5 substituents selected independently from the group consisting of $C_1$-$C_6$ alkoxy, $C_1$-$C_6$ alkylsulfonyl, $C_1$-$C_6$ haloalkoxy, $C_1$-$C_6$ haloalkyl, halogen and heterocyclyl.

Some embodiments of the present invention pertain to compounds of Formula 2c:

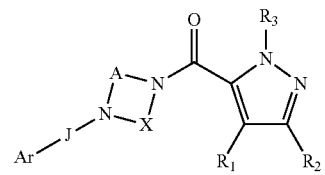

or a pharmaceutically acceptable salt, solvate or hydrate thereof;
wherein:
$R_1$ is H, fluoro, chloro, bromo, iodo or 2-methylphenyl;
$R_2$ is H, methyl, ethyl, isopropyl, t-butyl, phenyl, cyclopropyl, trifluoromethyl, furan-2-yl or nitro; or
$R_1$ and $R_2$ together with the carbon atoms to which they are bonded form a $C_5$ carbocyclyl;
$R_3$ is H, methyl, ethyl, t-butyl, phenyl or 4-methoxyphenyl;
A and X are each independently —$CH_2CH_2$— or —$CH(CH_3)CH_2$—;
J is —$CH_2CH_2$—, —$C(=NOMe)CH_2$—, —C=OCH$_2$—, —$CH(CH_3)CH_2$—, —$C(CH_3)_2CH_2$—, or —CHOHCH$_2$—; and
Ar is naphthyl, 2-methoxyphenyl, 4-methoxyphenyl, 4-methanesulfonylphenyl, 4-trifluoromethoxyphenyl, 4-trifluoromethylphenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl and 6-chloro-1,3-dihydro-indol-2-one.

Some embodiments of the present invention pertain to compounds of Formula 2e:

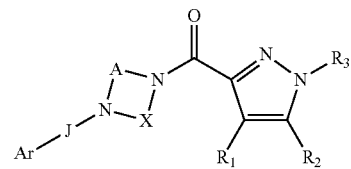

or a pharmaceutically acceptable salt, solvate or hydrate thereof;

wherein:
R₁ is H, halogen or C₁-C₆ alkylaryl;
R₂ is H, C₁-C₆ alkyl, aryl, C₃-C₇ cycloalkyl, C₁-C₆ haloalkyl, heteroaryl, or nitro; or
R₁ and R₂ together with the carbon atoms to which they are bonded form a C₃-C₇ carbocyclyl;
R₃ is H, C₁-C₆alkyl, aryl, or aryl substituted with C₁-C₆alkoxy;
A and X are each —CH₂CH₂—, each optionally substituted with C₁-C₃ alkyl;
J is —CH₂CH₂— optionally substituted with 1, 2, 3 or 4 substituents selected independently from the group consisting of C₁-C₃ alkyl, hydroxyl, oxo and =NO—C₁-C₃ alkyl; and
Ar is aryl or heteroaryl each optionally substituted with 1, 2, 3, 4 or 5 substituents selected independently from the group consisting of C₁-C₆alkoxy, C₁-C₆ alkylsulfonyl, C₁-C₆ haloalkoxy, C₁-C₆ haloalkyl, halogen and heterocyclyl.

Some embodiments of the present invention pertain to compounds of Formula 2e:

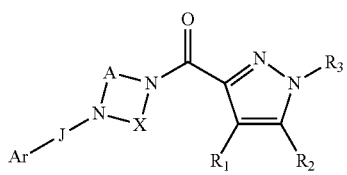

2e or a pharmaceutically acceptable salt, solvate or hydrate thereof;

wherein:

R₁ is H, fluoro, chloro, bromo, iodo or 2-methylphenyl;

R₂ is H, methyl, ethyl, isopropyl, t-butyl, phenyl, cyclopropyl, trifluoromethyl, furan-2-yl or nitro; or R₁ and R₂ together with the carbon atoms to which they are bonded form a C₅ carbocyclyl;

R₃ is H, methyl, ethyl, t-butyl, phenyl or 4-methoxyphenyl;

A and X are each independently —CH₂CH₂— or —CH(CH₃)CH₂—;

J is —CH₂CH₂—, —C(=NOMe)CH₂—, —C=OCH₂—, —CH(CH₃)CH₂—, —C(CH₃)₂CH₂—, or —CHOHCH₂—; and Ar is naphthyl, 2-methoxyphenyl, 4-methoxyphenyl, 4-methanesulfonylphenyl, 4-trifluoromethoxyphenyl, 4-trifluoromethylphenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl and 6-chloro-1,3-dihydro-indol-2-one.

In some embodiments, where R₁, R₂ and R₃ are all H; and A and X are both —CH₂CH₂—; and J is (CO)₂; then Ar is a moiety other than heteroaryl substituted with halogen.

Some embodiments of the present invention include every combination of one or more compounds selected from the following group shown in TABLE 4.

TABLE 4

| Cmpd No. | Chemical Structure | Chemical Name |
|---|---|---|
| 1 | 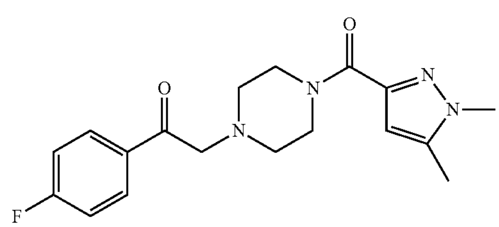 | 2-[4-(1,5-Dimethyl-1H-pyrazole-3-carbonyl)-piperazin-1-yl]-1-(4-fluoro-phenyl)-ethanone |
| 2 | 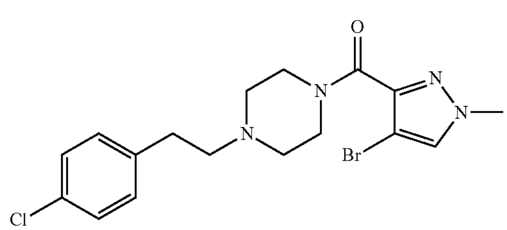 [SMILES: Cn1cc(Br)c(C(=O)N2CCN(CCc3ccc(Cl)cc3)CC2)n1] | (4-Bromo-1-methyl-1H-pyrazol-3-yl)-{4-[2-(4-chloro-phenyl)-ethyl]-piperazin-1-yl}-methanone |
| 3 | 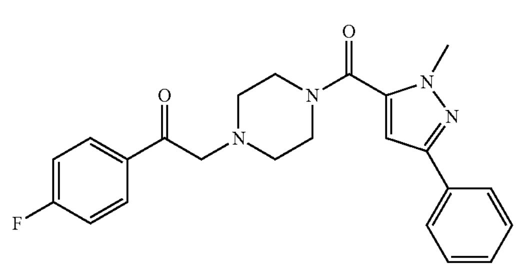 [SMILES: Cn1nc(-c2ccccc2)cc1C(=O)N1CCN(CC(=O)c2ccc(F)cc2)CC1] | 1-(4-Fluoro-phenyl)-2-[4-(2-methyl-5-phenyl-2H-pyrazole-3-carbonyl)-piperazin-1-yl]-ethanone |

TABLE 4-continued

| Cmpd No. | Chemical Structure | Chemical Name |
|---|---|---|
| 4 | 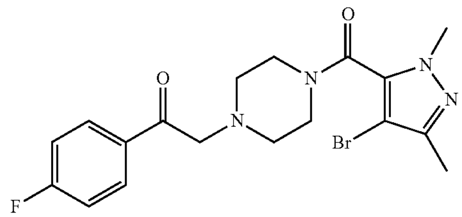 [SMILES: Cc1nn(C)c(C(=O)N2CCN(CC(=O)c3ccc(F)cc3)CC2)c1Br] | 2-[4-(4-Bromo-2,5-dimethyl-2H-pyrazole-3-carbonyl)-piperazin-1-yl]-1-(4-fluoro-phenyl)-ethanone |
| 5 | 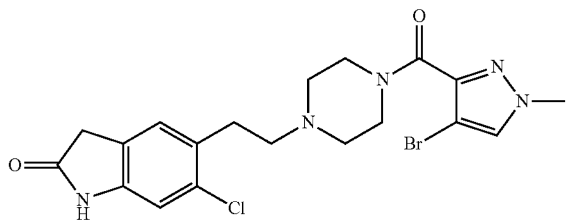 [SMILES: Cn1cc(Br)c(C(=O)N2CCN(CCc3cc4c(cc3Cl)NC(=O)C4)CC2)n1] | 5-{2-[4-(4-Bromo-1-methyl-1H-pyrazole-3-carbonyl)-piperazin-1-yl]-ethyl}-6-chloro-1,3-dihydro-indol-2-one |
| 6 | 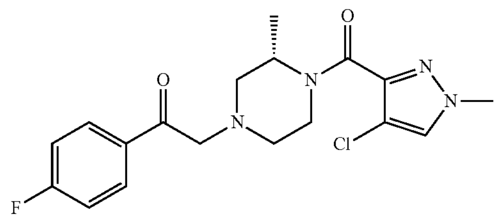 [SMILES: C[C@H]1CN(CC(=O)c2ccc(F)cc2)CCN1C(=O)c1nn(C)cc1Cl] | 2-[(S)-4-(4-Chloro-1-methyl-1H-pyrazole-3-carbonyl)-3-methyl-piperazin-1-yl]-1-(4-fluoro-phenyl)-ethanone |
| 7 | 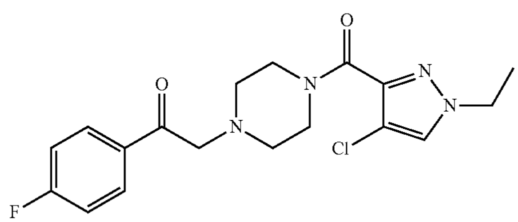 [SMILES: CCn1cc(Cl)c(C(=O)N2CCN(CC(=O)c3ccc(F)cc3)CC2)n1] | 2-[4-(4-Chloro-1-ethyl-1H-pyrazole-3-carbonyl)-piperazin-1-yl]-1-(4-fluoro-phenyl)-ethanone |
| 8 | 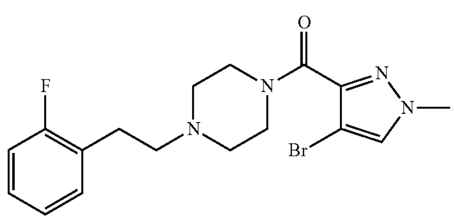 | (4-Bromo-1-methyl-1H-pyrazol-3-yl)-{4-[2-(2-fluoro-phenyl)-ethyl]-piperazin-1-yl}-methanone |
| 9 | 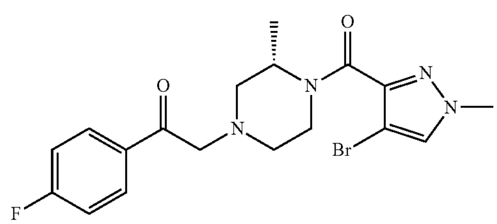 [SMILES: C[C@H]1CN(CC(=O)c2ccc(F)cc2)CCN1C(=O)c1nn(C)cc1Br] | 2-[(S)-4-(4-Bromo-1-methyl-1H-pyrazole-3-carbonyl)-3-methyl-piperazin-1-yl]-1-(4-fluoro-phenyl)-ethanone |
| 10 | 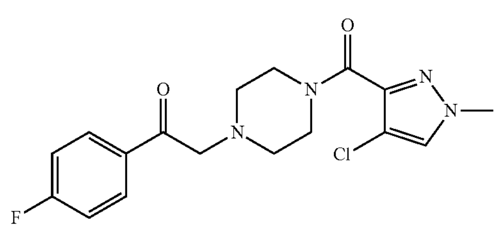 | 2-[4-(4-Chloro-1-methyl-1H-pyrazole-3-carbonyl)-piperazin-1-yl]-1-(4-fluoro-phenyl)-ethanone |

| Cmpd No. | Chemical Name |
|---|---|
| 11 | 1-(4-Fluoro-phenyl)-2-[4-(1,4,5,6-tetrahydro-cyclopentapyrazole-3-carbonyl)-piperazin-1-yl]-ethanone |
| 12 | 2-[(R)-4-(4-Chloro-1-methyl-1H-pyrazole-3-carbonyl)-2-methyl-piperazin-1-yl]-1-(4-fluoro-phenyl)-ethanone |
| 13 | 2-[4-(4-Bromo-1-methyl-1H-pyrazole-3-carbonyl)-piperazin-1-yl]-1-(4-fluoro-phenyl)-ethanone |
| 14 | 2-[4-(4-Bromo-1-methyl-1H-pyrazole-3-carbonyl)-piperazin-1-yl]-1-(3-fluoro-phenyl)-ethanone |
| 15 | 2-[(R)-4-(4-Bromo-1-methyl-1H-pyrazole-3-carbonyl)-2-methyl-piperazin-1-yl]-1-(4-fluoro-phenyl)-ethanone |
| 16 | (4-Chloro-1-ethyl-1H-pyrazol-3-yl)-{4-[2-(4-fluoro-phenyl)-ethyl]-piperazin-1-yl}-methanone |
| 17 | 2-[4-(1-tert-Butyl-5-methyl-1H-pyrazole-3-carbonyl)-piperazin-1-yl]-1-(4-fluoro-phenyl)-ethanone |

TABLE 4-continued

| Cmpd No. | Chemical Structure | Chemical Name |
|---|---|---|
| 18 | 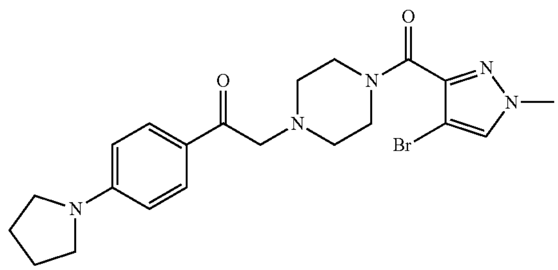 [SMILES: Cn1cc(Br)c(C(=O)N2CCN(CC(=O)c3ccc(N4CCCC4)cc3)CC2)n1] | 2-[4-(4-Bromo-1-methyl-1H-pyrazole-3-carbonyl)-piperazin-1-yl]-1-(4-pyrrolidin-1-yl-phenyl)-ethanone |
| 19 | 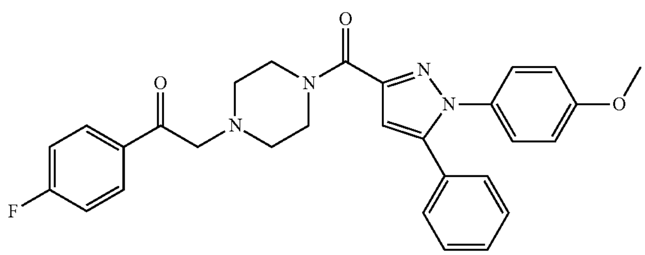 [SMILES: COc1ccc(-n2nc(C(=O)N3CCN(CC(=O)c4ccc(F)cc4)CC3)cc2-c2ccccc2)cc1] | 1-(4-Fluoro-phenyl)-2-{4-[1-(4-methoxy-phenyl)-5-phenyl-1H-pyrazole-3-carbonyl]-piperazin-1-yl}-ethanone |
| 20 | 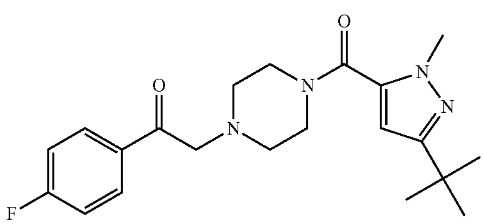 [SMILES: Cn1nc(C(C)(C)C)cc1C(=O)N1CCN(CC(=O)c2ccc(F)cc2)CC1] | 2-[4-(5-tert-Butyl-2-methyl-2H-pyrazole-3-carbonyl)-piperazin-1-yl]-1-(4-fluoro-phenyl)-ethanone |
| 21 | 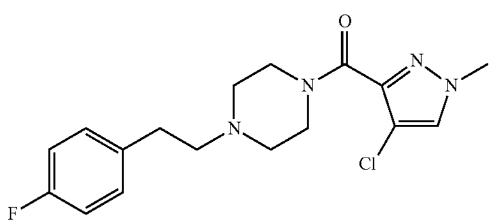 [SMILES: Cn1cc(Cl)c(C(=O)N2CCN(CCc3ccc(F)cc3)CC2)n1] | (4-Chloro-1-methyl-1H-pyrazol-3-yl)-{4-[2-(4-fluoro-phenyl)-ethyl]-piperazin-1-yl}-methanone |
| 22 | 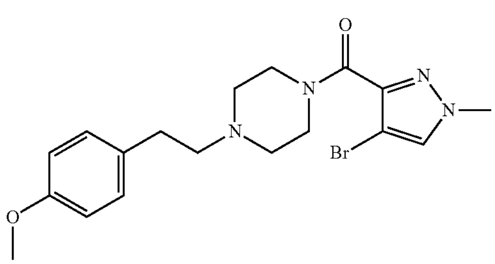 [SMILES: COc1ccc(CCN2CCN(C(=O)c3nn(C)cc3Br)CC2)cc1] | (4-Bromo-1-methyl-1H-pyrazol-3-yl)-{4-[2-(4-methoxy-phenyl)-ethyl]-piperazin-1-yl}-methanone |
| 23 | 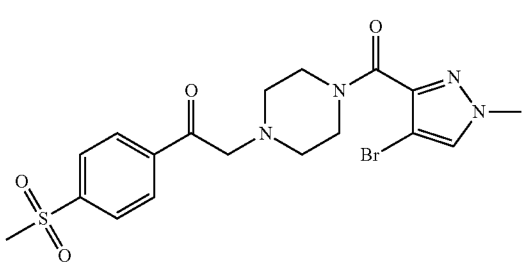 | 2-[4-(4-Bromo-1-methyl-1H-pyrazole-3-carbonyl)-piperazin-1-yl]-1-(4-methanesulfonyl-phenyl)-ethanone |

TABLE 4-continued

| Cmpd No. | Chemical Structure | Chemical Name |
|---|---|---|
| 24 | 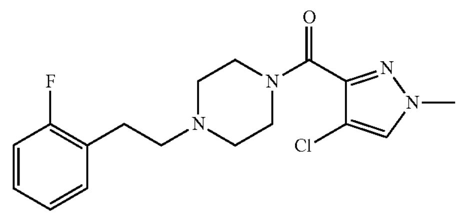 [SMILES: Cn1cc(Cl)c(C(=O)N2CCN(CCc3ccccc3F)CC2)n1] | (4-Chloro-1-methyl-1H-pyrazol-3-yl)-{4-[2-(2-fluoro-phenyl)-ethyl]-piperazin-1-yl}-methanone |
| 25 | 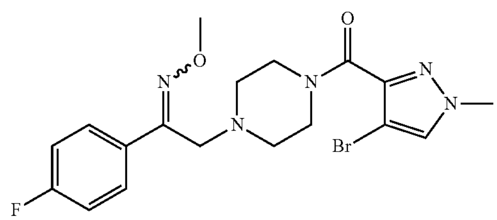 [SMILES: CON=C(CN1CCN(C(=O)c2nn(C)cc2Br)CC1)c1ccc(F)cc1] | 2-[4-(4-Bromo-1-methyl-1H-pyrazole-3-carbonyl)-piperazin-1-yl]-1-(4-fluoro-phenyl)-ethanone O-methyl-oxime |
| 26 | 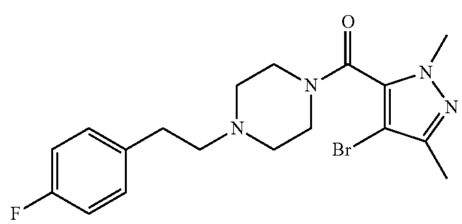 [SMILES: Cc1nn(C)c(C(=O)N2CCN(CCc3ccc(F)cc3)CC2)c1Br] | (4-Bromo-2,5-dimethyl-2H-pyrazol-3-yl)-{4-[2-(4-fluoro-phenyl)-ethyl]-piperazin-1-yl}-methanone |
| 27 | 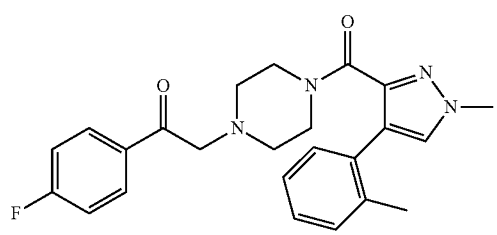 [SMILES: Cc1ccccc1-c1cn(C)nc1C(=O)N1CCN(CC(=O)c2ccc(F)cc2)CC1] | 1-(4-Fluoro-phenyl)-2-[4-(1-methyl-4-o-tolyl-1H-pyrazole-3-carbonyl)-piperazin-1-yl]-ethanone |
| 28 | 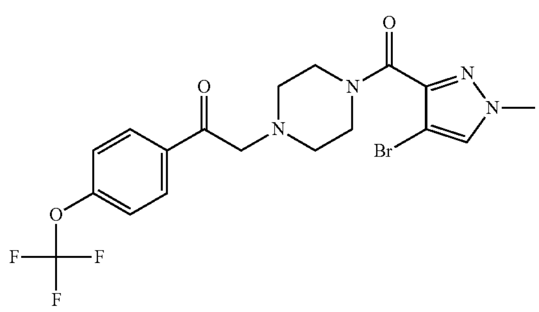 [SMILES: Cn1cc(Br)c(C(=O)N2CCN(CC(=O)c3ccc(OC(F)(F)F)cc3)CC2)n1] | 2-[4-(4-Bromo-1-methyl-1H-pyrazole-3-carbonyl)-piperazin-1-yl]-1-(4-trifluoromethoxy-phenyl)-ethanone |
| 29 | 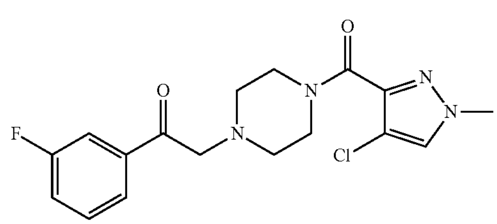 [SMILES: Cn1cc(Cl)c(C(=O)N2CCN(CC(=O)c3cccc(F)c3)CC2)n1] | 2-[4-(4-Chloro-1-methyl-1H-pyrazole-3-carbonyl)-piperazin-1-yl]-1-(3-fluoro-phenyl)-ethanone |

TABLE 4-continued

| Cmpd No. | Chemical Structure | Chemical Name |
|---|---|---|
| 30 | 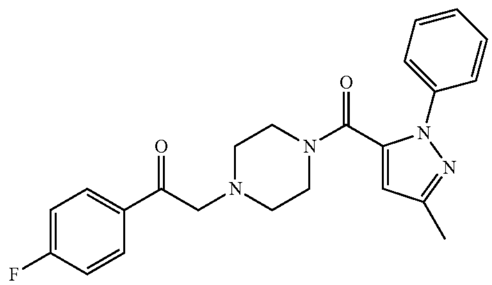 [SMILES: Cc1cc(C(=O)N2CCN(CC(=O)c3ccc(F)cc3)CC2)n(-c2ccccc2)n1] | 1-(4-Fluoro-phenyl)-2-[4-(5-methyl-2-phenyl-2H-pyrazole-3-carbonyl)-piperazin-1-yl]-ethanone |
| 31 | 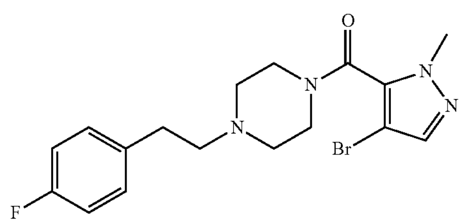 [SMILES: Cn1ncc(Br)c1C(=O)N1CCN(CCc2ccc(F)cc2)CC1] | (4-Bromo-2-methyl-2H-pyrazol-3-yl)-{4-[2-(4-fluoro-phenyl)-ethyl]-piperazin-1-yl}-methanone |
| 32 | 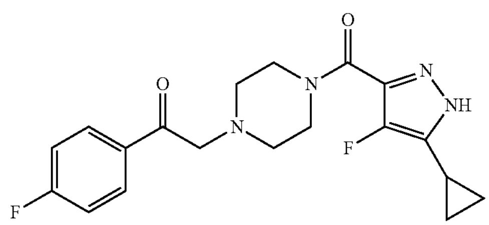 [SMILES: O=C(CN1CCN(C(=O)c2n[nH]c(C3CC3)c2F)CC1)c1ccc(F)cc1] | 2-[4-(5-Cyclopropyl-4-fluoro-1H-pyrazole-3-carbonyl)-piperazin-1-yl]-1-(4-fluoro-phenyl)-ethanone |
| 33 | 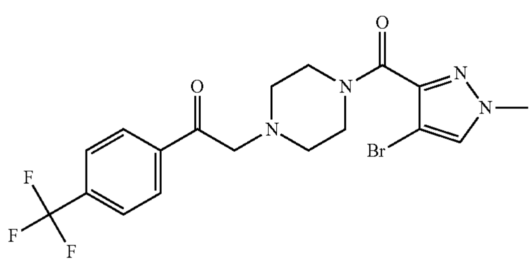 [SMILES: Cn1cc(Br)c(C(=O)N2CCN(CC(=O)c3ccc(C(F)(F)F)cc3)CC2)n1] | 2-[4-(4-Bromo-1-methyl-1H-pyrazole-3-carbonyl)-piperazin-1-yl]-1-(4-trifluoromethyl-phenyl)-ethanone |
| 34 | 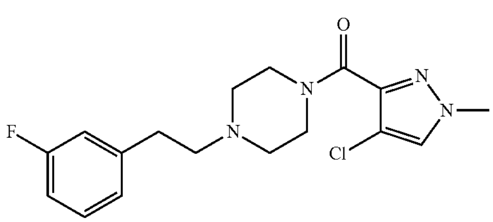 [SMILES: Cn1cc(Cl)c(C(=O)N2CCN(CCc3cccc(F)c3)CC2)n1] | (4-Chloro-1-methyl-1H-pyrazol-3-yl)-{4-[2-(3-fluoro-phenyl)-ethyl]-piperazin-1-yl}-methanone |
| 35 | 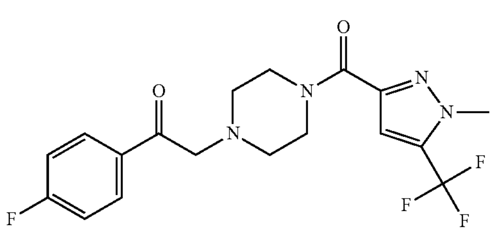 [SMILES: Cn1nc(C(=O)N2CCN(CC(=O)c3ccc(F)cc3)CC2)cc1C(F)(F)F] | 1-(4-Fluoro-phenyl)-2-[4-(1-methyl-5-trifluoromethyl-1H-pyrazole-3-carbonyl)-piperazin-1-yl]-ethanone |

TABLE 4-continued

| Cmpd No. | Chemical Structure | Chemical Name |
|---|---|---|
| 36 | 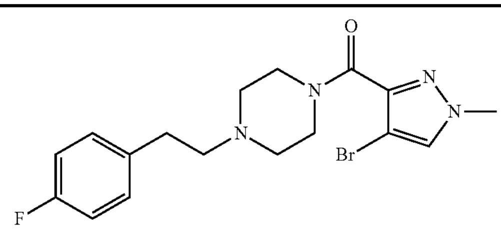 | (4-Bromo-1-methyl-1H-pyrazol-3-yl)-{4-[2-(4-fluoro-phenyl)-ethyl]-piperazin-1-yl}-methanone |
| 37 | 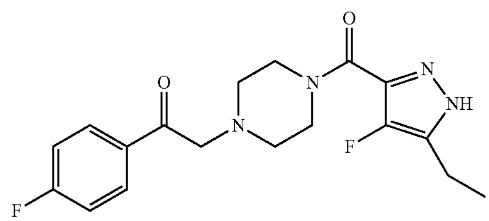 [SMILES: CCc1[nH]nc(C(=O)N2CCN(CC(=O)c3ccc(F)cc3)CC2)c1F] | 2-[4-(5-Ethyl-4-fluoro-1H-pyrazole-3-carbonyl)-piperazin-1-yl]-1-(4-fluoro-phenyl)-ethanone |
| 38 | 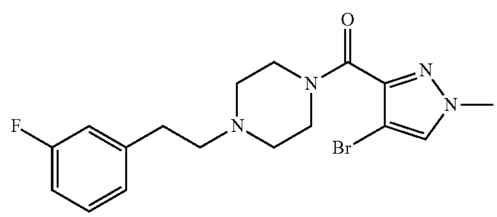 | (4-Bromo-1-methyl-1H-pyrazol-3-yl)-{4-[2-(3-fluoro-phenyl)-ethyl]-piperazin-1-yl}-methanone |
| 39 | 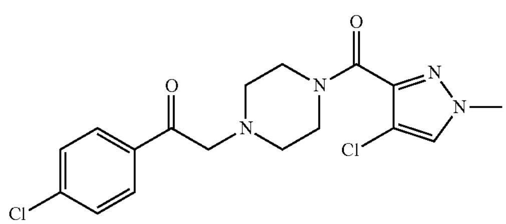 [SMILES: Cn1cc(Cl)c(C(=O)N2CCN(CC(=O)c3ccc(Cl)cc3)CC2)n1] | 2-[4-(4-Chloro-1-methyl-1H-pyrazole-3-carbonyl)-piperazin-1-yl]-1-(4-chloro-phenyl)-ethanone |
| 40 | 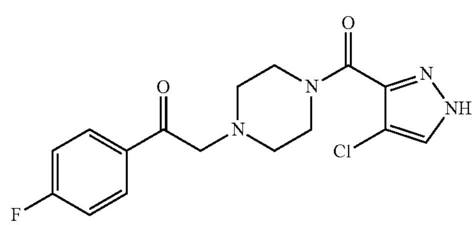 [SMILES: O=C(CN1CCN(C(=O)c2n[nH]cc2Cl)CC1)c1ccc(F)cc1] | 2-[4-(4-Chloro-1H-pyrazole-3-carbonyl)-piperazin-1-yl]-1-(4-fluoro-phenyl)-ethanone |
| 41 | 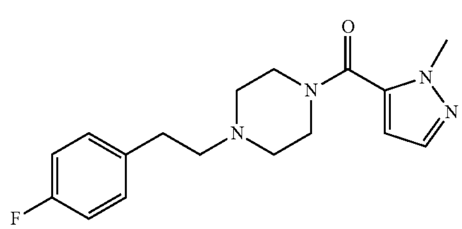 [SMILES: Cn1nccc1C(=O)N1CCN(CCc2ccc(F)cc2)CC1] | {4-[2-(4-Fluoro-phenyl)-ethyl]-piperazin-1-yl}-(2-methyl-2H-pyrazol-3-yl)-methanone |
| 42 | 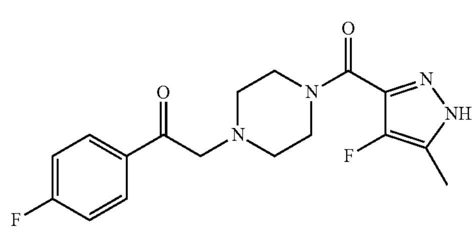 [SMILES: Cc1[nH]nc(C(=O)N2CCN(CC(=O)c3ccc(F)cc3)CC2)c1F] | 2-[4-(4-Fluoro-5-methyl-1H-pyrazole-3-carbonyl)-piperazin-1-yl]-1-(4-fluoro-phenyl)-ethanone |

| Cmpd No. | Chemical Structure | Chemical Name |
|---|---|---|
| 43 | 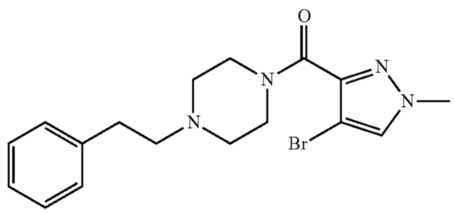 [SMILES: Cn1cc(Br)c(C(=O)N2CCN(CCc3ccccc3)CC2)n1] | (4-Bromo-1-methyl-1H-pyrazol-3-yl)-(4-phenethyl-piperazin-1-yl)-methanone |
| 44 | 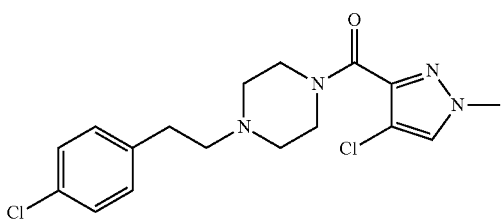 [SMILES: Cn1cc(Cl)c(C(=O)N2CCN(CCc3ccc(Cl)cc3)CC2)n1] | (4-Chloro-1-methyl-1H-pyrazol-3-yl)-{4-[2-(4-chloro-phenyl)-ethyl]-piperazin-1-yl}-methanone |
| 45 | 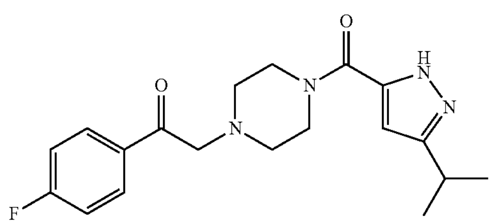 [SMILES: CC(C)c1cc(C(=O)N2CCN(CC(=O)c3ccc(F)cc3)CC2)[nH]n1] | 1-(4-Fluoro-phenyl)-2-[4-(5-isopropyl-2H-pyrazole-3-carbonyl)-piperazin-1-yl]-ethanone |
| 46 | 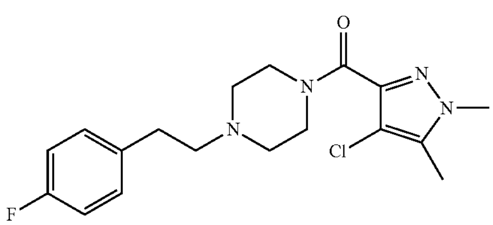 [SMILES: Cc1c(Cl)c(C(=O)N2CCN(CCc3ccc(F)cc3)CC2)nn1C] | (4-Chloro-1,5-dimethyl-1H-pyrazol-3-yl)-{4-[2-(4-fluoro-phenyl)-ethyl]-piperazin-1-yl}-methanone |
| 47 | 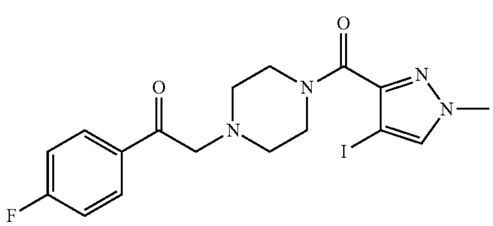 [SMILES: Cn1cc(I)c(C(=O)N2CCN(CC(=O)c3ccc(F)cc3)CC2)n1] | 1-(4-Fluoro-phenyl)-2-[4-(4-iodo-1-methyl-1H-pyrazole-3-carbonyl)-piperazin-1-yl]-ethanone |
| 48 | 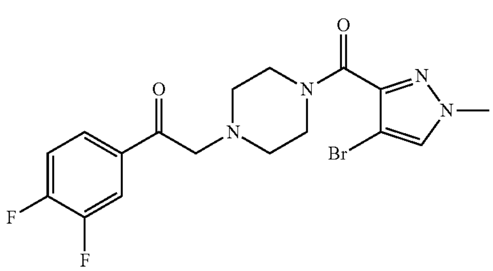 [SMILES: Cn1cc(Br)c(C(=O)N2CCN(CC(=O)c3ccc(F)c(F)c3)CC2)n1] | 2-[4-(4-Bromo-1-methyl-1H-pyrazole-3-carbonyl)-piperazin-1-yl]-1-(3,4-difluoro-phenyl)-ethanone |

TABLE 4-continued

| Cmpd No. | Chemical Structure | Chemical Name |
|---|---|---|
| 49 | 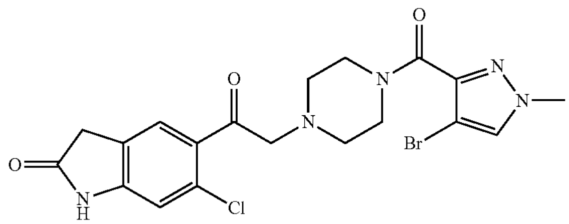 [SMILES: Cn1cc(Br)c(C(=O)N2CCN(CC(=O)c3cc4c(cc3Cl)NC(=O)C4)CC2)n1] | 5-{2-[4-(4-Bromo-1-methyl-1H-pyrazole-3-carbonyl)-piperazin-1-yl]-acetyl}-6-chloro-1,3-dihydro-indol-2-one |
| 50 | 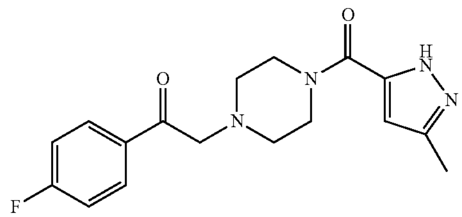 [SMILES: Cc1cc(C(=O)N2CCN(CC(=O)c3ccc(F)cc3)CC2)[nH]n1] | 1-(4-Fluoro-phenyl)-2-[4-(5-methyl-2H-pyrazole-3-carbonyl)-piperazin-1-yl]-ethanone |
| 51 | 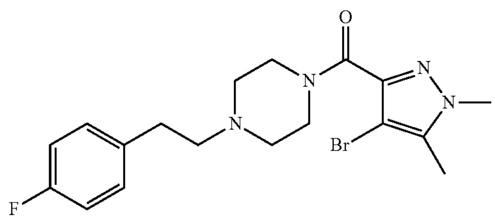 [SMILES: Cc1c(Br)c(C(=O)N2CCN(CCc3ccc(F)cc3)CC2)nn1C] | (4-Bromo-1,5-dimethyl-1H-pyrazol-3-yl)-{4-[2-(4-fluoro-phenyl)-ethyl]-piperazin-1-yl}-methanone |
| 52 | 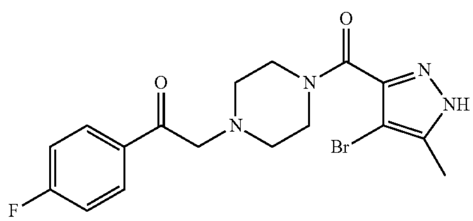 [SMILES: Cc1[nH]nc(C(=O)N2CCN(CC(=O)c3ccc(F)cc3)CC2)c1Br] | 2-[4-(4-Bromo-5-methyl-1H-pyrazole-3-carbonyl)-piperazin-1-yl]-1-(4-fluoro-phenyl)-ethanone |
| 53 | 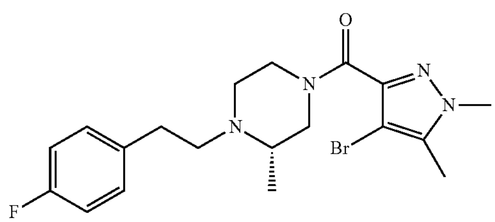 [SMILES: Cc1c(Br)c(C(=O)N2CCN(CCc3ccc(F)cc3)[C@@H](C)C2)nn1C] | (4-Bromo-1,5-dimethyl-1H-pyrazol-3-yl)-{(S)-4-[2-(4-fluoro-phenyl)-ethyl]-3-methyl-piperazin-1-yl}-methanone |
| 54 | 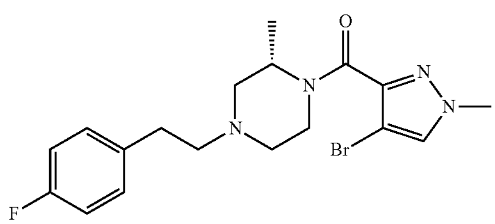 [SMILES: C[C@H]1CN(CCc2ccc(F)cc2)CCN1C(=O)c1nn(C)cc1Br] | (4-Bromo-1-methyl-1H-pyrazol-3-yl)-{(S)-4-[2-(4-fluoro-phenyl)-ethyl]-2-methyl-piperazin-1-yl}-methanone |
| 55 | 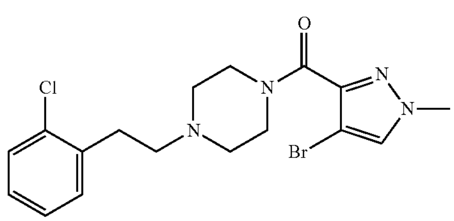 [SMILES: Cn1cc(Br)c(C(=O)N2CCN(CCc3ccccc3Cl)CC2)n1] | (4-Bromo-1-methyl-1H-pyrazol-3-yl)-{4-[2-(2-chloro-phenyl)-ethyl]-piperazin-1-yl}-methanone |

TABLE 4-continued

| Cmpd No. | Chemical Structure | Chemical Name |
|---|---|---|
| 56 | 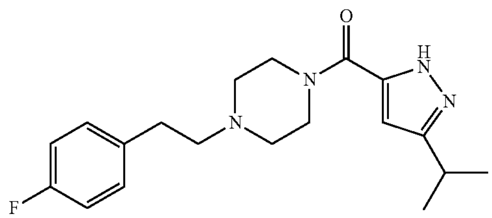 [SMILES: CC(C)c1cc(C(=O)N2CCN(CCc3ccc(F)cc3)CC2)[nH]n1] | {4-[2-(4-Fluoro-phenyl)-ethyl]-piperazin-1-yl}-(5-isopropyl-2H-pyrazol-3-yl)-methanone |
| 57 | 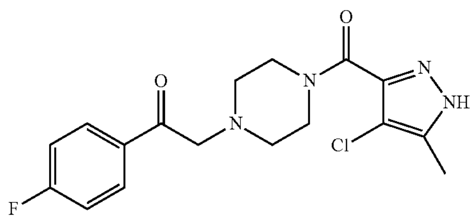 [SMILES: Cc1[nH]nc(C(=O)N2CCN(CC(=O)c3ccc(F)cc3)CC2)c1Cl] | 2-[4-(4-Chloro-5-methyl-1H-pyrazole-3-carbonyl)-piperazin-1-yl]-1-(4-fluoro-phenyl)-ethanone |
| 58 | 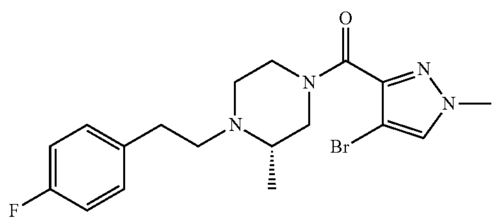 [SMILES: C[C@H]1CN(C(=O)c2nn(C)cc2Br)CCN1CCc1ccc(F)cc1] | (4-Bromo-1-methyl-1H-pyrazol-3-yl)-{(S)-4-[2-(4-fluoro-phenyl)-ethyl]-3-methyl-piperazin-1-yl}-methanone |
| 59 | 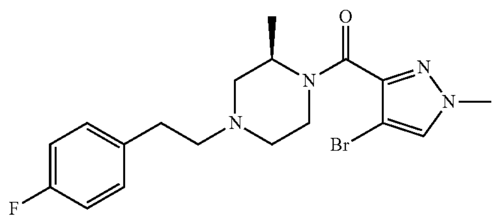 [SMILES: C[C@@H]1CN(CCc2ccc(F)cc2)CCN1C(=O)c1nn(C)cc1Br] | (4-Bromo-1-methyl-1H-pyrazol-3-yl)-{(R)-4-[2-(4-fluoro-phenyl)-ethyl]-2-methyl-piperazin-1-yl}-methanone |
| 60 | 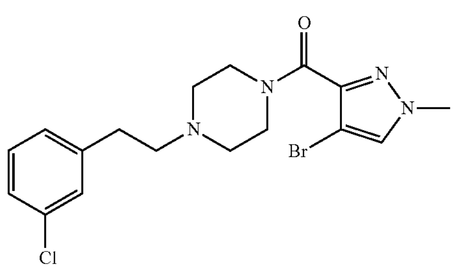 [SMILES: Cn1cc(Br)c(C(=O)N2CCN(CCc3cccc(Cl)c3)CC2)n1] | (4-Bromo-1-methyl-1H-pyrazol-3-yl)-{4-[2-(3-chloro-phenyl)-ethyl]-piperazin-1-yl}-methanone |
| 61 | 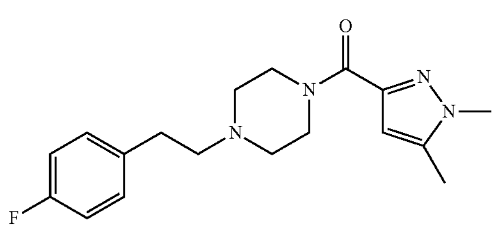 [SMILES: Cc1cc(C(=O)N2CCN(CCc3ccc(F)cc3)CC2)nn1C] | (1,5-Dimethyl-1H-pyrazol-3-yl)-{4-[2-(4-fluoro-phenyl)-ethyl]-piperazin-1-yl}-methanone |

TABLE 4-continued

| Cmpd No. | Chemical Structure | Chemical Name |
|---|---|---|
| 62 | 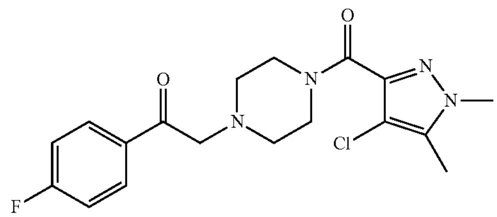 [SMILES: Cc1c(Cl)c(C(=O)N2CCN(CC(=O)c3ccc(F)cc3)CC2)nn1C] | 2-[4-(4-Chloro-1,5-dimethyl-1H-pyrazole-3-carbonyl)-piperazin-1-yl]-1-(4-fluoro-phenyl)-ethanone |
| 63 | 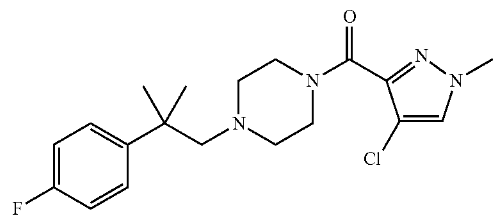 [SMILES: Cn1cc(Cl)c(C(=O)N2CCN(CC(C)(C)c3ccc(F)cc3)CC2)n1] | (4-Chloro-1-methyl-1H-pyrazol-3-yl)-{4-[2-(4-fluoro-phenyl)-2-methyl-propyl]-piperazin-1-yl}-methanone |
| 64 | 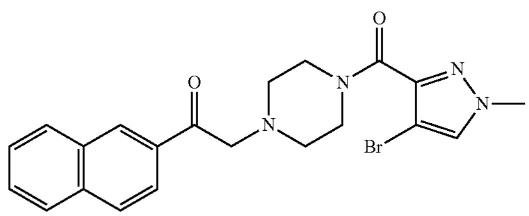 [SMILES: Cn1cc(Br)c(C(=O)N2CCN(CC(=O)c3ccc4ccccc4c3)CC2)n1] | 2-[4-(4-Bromo-1-methyl-1H-pyrazole-3-carbonyl)-piperazin-1-yl]-1-naphthalen-2-yl-ethanone |
| 65 | 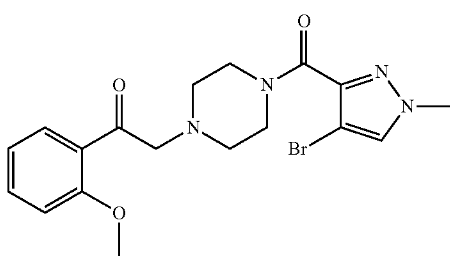 [SMILES: COc1ccccc1C(=O)CN1CCN(C(=O)c2nn(C)cc2Br)CC1] | 2-[4-(4-Bromo-1-methyl-1H-pyrazole-3-carbonyl)-piperazin-1-yl]-1-(2-methoxy-phenyl)-ethanone |
| 66 | 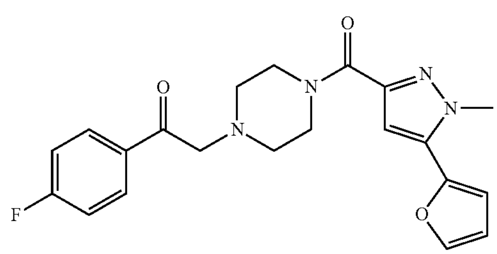 [SMILES: Cn1nc(C(=O)N2CCN(CC(=O)c3ccc(F)cc3)CC2)cc1-c1ccco1] | 1-(4-Fluoro-phenyl)-2-[4-(5-furan-2-yl-1-methyl-1H-pyrazole-3-carbonyl)-piperazin-1-yl]-ethanone |
| 67 | 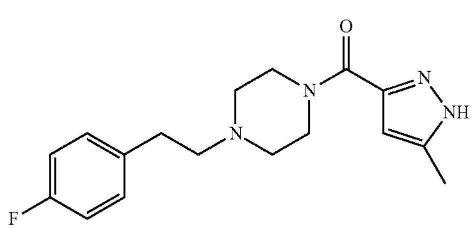 [SMILES: Cc1cc(C(=O)N2CCN(CCc3ccc(F)cc3)CC2)n[nH]1] | {4-[2-(4-Fluoro-phenyl)-ethyl]-piperazin-1-yl}-(5-methyl-1H-pyrazol-3-yl)-methanone |

TABLE 4-continued

| Cmpd No. | Chemical Structure | Chemical Name |
|---|---|---|
| 68 | 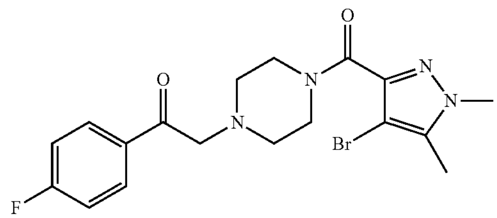 | 2-[4-(4-Bromo-1,5-dimethyl-1H-pyrazole-3-carbonyl)-piperazin-1-yl]-1-(4-fluoro-phenyl)-ethanone |
| 69 | 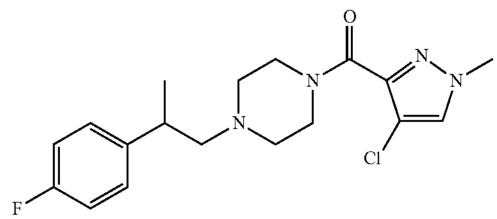 [SMILES: CC(CN1CCN(C(=O)c2nn(C)cc2Cl)CC1)c1ccc(F)cc1] | (4-Chloro-1-methyl-1H-pyrazol-3-yl)-{4-[2-(4-fluoro-phenyl)-propyl]-piperazin-1-yl}-methanone |
| 70 | 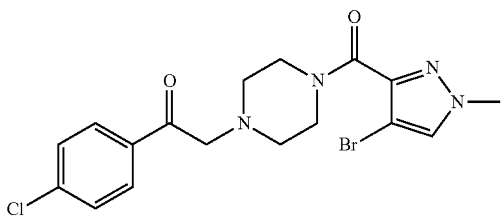 [SMILES: Cn1cc(Br)c(C(=O)N2CCN(CC(=O)c3ccc(Cl)cc3)CC2)n1] | 2-[4-(4-Bromo-1-methyl-1H-pyrazole-3-carbonyl)-piperazin-1-yl]-1-(4-chloro-phenyl)-ethanone |
| 71 | 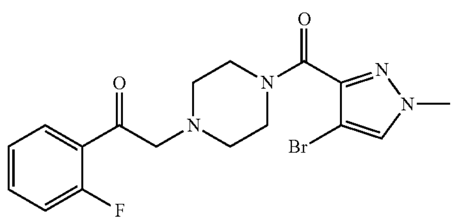 [SMILES: Cn1cc(Br)c(C(=O)N2CCN(CC(=O)c3ccccc3F)CC2)n1] | 2-[4-(4-Bromo-1-methyl-1H-pyrazole-3-carbonyl)-piperazin-1-yl]-1-(2-fluoro-phenyl)-ethanone |
| 72 | 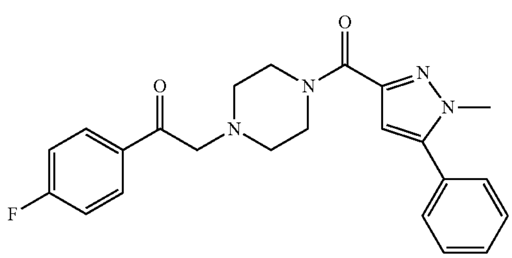 [SMILES: Cn1nc(C(=O)N2CCN(CC(=O)c3ccc(F)cc3)CC2)cc1-c1ccccc1] | 1-(4-Fluoro-phenyl)-2-[4-(1-methyl-5-phenyl-1H-pyrazole-3-carbonyl)-piperazin-1-yl]-ethanone |
| 73 | 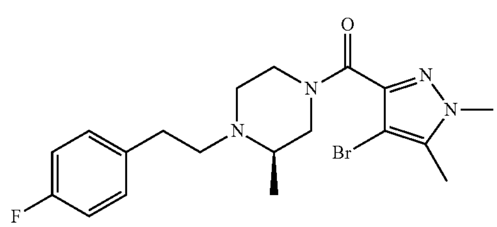 [SMILES: Cc1c(Br)c(C(=O)N2CCN(CCc3ccc(F)cc3)[C@H](C)C2)nn1C] | (4-Bromo-1,5-dimethyl-1H-pyrazol-3-yl)-{(R)-4-[2-(4-fluoro-phenyl)-ethyl]-3-methyl-piperazin-1-yl}-methanone |
| 74 | 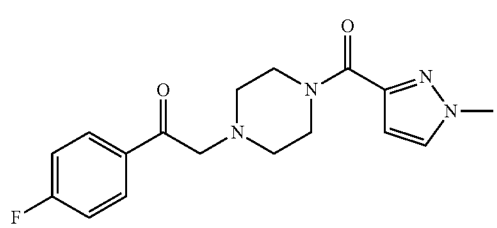 [SMILES: Cn1ccc(C(=O)N2CCN(CC(=O)c3ccc(F)cc3)CC2)n1] | 1-(4-Fluoro-phenyl)-2-[4-(1-methyl-1H-pyrazole-3-carbonyl)-piperazin-1-yl]-ethanone |

TABLE 4-continued

| Cmpd No. | Chemical Structure | Chemical Name |
|---|---|---|
| 75 | 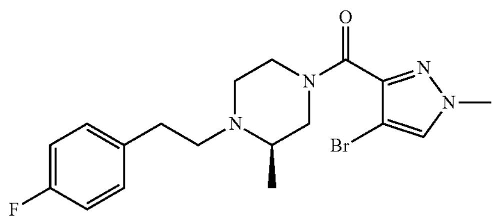 [SMILES: C[C@@H]1CN(C(=O)c2nn(C)cc2Br)CCN1CCc1ccc(F)cc1] | (4-Bromo-1-methyl-1H-pyrazol-3-yl)-{(R)-4-[2-(4-fluoro-phenyl)-ethyl]-3-methyl-piperazin-1-yl}-methanone |
| 76 | 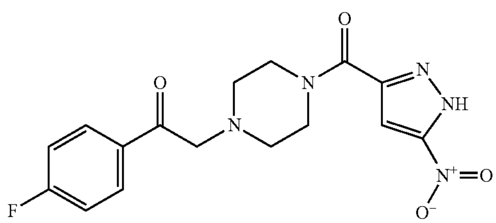 [SMILES: O=C(CN1CCN(C(=O)c2cc([N+](=O)[O-])[nH]n2)CC1)c1ccc(F)cc1] | 1-(4-Fluoro-phenyl)-2-[4-(5-nitro-1H-pyrazole-3-carbonyl)-piperazin-1-yl]-ethanone |
| 77 | 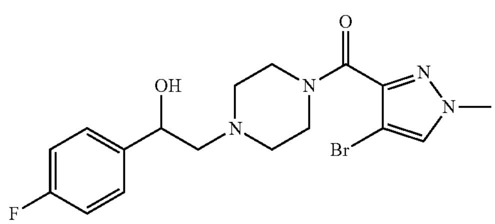 [SMILES: Cn1cc(Br)c(C(=O)N2CCN(CC(O)c3ccc(F)cc3)CC2)n1] | (4-Bromo-1-methyl-1H-pyrazol-3-yl)-{4-[2-(4-fluoro-phenyl)-2-hydroxy-ethyl]-piperazin-1-yl}-methanone |
| 78 | 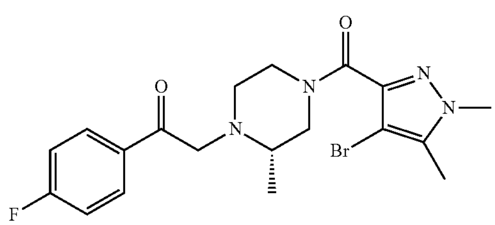 [SMILES: Cc1c(Br)c(C(=O)N2CCN(CC(=O)c3ccc(F)cc3)[C@@H](C)C2)nn1C] | 2-[(S)-4-(4-Bromo-1,5-dimethyl-1H-pyrazole-3-carbonyl)-2-methyl-piperazin-1-yl]-1-(4-fluoro-phenyl)-ethanone |
| 79 | 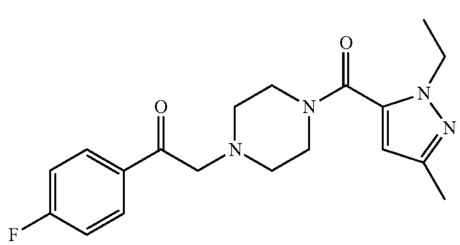 [SMILES: CCn1nc(C)cc1C(=O)N1CCN(CC(=O)c2ccc(F)cc2)CC1] | 2-[4-(2-Ethyl-5-methyl-2H-pyrazole-3-carbonyl)-piperazin-1-yl]-1-(4-fluoro-phenyl)-ethanone |
| 80 | 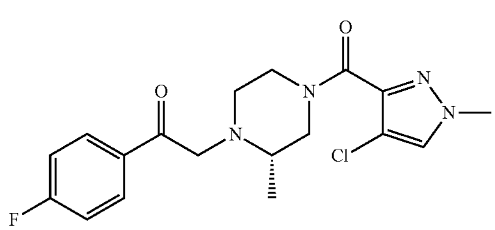 [SMILES: C[C@H]1CN(C(=O)c2nn(C)cc2Cl)CCN1CC(=O)c1ccc(F)cc1] | 2-[(S)-4-(4-Chloro-1-methyl-1H-pyrazole-3-carbonyl)-2-methyl-piperazin-1-yl]-1-(4-fluoro-phenyl)-ethanone |

TABLE 4-continued

| Cmpd No. | Chemical Structure | Chemical Name |
|---|---|---|
| 81 | 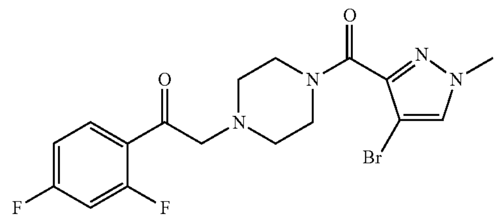 [SMILES: Cn1cc(Br)c(C(=O)N2CCN(CC(=O)c3ccc(F)cc3F)CC2)n1] | 2-[4-(4-Bromo-1-methyl-1H-pyrazole-3-carbonyl)-piperazin-1-yl]-1-(2,4-difluoro-phenyl)-ethanone |
| 82 | 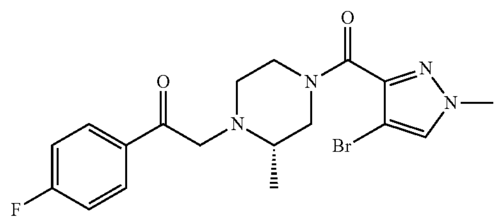 [SMILES: C[C@H]1CN(C(=O)c2nn(C)cc2Br)CCN1CC(=O)c1ccc(F)cc1] | 2-[(S)-4-(4-Bromo-1-methyl-1H-pyrazole-3-carbonyl)-2-methyl-piperazin-1-yl]-1-(4-fluoro-phenyl)-ethanone |
| 83 | 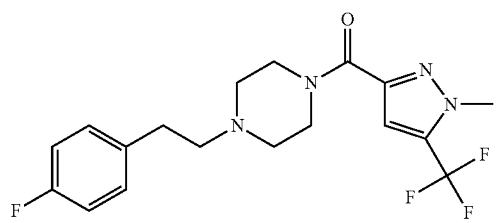 [SMILES: Cn1nc(C(=O)N2CCN(CCc3ccc(F)cc3)CC2)cc1C(F)(F)F] | {4-[2-(4-Fluoro-phenyl)-ethyl]-piperazin-1-yl}-(1-methyl-5-trifluoromethyl-1H-pyrazol-3-yl)-methanone |
| 84 | 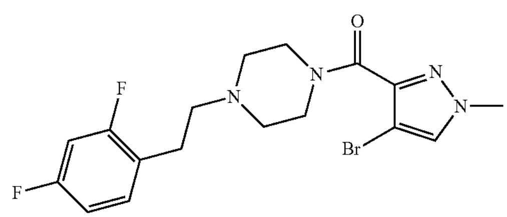 [SMILES: Cn1cc(Br)c(C(=O)N2CCN(CCc3ccc(F)cc3F)CC2)n1] | (4-Bromo-1-methyl-1H-pyrazol-3-yl)-{4-[2-(2,4-difluoro-phenyl)-ethyl]-piperazin-1-yl}-methanone |
| 85 | 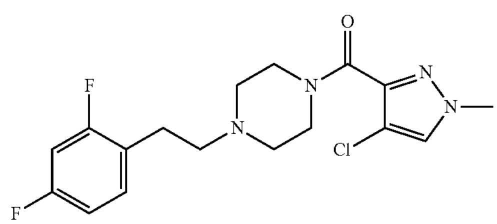 [SMILES: Cn1cc(Cl)c(C(=O)N2CCN(CCc3ccc(F)cc3F)CC2)n1] | (4-Chloro-1-methyl-1H-pyrazol-3-yl)-{4-[2-(2,4-difluoro-phenyl)-ethyl]-piperazin-1-yl}-methanone |

Additionally, individual compounds and chemical genera of the present invention, for example those compounds found in Table 4 including diastereomers and enantiomers thereof, encompass all pharmaceutically acceptable salts, solvates, and particularly hydrates thereof.

Some embodiments of the present invention pertain to 1-[3-(4-Bromo-2-methyl-2H-pyrazol-3-yl)-4-methoxy-phenyl]-3-(2,4-difluoro-phenyl)-urea.

One aspect of the present invention relates to novel, solid-dosage formulations of 1-[3-(4-Bromo-2-methyl-2H-pyrazol-3-yl)-4-methoxy-phenyl]-3-(2,4-difluoro-phenyl)-urea which provide one or more of the following: (a) high oral-bioavailability, comparable to that of liquid formulations; (b) physical stability with respect to crystalline form; and (c) chemical stability better than that of liquid formulations. Consequently, the solid-dosage formulations disclosed herein are useful for treating certain 5-HT$_{2A}$ serotonin receptor-related disorders, such as neuropsychiatric symptoms, including but not limited to hallucinations. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments the visual hallucinations are associated with a neurodegenerative disease such as Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments of the present invention pertain to N-(4-fluorophenylmethyl)-N-(1-methylpiperidin-4-yl)-N'-(4-(2-methylpropyloxy)phenylmethyl)carbamide or a pharmaceutically acceptable salt, hydrate, polymorph, or solvate thereof, which is also known as pimavanserin. Some embodiments of the present invention pertain to pruvanserin, eplivanserin, volinanserin, glemanserin, ketanserin, ritanserin, clozapine, or a pharmaceutically acceptable salt, hydrate, polymorph, or solvate thereof.

Additionally, compounds of the present invention, such as Formula (I) and related formulae, encompass all pharmaceutically acceptable salts, solvates, polymorphs, and particularly hydrates thereof.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Prophylaxis and/or Treatment of Lewy Body Dementia (LBD)

In addition to the foregoing beneficial uses for the modulators of 5-HT$_{2A}$ receptor activity disclosed herein, the compounds disclosed herein are believed to be useful in the treatment of Lewy Body dementia (LBD), and in the amelioration of symptoms thereof. In addition to the foregoing beneficial uses for the modulators of 5-HT$_{2A}$ receptor activity disclosed herein, the compounds disclosed herein are believed to be useful in the treatment of Lewy Body dementia (LBD) in subjects experiencing neuropsychiatric symptoms including but not limited to hallucinations, and in the amelioration of symptoms thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In addition to the foregoing beneficial uses for the modulators of 5-HT$_{2A}$ receptor activity disclosed herein, the compounds disclosed herein are believed to be useful in the treatment of Lewy Body dementia (LBD) in subjects experiencing visual hallucinations, and in the amelioration of symptoms thereof.

In some embodiments, the patient is an Adult subject aged 50 to 85, inclusive, with a diagnosis of probable Dementia with Lewy Bodies (DLB) and the presence of persistent neuropsychiatric symptoms including but not limited to hallucinations. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, the diagnosis of probable DLB will be defined by the presence of dementia and at least one of the following: At least two out of the following three Core Criteria: Visual hallucinations, Cognitive Fluctuations, and Parkinsonism; One of the Core Criteria and at least one of the following three Suggestive Criteria: REM Sleep Behavior Disorder, Severe Neuroleptic Sensitivity, and Low Dopamine Transporter Uptake on DaT SPECT Imaging Scan.

In some embodiments, the patient is an Adult subject aged 50 to 85, inclusive, with a diagnosis of probable Dementia with Lewy Bodies (DLB) and the presence of persistent visual hallucinations. In some embodiments, the diagnosis of probable DLB will be defined by the presence of dementia and at least one of the following: At least two out of the following three Core Criteria: Visual hallucinations, Cognitive Fluctuations, and Parkinsonism; One of the Core Criteria and at least one of the following three Suggestive Criteria: REM Sleep Behavior Disorder, Severe Neuroleptic Sensitivity, and Low Dopamine Transporter Uptake on DaT SPECT Imaging Scan.

In some embodiments, the presence of persistent hallucinations will be defined by having a score of four or greater on the hallucinations component of the Neuropsychiatric Inventory (NPI Item B) at screening and at the end of the two-week lead-in period, during which subjects may receive non-pharmacological brief psychosocial therapy. In addition, subjects must have a score of three or greater on SAPS-H at baseline. Subjects must again have an NPI Item B score of ≥4 and a SAPS-H score of ≥3 at the end of a two-week placebo run-in period prior to randomization. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, the presence of persistent visual hallucinations will be defined by having a score of four or greater on the hallucinations component of the Neuropsychiatric Inventory (NPI Item B) at screening and at the end of the two-week lead-in period, during which subjects may receive non-pharmacological brief psychosocial therapy. The hallucinations must be predominantly visual in nature, as reported by the patient and/or caregiver. In addition, subjects must have a score of three or greater on SAPS-H at baseline. Subjects must again have an NPI Item B score of ≥4 and a SAPS-H score of ≥3 at the end of a two-week placebo run-in period prior to randomization.

In some embodiments, treatment of Lewy Body dementia (LBD) in subjects experiencing hallucinations results in a change in the hallucinations component of the Scale for Assessment of Positive Symptoms (SAPS-H) after 43 days of treatment. In some embodiments, treatment of dementia with Lewy Bodies (LBD) in subjects experiencing hallucinations results in an improvement in the hallucinations component of the Scale for Assessment of Positive Symptoms (SAPS-H) after 43 days of treatment. In some embodiments, treatment of Lewy Body dementia (LBD) in subjects experiencing hallucinations results in a change in the hallucinations component of the Scale for Assessment of Positive Symptoms (SAPS-H) after 22 days of treatment. In some embodiments, treatment of Lewy Body dementia (LBD) in subjects experiencing hallucinations results in an improvement in the hallucinations component of the Scale for Assessment of Positive Symptoms (SAPS-H) after 22 days of treatment. In some embodiments, treatment of Lewy Body dementia (LBD) in subjects experiencing hallucinations results in a change in the delusions component of the Scale for Assessment of Positive Symptoms (SAPS-D) after 43 days of treatment. In some embodiments, treatment of Lewy Body dementia (LBD) in subjects experiencing hallucinations results in a change in the delusions component of the Scale for Assessment of Positive Symptoms (SAPS-D) after 22 days of treatment. In some embodiments, treatment of Lewy Body dementia (LBD) in subjects experiencing hallucinations results in an improvement in the delusions component of the Scale for Assessment of Positive Symptoms (SAPS-D) after 43 days of treatment. In some embodiments, treatment of Lewy Body dementia (LBD) in subjects experiencing hallucinations results in an improvement in the delusions component of the Scale for Assessment of Positive Symptoms (SAPS-D) after 22 days of treatment. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

In some embodiments, treatment of Lewy Body dementia (LBD) in subjects experiencing visual hallucinations results in a change in the hallucinations component of the Scale for Assessment of Positive Symptoms (SAPS-H) after 43 days of treatment. In some embodiments, treatment of dementia with Lewy Bodies (LBD) in subjects experiencing visual hallucinations results in an improvement in the hallucinations component of the Scale for Assessment of Positive Symptoms (SAPS-H) after 43 days of treatment. In some embodiments, treatment of Lewy Body dementia (LBD) in subjects experiencing visual hallucinations results in a change in the hallucinations component of the Scale for Assessment of Positive Symptoms (SAPS-H) after 22 days of treatment. In some embodiments, treatment of Lewy Body dementia (LBD) in subjects experiencing visual hallucinations results in an improvement in the hallucinations component of the Scale for Assessment of Positive Symptoms (SAPS-H) after 22 days of treatment. In some embodiments, treatment of Lewy Body dementia (LBD) in subjects experiencing visual hallucinations results in a change in the delusions component of the Scale for Assessment of Positive Symptoms (SAPS-D) after 43 days of treatment. In some embodiments, treatment of Lewy Body dementia (LBD) in subjects experiencing visual hallucinations results in a change in the delusions component of the Scale for Assessment of Positive Symptoms (SAPS-D) after 22 days of treatment. In some embodiments, treatment of Lewy Body dementia (LBD) in subjects experiencing visual hallucinations results in an improvement in the delusions component of the Scale for Assessment of Positive Symptoms (SAPS-D) after 43 days of treatment. In some embodiments, treatment of Lewy Body dementia (LBD) in subjects experiencing visual hallucinations results in an improvement in the delusions component of the Scale for Assessment of Positive Symptoms (SAPS-D) after 22 days of treatment.

In some embodiments, treatment of Lewy Body dementia (LBD) in subjects experiencing hallucinations results in a change in investigator assessments of global function as measured by a change in the CGI-I and CGI-S scores after 43 days of treatment. In some embodiments, treatment of Lewy Body dementia (LBD) in subjects experiencing hallucinations results in a change in investigator assessments of global function as measured by a change in the CGI-I and CGI-S scores after 22 days of treatment. In some embodiments, treatment of Lewy Body dementia (LBD) in subjects experiencing hallucinations results in an improvement in investigator assessments of global function as measured by the improvement in the CGI-I and CGI-S scores after 43 days of treatment. In some embodiments, treatment of Lewy Body dementia (LBD) in subjects experiencing hallucinations results in an improvement in investigator assessments of global function as measured by the change in the CGI-I and CGI-S scores after 22 days of treatment. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

In some embodiments, treatment of Lewy Body dementia (LBD) in subjects experiencing visual hallucinations results in a change in investigator assessments of global function as measured by a change in the CGI-I and CGI-S scores after 43 days of treatment. In some embodiments, treatment of Lewy Body dementia (LBD) in subjects experiencing visual hallucinations results in a change in investigator assessments of global function as measured by a change in the CGI-I and CGI-S scores after 22 days of treatment. In some embodiments, treatment of Lewy Body dementia (LBD) in subjects experiencing visual hallucinations results in an improvement in investigator assessments of global function as measured by the improvement in the CGI-I and CGI-S scores after 43 days of treatment. In some embodiments, treatment of Lewy Body dementia (LBD) in subjects experiencing visual hallucinations results in a change in investigator assessments of global function as measured by the change in the CGI-I and CGI-S scores after 22 days of treatment.

In some embodiments, treatment of Lewy Body dementia (LBD) in subjects experiencing hallucinations results in a change in caregiver burden as measured by the Zarit Caregiver Burden Score after 43 days of treatment. In some embodiments, treatment of dementia with Lewy Bodies (LBD) in subjects experiencing hallucinations results in a change in caregiver burden as measured by the Zarit Caregiver Burden Score after 22 days of treatment. In some embodiments, treatment of Lewy Body dementia (LBD) in subjects experiencing hallucinations results in an improvement in caregiver burden as measured by the Zarit Caregiver Burden Score after 43 days of treatment. In some embodiments, treatment of Lewy Body dementia (LBD) in subjects experiencing hallucinations results in an improvement in caregiver burden as measured by the Zarit Caregiver Burden Score after 22 days of treatment. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

In some embodiments, treatment of Lewy Body dementia (LBD) in subjects experiencing visual hallucinations results in a change in caregiver burden as measured by the Zarit Caregiver Burden Score after 43 days of treatment. In some embodiments, treatment of dementia with Lewy Bodies (LBD) in subjects experiencing visual hallucinations results in a change in caregiver burden as measured by the Zarit Caregiver Burden Score after 22 days of treatment. In some embodiments, treatment of Lewy Body dementia (LBD) in subjects experiencing visual hallucinations results in an improvement in caregiver burden as measured by the Zarit Caregiver Burden Score after 43 days of treatment. In some embodiments, treatment of Lewy Body dementia (LBD) in subjects experiencing visual hallucinations results in an improvement in caregiver burden as measured by the Zarit Caregiver Burden Score after 22 days of treatment.

In some embodiments, treatment of Lewy Body dementia (LBD) in subjects experiencing hallucinations results in a change in subjective sleep quality as measured by change in the SCOPA-night and SCOPA day wake scores after 43 days of treatment. In some embodiments, treatment of Lewy Body dementia (LBD) in subjects experiencing hallucinations results in a change in subjective sleep quality as measured by change in the SCOPA-night and SCOPA day wake scores after 22 days of treatment. In some embodiments, treatment of Lewy Body dementia (LBD) in subjects experiencing hallucinations results in an improvement in subjective sleep quality as measured by improvement in the SCOPA-night and SCOPA day wake scores after 43 days of treatment. In some embodiments, treatment of Lewy Body dementia (LBD) in subjects experiencing hallucinations results in an improvement in subjective sleep quality as measured by improvement in the SCOPA-night and SCOPA day wake scores after 22 days of treatment. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

In some embodiments, treatment of Lewy Body dementia (LBD) in subjects experiencing visual hallucinations results in a change in subjective sleep quality as measured by change in the SCOPA-night and SCOPA day wake scores after 43 days of treatment. In some embodiments, treatment of Lewy Body dementia (LBD) in subjects experiencing visual hallucinations results in a change in subjective sleep quality as measured by change in the SCOPA-night and SCOPA day wake scores after 22 days of treatment. In some embodiments, treatment of Lewy Body dementia (LBD) in subjects experiencing visual hallucinations results in an improvement in subjective sleep quality as measured by improvement in the SCOPA-night and SCOPA day wake scores after 43 days of treatment. In some embodiments, treatment of Lewy Body dementia (LBD) in subjects experiencing visual hallucinations results in an improvement in subjective sleep quality as measured by improvement in the SCOPA-night and SCOPA day wake scores after 22 days of treatment.

In addition to the foregoing beneficial uses for the modulators of 5-HT$_{2A}$ receptor activity disclosed herein, the compounds disclosed herein are believed to be useful in the treatment of hallucinations, delusions, agitation, Alzheimer's agitation, aggression, REM sleep behavior disorder, schizophrenia, and any combination thereof, and in the amelioration of the symptoms thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One aspect of the present invention encompasses methods for modulating the activity of a 5-HT$_{2A}$ serotonin receptor by contacting the receptor with a compound according to any of the embodiments described herein or a pharmaceutical composition comprising a compound according to any of the embodiments described herein.

One aspect of the present invention encompasses methods for prophylaxis and/or treatment of Lewy Body dementia (LBD) in a subject comprising administering to said subject in need thereof a therapeutically effective amount of a compound according to any of the embodiments described herein or a pharmaceutical composition comprising a compound according to any of the embodiments described herein. In some embodiments, the subject may also have another neurological condition, such as, but not limited to Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

One aspect of the present invention encompasses processes for preparing a composition comprising admixing a compound according any embodiments described herein and a pharmaceutically acceptable carrier.

One aspect of the present invention is the use of a compound for the production of a medicament for use in the prophylaxis and/or treatment of a 5-HT$_{2A}$ serotonin receptor-related disorder.

One embodiment of the present invention is the use of a compound for the production of a medicament for use in the prophylaxis and/or treatment of a 5-HT$_{2A}$ serotonin receptor-related disorder wherein the disorder is Lewy Body dementia (LBD).

One aspect of the present invention are compounds according to any of the embodiments described herein for use in a method of treatment of the human or animal body by therapy.

One aspect of the present invention are compounds according to any of the embodiments described herein for use in a method for the prophylaxis and/or treatment of a 5-HT$_{2A}$ serotonin receptor-related disorder, as described herein, in the human or animal body by therapy.

One aspect of the present invention are compounds according to any of the embodiments described herein for use in a method for the prophylaxis and/or treatment of Lewy Body dementia (LBD), as described herein, in the human or animal body by therapy.

One aspect of the present invention pertains to pharmaceutical compositions comprising: (a) 1-[3-(4-bromo-2-methyl-2H-pyrazol-3-yl)-4-methoxy-phenyl]-3-(2,4-difluoro-phenyl)-urea; and (b) an excipient selected from PVP and coPVP.

One aspect of the present invention pertains to kits for treating a 5-HT$_{2A}$ serotonin receptor-related disorder in a subject comprising a container and a pharmaceutical composition of the present invention.

One aspect of the present invention pertains to methods for treating a 5-HT$_{2A}$ serotonin receptor-related disorder in a subject comprising administering to the subject in need thereof a therapeutically effective amount of a pharmaceutical composition of the present invention.

In some embodiments, the subject is a mammal. In some embodiments, the mammal is a human.

In some embodiments, the pharmaceutical composition is administered orally, nasally sublingually, buccally, transdermally, vaginally or rectally.

In some embodiments, the pharmaceutical composition is administered orally.

One aspect of the present invention pertains to the use of a pharmaceutical composition of the present invention in the manufacture of a medicament for the treatment of a 5-HT$_{2A}$ serotonin receptor-related disorder.

One aspect of the present invention pertains to the use of a pharmaceutical composition of the present invention in the manufacture of a medicament for the treatment of neuropsychiatric symptoms including but not limited to hallucinations. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One aspect of the present invention pertains to the use of a pharmaceutical composition of the present invention in the manufacture of a medicament for the treatment of Lewy Body Dementia (LBD).

One aspect of the present invention is directed to methods for treating a $5\text{-}HT_{2A}$ serotonin receptor-related disorder in a subject comprising administering to the subject in need thereof a therapeutically effective amount of a composition of the present invention.

One aspect of the present invention pertains to the use of a composition of the present invention in the manufacture of a medicament for the treatment of a $5\text{-}HT_{2A}$ serotonin receptor-related disorder.

One aspect of the present invention pertains to the use of a composition of the present invention in the manufacture of a medicament for the treatment of neuropsychiatric symptoms including but not limited to hallucinations. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One aspect of the present invention pertains to the use of a composition of the present invention in the manufacture of a medicament for the treatment of Lewy Body dementia (LBD).

Prophylaxis and/or Treatment of Hallucinations Associated with Lewy Body Dementia Dementia with Lewy bodies (DLB) is a progressive neurocognitive illness characterized pathologically by the presence of diffuse clusters comprised of alpha synuclein and other proteins that aggregate in the brain and disrupt cognitive function. DLB is considered to be the second most prevalent cause of degenerative dementia in the elderly population, accounting for up to 15%-25% of dementia presentations and 15%-20% of all autopsy confirmed dementias in old age. Between 50% and 80% of subjects with Parkinson's disease may experience dementia over the course of their illness. While few studies of the exact prevalence of DLB have been published, the Lewy Body Dementia Association estimates that 1.1 million individuals are affected by DLB in the U.S. alone. In addition to the foregoing beneficial uses for the modulators of $5\text{-}HT_{2A}$ receptor activity disclosed herein, the compounds disclosed herein are believed to be useful in the treatment of neuropsychiatric symptoms including but not limited to hallucinations associated with a neurodegenerative disease such as, Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof, and in the amelioration of symptoms thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

Representative Methods of the Invention

One aspect of the present invention encompasses methods for prophylaxis and/or treatment of neuropsychiatric symptoms including but not limited to hallucinations associated with Lewy Body dementia in an individual comprising administering to said individual in need thereof a therapeutically effective amount of a compound according to any of the embodiments described herein or a pharmaceutical composition comprising a compound according to any of the embodiments described herein. In some embodiments, the individual may also have another neurological condition, such as, but not limited to Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One aspect of the present invention encompasses methods for prophylaxis and/or treatment of visual hallucinations associated with Lewy Body dementia in an individual comprising administering to said individual in need thereof a therapeutically effective amount of a compound according to any of the embodiments described herein or a pharmaceutical composition comprising a compound according to any of the embodiments described herein. In some embodiments, the individual may also have another neurological condition, such as, but not limited to Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

One aspect of the present invention encompasses processes for preparing a composition comprising admixing a compound according to any embodiments described herein and a pharmaceutically acceptable carrier.

One aspect of the present invention is the use of a compound for the production of a medicament for use in the prophylaxis and/or treatment of neuropsychiatric symptoms including but not limited to hallucinations associated with a neurodegenerative disease such as Lewy Body dementia. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One embodiment of the present invention is the use of a compound for the production of a medicament for use in the prophylaxis and/or treatment of visual hallucinations associated with a neurodegenerative disease such as Lewy Body dementia. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One aspect of the present invention are compounds according to any of the embodiments described herein for use in a method of treatment of the human or animal body by therapy.

One aspect of the present invention are compounds according to any of the embodiments described herein for use in a method for the prophylaxis and/or treatment of visual hallucinations associated with a neurodegenerative disease such as Lewy Body dementia, as described herein, in the human or animal body by therapy. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One aspect of the present invention are compounds according to any of the embodiments described herein for use in a method for the prophylaxis and/or treatment of visual hallucinations associated with a neurodegenerative disease such as Lewy Body dementia, as described herein, in the human or animal body by therapy.

One aspect of the present invention pertains to pharmaceutical compositions comprising: (a) 1-[3-(4-bromo-2-methyl-2H-pyrazol-3-yl)-4-methoxy-phenyl]-3-(2,4-difluoro-phenyl)-urea; and (b) an excipient selected from: PVP and coPVP and their use in the treatment and prophylaxis of neuropsychiatric symptoms including but not limited to hallucinations associated with a neurodegenerative disease such as Lewy Body dementia. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One aspect of the present invention pertains to pharmaceutical compositions comprising: (a) 1-[3-(4-bromo-2-methyl-2H-pyrazol-3-yl)-4-methoxy-phenyl]-3-(2,4-difluoro-phenyl)-urea; and (b) an excipient selected from: PVP and coPVP and their use in the treatment and prophylaxis of visual hallucinations associated with a neurodegenerative disease such as Lewy Body dementia.

One aspect of the present invention pertains to kits for the prophylaxis and/or treatment of neuropsychiatric symptoms including but not limited to hallucinations associated with a neurodegenerative disease such as Lewy Body dementia in an individual comprising a container and a pharmaceutical composition of the present invention comprising a compound according to any of the embodiments described herein. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One aspect of the present invention pertains to kits for the prophylaxis and/or treatment of visual hallucinations associated with a neurodegenerative disease such as Lewy Body dementia in an individual comprising a container and a pharmaceutical composition of the present invention comprising a compound according to any of the embodiments described herein.

One aspect of the present invention encompasses methods for the prophylaxis and/or treatment of neuropsychiatric symptoms including but not limited to hallucinations associated with a neurodegenerative disease such as Lewy Body dementia, in an individual comprising administering to said individual in need thereof a therapeutically effective amount of a compound according to any of the embodiments described herein or a pharmaceutical composition. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

One aspect of the present invention encompasses methods for the prophylaxis and/or treatment of visual hallucinations associated with a neurodegenerative disease such as Lewy Body dementia, in an individual comprising administering to said individual in need thereof a therapeutically effective amount of a compound according to any of the embodiments described herein or a pharmaceutical composition.

Some embodiments are directed to methods for the prophylaxis and/or treatment of neuropsychiatric symptoms including but not limited to hallucinations associated with a neurodegenerative disease such as Lewy Body dementia, in a subject in need thereof comprising administering to said subject a therapeutically effective amount of a 5-HT$_{2A}$ inverse agonist. In some embodiments, administration of a therapeutically effective amount of a 5-HT$_{2A}$ inverse agonist results in treatment, and/or prophylaxis of hallucinations associated with a neurodegenerative disease such as Lewy Body dementia. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

Some embodiments are directed to methods for the prophylaxis and/or treatment of visual hallucinations associated with a neurodegenerative disease such as Lewy Body dementia, in a subject in need thereof comprising administering to said subject a therapeutically effective amount of a 5-HT$_{2A}$ inverse agonist. In some embodiments, administration of a therapeutically effective amount of a 5-HT$_{2A}$ inverse agonist results in treatment, and/or prophylaxis of visual hallucinations associated with a neurodegenerative disease such as Lewy Body dementia.

Some embodiments are directed to methods for the prophylaxis and/or treatment of neuropsychiatric symptoms including but not limited to hallucinations, in a subject in need thereof, comprising administering to said subject a therapeutically effective amount of a $5\text{-HT}_{2A}$ inverse agonist. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

Some embodiments are directed to methods for the prophylaxis and/or treatment of visual hallucinations, in a subject in need thereof, comprising administering to said subject a therapeutically effective amount of a $5\text{-HT}_{2A}$ inverse agonist.

In some embodiments, the $5\text{-HT}_{2A}$ inverse agonist is selected from nelotanserin, pimavanserin, pruvanserin, eplivanserin, volinanserin, glemanserin, ketanserin, ritanserin, clozapine, or a pharmaceutically acceptable salt, hydrate, polymorph, or solvate thereof. In some embodiments, the $5\text{-HT}_{2A}$ inverse agonist is nelotanserin or a pharmaceutically acceptable salt, hydrate, polymorph, or solvate thereof. In some embodiments, the nelotanserin or a pharmaceutically acceptable salt, hydrate, polymorph, or solvate thereof is selected from the group consisting of Form I of 1-[3-(4-bromo-2-methyl-2H-pyrazol-3-yl)-4-methoxy-phenyl]-3-(2,4-difluoro-phenyl)-urea, Form II of 1-[3-(4-bromo-2-methyl-2H-pyrazol-3-yl)-4-methoxy-phenyl]-3-(2,4-difluoro-phenyl)-urea and a combination thereof. In some embodiments, the therapeutically effective amount of nelotanserin or a pharmaceutically acceptable salt, hydrate, polymorph, or solvate thereof is from 10 mg to about 160 mg. In some embodiments, the therapeutically effective amount of nelotanserin or a pharmaceutically acceptable salt, hydrate, polymorph, or solvate thereof is about 10 mg, about 20 mg, about 40 mg, about 80 mg, or about 160 mg. In some embodiments, the therapeutically effective amount of nelotanserin is about 10 mg, about 20 mg, about 40 mg, about 80 mg, or about 160 mg. In some embodiments, the therapeutically effective amount of nelotanserin is about 10 mg. In some embodiments, the therapeutically effective amount of nelotanserin is about 20 mg. In some embodiments, the therapeutically effective amount of nelotanserin is about 40 mg. In some embodiments, the therapeutically effective amount of nelotanserin is about 80 mg. In some embodiments, the therapeutically effective amount of nelotanserin is about 160 mg. In some embodiments, the therapeutically effective amount of the $5\text{-HT}_{2A}$ inverse agonist is administered once a day, twice a day, three times a day, or four times a day. In some embodiments, the $5\text{-HT}_{2A}$ inverse agonist is in a pharmaceutical composition configured for immediate release, for extended release, for delayed release, or any combination thereof. In some embodiments, the $5\text{-HT}_{2A}$ inverse agonist is in a pharmaceutical composition, and wherein the pharmaceutical composition is formulated for oral administration. In some embodiments, the therapeutically effective amount of the $5\text{-HT}_{2A}$ inverse agonist is administered about one to about four times per day, once daily in the morning, once daily about 1 hour prior to the subject's bedtime, or twice daily.

In some embodiments, the subject is a human. In some embodiments, the human is an adult with a diagnosis of a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the human has a concurrent diagnosis of neuropsychiatric symptoms including but not limited to hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, the human has a concurrent diagnosis of visual hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the human has a diagnosis of probable Dementia with Lewy Bodies. In some embodiments, the diagnosis of probable DLB is defined by the presence of dementia and at least one of: at least two Core Criteria selected from visual hallucinations, cognitive fluctuations, and Parkinsonism, and any combination thereof; and one Core Criteria selected from visual hallucinations, cognitive fluctuations, and Parkinsonism, and any combination thereof; and at least one Suggestive Criteria selected from REM Sleep Behavior Disorder, Severe Neuroleptic Sensitivity, Low Dopamine Transporter Uptake on DaT SPECT Imaging Scan; and any combination thereof. In some embodiments, the human has a diagnosis of Dementia with Lewy Bodies. In some embodiments, the human has a Mini Mental State Examination score of greater than, or equal to, about 18. In some embodiments, the human is an adult with a diagnosis of visual hallucinations associated with Dementia with Lewy Bodies. In some embodiments, the human is an adult aged 50-85 inclusive. In some embodiments, the human has experienced persistent visual hallucinations. In some embodiments, the presence of persistent hallucinations is defined by a score of four or greater on the hallucinations component of the Neuropsychiatric Inventory (NPI Item B) at screening. In some embodiments, the human has experienced visual hallucinations on at least five days in a week.

In some embodiments, administration of a therapeutically effective amount of a $5\text{-HT}_{2A}$ inverse agonist results in treatment, and/or prophylaxis of neuropsychiatric symptoms including but not limited to hallucinations. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, treating or prophylaxis results in a decrease in the frequency, severity, or a combination thereof of hallucinations. In some embodiments, administration of a therapeutically effective amount of a $5\text{-HT}_{2A}$ inverse agonist results in treatment, and/or prophylaxis of visual hallucinations. In some embodiments, treating or prophylaxis results in a decrease in the frequency, severity, or a combination thereof of visual hallucinations. In some embodiments, the subject has a score of three or greater on SAPS-H prior to administration of a therapeutically effective amount of a $5\text{-HT}_{2A}$ inverse agonist. In some embodiments, treatment results in an improvement in the hallucinations component of the Scale for Assessment of Positive Symptoms (SAPS-H) after 22 days of treatment. In some embodiments, treatment results in an improvement in the hallucinations component of the Scale for Assessment of Positive Symptoms (SAPS-H) after 43 days of treatment. In some embodiments, treatment results in an improvement in the delusions component of the Scale for Assessment of Positive Symptoms (SAPS-D) after 22 days of treatment. In some embodiments, treatment results in an improvement in the delusions component of the Scale for Assessment of Positive Symptoms (SAPS-D) after 43 days of treatment. In some embodiments, treatment results in an improvement in investigator assessments of global function as measured by the change in the CGI-I and CGI-S scores after 22 days of treatment. In some embodiments, treatment results in an improvement in investigator assessments of global function as measured by the change in the CGI-I and CGI-S scores after 43 days of treatment. In some embodiments, treatment results in an improvement in caregiver burden as measured by the Zarit Caregiver Burden Score after 22 days of treatment. In some embodiments, treatment results in an improvement in caregiver burden as measured by the Zarit Caregiver Burden Score after 43 days of treatment. In some embodiments, treatment results in an improvement in subjective sleep quality as measured by change in the SCOPA-night and SCOPA day wake scores after 22 days of treatment. In some embodiments, treatment results in an improvement in subjective sleep quality as measured by change in the SCOPA-night and SCOPA day wake scores after 43 days of treatment. In some embodiments, treating or prophylaxis results in an improvement in the subject's Mini-Mental State Examination score, cognition, attention, Clinician's Interview-Based Impression of Change with caregiver input (CIBIC+) rating, neuropsychiatric inventory (NPI), North-East Visual Hallucinations Interview (NEVHI), Cognitive Drug Research (CDR) computerized assessment system, Scale for the Assessment of Positive Symptoms (SAPS), Parkinson's Disease-adapted Scale for the Assessment of Positive Symptoms (SAPS-PD), Positive and Negative Syndrome Scale (PANSS), Clinical Global Impression (CGI) scale, or any combination thereof. In some embodiments, treating or prophylaxis results in fluctuations in cognition, attention or a combination thereof.

Some embodiments are directed to methods for the prophylaxis and/or treatment of neuropsychiatric symptoms including but not limited to hallucinations associated with Lewy Body Dementia, in a subject in need thereof comprising administering to said subject a daily dose of about 40 mg of nelotanserin. In some embodiments, the daily dose of about 40 mg of nelotanserin is administered once a day, twice a day, three times a day, or four times a day. In some embodiments, the subject has a concurrent diagnosis of neuropsychiatric symptoms including but not limited to hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

Some embodiments are directed to methods for the prophylaxis and/or treatment of visual hallucinations associated with Lewy Body Dementia, in a subject in need thereof comprising administering to said subject a daily dose of about 40 mg of nelotanserin. In some embodiments, the daily dose of about 40 mg of nelotanserin is administered once a day, twice a day, three times a day, or four times a day. In some embodiments, the subject has a concurrent diagnosis of visual hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of neuropsychiatric symptoms including but not limited to hallucinations, in a subject in need thereof, comprising administering to said subject a daily oral dose of about 40 mg of nelotanserin. In some embodiments, the daily dose of about 40 mg of nelotanserin is administered once a day, twice a day, three times a day or four times a day. In some embodiments, the subject has a concurrent diagnosis of neuropsychiatric symptoms including but not limited to hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

Some embodiments are directed to methods for the prophylaxis and/or treatment of visual hallucinations, in a subject in need thereof, comprising administering to said subject a daily oral dose of about 40 mg of nelotanserin. In some embodiments, the daily dose of about 40 mg of nelotanserin is administered once a day, twice a day, three times a day or four times a day. In some embodiments, the subject has a concurrent diagnosis of visual hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of neuropsychiatric symptoms including but not limited to hallucinations, in a subject in need thereof, comprising administering to said subject a daily oral dose of about 80 mg of nelotanserin. In some embodiments, the daily dose of about 80 mg of nelotanserin is administered once a day, twice a day, three times a day or four times a day. In some embodiments, the subject has a concurrent diagnosis of neuropsychiatric symptoms including but not limited to hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

Some embodiments are directed to methods for the prophylaxis and/or treatment of visual hallucinations, in a subject in need thereof, comprising administering to said subject a daily oral dose of about 80 mg of nelotanserin. In some embodiments, the daily dose of about 80 mg of nelotanserin is administered once a day, twice a day, three times a day or four times a day. In some embodiments, the subject has a concurrent diagnosis of visual hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of neuropsychiatric symptoms including but not limited to hallucinations, in a subject in need thereof, comprising administering to said subject a daily oral dose of about 160 mg of nelotanserin. In some embodiments, the daily dose of about 160 mg of nelotanserin is administered once a day, twice a day, three times a day or four times a day. In some embodiments, the subject has a concurrent diagnosis of neuropsychiatric symptoms including but not limited to hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

Some embodiments are directed to methods for the prophylaxis and/or treatment of visual hallucinations, in a subject in need thereof, comprising administering to said subject a daily oral dose of about 160 mg of nelotanserin. In some embodiments, the daily dose of about 160 mg of nelotanserin is administered once a day, twice a day, three times a day or four times a day. In some embodiments, the subject has a concurrent diagnosis of visual hallucinations and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of neuropsychiatric symptoms including but not limited to hallucinations in a subject in need thereof comprising administering to said subject a dose of about 40 mg of nelotanserin for a first time period followed by administering to said subject a dose of about 80 mg of nelotanserin for a second time period. In some embodiments, the subject is a human adult with a diagnosis of a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

Some embodiments are directed to methods for the prophylaxis and/or treatment of visual hallucinations in a subject in need thereof comprising administering to said subject a dose of about 40 mg of nelotanserin for a first time period followed by administering to said subject a dose of about 80 mg of nelotanserin for a second time period. In some embodiments, the subject is a human adult with a diagnosis of a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

Some embodiments are directed to methods for the prophylaxis and/or treatment of dementia with Lewy Bodies in a subject in need thereof, comprising administering to said subject a therapeutically effective amount of a $5\text{-HT}_{2A}$ inverse agonist. In some embodiments, the $5\text{-HT}_{2A}$ inverse agonist is selected from nelotanserin, pimavanserin, pruvanserin, eplivanserin, volinanserin, glemanserin, ketanserin, ritanserin, clozapine, or a pharmaceutically acceptable salt, hydrate, polymorph, or solvate thereof. In some embodiments, the $5\text{-HT}_{2A}$ inverse agonist is nelotanserin or a pharmaceutically acceptable salt, hydrate, polymorph, or solvate thereof. In some embodiments, the nelotanserin or a pharmaceutically acceptable salt, hydrate, polymorph, or solvate thereof is selected from the group consisting of Form I of 1-[3-(4-bromo-2-methyl-2H-pyrazol-3-yl)-4-methoxy-phenyl]-3-(2,4-difluoro-phenyl)-urea, Form II of 1-[3-(4-bromo-2-methyl-2H-pyrazol-3-yl)-4-methoxy-phenyl]-3-(2,4-difluoro-phenyl)-urea and a combination thereof. In some embodiments, the therapeutically effective amount of nelotanserin or a pharmaceutically acceptable salt, hydrate, polymorph, or solvate thereof is from 10 mg to about 160 mg. In some embodiments, the therapeutically effective amount of nelotanserin or a pharmaceutically acceptable salt, hydrate, polymorph, or solvate thereof is about 10 mg, about 20 mg, about 40 mg, about 80 mg, or about 160 mg. In some embodiments, the therapeutically effective amount of nelotanserin is about 10 mg, about 20 mg, about 40 mg, about 80 mg, or about 160 mg. In some embodiments, the therapeutically effective amount of nelotanserin is about 10 mg. In some embodiments, the therapeutically effective amount of nelotanserin is about 20 mg. In some embodiments, the therapeutically effective amount of nelotanserin is about 40 mg. In some embodiments, the therapeutically effective amount of nelotanserin is about 80 mg. In some embodiments, the therapeutically effective amount of nelotanserin is about 160 mg. In some embodiments, the therapeutically effective amount of the $5\text{-HT}_{2A}$ inverse agonist is administered once a day, twice a day, three times a day, or four times a day. In some embodiments, the $5\text{-HT}_{2A}$ inverse agonist is in a pharmaceutical composition configured for immediate release, for extended release, for delayed release, or any combination thereof. In some embodiments, the $5\text{-HT}_{2A}$ inverse agonist is in a pharmaceutical composition, and wherein the pharmaceutical composition is formulated for oral administration. In some embodiments, the therapeutically effective amount of the $5\text{-HT}_{2A}$ inverse agonist is administered In some embodiments, the dose is administered about one to about four times per day, once daily in the morning, once daily about 1 hour prior to the subject's bedtime, or twice daily.

In some embodiments, the subject is a human. In some embodiments, the human is an adult with a diagnosis of a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the human has a concurrent diagnosis of neuropsychiatric symptoms including but not limited to hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, the human has a concurrent diagnosis of visual hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof. In some embodiments, the human has a diagnosis of probable Dementia with Lewy Bodies. In some embodiments, the diagnosis of probable Dementia with Lewy Bodies is defined by the presence of dementia and at least one of: at least two Core Criteria selected from visual hallucinations, cognitive fluctuations, and Parkinsonism, and any combination thereof; and one Core Criteria selected from visual hallucinations, cognitive fluctuations, and Parkinsonism, and any combination thereof; and at least one Suggestive Criteria selected from REM Sleep Behavior Disorder, Severe Neuroleptic Sensitivity, Low Dopamine Transporter Uptake on DaT SPECT Imaging Scan; and any combination thereof. In some embodiments, the human has a diagnosis of Dementia with Lewy Bodies. In some embodiments, the human has a Mini Mental State Examination score of greater than, or equal to, about 18. In some embodiments, the human is an adult with a diagnosis of neuropsychiatric symptoms including but not limited to hallucinations associated with Dementia with Lewy Bodies. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, the human is an adult aged 50-85 inclusive. In some embodiments, the human has experienced persistent hallucinations. In some embodiments, the human is an adult with a diagnosis of visual hallucinations associated with Dementia with Lewy Bodies. In some embodiments, the human is an adult aged 50-85 inclusive. In some embodiments, the human has experienced persistent visual hallucinations. In some embodiments, the presence of persistent hallucinations is defined by a score of four or greater on the hallucinations component of the Neuropsychiatric Inventory (NPI Item B) at screening. In some embodiments, the human has experienced visual hallucinations on at least five days in a week.

In some embodiments, the subject is concurrently receiving a therapeutically effective amount of at least one additional therapeutic agent selected from the group consisting of melatonin, quetiapine, clonazepam, levodopa, carbidopa, an antiparkinsonian drug, an acetylcholinesterase inhibitor, an NMDA receptor antagonist, and a combination thereof. In some embodiments, the antiparkinsonian drug is selected from an MAO-B inhibitor, a COMT inhibitor, a dopamine agonist or any combination thereof. In some embodiments, the acetylcholinesterase inhibitor is selected from the group consisting of donepezil, rivastigmine, galantamine, and pharmaceutically acceptable salts, hydrates, polymorphs, or solvates thereof. In some embodiments, the acetylcholinesterase inhibitor is donepezil or a pharmaceutically acceptable salt, hydrate, polymorph, or solvate thereof. In some embodiments, the acetylcholinesterase inhibitor is rivastigmine or a pharmaceutically acceptable salt, hydrate, polymorph, or solvate thereof. In some embodiments, the acetylcholinesterase inhibitor is galantamine or a pharmaceutically acceptable salt, hydrate, polymorph, or solvate thereof. In some embodiments, NMDA receptor antagonist is selected from the group consisting of memantine, amantadine, ketamine, and pharmaceutically acceptable salts, hydrates, polymorphs, or solvates thereof. In some embodiments, the NMDA receptor antagonist is memantine or a pharmaceutically acceptable salt, hydrate, polymorph, or solvate thereof. In some embodiments, the NMDA receptor antagonist is amantadine or a pharmaceutically acceptable salt, hydrate, polymorph, or solvate thereof.

In some embodiments, administration of a therapeutically effective amount of a 5-HT$_{2A}$ inverse agonist results in treatment, and/or prophylaxis of Lewy Body Dementia or the symptom thereof in a subject experiencing neuropsychiatric symptoms including but not limited to hallucinations. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations. In some embodiments, treating or prophylaxis results in an improvement in the subject's Mini-Mental State Examination score, cognition, attention, Clinician's Interview-Based Impression of Change with caregiver input (CIBIC+) rating, neuropsychiatric inventory (NPI), North-East Visual Hallucinations Interview (NEVHI), Cognitive Drug Research (CDR) computerized assessment system, Scale for the Assessment of Positive Symptoms (SAPS), Parkinson's Disease-adapted Scale for the Assessment of Positive Symptoms (SAPS-PD), Positive and Negative Syndrome Scale (PANSS), Clinical Global Impression (CGI) scale, or any combination thereof. In some embodiments, treating or prophylaxis results in fluctuations in cognition, attention or a combination thereof.

In some embodiments, administration of a therapeutically effective amount of a 5-HT$_{2A}$ inverse agonist results in treatment, and/or prophylaxis of Lewy Body Dementia or the symptom thereof in a subject experiencing visual hallucinations. In some embodiments, treating or prophylaxis results in an improvement in the subject's Mini-Mental State Examination score, cognition, attention, Clinician's Interview-Based Impression of Change with caregiver input (CIBIC+) rating, neuropsychiatric inventory (NPI), North-East Visual Hallucinations Interview (NEVHI), Cognitive Drug Research (CDR) computerized assessment system, Scale for the Assessment of Positive Symptoms (SAPS), Parkinson's Disease-adapted Scale for the Assessment of Positive Symptoms (SAPS-PD), Positive and Negative Syndrome Scale (PANSS), Clinical Global Impression (CGI) scale, or any combination thereof. In some embodiments, treating or prophylaxis results in fluctuations in cognition, attention or a combination thereof.

In some embodiments, the subject is concurrently receiving a therapeutically effective amount of at least one additional therapeutic agent selected from the group consisting of melatonin, quetiapine, clozapine, risperidone, clonazepam, levodopa, carbidopa, an antiparkinsonian drug, an acetylcholinesterase inhibitor, NMDA receptor antagonist, an atypical antipsychotic agent, a dopaminergic agent, a benzodiazepine, an antidepressant, and a combination thereof. In some embodiments, the therapeutically effective amount of melatonin is about 1 mg to about 5 mg. In some embodiments, the therapeutically effective amount of quetiapine is about 12.5 mg to about 100 mg. In some embodiments, the therapeutically effective amount of quetiapine is less than about 25 mg. In some embodiments, the therapeutically effective amount of clonazepam is about 0.0625 mg to about 5 mg. In some embodiments, the antiparkinsonian drug is selected from an MAO-B inhibitor, a COMT inhibitor, a dopamine agonist or any combination thereof. In some embodiments, the therapeutically effective amount of levodopa or a pharmaceutically acceptable salt, hydrate, polymorph, or solvate thereof is from about 0.001 mg to about 10,000 mg, or about 0.001 mg to about 8,000 mg. In some embodiments, the therapeutically effective amount of levodopa or a pharmaceutically acceptable salt, hydrate, polymorph, or solvate thereof is about 285 mg, about 300 mg, about 400 mg, about 435 mg, about 500 mg, about 585 mg, about 600 mg, about 700 mg, about 735 mg, about 750 mg, about 800 mg, about 980 mg, about 1,000 mg, about 1,225 mg, about 1,250 mg, about 1,470 mg, about 1,500 mg, about 1,715 mg, about 1,750 mg, about 1,960 mg, about 2,000 mg, about 2,205 mg, about 2,250 mg, about 2,450 mg, about 2,500 mg, about 2,750 mg, about 3,000 mg, about 3,250 mg, about 3,500 mg, about 3,750 mg, about 4,000 mg, about 4,250 mg, about 5,000 mg, about 5,250 mg, about 5,500 mg, about 5,750 mg, about 6,000 mg, about 6,250 mg, about 6,500 mg, about 6,750 mg, about 7,000 mg, about 7,250 mg, about 7,500 mg, about 7,750 mg, or about 8,000 mg. In some embodiments, the therapeutically effective amount of carbidopa or a pharmaceutically acceptable salt, hydrate, polymorph, or solvate thereof is configured for immediate release, for extended release, for delayed release, or any combination thereof. In some embodiments, the therapeutically effective amount of carbidopa is from about 0.001 mg to about 1,000 mg, or from about 0.001 mg to about 700 mg. In some embodiments, the therapeutically effective amount of carbidopa is about 30 mg, about 40 mg, about 50 mg, about 60 mg, about 70 mg, about 71.25 mg, about 80 mg, about 108.75 mg, about 146.25 mg, 183.75 mg, about 245 mg, about 245 mg, about 306.25 mg, about 367.5 mg, about 428.75 mg, about 490 mg, about 551.25 mg, or about 612.5 mg. In some embodiments, the acetylcholinesterase inhibitor is selected from the group consisting of donepezil, rivastigmine, galantamine, and pharmaceutically acceptable salts, hydrates, polymorphs, or solvates thereof. In some embodiments, the acetylcholinesterase inhibitor is donepezil or a pharmaceutically acceptable salt, hydrate, polymorph, or solvate thereof. In some embodiments, the therapeutically effective amount of donepezil or a pharmaceutically acceptable salt, hydrate, polymorph, or solvate thereof is configured for immediate release, for extended release, for delayed release, or any combination thereof. In some embodiments, the therapeutically effective amount of donepezil or a pharmaceutically acceptable salt, hydrate, polymorph, or solvate thereof is from about 0.001 mg to about 1,000 mg, or about 0.001 mg to about 30 mg. In some embodiments, the therapeutically effective amount of donepezil or a pharmaceutically acceptable salt, hydrate, polymorph, or solvate thereof is about 5 mg, 10 mg, or 23 mg. In some embodiments, the acetylcholinesterase inhibitor is rivastigmine or a pharmaceutically acceptable salt, hydrate, polymorph, or solvate thereof. In some embodiments, the therapeutically effective amount of rivastigmine or a pharmaceutically acceptable salt, hydrate, polymorph, or solvate thereof is from about 0.001 mg to about 1,000 mg, or about 0.001 mg to about 15 mg. In some embodiments, the therapeutically effective amount of rivastigmine or a pharmaceutically acceptable salt, hydrate, polymorph, or solvate thereof is about 1.5 mg, about 3 mg, about 4.5 mg, about 6 mg, about 9 mg, about 9.5 mg, about 12 mg, or about 13.3 mg. In some embodiments, the therapeutically effective amount of rivastigmine or a pharmaceutically acceptable salt, hydrate, polymorph, or solvate thereof is configured for immediate release, for extended release, for delayed release, or any combination thereof. In some embodiments, the acetylcholinesterase inhibitor is galantamine or a pharmaceutically acceptable salt, hydrate, polymorph, or solvate thereof. In some embodiments, the therapeutically effective amount of galantamine or a pharmaceutically acceptable salt, hydrate, polymorph, or solvate thereof is configured for immediate release, for extended release, for delayed release, or any combination thereof. In some embodiments, the therapeutically effective amount of galantamine or a pharmaceutically acceptable salt, hydrate, polymorph, or solvate thereof is from about 0.001 mg to about 1,000 mg, or about 0.001 mg to about 30 mg. In some embodiments, the therapeutically effective amount of galantamine or a pharmaceutically acceptable salt, hydrate, polymorph, or solvate thereof is about 4 mg, about 8 mg, about 12 mg, about 16 mg, or about 24 mg. In some embodiments, NMDA receptor antagonist is selected from the group consisting of memantine, amantadine, ketamine, and pharmaceutically acceptable salts, hydrates, polymorphs, or solvates thereof. In some embodiments, the NMDA receptor antagonist is memantine or a pharmaceutically acceptable salt, hydrate, polymorph, or solvate thereof. In some embodiments, the therapeutically effective amount of memantine or a pharmaceutically acceptable salt, hydrate, polymorph, or solvate thereof is configured for immediate release, for extended release, for delayed release, or any combination thereof. In some embodiments, the therapeutically effective amount of memantine or a pharmaceutically acceptable salt, hydrate, polymorph, or solvate thereof is from about 0.001 mg to about 1,000 mg, or about 0.001 mg to about 30 mg. In some embodiments, the therapeutically effective amount of memantine or a pharmaceutically acceptable salt, hydrate, polymorph, or solvate thereof is about 5 mg, about 7 mg, about 10 mg, about 14 mg, about 20 mg, about 21 mg, or about 28 mg. In some embodiments, the therapeutically effective amount of memantine or a pharmaceutically acceptable salt, hydrate, polymorph, or solvate thereof is configured for extended release, for delayed release or a combination thereof. In some embodiments, the NMDA receptor antagonist is amantadine or a pharmaceutically acceptable salt, hydrate, polymorph, or solvate thereof. In some embodiments, the therapeutically effective amount of amantadine or a pharmaceutically acceptable salt, hydrate, polymorph, or solvate thereof is configured for immediate release, for extended release, for delayed release, or any combination thereof. In some embodiments, the therapeutically effective amount of amantadine or a pharmaceutically acceptable salt, hydrate, polymorph, or solvate thereof is from about 0.001 mg to about 1,000 mg, or about 0.001 mg to about 500 mg. In some embodiments, the therapeutically effective amount of amantadine or a pharmaceutically acceptable salt, hydrate, polymorph, or solvate thereof is from about 100 mg to about 400 mg. In some embodiments, the therapeutically effective amount of amantadine or a pharmaceutically acceptable salt, hydrate, polymorph, or solvate thereof is about 100 mg, about 200 mg, about 300 mg or about 400 mg.

In some embodiments, the at least one additional therapeutic agent is 3-phenylsulfonyl-8-piperazinyl-1yl-quinoline. In some embodiments, 3-phenylsulfonyl-8-piperazinyl-1yl-quinoline is administered in a therapeutically effective amount. In some embodiments, the therapeutically effective amount of 3-phenylsulfonyl-8-piperazinyl-1yl-quinoline or pharmaceutically acceptable salts, hydrates or solvates thereof is configured for extended release, and the additional therapeutic agent useful for treating a neurodegenerative disease is configured for immediate release, for sustained release, for extended release, or any combination thereof. In some embodiments, the therapeutically effective amount of 3-phenylsulfonyl-8-piperazinyl-1yl-quinoline or a pharmaceutically acceptable salt, hydrate, polymorph, or solvate thereof is from about 0.001 mg to about 1,000 mg, about 0.001 mg to about 200 mg, about 0.001 mg to about 175 mg, or 0.001 mg to about 70 mg. In some embodiments, the therapeutically effective amount of 3-phenylsulfonyl-8-piperazinyl-1yl-quinoline or a pharmaceutically acceptable salt, hydrate, polymorph, or solvate thereof is about 15 mg, about 35 mg, or about 70 mg.

In some embodiments, the at least one additional therapeutic agent is a monoclonal antibody. In some embodiments, the second therapeutic agent is a human monoclonal antibody. In some embodiments, the second therapeutic agent is a humanized monoclonal antibody. In some embodiments the monoclonal antibody targets beta amyloid. In some embodiments the beta amyloid may comprise aggregated beta amyloid such as but not limited to soluble oligomers, insoluble fibrils deposited into amyloid plaque, or a combination thereof. In some embodiments, the monoclonal antibody is Aducanumab (B11B037), Gantenerumab, Bapineuzumab, Crenezumab, Ponezumab, Solanezumab, SAR228810, MEDI1814, BAN2401, or any combination thereof. In some embodiments, the monoclonal antibody targets alpha-synuclein. In some embodiments, the monoclonal antibody targeting alpha-synuclein is RG-7935, Posiphen, Affitope PD03A, Affitope PDOIA, or any combination thereof.

In some embodiments, the at least one additional therapeutic agent is a BACE enzyme inhibitor. In some embodiments, the BACE enzyme inhibitor is CTS-21166, MK-8931, AZD3293, LY3314814, BI 1181181, LY2886721, E2609, RG7129, JNJ-5486911, TAK-070, or any combination thereof.

In some embodiments, the at least one additional therapeutic agent is a RAGE inhibitor. In some embodiments, the RAGE inhibitor is TTP488 (Azeliragon), TTP4000, FPS-ZM1, or any combination thereof.

In some embodiments, the at least one additional therapeutic agent is an antibody targeting Tau. In some embodiments, the antibody targeting Tau is AADVAC1-1, AADVAC1-2, AC1-35, BMS-986168, RG7345, TRx-237-015 (LMTX), AV-1451, AV-680, Posiphen, or any combination thereof.

In some embodiments, the at least one additional therapeutic agent is a α7 nicotinic acetylcholine receptor modulator. In some embodiments, the α7 nicotinic acetylcholine receptor modulator is Encenicline (EVP-6124), ABT-126, ABT 418, RG3487, Varenicline, A-867744, TC-5219, AVL3288, BMS933043, DSP-3748, or any combination thereof.

In some embodiments, the at least one additional therapeutic agent may include one or more treatments for Alzheimer's disease such as Namzaric™, Exelon®, Aricept® (donepezil hydrochloride), Namenda® (memantine hydrochloride), or galantamine hydrobromide. In some embodiments, described compositions and formulations may be administered in combination with one or more treatments for Parkinson's Disease such as ABT-126 (Abbott Laboratories), pozanicline (Abbott Laboratories), MABT-5102A (AC Immune), Affitope AD-01 (AFFiRiS GmbH), Affitope AD-02 (AFFiRiS GmbH), davunetide (Allon Therapeutics Inc), nilvadipine derivative (Archer Pharmaceuticals), Anapsos (ASAC Pharmaceutical International AIE), ASP-2535 (Astellas Pharma Inc), ASP-2905 (Astellas Pharma Inc), 11C-AZD-2184 (AstraZeneca pic), 11C-AZD-2995 (AstraZeneca pic), 18F-AZD-4694 (AstraZeneca pic), AV-965 (Avera Pharmaceuticals Inc), AVN-101 (Avineuro Pharmaceuticals Inc), immune globulin intravenous (Baxter International Inc), EVP-6124 (Bayer AG), nimodipine (Bayer AG), BMS-708163 (Bristol-Myers Squibb Co), CERE-110 (Ceregene Inc), CLL-502 (CLL Pharma), CAD-106 (Cytos Biotechnology AG), mimopezil ((Debiopharm SA), DCB-AD1 (Development Centre for Biotechnology), EGb-761 ((Dr Willmar Schwabe GmbH & Co), E-2012 (Eisai Co Ltd), ACC1-001 (Elan Corp pic), bapineuzumab (Elan Corp pic), ELND-006 (Elan Pharmaceuticals Inc), atomoxetine (Eli Lilly & Co), LY-2811376 (Eli Lilly & Co), LY-451395 (Eli Lilly & Co), m266 (Eli Lilly & Co), semagacestat (Eli Lilly & Co), solanezumab (Eli Lilly & Co), AZD-103 (Ellipsis Neurotherapeutics Inc), FGLL (ENKAM Pharmaceuticals A/S), EHT-0202 (ExonHit Therapeutics SA), celecoxib (GD Searle & Co), GSK-933776A (GlaxoSmithKline pic), rosiglitazone XR (GlaxoSmithKline pic), SB-742457 (GlaxoSmithKline pic), R-1578 (Hoffmann-La Roche AG), HF-0220 (Hunter-Fleming Ltd), oxiracetam (ISF Societa Per Azioni), KD-501 (Kwang Dong Pharmaceutical Co Ltd), NGX-267 (Life Science Research Israel), huperzine A (Mayo Foundation), Dimebon (Medivation Inc), MEM-1414 (Memory Pharmaceuticals Corp), MEM-3454 (Memory Pharmaceuticals Corp), MEM-63908 (Memory Pharmaceuticals Corp), MK-0249 (Merck & Co Inc), MK-0752 (Merck & Co Inc), simvastatin (Merck & Co Inc), V-950 (Merck & Co Inc), memantine (Merz & Co GmbH), neramexane (Merz & Co GmbH), Epadel (Mochida Pharmaceutical Co Ltd), 1231-MNI-330 (Molecular Neuroimaging Lie), gantenerumab (MorphoSys AG), NIC5-15 (Mount Sinai School of Medicine), huperzine A (NeuroHitech Inc), OXIGON (New York University), NP-12 (Noscira SA), NP-61 (Noscira SA), rivastigmine (Novartis AG), ECT-AD (NsGene A/S), arundic acid (Ono Pharmaceutical Co Ltd), PF-3084014 (Pfizer Inc), PF-3654746 (Pfizer Inc), RQ-00000009 (Pfizer Inc), PYM-50028 (Phytopharm pic), Gero-46 (PN Gerolymatos SA), PBT-2 (Prana Biotechnology Ltd), PRX-03140 (Predix Pharmaceuticals Inc), Exebryl-1 (ProteoTech Inc), PF-4360365 (Rinat Neuroscience Corp), HuCAL anti-beta amyloid monoclonal antibodies (Roche AG), EVT-302 (Roche Holding AG), nilvadipine (Roskamp Institute), galantamine (Sanochemia Pharmazeutika AG), SAR-110894 (sanofi-aventis), INM-176 (Scigenic & Scigen Harvest), mimopezil (Shanghai Institute of Materia Medica of the Chinese Academy of Sciences), NEBO-178 (Stegram Pharmaceuticals), SUVN-502 (Suven Life Sciences), TAK-065 (Takeda Pharmaceutical), ispronicline (Targacept Inc), rasagiline (Teva Pharmaceutical Industries), T-817MA (Toyama Chemical), PF-4494700 (TransTech Pharma Inc), CX-717 (University of California), 18F-FDDNP (University of California Los Angeles), GTS-21 (University of Florida), 18F-AV-133 (University of Michigan), 18F-AV-45 (University of Michigan), tetrathiomolybdate (University of Michigan), 1231-IMPY (University of Pennsylvania), 18F-AV-1/ZK (University of Pennsylvania), 11C-6-Me-BTA-1 (University of Pittsburgh), 18F-6-OH-BTA-1 (University of Pittsburgh), MCD-386 (University of Toledo), leuprolide acetate implant (Voyager Pharmaceutical Corp), aleplasinin (Wyeth), begacestat (Wyeth), GSI-136 (Wyeth), NSA-789 (Wyeth), SAM-531 (Wyeth), CTS-21166 (Zapaq), and ZSET-1446 (Zenyaku Kogyo).

In some embodiments, the at least one additional therapeutic agent may include one or more agents useful for the treatment of motor neuronal disorders, such as AEOL-10150 (Aeolus Pharmaceuticals Inc), riluzole (Aventis Pharma AG), ALS-08 (Avicena Group Inc), creatine (Avicena Group Inc), arimoclomol (Biorex Research and Development Co), mecobalamin (Eisai Co Ltd), talampanel (Eli Lilly & Co), R-7010 (F Hoffmann-La Roche Ltd), edaravone (Mitsubishi-Tokyo Pharmaceuticals Inc), arundic acid (Ono Pharmaceutical Co Ltd), PYM-50018 (Phytopharm pic), RPI-MN (ReceptoPharm Inc), SB-509 (Sangamo Biosciences Inc), olesoxime (Trophos SA), sodium phenylbutyrate (Ucyclyd Pharma Inc), and R-pramipexole (University of Virginia).

In some embodiments, the at least one additional therapeutic agent may be an agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT$_4$ receptor partial agonists or 5HT$_{1A}$ receptor antagonists and NMDA receptor antagonists or modulators, glutamate antagonists, GABA-ergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies, an antidepressants, for example a tricyclic, a MAOI (Monoamine oxidase inhibitor) a SSRI (Selective Serotonin Reuptake Inhibitor), a SNRI (Serotonin and Noradrenaline Reuptake Inhibitor) or a NaSSA (noradrenergeric and specific serotonergic antidepressant). Examples of specific antidepressant compounds include amitriptyline, clomipramine, citalopram, dosulepin, doxepin, fluoxetine, imipramine, lofepramine, mirtazapine, moclobemide, nortriptyline, paroxetine, phenelzine, reboxetine, sertraline, tranylcypromine, trazodone, or venlafaxine. In some embodiments, additional therapeutic agents may include antipsychotic drugs, such as olanzapine, clozapine, risperidone, quetiapine, aripiprazole or paliperiden.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

One aspect of the present invention pertains to pharmaceutical compositions comprising a therapeutically effective amount of 1-[3-(4-bromo-2-methyl-2H-pyrazol-3-yl)-4-methoxy-phenyl]-3-(2,4-difluoro-phenyl)-urea; and PVP, methyl cellulose, or a mixture thereof. One aspect of the present invention pertains to pharmaceutical compositions comprising a therapeutically effective amount of 1-[3-(4-bromo-2-methyl-2H-pyrazol-3-yl)-4-methoxy-phenyl]-3-(2,4-difluoro-phenyl)-urea. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 0.0001 to about 1,000 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 10 to about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 10 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 20 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 40 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 80 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 160 mg.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

One aspect of the present invention pertains to methods for preparing a pharmaceutical composition of the present invention comprising: (a) 1-[3-(4-bromo-2-methyl-2H-pyrazol-3-yl)-4-methoxy-phenyl]-3-(2,4-difluoro-phenyl)-urea; and (b) an excipient selected from: PVP and coPVP; comprising blending the 1-[3-(4-bromo-2-methyl-2H-pyrazol-3-yl)-4-methoxy-phenyl]-3-(2,4-difluoro-phenyl)-urea and the excipient in a blender.

One aspect of the present invention pertains to dosage forms comprising a therapeutically effective amount of 1-[3-(4-bromo-2-methyl-2H-pyrazol-3-yl)-4-methoxy-phenyl]-3-(2,4-difluoro-phenyl)-urea; and PVP, methyl cellulose, or a mixture thereof. One aspect of the present invention pertains to dosage forms comprising a therapeutically effective amount of 1-[3-(4-bromo-2-methyl-2H-pyrazol-3-yl)-4-methoxy-phenyl]-3-(2,4-difluoro-phenyl)-urea. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 0.0001 to about 1,000 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is from about 10 to about 160 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 10 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 20 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 40 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 80 mg. In some embodiments, the therapeutically effective amount of 1-[3-(4-bromo-2-methyl-2H-pyrazol-3-yl)-4-methoxy-phenyl]-3-(2,4-difluoro-phenyl)-urea is about 160 mg.

In some embodiments, the pharmaceutical compositions described herein may comprise at least one additional therapeutic agent.

In some embodiments, the at least one additional therapeutic agent is selected from the group consisting of melatonin, quetiapine, clozapine, risperidone, clonazepam, levodopa, carbidopa, an antiparkinsonian drug, an acetylcholinesterase inhibitor, NMDA receptor antagonist, an atypical antipsychotic agent, a dopaminergic agent, a benzodiazepine, an antidepressant, and a combination thereof. In some embodiments, the antiparkinsonian drug is selected from an MAO-B inhibitor, a COMT inhibitor, a dopamine agonist or any combination thereof. In some embodiments, the acetylcholinesterase inhibitor is selected from the group consisting of donepezil, rivastigmine, galantamine, and pharmaceutically acceptable salts, hydrates, polymorphs, or solvates thereof. In some embodiments, the acetylcholinesterase inhibitor is donepezil or a pharmaceutically acceptable salt, hydrate, polymorph, or solvate thereof. In some embodiments, NMDA receptor antagonist is selected from the group consisting of memantine, amantadine, ketamine, and pharmaceutically acceptable salts, hydrates, polymorphs, or solvates thereof.

In some embodiments, the at least one additional therapeutic agent is 3-phenylsulfonyl-8-piperazinyl-1yl-quinoline.

In some embodiments, the at least one additional therapeutic agent is a monoclonal antibody. In some embodiments, the second therapeutic agent is a human monoclonal antibody. In some embodiments, the second therapeutic agent is a humanized monoclonal antibody. In some embodiments the monoclonal antibody targets beta amyloid. In some embodiments the beta amyloid may comprise aggregated beta amyloid such as but not limited to soluble oligomers, insoluble fibrils deposited into amyloid plaque, or a combination thereof. In some embodiments, the monoclonal antibody is Aducanumab (BIIB037), Gantenerumab, Bapineuzumab, Crenezumab, Ponezumab, Solanezumab, SAR228810, MEDI1814, BAN2401, or any combination thereof. In some embodiments, the monoclonal antibody targets alpha-synuclein. In some embodiments, the monoclonal antibody targeting alpha-synuclein is RG-7935, Posiphen, Affitope PD03A, Affitope PD01A, or any combination thereof.

In some embodiments, the at least one additional therapeutic agent is a BACE enzyme inhibitor. In some embodiments, the BACE enzyme inhibitor is CTS-21166, MK-8931, AZD3293, LY3314814, BI 1181181, LY2886721, E2609, RG7129, JNJ-5486911, TAK-070, or any combination thereof.

In some embodiments, the at least one additional therapeutic agent is a RAGE inhibitor. In some embodiments, the RAGE inhibitor is TTP488 (Azeliragon), TTP4000, FPS-ZM1, or any combination thereof.

In some embodiments, the at least one additional therapeutic agent is an antibody targeting Tau. In some embodiments, the antibody targeting Tau is AADVAC1-1, AADVAC1-2, AC1-35, BMS-986168, RG7345, TRx-237-015 (LMTX), AV-1451, AV-680, Posiphen, or any combination thereof.

In some embodiments, the at least one additional therapeutic agent is a α7 nicotinic acetylcholine receptor modulator. In some embodiments, the α7 nicotinic acetylcholine receptor modulator is Encenicline (EVP-6124), ABT-126, ABT 418, RG3487, Varenicline, A-867744, TC-5219, AVL3288, BMS933043, DSP-3748, or any combination thereof.

In some embodiments, the at least one additional therapeutic agent may include one or more treatments for Alzheimer's disease such as Namzaric™, Exelon®, Aricept® (donepezil hydrochloride), Namenda® (memantine hydrochloride), or galantamine hydrobromide. In some embodiments, described compositions and formulations may be administered in combination with one or more treatments for Parkinson's Disease such as ABT-126 (Abbott Laboratories), pozanicline (Abbott Laboratories), MABT-5102A (AC Immune), Affitope AD-01 (AFFiRiS GmbH), Affitope AD-02 (AFFiRiS GmbH), davunetide (Allon Therapeutics Inc), nilvadipine derivative (Archer Pharmaceuticals), Anapsos (ASAC Pharmaceutical International AIE), ASP-2535 (Astellas Pharma Inc), ASP-2905 (Astellas Pharma Inc), 11C-AZD-2184 (AstraZeneca pic), 11C-AZD-2995 (AstraZeneca pic), 18F-AZD-4694 (AstraZeneca pic), AV-965 (Avera Pharmaceuticals Inc), AVN-101 (Avineuro Pharmaceuticals Inc), immune globulin intravenous (Baxter International Inc), EVP-6124 (Bayer AG), nimodipine (Bayer AG), BMS-708163 (Bristol-Myers Squibb Co), CERE-110 (Ceregene Inc), CLL-502 (CLL Pharma), CAD-106 (Cytos Biotechnology AG), mimopezil ((Debiopharm SA), DCB-AD1 (Development Centre for Biotechnology), EGb-761 ((Dr Willmar Schwabe GmbH & Co), E-2012 (Eisai Co Ltd), ACC1-001 (Elan Corp pic), bapineuzumab (Elan Corp pic), ELND-006 (Elan Pharmaceuticals Inc), atomoxetine (Eli Lilly & Co), LY-2811376 (Eli Lilly & Co), LY-451395 (Eli Lilly & Co), m266 (Eli Lilly & Co), semagacestat (Eli Lilly & Co), solanezumab (Eli Lilly & Co), AZD-103 (Ellipsis Neurotherapeutics Inc), FGLL (ENKAM Pharmaceuticals A/S), EHT-0202 (ExonHit Therapeutics SA), celecoxib (GD Searle & Co), GSK-933776A (GlaxoSmithKline pic), rosiglitazone XR (GlaxoSmithKline pic), SB-742457 (GlaxoSmithKline pic), R-1578 (Hoffmann-La Roche AG), HF-0220 (Hunter-Fleming Ltd), oxiracetam (ISF Societa Per Azioni), KD-501 (Kwang Dong Pharmaceutical Co Ltd), NGX-267 (Life Science Research Israel), huperzine A (Mayo Foundation), Dimebon (Medivation Inc), MEM-1414 (Memory Pharmaceuticals Corp), MEM-3454 (Memory Pharmaceuticals Corp), MEM-63908 (Memory Pharmaceuticals Corp), MK-0249 (Merck & Co Inc), MK-0752 (Merck & Co Inc), simvastatin (Merck & Co Inc), V-950 (Merck & Co Inc), memantine (Merz & Co GmbH), neramexane (Merz & Co GmbH), Epadel (Mochida Pharmaceutical Co Ltd), 1231-MNI-330 (Molecular Neuroimaging Lie), gantenerumab (MorphoSys AG), NIC5-15 (Mount Sinai School of Medicine), huperzine A (NeuroHitech Inc), OXIGON (New York University), NP-12 (Noscira SA), NP-61 (Noscira SA), rivastigmine (Novartis AG), ECT-AD (NsGene A/S), arundic acid (Ono Pharmaceutical Co Ltd), PF-3084014 (Pfizer Inc), PF-3654746 (Pfizer Inc), RQ-00000009 (Pfizer Inc), PYM-50028 (Phytopharm pic), Gero-46 (PN Gerolymatos SA), PBT-2 (Prana Biotechnology Ltd), PRX-03140 (Predix Pharmaceuticals Inc), Exebryl-1 (ProteoTech Inc), PF-4360365 (Rinat Neuroscience Corp), HuCAL anti-beta amyloid monoclonal antibodies (Roche AG), EVT-302 (Roche Holding AG), nilvadipine (Roskamp Institute), galantamine (Sanochemia Pharmazeutika AG), SAR-110894 (sanofi-aventis), INM-176 (Scigenic & Scigen Harvest), mimopezil (Shanghai Institute of Materia Medica of the Chinese Academy of Sciences), NEBO-178 (Stegram Pharmaceuticals), SUVN-502 (Suven Life Sciences), TAK-065 (Takeda Pharmaceutical), ispronicline (Targacept Inc), rasagiline (Teva Pharmaceutical Industries), T-817MA (Toyama Chemical), PF-4494700 (TransTech Pharma Inc), CX-717 (University of California), 18F-FDDNP (University of California Los Angeles), GTS-21 (University of Florida), 18F-AV-133 (University of Michigan), 18F-AV-45 (University of Michigan), tetrathiomolybdate (University of Michigan), 1231-IMPY (University of Pennsylvania), 18F-AV-1/ZK (University of Pennsylvania), 11C-6-Me-BTA-1 (University of Pittsburgh), 18F-6-OH-BTA-1 (University of Pittsburgh), MCD-386 (University of Toledo), leuprolide acetate implant (Voyager Pharmaceutical Corp), aleplasinin (Wyeth), begacestat (Wyeth), GSI-136 (Wyeth), NSA-789 (Wyeth), SAM-531 (Wyeth), CTS-21166 (Zapaq), and ZSET-1446 (Zenyaku Kogyo).

In some embodiments, the at least one additional therapeutic agent may include one or more agents useful for the treatment of motor neuronal disorders, such as AEOL-10150 (Aeolus Pharmaceuticals Inc), riluzole (Aventis Pharma AG), ALS-08 (Avicena Group Inc), creatine (Avicena Group Inc), arimoclomol (Biorex Research and Development Co), mecobalamin (Eisai Co Ltd), talampanel (Eli Lilly & Co), R-7010 (F Hoffmann-La Roche Ltd), edaravone (Mitsubishi-Tokyo Pharmaceuticals Inc), arundic acid (Ono Pharmaceutical Co Ltd), PYM-50018 (Phytopharm pic), RPI-MN (ReceptoPharm Inc), SB-509 (Sangamo Biosciences Inc), olesoxime (Trophos SA), sodium phenylbutyrate (Ucyclyd Pharma Inc), and R-pramipexole (University of Virginia).

In some embodiments, the at least one additional therapeutic agent may be an agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT$_4$ receptor partial agonists or 5HT$_{1A}$ receptor antagonists and NMDA receptor antagonists or modulators, glutamate antagonists, GABA-ergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies, an antidepressants, for example a tricyclic, a MAOI (Monoamine oxidase inhibitor) a SSRI (Selective Serotonin Reuptake Inhibitor), a SNRI (Serotonin and Noradrenaline Reuptake Inhibitor) or a NaSSA (noradrenergeric and specific serotonergic antidepressant). Examples of specific antidepressant compounds include amitriptyline, clomipramine, citalopram, dosulepin, doxepin, fluoxetine, imipramine, lofepramine, mirtazapine, moclobemide, nortriptyline, paroxetine, phenelzine, reboxetine, sertraline, tranylcypromine, trazodone, or venlafaxine. In some embodiments, additional therapeutic agents may include antipsychotic drugs, such as olanzapine, clozapine, risperidone, quetiapine, aripiprazole or paliperiden.

Conventional excipients, such as binding agents, fillers, acceptable wetting agents, tableting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

While it is possible that, for use in the prophylaxis and/or treatment, a compound of the invention may, in an alternative use, be administered as a raw or pure chemical, it is preferable to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insulation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as 5-$HT_{2A}$ receptor modulators. The term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present invention include, but are not limited to, about 0.0001 to about 1,000 mg, about 10 to about 160 mg, about 10 mg, about 20 mg, about 40 mg, about 80 mg or about 160 mg. Multiple doses may be administered during the day, especially when relatively large amounts are deemed to be needed, for example 2, 3 or 4, doses. In some embodiments, the dose is administered once daily in the morning, twice daily, or once daily about 1 hour prior to the subject's bedtime. In some embodiments, the dose is administered about one to about four times per day, once daily in the morning, once daily about 1 hour prior to the subject's bedtime, or twice daily. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human. However, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, whether an acute or chronic disease state is being treated or prophylaxis is conducted, or whether further active compounds are administered in addition to the compounds of the present invention and as part of a drug combination. The dosage regimen for treating a disease condition with the compounds and/or compositions of this invention is selected in accordance with a variety of factors as cited above. Thus, the actual dosage regimen employed may vary widely and therefore may deviate from a preferred dosage regimen. One skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier, providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved, for example, by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well-known to a person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethanesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed in Journal of Pharmaceutical Science, 66, 2 (1977); incorporated herein by reference in its entirety.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art, and when administered into an individual, these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, "Pro-drugs as Novel Delivery Systems," Vol. 14 of the A.C.S. Symposium Series; and in Bioreversible Carriers in Drug Design, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the $5\text{-HT}_{2A}$ receptor modulators are utilized as active ingredients in a pharmaceutical composition, these are not intended for use only in humans, but in other non-human mammals as well. Indeed, recent advances in the area of animal healthcare mandate that consideration be given for the use of active agents, such as $5\text{-HT}_{2A}$ receptor modulators, for the treatment of a $5\text{-HT}_{2A}$ mediated disease or disorder in domestic animals (e.g., cats and dogs) and in other domestic animals (e.g., such as cows, chickens, fish, etc.). Those of ordinary skill in the art are readily credited with understanding the utility of such compounds in such settings.

Embodiments of the invention are not limited to any particular agent encompassed by the classes of agents described above, and any agent that falls within any of these categories may be utilized in embodiments of the invention. Non-limiting examples of such agents are provided for clarity. Any of the secondary agents described above may be useful in embodiments of the invention.

The embodiments for disease states, subject type, daily dose amounts, therapeutically effective amounts, no observable adverse effect level dose amounts, non-effective dose amounts, pharmaceutical compositions, and chiral purities for the methods of the invention, which are described herein separately for the sake of brevity, can be joined in any suitable combination.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

EXAMPLES

Example 1—A Phase 2, Double-Blind, Randomized Placebo-Controlled Study of Nelotanserin Versus Placebo in Dementia with Lewy Bodies (DLB) Subjects Experiencing Visual Hallucinations Primary Objectives: To assess the effects of nelotanserin versus placebo on hallucinations as measured by the change in the hallucinations component of the Scale for Assessment of Positive Symptoms (SAPS-H) after 43 days of treatment.

Secondary Objectives: To assess the effects of nelotanserin versus placebo on delusions as measured by the change in the delusions component of the Scale for Assessment of Positive Symptoms (SAPS-D) after 43 days of treatment.

To assess the effects of nelotanserin versus placebo on investigator assessments of global function as measured by the change in the CGI-I and CGI-S scores after 43 days of treatment.

To assess the effects of nelotanserin versus placebo on caregiver burden as measured by the Zarit Caregiver Burden Score after 43 days of treatment.

To assess the effects of nelotanserin on subjective sleep quality as measured by change in the SCOPA-night and SCOPA day wake scores after 43 days of treatment.

To assess the effects of nelotanserin versus placebo on all measures of efficacy described above after 22 days of treatment.

To assess the safety and tolerability of nelotanserin.

Target Population: Adult subjects aged 50 to 85, inclusive, with a diagnosis of probable Dementia with Lewy Bodies (DLB) and the presence of persistent visual hallucinations. The diagnosis of probable DLB will be defined by the presence of dementia and at least one of the following:

At least two out of the following three Core Criteria: Visual hallucinations; Cognitive Fluctuations; Parkinsonism or one of the Core Criteria and at least one of the following three Suggestive Criteria: REM Sleep Behavior Disorder; Severe Neuroleptic Sensitivity; Low Dopamine Transporter Uptake on DaT SPECT Imaging Scan.

The presence of persistent hallucinations will be defined by having a score of four or greater on the hallucinations component of the Neuropsychiatric Inventory (NPI Item B) at screening and at the end of the two-week lead-in period, during which subjects will receive non-pharmacological brief psychosocial therapy. The hallucinations must be predominantly visual in nature, as reported by the patient and/or caregiver. In addition, subjects must have a score of three or greater on SAPS-H at baseline. Subjects must again have an NPI Item B score of >4 and a SAPS-H score of >3 at the end of a two-week placebo run-in period prior to randomization.

The use of antipsychotic drugs in the study will be prohibited, with the exception of stable low dose quetiapine (<25 mg QD). Subjects on a low dose of quetiapine during the study must have been on a stable dose <25 mg QD for at least three weeks prior to screening. All other subjects receiving any other antipsychotic (or any other dose of quetiapine) within three weeks prior to screening will be excluded from the study. Target stratification for the study will be to include subjects on a stable low dose of quetiapine to comprise approximately 50% of study participants and no more than 60%.

Stable cholinesterase inhibitor therapy (for at least two months prior to screening) will be allowed during the study.

Number of subjects planned: Approximately 225 randomized subjects (Nelotanserin 80 mg QD: 75 subjects; Nelotanserin 40 mg QD: 75 subjects; Placebo: 75 subjects).

Number of Study Centers planned: Approximately 40.

Study Design: This is a multi-center, double-blind, randomized, placebo-controlled, parallel-group study in subjects with probable DLB experiencing visual hallucinations. The efficacy and safety of nelotanserin at doses of 80 mg and 40 mg daily will be evaluated over a 6-week treatment period when given to subjects experiencing frequent and recurrent visual hallucinations. Stable cholinesterase therapy (a stable dose for at least two months prior to screening) will be allowed during the study. The use of antipsychotic drugs will be prohibited during the study, with the exception of low dose quetiapine (<25 mg QD) in subjects on a stable dose for at least three weeks prior to screening. All subjects on a stable dose of quetiapine or cholinesterase inhibitors will continue to remain on them for the duration of the study.

The randomization ratio will be 1:1:1 (80 mg nelotanserin:40 mg nelotanserin:placebo), with a target study stratification of 50% (and no greater than 60%) of participants receiving a stable low dose of quetiapine. DLB subjects with an MMSE score of >18 will be included in the study. All subjects will undergo a DaT SPECT Imaging Scan. The results of this scan will be supportive of a diagnosis of probable DLB but will not be a requirement for such a diagnosis if the other criteria are met.

After screening, subjects will enter into a two-week lead-in period during which they will undergo non-pharmacological brief psychosocial therapy. At the end of this lead-in period, all subjects will again undergo NPI and SAPS testing, and those with an NPI Item B (hallucinations) score of <4, a SAPS-H score of <3, or the presence of hallucinations that are predominantly non-visual in nature will be excluded from the study.

Following the lead-in period, subjects will then undergo a two-week single arm placebo run-in period. At the end of this placebo run-in period, all subjects will again undergo NPI and SAPS testing, and those with an NPI Item B (hallucinations) score of <4, a SAPS-H score of <3, or the presence of hallucinations that are predominantly non-visual in nature will be excluded from the study.

Following this two week placebo run-in period, subjects in the study will be randomized 1:1:1 to receive either 80 mg or 40 mg of nelotanserin or placebo, once daily. Safety data will be collected throughout the study. Efficacy data on the primary and secondary endpoints will be collected at the pre-specified primary endpoint at 6 weeks of treatment, as well as at 3 week and baseline.

Duration of Treatment: Study participation will last approximately 16 weeks: 0 to 28 days for Screening, a two-week lead-in period with non-pharmacological brief psychosocial therapy, a two-week placebo run-in period, a six-week randomized treatment period, and a two-week follow-up period.

Following the six-week randomized treatment period, all subjects will be eligible to participate in a 40-week open-label extension study with nelotanserin at the most efficacious and tolerated dose.

Criteria for Evaluation: Primary efficacy measures: The primary efficacy response will be an assessment of change at 43 days from baseline in hallucinations as evaluated by the SAPS-H scale.

Secondary efficacy measures: Measurements at 43 days, including: additional measures of psychosis, including SAPS-D; investigator assessments of global function as measured by change in CGI-I and CGI-S scores; effects on caregiver burden as measured by Zarit Caregiver Burden Score; effects on sleep as measured by SCOPA scores. Measurement of all primary and secondary measures after 22 days of treatment.

Safety evaluation: Safety will be evaluated based on adverse events (AEs), physical examinations, vital signs, electrocardiograms (ECGs), and routine clinical laboratory assessments.

Although the present invention has been described in considerable detail with reference to certain preferred embodiments thereof, other versions are possible. Therefore the spirit and scope of the appended claims should not be limited to the description and the preferred versions contained within this specification.

Example 2—A Phase 1b, Double-Blind, Randomized, Placebo-Controlled Cross-Over Study of Nelotanserin Versus Placebo in Lewy Body Dementia (LBD) Subjects Experiencing Visual Hallucinations Indication Rationale: Evaluation of Nelotanserin for the treatment of visual hallucinations associated with LBD is warranted by the following: (1) markedly increased 5-HT$_2$a receptor density in subjects with Lewy body disease as determined by PET radiotracer imaging, with evidence of relative preservation of 5-HT$_2$ receptors in the temporal cortex being a differentiating feature between hallucinating and non-hallucinating DLB cases; (2) evidence that other agents that block 5-HT$_2$a neurotransmission, for example pimavanserin and low dose clozapine, demonstrate efficacy in psychotic symptoms associated with Parkinson's Disease; (3) the off-label use of low-dose atypical antipsychotics such as quetiapine for treatment of hallucinations associated with DLB and PDD; and, (4) an acceptable safety and tolerability profile of Nelotanserin based on previous clinical studies to date in the proposed dose range.

Dose Rationale: A daily dose of 80 mg Nelotanserin was selected for this study based on the favorable tolerability and PK/PD profile at this dose in studies completed to date.

Objectives And Endpoints

| Objectives | Endpoints |
|---|---|
| Primary | |
| To assess the safety of Nelotanserin DLB subjects with visual hallucinations after 28 days of treatment | Safety will be assessed by analyzing adverse events, laboratory values, vital signs, and physical examinations<br>Extrapyramidal signs are assessed with the motor subsection of the Unified Parkinson's Disease Rating Scale (UPDRS, Parts II and III). |
| Secondary | |
| To assess the effects of Nelotanserin versus placebo on the frequency of visual hallucinations after 28 days of treatment, as recorded in a daily diary completed by the subject and his/her primary caregiver | Change in the frequency of visual hallucinations from baseline to day 28 based on a daily diary completed by the subject and his/her caregiver |
| To assess the effects of Nelotanserin versus placebo on the frequency and severity of visual hallucinations after 28 days of treatment, as measured by a visual analog scale (VAS) completed by the subject and his/her primary caregiver | Change in VAS score from baseline to day 28 based on scoring by the subject and his/her caregiver |
| To assess the effects of Nelotanserin versus placebo on hallucinations and delusions after 28 days of treatment as measured by the Scale for Assessment of Positive Symptoms (SAPS) | Change in SAPS-Hallucinations and SAPS-Delusions subscores from baseline to day 28 |
| To assess the effects of Nelotanserin versus placebo on cognition after 28 days of treatment as measured by the Cognitive Drug Research Power of Attention computerized test | Change in Power of Attention score from baseline to day 28 |

Study Design: This is a multi-center, double-blind, randomized, placebo-controlled, cross-over study in DLB subjects experiencing frequent and recurrent visual hallucinations. The primary objective of the study will be to evaluate the safety of Nelotanserin. Secondary objectives of the study include the evaluation of the effects of Nelotanserin on visual hallucinations.

Following an initial screening, eligible subjects will enter a two-week single blind placebo run-in period. At the end of this period, all subjects who continue to meet the eligibility criteria will enter the four-week double-blind Treatment Period 1. Following the completion of Treatment Period 1, subjects will undergo a washout period of four weeks during which subjects will not receive any study medication. After the washout, subjects will then enter the four-week double-blind Treatment Period 2.

Each subject will be randomized 1:1, stratified by DLB and PDD, to one of the following sequences:
1. AB=Nelotanserin Period 1 and placebo in Period 2
2. BA=placebo in Period 1 and Nelotanserin Period 2

During each treatment period, subjects receiving Nelotanserin will receive a 40 mg dose for the first three days, and will then receive an 80 mg dose for the remainder of the treatment period. Following the final visit, all subjects will be eligible to participate in an open-label extension period with Nelotanserin.

Type and Number of Subjects: Up to 20 subjects with visual hallucinations associated with Lewy Body Dementia will be enrolled, at least 10 of whom will have visual hallucinations associated with Dementia with Lewy Bodies (DLB) and approximately 10 will have visual hallucinations associated with Parkinson's Disease Dementia (PDD).

Inclusion Criteria: Diagnosis of DLB based on DSM-5 diagnostic criteria or diagnosis of PDD based on DSM-5 diagnostic criteria; Presence of visual hallucinations that occur at least five days per week during each of the past four weeks; Mini Mental state examination score ≥18; Stable quetiapine treatment will be allowed, if at a stable dose of ≤25 mg/day for at least four weeks prior to screening; Subjects taking antiparkinsonian drugs (e.g., levodopa) must be on stable dosage for at least 1 month prior to screening and expect to continue the stable regimen throughout the study; Subjects taking acetylcholinesterase inhibitors (AchEIs) or memantine must be on stable dosage for at least 1 month prior to screening and expect to continue the stable regimen throughout the study; Subjects must have a caregiver or family member who can serve as a collateral informant for study assessments and, if necessary, provide proxy consent to participate in the study; Female subjects who are premenopausal or postmenopausal less than 1 year and who have not had surgical sterilization (i.e., tubal ligation, partial or complete hysterectomy) must have a negative serum pregnancy test, be nonlactating, and willing to use adequate and reliable contraception throughout the study (e.g., barrier with additional spermicidal foam or jelly, intra-uterine device, hormonal contraception).

Exclusion Criteria: Subjects have a current diagnosis of significant psychotic disorders including, but not limited to, schizophrenia or bipolar disorder; Subjects with visual hallucinations that occur fewer than five days per week during any of the past four weeks; Subjects' psychotic symptoms are secondary to or better counted for by another medical condition, psychiatric disorder, or substance abuse; Subjects have been refractory to antipsychotic drug treatment for psychosis; Use of any antipsychotic medication other than stable quetiapine at a dose of >25 mg/day; Any significant change in the subject's environment within the past four weeks; Subjects with a history of significant cerebrovascular events; Subjects with a history of seizures; Subjects with a current serious and/or unstable cardiovascular, respiratory, thyroid, gastrointestinal, renal, hematologic or other medical disorder; Subjects who have used any investigational medication within 30 days prior to the first dose of study medication; Subjects with evidence of impaired liver function at screening (laboratory test values ≥3 times the upper limit of the laboratory reference (normal) range (ULN) for aspartate transaminase [AST/SGOT] or alanine transaminase [ALT/SGPT]); Subjects who are allergic or hypersensitive to nelotanserin.

Other Eligibility Criteria Considerations: To assess any potential impact on subject eligibility with regard to safety, the investigator must refer to the following document(s) for detailed information regarding warnings, precautions, contraindications, AEs, and other significant data pertaining to the investigational product(s) being used in this study: Nelotanserin Clinical Investigator's Brochure.

Withdrawal Criteria—Reasons for Withdrawal: A withdrawal from the study is defined as withdrawing any time after entering the Single-Blind Run-In Phase and before completion of the Week 12 visit (visit 7). Subjects who permanently discontinue use of theinvestigational product will be considered to be withdrawn from the study. Subjects may withdraw from the study at any time and for any reason. The investigator (or designee) must document the reason for withdrawal in the Study Conclusion section of the electronic case report form (eCRF). Information related to AEs will continue to be collected as per usual procedures on subjects who have discontinued investigational product. Withdrawn subjects will not be replaced. The reasons for subject withdrawal will be recorded and may include, but are not limited to: Any clinical AE, laboratory abnormality, or other medical condition or situation occurs such that continued participation in the study would not be in the best interest of the subject in the opinion of the investigator; Pregnancy of female subject (discontinuation of treatment, but will be followed until the outcome of pregnancy is known); Significant protocol violation; Subject requests to discontinue for any reason; it is important to determine whether the withdrawal of consent is primarily due to an AE, lack of efficacy, or other reason; Subjects don't meet the eligibility criteria at baseline (Visit 3). The above reasons do not automatically lead to withdrawal from the study in all cases. The final decision will be based on consultation between the principal investigator and the study Medical Monitor, with the ultimate decision by the principal investigator or subject. Subjects may discontinue from treatment with study IP but may agree to continue to be followed for additional safety evaluation.

Investigational Product and Other Study Treatment: Nelotanserin 20 mg tablets and matching placebo tablets are composed of an immediate-release, blue, oblong shaped tablet containing common pharmaceutical excipients in a compacted powder blend. The excipients used for the proposed clinical program are commonly available, generally regarded as safe, and tested against appropriate compendial acceptance criteria. The tablets are coated with a cosmetic colored film-coat. Lactose monohydrate is the only excipient used in the manufacture of RVT-102 tablets that is animal-sourced. The vendor source of this excipient has certified that ingredients used in the manufacture of lactose monohydrate are BSE/TSE free.

Randomization/Treatment Assignment: During the screening and the placebo run-in period, subjects will be identified by their initials, screening number and date of birth. Subjects who meet all screening eligibility criteria at Visit 2 will receive single-blind placebo for 2 weeks during the run-in period. The tablet will be administered once-daily in the morning (around the same time each day). At Visit 3, if subjects continue to meet all eligibility criteria, they will be randomized and assigned a randomization identification number (three digits). Both screening and randomization numbers will be used to identify the subject on any related study documents. The Investigator will keep a record relating the names of the subjects to their identification numbers, to allow easy checking of data in subject files, when required. Investigators are instructed to assign randomization numbers in ascending order, according to their current supply.

Eligible subjects will be randomized to receive study treatments A or B according to one of the treatment sequences listed in table 5 below.

TABLE 5

Randomization of subjects

| Treatment Sequence | Treatment Period 1 | Treatment Period 2 |
|---|---|---|
| 1 | A | B |
| 2 | B | A |

Where:
A = Nelotanserin (RVT-102)
B = Placebo

Where:
   A=Nelotanserin (RVT-102)
   B=Placebo

The study medication used in the trial are Nelotanserin 20 mg and matching placebo tablets. During each treatment period, subjects randomized to Nelotanserin will receive a 40 mg dose (2×20 mg tablets) initially for 3 days and their dose will be titrated up to 80 mg (4×20 mg tablets) for the remainder of the treatment period. No study drug will be administered during the 4-week washout period between Treatment Periods 1 and 2.

Blinding: The 20 mg Nelotanserin and matching placebo tablets will be identical in appearance.

Concomitant Medications and Non-Drug Therapies

Permitted Medications and Non-Drug Therapies: Stable quetiapine treatment will be allowed, if at a stable dose of ≤25 mg/day for at least four weeks prior to screening; Subjects taking antiparkinsonian drugs (e.g., levodopa) must be on stable dosage for at least 1 month prior to screening and expect to continue the stable regimen throughout the study; Subjects taking acetylcholinesterase inhibitors (AchEIs) or memantine must be on stable dosage for at least 1 month prior to screening and expect to continue the stable regimen throughout the study.

Prohibited Medications and Non-Drug Therapies: Prohibited medications include any medications that may interfere with study assessment during the run-in and treatment periods as shown in Table 6.

TABLE 6

List of Prohibited Medications

| CYP 3A4 inhibitors | CYP 3A4 Inducers | Antipsychotics |
|---|---|---|
| macrolide antibiotics: (e.g., erythromycin, clarithromycin) | Carbamazepine (Tegretol) Dexamethasone Phenobarbital | All antipsychotics, except for quetiapine |

TABLE 6-continued

List of Prohibited Medications

| CYP 3A4 inhibitors | CYP 3A4 Inducers | Antipsychotics |
|---|---|---|
| Azole antifungals: (e.g., ketoconazole, itraconazole, fluconazole) | Phenytoin (Dilantin) Rifampin (Rifadin, Rimactane) | ≤25 mg/day |
| Protease inhibitors: indinivir, ritinivir | | |
| SSRis: (e.g., fluvoxamine, fluoxetine, paroxetine) | | |
| SNRI antidepressants: (e.g., venlafaxine) | | |
| Verapamil | | |
| Propoxyphene (Darvon) | | |
| Cimetidine (Tagament) | | |
| Diltiazem (Cardizem) | | |

Any other medications used to treat visual hallucinations than those allowed in the study.

Lifestyle and/or Dietary Restrictions

Meals and Dietary Restrictions: The study medication can be administered with or without food.

Study Assessments And Procedures: Protocol waivers or exemptions are not allowed, with the exception of immediate safety concerns. Therefore, adherence to the study design requirements, including those specified in the Time and Events Table, are essential and required for study conduct.

Time and Events: The Time and Events Schedule displays each study assessment and procedure along with the time of occurrence. All study assessments should be conducted by the investigator, and/or a suitably qualified designee approved and documented for this study. All raters will be trained and certified to perform the specific rating scales in this study. It is important that all visits should be scheduled relative to the baseline visit. If the visit window is used, the subsequent visit should remain according to the planned visit schedule (i.e., the subsequent visit date should not be re-calculated from the date of the previous visit but should remain relative to baseline). Information will be recorded in the source documents and, where appropriate, the eCRF. If medical assessments are scheduled for the same nominal time, then the assessments should be given after cognitive testing and occur in the following order whenever possible: 12-lead ECG; Vital Signs; and Blood draws.

Screening Period (up to 28 days before Visit 2): Subjects will be screened for eligibility during the Screening Period. An ICF will be signed by each subject, if they are able, or by the caregiver with subject assent. An ICF will also be signed by the caregiver before any study-specific procedures are performed. Subjects who do not qualify for the study during this period will be considered screen failures. Subjects will be screened according to study inclusion/exclusion criteria. This Screening Period may be extended for up to an additional 14 days if needed to complete assessment activities after approval by the study Medical Monitor. Subjects who are screen failures during the Screening Period may be rescreened after discussion with the Medical Monitor. Note: subjects who are screen failures may be rescreened only once.

Single-Blind Run-In Period (14 days before Visit 3): At Visit 2, subjects who meet all study screening criteria will enter a Single-Blind Run-In Period. Investigational product will be dispensed. Subjects will be instructed to take the investigational product once daily in the morning. Subjects will be instructed to take the first Run-In investigational product (single-blind placebo) during the study visit. Visit 2 assessments will be performed according to Table 7 below. To qualify for randomization at Baseline (Visit 3) subjects must return unused study medication, be considered capable of completing study assessments, remain within study-specified criteria for MMSE, and meet all other eligibility requirements.

Baseline (Visit 3—Day 0) and Treatment Period 1 (Visit 4 and Visit 5—Day 14 and Day 28): At Visit 3 (Day 0), prior to ingestion of double-blind investigational product, baseline assessments will be performed to determine subject eligibility. Eligible subjects will be randomized to one of two groups, Nelotanserin or placebo, stratified by PDD or LBD, for the first four week double-blind treatment period. Subjects receiving Nelotanserin during Treatment Period 1 will receive a 40 mg dose (2×20 mg tablets) for the first three days of the treatment period, and will then receive an 80 mg dose (4×20 mg tablets) for the remainder of the treatment period. Double-blind investigational product will be dispensed at Visit 3. At the baseline visit, subjects will ingest the first dose of investigational product in the clinic in the presence of study center personnel. All additional doses will be ingested as outpatients. At each visit, subjects will be reminded to take the blinded investigational product each morning. Note: no investigational product will be dispensed at Visit 4 (Week 2) since subjects will have been provided a four-week supply of study medication at Visit 3. However, compliance with investigational product should be assessed at Visit 4, and study medication bottles returned to subjects to continue until Visit 5 (Day 28±3 days) when the next bottles will be dispensed.

All clinic visits will be scheduled according to specified visit windows, and all specified assessments will be completed (Table 7). The administration of the Cognitive Drug Research Power of Attention test should be kept within a +/−one-hour window of the time of day of the Baseline assessment for each subject to diminish the potential impact of circadian fluctuations in cognition. This should be taken into consideration when scheduling and performing baseline Power of Attention assessments.

The order of assessments should remain consistent. If possible, other assessments, including ECG, vital signs, and blood draws, should be performed after cognitive testing. Subjects who prematurely discontinue double-blind investigational product should be encouraged to return to the clinic for an Early Termination Visit, and the Visit 5 assessments and procedures will be completed.

Washout Period (Visit 5, Day 28—Visit 6, Day 56): No investigational product will be given to subjects during the washout period.

All clinic visits will be scheduled according to specified visit windows, and all specified assessments will be completed (Table 7). The administration of the Cognitive Drug Research Power of Attention test should be kept within a +/−one-hour window of the time of day of the Baseline assessment for each subject to diminish the potential impact of circadian fluctuations in cognition. This should be taken into consideration when scheduling and performing baseline Power of Attention assessments.

The order of assessments should remain consistent. If possible, other assessments, including ECG, vital signs, and blood draws, should be performed after cognitive testing. Subjects who prematurely discontinue double-blind investigational product should be encouraged to return to the clinic for an Early Termination Visit, and the Visit 6 assessments and procedures will be completed (except for dispensing study drug).

Treatment Period 2 (Visit 6, Day 56—Visit 8, Day 84): Subjects who received Nelotanserin during Treatment Period 1 will receive placebo during Treatment Period 2; subjects who received placebo during Treatment Period I will receive Nelotanserin during Treatment Period 2. Subjects receiving Nelotanserin during Treatment Period 2 will receive a 40 mg dose (2×20 mg tablets) for the first three days of the treatment period, and will then receive an 80 mg dose (4×20 mg tablets) for the remainder of the treatment period. Double-blind investigational product will be dispensed at Visit 6. At the baseline visit, subjects will ingest the first dose of investigational product in the clinic in the presence of study center personnel. All additional doses will be ingested as outpatients. At each visit, subjects will be reminded to take the blinded investigational product each morning. Note: no investigational product will be dispensed at Visit 7 (Week 10) since subjects will have been provided a four-week supply of study medication at Visit 6. However, compliance with investigational product should be assessed at Visit 7, and study medication bottles returned to subjects to continue until Visit 8 (Day 84±3 days).

All clinic visits will be scheduled according to specified visit windows, and all specified assessments will be completed (Table 7). The administration of the Cognitive Drug Research Power of Attention test should be kept within a +/−one-hour window of the time of day of the Baseline assessment for each subject to diminish the potential impact of circadian fluctuations in cognition. This should be taken into consideration when scheduling and performing baseline Power of Attention assessments.

The order of assessments should remain consistent. If possible, other assessments, including ECG, vital signs, and blood draws, should be performed after cognitive testing. Subjects who prematurely discontinue double-blind investigational product should be encouraged to return to the clinic for an Early Termination Visit, and the Visit 8 assessments and procedures will be completed.

TABLE 7

Time and Events Schedule

| | Screening | Placebo Run-in | Baseline | Treatment Period 1 | | Washout Period | Treatment Period 2 | |
|---|---|---|---|---|---|---|---|---|
| Study Visit Number: | V1 | V2 | V3/Pre-dose* | V4 | V5 | V6/Pre-dose* | V7 | V8 |
| Study Week: | W(−6) | W(−2) | W(0) | W(2) | W(4) | W(8) | W(10) | W(12) |
| Study Day: (relative to Baseline unless specified) | Up to −42 | −14 | | 14 | 28 | 56 | 70 | 84 | Early Termination |
| Informed consent | X | | | | | | | | |
| Inclusion and exclusion criteria | X | | X | | | | | | |
| Medical history with demographics | X | | | | | | | | |
| Concomitant medications review | X | X | X | X | X | X | X | X | X |
| Blood alcohol and drug screen | X | | | | | | | | |
| Columbia Suicide Severity Rating Scale, physician administered | X | | | | X | | | X | X |
| Neurological examination | X | | X | | X | X | | X | X |
| Physical Exam | X | X | X | X | X | X | X | X | X |
| 12-lead ECG | X | X | X | X | X | X | | | |
| Vital Signs | X | X | X | X | X | X | X | X | X |
| Review adverse events | X | X | X | X | X | X | X | X | |
| Labs: Serum Chemistry, Hematology, Urinalysis | X | | X | X | X | X | X | X | X |
| MMSE | X | | X | | | | | | |
| Review of visual hallucinations diary | | | X | X | X | X | X | X | X |
| Review of visual analog scale (VAS) | | | X | X | X | X | X | X | X |
| Scale for Assessment of Positive Symptoms | X | | X | X | X | X | X | X | X |
| Cognitive Drug Research Power of Attention computerized test | | | X | | X | X | | X | X |
| Unified Parkinson's Disease Rating Scale, Part II and Part III | | | X | | X | X | | X | X |
| Dispense Study Drug | | X | X | | | X | | | |

*Pre-dose assessments will be performed (to establish baseline for each treatment period)

Critical Baseline Assessments: Subjects need to continue to meet the eligibility criteria for visual hallucinations: visual hallucinations present for at least five days per week during each of the 2 weeks during the placebo run-in period.

Study Assessments and Procedures

Efficacy Assessments: All study assessments should be conducted by the investigator, and/or a suitably qualified designee, all of whom will be trained and certified to administer these measures for this study. Every effort should be made for the same person to conduct specific assessments on each individual subject at each study visit. Assessments will be monitored for quality. Screening assessments along with accompanying data will be reviewed to ensure that subjects meet the inclusion criteria. Other assessments will be monitored by using data collected.

Mini-Mental State Examination: The MMSE (Folstein et al, 1975) consists of 11 tests of orientation, memory (recent and immediate), concentration, language, and praxis. Scores range from 0 to 30, with lower scores indicating greater cognitive impairment. It is based on the performance of the subject and takes approximately 5 to 10 minutes to administer.

Daily Visual Hallucinations Diary: Subjects and caregivers will together complete a daily visual hallucinations diary, in which they will document the frequency and severity of visual hallucinations experienced by the subject. This diary will be completed each evening at a defined time (i.e. within one hour of the time at which the diary is first completed during the study). The subject and caregiver will note whether the subject experiences any visual hallucinations over the course of the day, and will describe the approximate number of hallucinations, the quality of the hallucinations, and the degree to which the hallucinations are disturbing to the subject and caregiver. This daily visual hallucinations diary will be reviewed by the investigator according to the time and events schedule described above, and the number of days since the last visit in which a subject experiences at least one visual hallucination will be recorded. An example of the Daily Visual Hallucinations Diary is shown below:

Visual Hallucinations Diary

As part of this investigation we will be looking at whether treatment is changing the number and type of visual hallucinations that patients are experiencing. By visual hallucinations, we mean occasions when patients report or acknowledge seeing false visions. This might take the form of patients seeing things that they know are unlikely to be real. The occurrence of visual hallucinations can also be evident from the way the patient acts, such as by talking to people that aren't there, or behaving as though they are seeing things that are not seen by other people.

Section A—to be jointly completed by the patient & caregiver

Date _____

Number of study tablets taken today _____

1. Have you experienced any visual hallucination today? Yes/no
2. How many times _____?
3. Describe what you saw:

Section B—for completion by the informant/caregiver

Figure 2A:
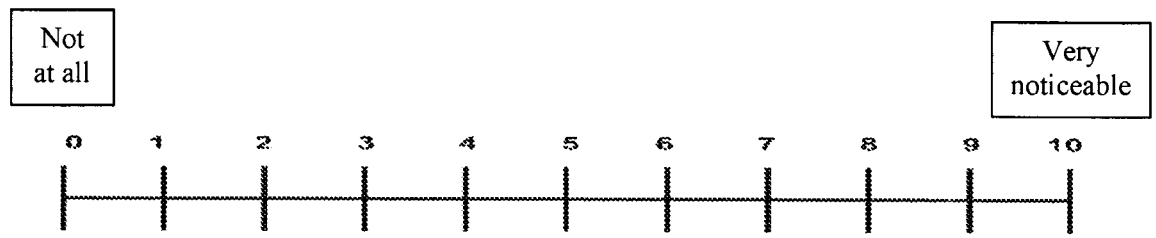
FIGS. 2A-2D each depict a visual analog scale (VAS) that is completed by the subject and the caregiver.
Figure 2B:
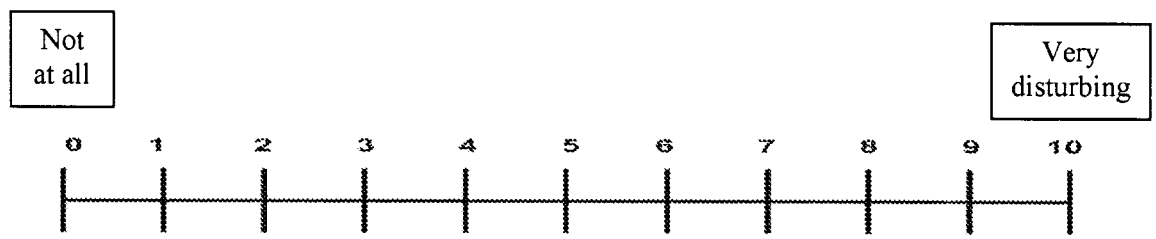

1. How noticeable were the visual hallucinations today (please place an X on the line shown in FIG. 2A)?
2. How disturbing were the visual hallucinations (please place an X on the line shown in FIG. 2B)

Section C—for completion by the patient

Figure 2C:
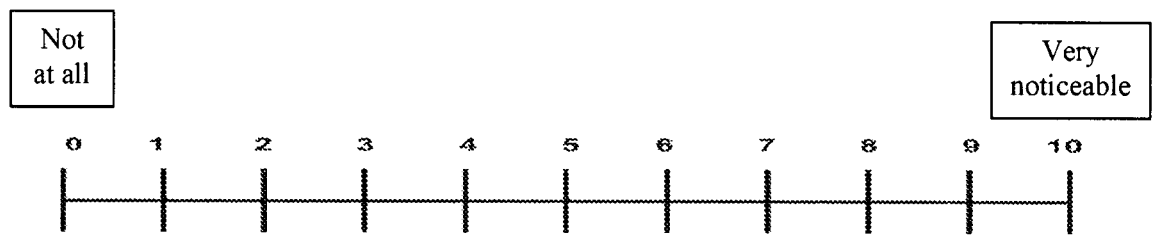
Figure 2D:
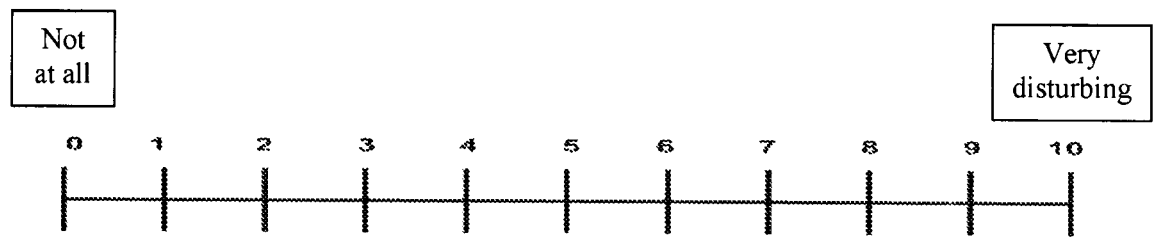

3. How noticeable were the visual hallucinations today (please place an X on the line shown in FIG. 2C)?
4. How disturbing were the visual hallucinations (please place an X on the line shown in FIG. 2D)

Visual Analog Scale: The visual analog scale (VAS) is a psychometric tool that enables an individual to quantify subjective assessments. The scale is usually a horizontal line, typically 100 mm in length, anchored at each end by a word description. The individual completing the VAS will place a mark on the line representing the degree to which they find the symptom in question impairing, and the VAS is scored by measuring the physical distance from either end of the line. The VAS will be completed by both the subject and his/her caregiver in accordance with the time and events schedule described above.

Scale for the Assessment of Positive Symptoms: The Scale for Assessment of Positive Symptoms (SAPS) was originally developed for the assessment of psychotic symptoms in schizophrenia. The SAPS assesses four symptom clusters (hallucinations, delusions, bizarre behavior, and positive formal thought disorder). The items assessed in each of these clusters are rated based on frequency, and the global score item in each cluster is based on both the frequency and extent to which symptoms disrupt functioning. For this study, the use of a shortened form of the SAPS that focuses only on hallucinations and delusions will be used, as the other components of the SAPS are not as directly relevant to patients with DLB and PDD. The SAPS will be assessed in accordance with the time and events schedule described above.

Cognitive Drug Research Power of Attention Computerized Test: The Power of Attention is a computerized battery of tests used to evaluate attention and alertness. The battery is comprised of three key latency measures from the cognitive drug research assessment: simple reaction time, choice reaction time, and the digit vigilance task. A typical single assessment of the tests that comprise the Power of Attention requires less than 10 minutes. The Power of Attention battery and its constituent components have been employed to evaluate attention and alertness in multiple studies of DLB and PDD.

Safety and Screening Assessments

Adverse Events: The investigator or site staff is responsible for detecting, documenting, and reporting events that meet the definition of an AE or SAE.

Definition of Adverse Events: An AE is any untoward medical occurrence associated with the use of a drug in humans, whether or not considered drug related. Therefore an AE can be ANY unfavorable and unintended sign (including an abnormal laboratory finding or vital sign measurement), symptom, or disease temporally associated with the use of a medicinal product, without any judgment about causality.

Events meeting the definition of an AE include:

Exacerbation of a chronic or intermittent pre-existing condition including either an increase in frequency and/or intensity of the condition.

New conditions detected or diagnosed after investigational product administration even though it may have been present prior to the start of the study.

Signs, symptoms, or the clinical sequelae of a suspected drug interaction.

Signs, symptoms, or the clinical sequelae of a suspected overdose of either investigational product or a concomitant medication.

Clinically significant abnormal findings (laboratory test results, vital signs, physical examination findings, ECGs, radiologic exams or other studies) should be recorded as AEs. A "clinically significant" finding is one that affects clinical management, including additional visits, monitoring or referrals, diagnostic tests or alteration of treatment, or that is considered clinically significant by the investigator. A clinically significant finding may be a change in a test that has previously been abnormal but now requires additional action.

When a medical or surgical procedure is performed, the condition that leads to the procedure should be recorded as the AE.

Events that do not meet the definition of an AE include:

Anticipated day-to-day fluctuations or expected progression of pre-existing disease(s) or condition(s) present or detected at the start of the study unless judged by investigator to be more severe than expected for the subject's underlying condition.

Abnormal laboratory, ECG, or vital sign measurements that are not labelled clinically significant (see definition above).

Situations where an untoward medical occurrence did not occur (social and/or convenience admission to a hospital).

Overdose in the absence of other AEs will not be reported as an AE in its own right.

Changes in C-SSRS during the course of the study indicating worsening should be evaluated by the investigator for clinical significance, and if clinically significant (e.g., alteration in medical care or intervention is required), an associated AE should be recorded, if present. The AE should be the primary underlying clinical manifestation assessed as clinically significant, and not the change in score itself.

Adverse events are recorded from the time that informed consent is signed, including those that occur during the Single-Blind Run-in Period. Treatment emergent adverse events are defined as those that occur on or after the date of the first dose of investigational product.

Definition of Serious Adverse Event: An AE is considered serious if, in the view of either investigator or sponsor, it results in any of the following outcomes: Death; A life-threatening AE, (An AE is considered "life-threatening" if, in the view of either the investigator or sponsor, its occurrence places the patient or subject at immediate risk of death. It does not include an AE that, had it occurred in a more severe form, might have caused death. The determination of whether an AE is life threatening can be based on the opinion of either the investigator or sponsor. Thus, if either believes that it meets the definition of life-threatening, it must be considered life-threatening for reporting purposes); Inpatient hospitalization or prolongation of existing hospitalization; A persistent or significant incapacity or substantial disruption of the ability to conduct normal life functions; or A congenital anomaly/birth defect.

Important medical events that may not result in death, be life threatening, or require hospitalization may be considered serious when, based upon appropriate medical judgment, they may jeopardize the patient or subject and may require medical or surgical intervention to prevent one of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse.

This definition of an SAE permits either the sponsor or the investigator to decide if an event is serious. Because SAEs are critically important for the identification of significant safety problems, FDA believes taking into account both the investigator's and the sponsor's assessment is important. For example, the investigator's perspective may be informed by having actually observed the event, and the sponsor is likely to have broader knowledge of the drug and its effects to inform its evaluation of the significance of the event. If either the sponsor or investigator believes that the event is serious, the event must be considered serious and evaluated by the sponsor for possible expedited reporting.

Time Period and Frequency for Collecting Adverse Event and Serious Adverse Event Information: Collection of AEs and SAEs will begin at the time a subject signs informed consent and continues until the follow-up contact, as shown in the Time and Events Schedule. All SAEs will be recorded and reported within 24 hours of the investigator becoming aware of the SAE. Investigators are not obligated to actively seek AEs or SAEs in former study subjects. However, if the investigator learns of any SAE, including a death, at any time after a subject has been discharged from the study, and he/she considers the event reasonably related to the investigational product or study participation, the investigator must promptly notify the sponsor or sponsor representative.

Assessment of Adverse Events: The severity of each AE will be assessed by the investigator, or designee approved and documented for this study, as mild, moderate, or severe based on the below definitions:

Mild: Event that is usually transient and may require only minimal treatment or therapeutic intervention. The event does not generally interfere with usual activities of daily living Moderate: Event that is usually alleviated with additional specific therapeutic intervention. The event interferes with usual activities of daily living, causing discomfort, but poses no significant or permanent risk of harm to the subject.

Severe: Event that interrupts usual activities of daily living or significantly affects clinical status, or may require intensive therapeutic intervention.

Note that severity is not the same as "seriousness," which is defined herein. Outcome will be assessed using the following categories: recovered/resolved, not recovered/not resolved, recovered/resolved with sequelae, fatal, or unknown.

Method of Detecting Adverse Events and Serious Adverse Events: Care will be taken not to introduce bias when detecting AEs and/or SAEs. Open-ended and non-leading verbal questioning is the preferred method to inquire about AE occurrence. Appropriate questions include: "How are you feeling?"; "Have you had any (other) medical problems since your last visit/contact?" or "Have you taken any new medicines, other than those provided in this study, since your last visit/contact?"

Follow-up of Adverse Events and Serious Adverse Events: After the initial AE/SAE report, the investigator is required to proactively follow each subject at subsequent visits/contacts. All AEs and SAEs will be followed until resolution, until the condition stabilizes, until the event is otherwise explained, or until the subject is lost to follow-up.

Physical Examinations: Physical examinations will be performed as indicated in Table 7. A complete physical examination will include, at a minimum, assessment of the cardiovascular, respiratory, gastrointestinal, and neurological systems. Neurological examinations will include assessment of gait, balance, coordination, cranial nerves and motor and sensory systems. A brief, symptoms-directed physical examination will include, at a minimum, assessments of the lungs, cardiovascular system, and abdomen (liver and spleen). Physical examinations at Screening and Visit 8 will be full examinations; at all other study visits, an abbreviated physical examination is required.

Vital Signs: Vital signs will be measured after the subject has been in the seated position for 5 minutes and will include temperature, systolic and diastolic blood pressures, pulse rate, and respiratory rate. Postural changes will be measured within 3 minutes of appropriate body position change. Body weight will also be recorded at each visit and height will be recorded at Screening.

Electrocardiogram: Single 12-lead ECGs will be obtained at each time point during the study using an ECG machine that automatically calculates the heart rate and measures PR, QRS, QT, and QTc intervals with the subject in the supine position. The investigator or designated qualified physician at the site will evaluate the Screening ECG for any abnormalities that should exclude the subject from the study or require acute additional evaluation or intervention. They should also evaluate the ECG printouts for all subsequent visits for any new abnormalities. Any abnormality should include a determination of clinical significance. A clinically significant ECG finding is one that requires additional medical evaluation or treatment.

Clinical Safety Laboratory Assessments: All protocol-required laboratory assessments, as defined in Table 8, must be conducted in accordance with the Study Procedures Manual and Protocol Time and Events Schedule (Table 7). Laboratory requisition forms must be completed and samples must be clearly labelled with the subject number, protocol number, site/center number, and visit date. Details for the preparation and shipment of samples will be provided by the laboratory and are detailed in the Study Procedures Manual. Reference ranges for all safety parameters will be provided to the site by the laboratory responsible for the assessments.

Abnormal laboratory tests that are clinically significant should also be recorded as AEs on the eCRF. Clinically significant means that the confirmed abnormal test result has an impact on patient management, including additional monitoring diagnostic tests, or changes in treatment.

The same standard applies to additional non-protocol specified laboratory assessments that are performed at the institution's local laboratory and result in a change in subject management (i.e., monitoring, diagnostic tests, or any alteration in treatment).

Refer to the Study Procedures Manual for appropriate processing and handling of samples to avoid duplicate and/or additional blood draws.

Hematology, clinical chemistry, urinalysis, and other screening laboratory parameters to be tested are listed in Table 8.

TABLE 8

Protocol-Required Screening and Safety Laboratory Assessments

| Laboratory Assessments | Parameters | | |
|---|---|---|---|
| Hematology | Platelet count<br>RBC count<br>Hemoglobin<br>Hematocrit | RBC Indices<br>MCV<br>MCH | WBC Count with Differential<br>Neutrophils<br>Lymphocytes<br>Monocytes<br>Eosinophils<br>Basophils |
| Clinical Chemistry | BUN<br>Creatinine<br>Glucose | Potassium<br>Sodium<br>Calcium<br>Chloride<br>Bicarbonate | AST<br>ALT<br>Alkaline phosphatase<br>Total and direct bilirubin<br>Total protein<br>Albumin<br>GGT |

TABLE 8-continued

Protocol-Required Screening and Safety Laboratory Assessments

| Laboratory Assessments | Parameters |
|---|---|
| Routine Urinalysis | Specific gravity<br>pH, glucose, protein, blood, and ketones by dipstick<br>Microscopic examination (if blood or protein is abnormal) |
| Screening Tests only | Drugs and alcohol screen<br>HBsAg<br>Hepatitis C antibody<br>TSH<br>Vitamin $B_{12}$<br>Syphilis serology<br>Serum or urine hCG pregnancy test (as needed for women of child bearing potential) |

Abbreviations:
ALT = alanine aminotransferase;
AST = aspartate aminotransferase;
BUN = blood urea nitrogen;
FSH = follicle stimulating hormone;
GGT = gamma glutamyltransferase;
HBsAg = hepatitis B surface antigen;
hCG = human chorionic gonadotropin;
MCH = mean corpuscular hemoglobin;
MCV = mean corpuscular volume;
RBC = red blood cell;
TSH = thyroid stimulating hormone;
WBC = white blood cell.

All laboratory tests with values that are considered clinically significantly abnormal during participation in the study or within 7 days after the last dose of investigational product should be repeated until the values return to normal or baseline or until the value stabilizes. If such values do not return to normal within a period judged reasonable by the investigator, the etiology should be identified and the Medical Monitor notified.

Assessment of Suicidality: Subjects will be assessed for suicidality before and during the study using the Columbia Suicide Severity Rating Scale (C-SSRS). Subjects considered to be at significant risk will be excluded from the study. The C-SSRS is a brief measure which is designed to assess severity and change of suicidality by integrating both behavior and ideation. It assesses intensity of ideation (a potentially important marker of severity), specifically asking about frequency, duration, controllability, deterrents, and reasons for the ideation which was most severe during the respectively assessed timeframe. Suicidal behavior is also assessed by asking further questions to categorize the behaviors into actual, interrupted, or aborted attempts; as well as preparatory and non-suicidal self-injurious behavior. The C-SSRS will be completed by a rater trained and certified to administer this scale. Any change in C-SSRS score indicating the presence of suicidality should be evaluated by the investigator for clinical significance to determine continued study eligibility and appropriate clinical actions (including but not limited to a referral to a mental health professional). Clinically meaningful suicidal ideation, suicidal behavior and completed suicide should be recorded as adverse events.

Assessment of Parkinsonism: Subjects will be assessed for signs of Parkinsonism before and during the study using the Unified Parkinson's Disease Rating Scale (UPDRS) Part II and Part III. The UPDRS Part II is a patient self-evaluation of the activities of daily life (ADLs) including speech, swallowing, handwriting, dressing, falling, salivating, walking, and tremor. The UPDRS Part III is clinician-scored motor evaluation including rigidity, figure taps, tremor at rest, posture, leg agility, bradykinesia.

Pregnancy: Details of all pregnancies in female subjects will be collected after the start of dosing and until 30 days after the last dose of investigational product. If a pregnancy is reported, then the investigator should inform the Medical Monitor within 24 hours of learning of the pregnancy. The pregnancy must be followed up to determine outcome (including premature termination) and status of mother and child. Pregnancy complications and elective terminations for medical reasons must be reported as an AE or SAE. Spontaneous abortions must be reported as an SAE. Any SAE occurring in association with a pregnancy brought to the investigator's attention after the subject has completed the study and considered by the investigator as possibly related to the investigational product must be promptly reported to the sponsor or the sponsor's representative. The investigator must attempt to collect pregnancy information on any female partners of male study subjects who become pregnant while the subject is enrolled in the study. Pregnancy information must be reported to the sponsor or the sponsor's representative as described above. The partner will also be followed to determine the outcome of the pregnancy. Information on the status of the mother and child will be forwarded to sponsor or the sponsor's representative. Generally, follow-up will be no longer than 6 to 8 weeks following the estimated delivery date. Any premature termination of the pregnancy will be reported.

Statistical Considerations And Data Analyses

Hypotheses: No formal hypotheses are planned for the study. The primary statistical framework will be to evaluate the safety of Nelotanserin as compared to placebo following treatment for four weeks. The estimation approach using a mixed-effect model will be performed to estimate the between treatment difference in the secondary efficacy endpoints of interest.

Sample Size Considerations: The primary comparison of interest is to compare the safety of Nelotanserin to placebo after a four week treatment period in patients with Lewy Body Dementia. A sample size of up to approximately 20 patients (comprised of approximately 10 DLB patients and up to 10 PDD patients) in a crossover design will enable appropriate evaluation of key safety parameters after treatment with Nelotanserin.

Data Analysis Considerations

Analysis Populations: The primary population for safety analyses will be the Safety Population, which will consist of all subjects who were randomized and took at least one dose of investigational product. The efficacy analysis population will consist of all randomized subjects who have taken at least one dose of investigational product and who have at least one post-baseline efficacy assessment. This will be the primary population used for the efficacy analysis.

Key Elements of Analysis Plan: The primary objective of this study is to evaluate the safety and tolerability of Nelotanserin. Evaluation of the efficacy of Nelotanserin is not a primary objective of the study. All efficacy and safety measures over the course of the study will be presented. Continuous data will be summarized by means, SDs, medians, maximum, minimum, and number of subjects. Categorical data will be summarized by counts and percentages. Listings will be sorted by sequence subject, period and time. Summaries will be presented by treatment and time. Version 9.2 or higher of the SAS system will be used to analyze the data as well as to generate tables, figures, and listings. Further details of analyses to be performed will be provided in the statistical analysis plan. Analysis datasets will be constructed using version SAS 9.2 or later following current CDISC guidelines.

Safety Analyses: The safety analyses will be based on the Safety Population. Safety will be assessed by summarizing and analyzing AEs, laboratory analytes, vital signs, ECG parameters, physical examination findings, and concomitant medications.

Adverse Events: AEs will be considered treatment-emergent (TEAEs) if they start or worsen after first dose of the double-blinded treatment. If an AE begins or worsens on the first day of investigational product administration, a CRF and source data note will be provided to clarify whether it occurred prior to or after investigational product administration. TEAEs, SAEs including deaths, AEs that lead to discontinuation of investigational product, and AEs by maximum severity and relationship to investigational product will be summarized by MedDRA system organ class (SOC) and preferred term. TEAEs will also be summarized by preferred term, sorted by decreasing frequency within SOC. AEs will be summarized separately for the Single-Blind Run-In Period, the Double-Blind Treatment Period, and the Follow-up Period.

Clinical Laboratory Tests: Summaries of clinical laboratory data will be provided for subjects in the Safety Population. No inferential statistics will be provided. Quantitative values and change from baseline in quantitative values will be summarized by planned nominal time and treatment for each quantitative laboratory value. Listings of all laboratory results and reference ranges will be provided. For multiple lab assessments at the same time point, the worst value will be used for the data summaries. Laboratory values that fall outside of the reference range will be flagged as H=High or L=low. A lab shift table may be provided to show the baseline to the worst post value. Laboratory values that do not meet the laboratory abnormalities will be assigned N=normal in the shift table.

Vital Signs, Electrocardiograms, Physical Findings, and Other Safety Evaluations: Descriptive summaries of medical history, vital signs, weight, and ECG parameters will be presented separately for each study visit and treatment group. Clinically significant abnormal morphological ECG findings will be summarized by study visit. Abnormal physical examination findings will be summarized to include the number and percentage of subjects experiencing each treatment-emergent abnormal physical finding. Concomitant medications will be coded using the WHO ATC classification and these data will be summarized by treatment group.

Secondary Efficacy Analyses: Efficacy data will be summarized and listed by treatment and assessment time by period and overall. The between treatment differences for the efficacy endpoints of interest will be estimated using a mixed effect model with sequence, period, and treatment as fixed effect and subject-within-sequence as random effect. The least squares means, treatment difference and 95% CIs, P-values will be estimated for the following efficacy endpoints: Change in the global severity of visual hallucinations from baseline to four weeks, as recorded by a visual analog scale (VAS) completed by the patient and his/her primary caregiver; Change in the frequency and severity of hallucinations and delusions from baseline to four weeks as measured by the Scale for Assessment of Positive Symptoms (SAPS) hallucinations and delusions subscores; Change in cognition from baseline to four weeks as measured by the Cognitive Drug Research Power of Attention computerized test; or Change in frequency of visual hallucinations from baseline to four weeks, as recorded by daily patient and caregiver diary.

Carry over effect will be tested and evaluated based on the pre-dose assessment in each treatment period. The between treatment comparisons will also be performed using an analysis of covariance model based on Treatment Period 1 data.

Other Analyses: Additional analyses of the data may be conducted as deemed appropriate and will be detailed in the SAP. Further analyses of the data not specified in the SAP may be undertaken as post hoc analyses after completion of the study. Results of all study assessments will be included in an appendix to the study report.

Example 3—Patient Diary

Visual Hallucinations

1. How often did you experience visual hallucinations today? Place an "X" in one of the boxes below.

| 0 | = not at all |
|---|---|
| 1 | |
| 2 | |
| 3 | |
| 4 | |
| 5 | |
| 6 | |
| 7 | |
| 8 | |
| 9 | |

| 10 | = All the time |
|----|----------------|

2. How disturbing were your visual hallucinations today (rate the most disturbing visual hallucination if you had more than one)? Seeing things that were not real. Place an "X" in one of the boxes below

| 0 | = not at all |
|----|----------------|
| 1 | |
| 2 | |
| 3 | |
| 4 | |
| 5 | |
| 6 | |
| 7 | |
| 8 | |
| 9 | |
| 10 | = Extremely disturbing |

3. Describe your visual hallucinations. How long did they last? What did you see? How did you feel? Did you believe what you saw was real?

Auditory Hallucinations

4. How often did you experience auditory hallucinations today? Hearing things that were not real. Place an "X" in one of the boxes below.

| 0 | = not at all |
|----|----------------|
| 1 | |
| 2 | |
| 3 | |
| 4 | |
| 5 | |
| 6 | |
| 7 | |

| 8 | |
|---|---|
| 9 | |
| 10 | = All the time |

5. How disturbing were your auditory hallucinations today (rate the most disturbing visual hallucination if you had more than one)? Place an "X" in one of the boxes below

| 0 | = not at all |
|---|---|
| 1 | |
| 2 | |
| 3 | |
| 4 | |
| 5 | |
| 6 | |
| 7 | |
| 8 | |
| 9 | |
| 10 | = Extremely disturbing |

6. Describe your auditory hallucinations. How long did they last? What did you see? How did you feel?

Other Hallucinations (non-visual and non-auditory)

7. How often did you experience other types of hallucinations today – non-visual and non-auditory? Experiencing things that were not real in ways other than seeing or hearing. Place an "X" in one of the boxes below.

| 0 | = not at all |
|---|---|
| 1 | |
| 2 | |
| 3 | |
| 4 | |

| | |
|---|---|
| 5 | |
| 6 | |
| 7 | |
| 8 | |
| 9 | |
| 10 | = All the time |

8. How disturbing were these other non-visual and non-auditory hallucinations today (rate the most disturbing visual hallucination if you had more than one)? Place an "X" in one of the boxes below.

| | |
|---|---|
| 0 | = not at all |
| 1 | |
| 2 | |
| 3 | |
| 4 | |
| 5 | |
| 6 | |
| 7 | |
| 8 | |
| 9 | |
| 10 | = Extremely disturbing |

9. Describe these other types of hallucinations. How long did they last? What did you see? How did you feel? Did you believe what you experienced was real?

Study Partner Observation on Hallucinations

10. Does it seem like the patient was responding to or disturbed by the hallucinations today?

If yes, please rate the severity of these reactions on the following scale (place an X on the line corresponding to the severity)

Minimal  Severe

Study Partner Observation on Sleep Behaviors

11. Did the patient have any excessive arm or leg movements last night?  Yes / No a. If yes, how many times during the night? _____ b. If yes, please rate the severity of these excessive arm or leg movements on the following scale (place an X on the line corresponding to the severity)

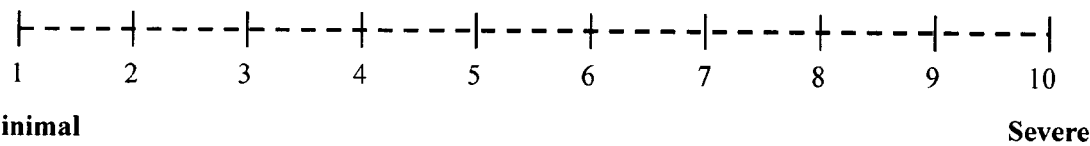

Minimal                                                                        Severe c. Were you injured by the patient's excessive arm or leg movements? Yes / No
       If yes, describe:

d. Was the patient injured?  Yes / No
       If yes, describe:

12. Did the patient appear to act out any nightmares last night? Yes / No e. If yes, please describe the content of the dreams or nightmares as reported by the patient, including how emotionally distressing they were to the patient f. If yes, please rate the severity of these nightmares as reported by the patient. Please use the following scale (place an X on the line corresponding to the severity)

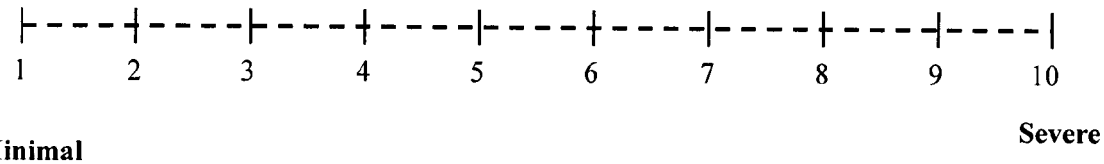

Minimal                                                                        Severe

[533]     Example 4 – Patient Diary

[534] Visual Hallucinations Diary

[535] As part of this investigation we will be looking at whether treatment affects the duration, frequency, and type of visual hallucinations that patients experience. By visual hallucinations, we mean occasions when patients see false visions. This might take the form of patients seeing things that they know are unlikely to be real. The occurrence of visual hallucinations can also be evident from the way the patient behaves. For example, patients may talk to or interact with people that are not actually present. This diary should be completed at the same time each evening (ideally one hour before bedtime) and jointly by the patient and caregiver together in discussion with one another.

[536] Section A – to be jointly completed by the patient & caregiver

Date _____

Number of study tablets taken today _____

1. How many visual hallucinations did you have today? For example, if you saw an animal that wasn't real at breakfast and a person who wasn't real at lunch, that would count as 2 hallucinations. _____

2. On average how long did a typical visual hallucination last today? For example, if you saw an animal that wasn't real and that lasted for 30 minutes at breakfast, and you saw a person who wasn't real and that lasted for 60 minutes at lunch, then your visual hallucinations lasted for 45 minutes on average. _____ (min)

3. Describe the visual hallucinations you experienced today that affected you the most. How long did it/they last? What did you see? Were they vivid images (describe the color and size of what you saw), like shadows, or just a feeling? How did you feel? Do you believe what you saw was real?

[537] If visual hallucinations occurred today, proceed to Section B

[538] Section B

[539] To be completed by the caregiver

1. How many times did you see the patient responding to/disturbed by visual hallucinations? _____

2. How disturbing were the visual hallucinations experienced by the patient today (please rate on a 1-10 numerical rating scale, where 1 represents "not at all disturbing" and 10 represents "very disturbing")? _____

3.

[540] To be completed by the patient

1. How disturbing were the visual hallucinations today (please rate on a 1-10 numerical rating scale, where 1 represents "not at all disturbing" and 10 represents "very disturbing")? _____

What is claimed:

1. A method for the treatment of visual hallucinations, in a subject in need thereof, comprising administering to said subject a therapeutically effective amount of a 5-HT$_{2A}$ inverse agonist, wherein the 5-HT$_{2A}$ inverse agonist is nelotanserin or a pharmaceutically acceptable salt, hydrate, polymorph, or solvate thereof.

2. The method of claim 1, wherein the nelotanserin or a pharmaceutically acceptable salt, hydrate, polymorph, or solvate thereof is selected from the group consisting of Form I of 1-[3-(4-bromo-2-methyl-2H-pyrazol-3-yl)-4-methoxy-phenyl]-3-(2,4-difluoro-phenyl)-urea, Form II of 1-[3-(4-bromo-2-methyl-2H-pyrazol-3-yl)-4-methoxy-phenyl]-3-(2,4-difluoro-phenyl)-urea and a combination thereof.

3. The method of claim 1, wherein the therapeutically effective amount of nelotanserin or a pharmaceutically acceptable salt, hydrate, polymorph, or solvate thereof is from about 10 mg to about 160 mg.

4. The method of claim 1, wherein the therapeutically effective amount of nelotanserin or a pharmaceutically acceptable salt, hydrate, polymorph, or solvate thereof is about 10 mg, about 20 mg, about 40 mg, about 80 mg, or about 160 mg.

5. The method of claim 1, wherein the therapeutically effective amount of nelotanserin is about 10 mg, about 20 mg, about 40 mg, about 80 mg, or about 160 mg.

6. The method of claim 1, wherein the therapeutically effective amount of nelotanserin is about 10 mg.

7. The method of claim 1, wherein the therapeutically effective amount of nelotanserin is about 20 mg.

8. The method of claim 1, wherein the therapeutically effective amount of nelotanserin is about 40 mg.

9. The method of claim 1, wherein the therapeutically effective amount of nelotanserin is about 80 mg.

10. The method of claim 1, wherein the therapeutically effective amount of nelotanserin is about 160 mg.

11. The method of claim 1, wherein the therapeutically effective amount of the 5-HT$_{2A}$ inverse agonist is administered once a day, twice a day, three times a day, or four times a day.

12. The method of claim 1, wherein the 5-HT$_{2A}$ inverse agonist is in a pharmaceutical composition configured for immediate release, for extended release, for delayed release, or any combination thereof.

13. The method of claim 1, wherein the 5-HT$_{2A}$ inverse agonist is in a pharmaceutical composition, and wherein the pharmaceutical composition is formulated for oral administration.

14. The method of claim 1, wherein the therapeutically effective amount of the 5-HT$_{2A}$ inverse agonist is administered about one to about four times per day, once daily in the morning, once daily about 1 hour prior to the subject's bedtime, or twice daily.

15. The method of claim 1, wherein the subject is a human.

16. The method of claim 15, wherein the human is an adult with a diagnosis of a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

17. The method of claim 15, wherein the human has a concurrent diagnosis of visual hallucinations, and a condition selected from Lewy Body Dementia, probable Dementia with Lewy bodies, Dementia with Lewy bodies, Parkinson's disease dementia, Parkinson's disease, multiple system atrophy, Alzheimer's disease, vascular dementia, dementia, mild cognitive impairment, Parkinson's disease psychosis, Alzheimer's disease psychosis, a sleep disturbance, insomnia, delusions, agitation, Alzheimer's agitation, aggression, REM sleep behavior disorder, schizophrenia, and any combination thereof.

18. The method of claim 15, wherein the human has a diagnosis of probable Dementia with Lewy Bodies.

19. The method of claim 18, wherein the diagnosis of probable Dementia with Lewy bodies is defined by the presence of dementia and at least one of:
   at least two Core Criteria selected from visual hallucinations, cognitive fluctuations, and Parkinsonism, and any combination thereof, and
   one Core Criteria selected from visual hallucinations, cognitive fluctuations, and Parkinsonism, and any combination thereof; and at least one Suggestive Criteria selected from REM Sleep Behavior Disorder, Severe Neuroleptic Sensitivity, Low Dopamine Transporter Uptake on DaT SPECT Imaging Scan; and any combination thereof.

20. The method of claim 15, wherein the human has a diagnosis of Dementia with Lewy Bodies.

21. The method of claim 15, wherein the human has a Mini Mental State Examination score of greater than, or equal to, about 18.

22. The method of claim 15, wherein the human is an adult with a diagnosis of visual hallucinations associated with Dementia with Lewy Bodies.

23. The method of claim 15, wherein the human is an adult aged 50-85 inclusive.

24. The method of claim 15, wherein the human has experienced persistent visual hallucinations.

25. The method of claim 24, wherein the presence of persistent hallucinations is defined by a score of four or greater on the hallucinations component of the Neuropsychiatric Inventory (NPI Item B) at screening.

26. The method of claim 15, wherein the human has experienced visual hallucinations on at least five days in a week.

27. The method of claim 1, wherein the subject is concurrently receiving a therapeutically effective amount of at least one additional therapeutic agent selected from the group consisting of melatonin, quetiapine, clonazepam, levodopa, carbidopa, an antiparkinsonian drug, an acetylcholinesterase inhibitor, NMDA receptor antagonist, and a combination thereof.

28. The method of claim 27, wherein the antiparkinsonian drug is selected from an MAO-B inhibitor, a COMT inhibitor, a dopamine agonist and any combination thereof.

\* \* \* \* \*